(12) United States Patent
Braddock et al.

(10) Patent No.: US 12,157,903 B2
(45) Date of Patent: Dec. 3, 2024

(54) COMPOSITIONS AND METHODS FOR REDUCING PROGRESSION OF NEPHROLITHIASIS

(71) Applicant: YALE UNIVERSITY, New Haven, CT (US)

(72) Inventors: Demetrios Braddock, Guilford, CT (US); Clemens Bergwitz, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 17/052,199

(22) PCT Filed: May 7, 2019

(86) PCT No.: PCT/US2019/031049
§ 371 (c)(1),
(2) Date: Nov. 1, 2020

(87) PCT Pub. No.: WO2019/217373
PCT Pub. Date: Nov. 14, 2019

(65) Prior Publication Data
US 2021/0363506 A1 Nov. 25, 2021

Related U.S. Application Data

(60) Provisional application No. 62/668,293, filed on May 8, 2018.

(51) Int. Cl.
*C12N 9/14* (2006.01)
*A61P 13/12* (2006.01)
*A61K 38/00* (2006.01)

(52) U.S. Cl.
CPC ............. *C12N 9/14* (2013.01); *A61P 13/12* (2018.01); *A61K 38/00* (2013.01); *C07K 2319/02* (2013.01); *C07K 2319/30* (2013.01); *C07K 2319/31* (2013.01); *C12Y 306/01009* (2013.01)

(58) Field of Classification Search
CPC .................................. C12N 9/14; A61P 13/12
See application file for complete search history.

(56) References Cited

U.S. PATENT DOCUMENTS

| | | | |
|---|---|---|---|
| 5,968,508 A | 10/1999 | Goldfine et al. | |
| 9,744,219 B2* | 8/2017 | Braddock | A61P 9/10 |
| 10,064,917 B2* | 9/2018 | Braddock | C12Q 1/6883 |
| 10,357,541 B2* | 7/2019 | Braddock | A61K 38/46 |
| 10,517,927 B2* | 12/2019 | Braddock | A01K 67/0271 |
| 10,583,170 B2* | 3/2020 | Braddock | A61P 13/12 |
| 10,624,958 B2* | 4/2020 | Braddock | A61P 19/08 |
| 10,960,050 B2* | 3/2021 | Braddock | A61K 38/465 |
| 11,266,722 B2* | 3/2022 | Braddock | A61P 9/10 |
| 2010/0203076 A1* | 8/2010 | Fotin-Mleczek | A61P 35/00 424/193.1 |
| 2014/0349369 A1 | 11/2014 | Buechler et al. | |
| 2016/0184458 A1* | 6/2016 | Heartlein | A61K 48/0075 514/44 R |
| 2017/0340713 A1 | 11/2017 | Braddock et al. | |
| 2018/0085492 A1 | 3/2018 | Ameer et al. | |

FOREIGN PATENT DOCUMENTS

| | | |
|---|---|---|
| JP | H04292169 A | 10/1992 |
| JP | 2014509617 A | 4/2014 |
| JP | 2016530899 A | 10/2016 |
| JP | 201718330 A | 8/2018 |
| WO | 0239994 A2 | 5/2002 |
| WO | 03040340 A2 | 5/2003 |
| WO | 2006135925 A2 | 12/2006 |
| WO | 2006135935 A1 | 12/2006 |
| WO | 2008105911 A2 | 9/2008 |
| WO | 2014126965 A2 | 8/2014 |
| WO | 2016187408 A1 | 11/2016 |
| WO | 2017191274 A2 | 11/2017 |

OTHER PUBLICATIONS

Moochhala SH et al. Renal calcium stones: insights from the control of bone mineralization. Experimental Physiology. 2007. 93.1. pp. 43-49 (Year: 2007).*
Buckley, et al., "Plasma cell membrane glycoprotein PC-1. cDNA cloning of the human molecule, amino acid sequence, and chromosomal location", J Biol Chem. 265(29), Oct. 1990, 17506-17511.
Robbie, et al. "A novel investigational Fc-modified humanized monoclonal antibody, motavizumab-YTE, has an extended half-life in healthy adults." Antimicrobial agents and chemotherapy 57.12 (2013): 6147-6153.
Okawa, et al., "Mutation in Npps in a mouse model of ossification of the posterior longitudinal ligament of the spine", Nat Genet. 19(3), Jul. 1998, 271-273.
Johnson, et al. "The nucleoside triphosphate pyrophosphohydrolase isozyme PC-1 directly promotes cartilage calcification through chondrocyte apoptosis and increased calcium precipitation by mineralizing vesicles." The Journal of Rheumatology 28.12 (2001): 2681-2691.
Li, et al. "Serum phosphate concentration and incidence of stroke: a systemic review and meta-analysis." Neurological sciences 35.12 (2014): 1877-1882.
Kassim (Clinical Advances in Hematology & Oncology vol. 14, Issue May 5, 2016 pp. 307-309).
Sayer "Progress in understanding the genetics of calcium-containing nephrolithiasis." Journal of the American Society of Nephrology 28.3 (2017): 748-759.
Extended European Search Report for European Patent Application No. 19798912.2 dated Feb. 9, 2022.

(Continued)

*Primary Examiner* — Paul J Holland
(74) *Attorney, Agent, or Firm* — Saul Ewing LLP; Kathryn Doyle; Domingos J. Silva

(57) ABSTRACT

The present invention includes compositions and methods for treating and/or preventing renal and/or kidney stones in a human subject. In certain embodiments, the subject is administered certain ENPP1 polypeptides or ENPP3 polypeptides, mutants, or mutant fragments thereof.

9 Claims, 7 Drawing Sheets
Specification includes a Sequence Listing.

(56) References Cited

OTHER PUBLICATIONS

Albright, et al., "ENPP1-Fc prevents mortality and vascular calcifications in rodent model of generalized arterial calcification of infancy", Nat Commun., Jun. 2015, 10006.
Caballero, et al., "Impaired urinary osteopontin excretion in Npt2a−/− mice", Am J Physiol Renal Physiol. 312(1), 2017, F77-F83.
Dasgupta, et al., "Mutations in SLC34A3/NPT2c are associated with kidney stones and nephrocalcinosis", J Am Soc Nephrol. 25(10), 2014, 2366-2375.
Fleisch, et al., "Inhibitors and promoters of stone formation", Kidney Int. 13(5), 1978, 361-371.
Jansen, et al., "Proteolytic maturation and activation of autotaxin (NPP2), a secreted metastasis-enhancing lysophospholipase D", J Cell Sci. 118(Pt 14), 2005, 3081-3089.
Li, et al., "Response of Npt2a knockout mice to dietary calcium and phosphorus", PLoS One. 12(4), 2017, e0176232.
Ratkalkar, et al., "Mechanisms of Stone Formation", Clin Rev Bone Miner Metab. 9(3-4), 2011, 187-197.

* cited by examiner

Comparison of partially purified ENPP3 to crude starting material: SDS-PAGE

COMPOSITIONS AND METHODS FOR REDUCING PROGRESSION OF NEPHROLITHIASIS

CROSS-REFERENCE TO RELATED APPLICATIONS

The present application is a 35 U.S.C. § 371 national phase application from, and claiming priority to, International Application No. PCT/US2019/031049, filed May 7, 2019, which claims priority under 35 U.S.C. § 119(e) to U.S. Provisional Patent Application No. 62/668,293, filed May 8, 2018, all of which applications are incorporated herein by reference in their entireties.

STATEMENT REGARDING FEDERALLY SPONSORED RESEARCH OR DEVELOPMENT

This invention was made with government support under DK079310 awarded by National Institutes of Health. The government has certain rights in the invention.

BACKGROUND OF THE INVENTION

Renal (kidney) calcifications include two distinct pathogenesis: nephrocalcinosis, which corresponds to generalized kidney calcification, affecting the soft tissue of the kidney; and nephrolithiasis (commonly referred to as renal stones or kidney stones), which corresponds to calcifications within the kidney tubules.

Nephrocalcinosis most often results from severe diseases such as end-stage renal disease (ESRD), generalized arterial calcification of infancy (GACI), diabetes mellitus II, autosomal-recessive hypophosphatemic rickets, cardiovascular disorder, atherosclerosis, chronic kidney disease (CKD), and/or pseudoxanthoma elasticum (PXE). Nephrocalcinosis may or may not involve kidney stones in addition to soft tissue calcification.

Nephrolithiasis or common kidney stone disease (where a subject not affected by a severe disease of tissue calcification develops kidney stones) may be asymptomatic, or may be associated with one or several of the following: flank pain, gross or microscopic hematuria, obstruction of one or both kidneys, and urinary infections. Signs and symptoms of kidney stones can include severe pain, nausea, vomiting, fever, chills and blood discharge in urine. The pain is typically severe and comes in waves, along with microscopic or gross hematuria.

Oral phosphate supplements and thiazide diuretics are used to reduce nephrolithiasis. Reduced protein and sodium intake, acidification of the urine with citric acid, and high fluid intake are additional non-specific treatment strategies for kidney stones. However, these treatments are often poorly tolerated (i.e., phosphate supplements), or ineffective in preventing recurrent stone formation or resolving existing stones.

The human ENPP (ectonucleotide pyrophosphatase) protein family consists of seven extracellular, glycosylated proteins (i.e., ENPP1, ENPP2, ENPP3, ENPP4, ENPP5, ENPP6, and ENPP7) that hydrolyze phosphodiester bonds. ENPPs are cell-surface enzymes, with the exception of ENPP2, which is exported to the plasma membrane but cleaved by furin and released into the extracellular fluid. The enzymes have high degrees of sequence and structural homology, but exhibit a diverse substrate specificity that encompasses nucleotides to lipids.

The construct ENPP1-Fc reduces generalized arterial calcifications in mice homozygous for an ENPP1 mutation (ENPP1$^{asi/asi}$) (Albright, et al., 2015, Nature Comm. 10006). The ENPP1$^{asi/asi}$ mouse serves as an animal model of GACI (generalized arterial calcification of infants), a severe disease occurring in infants and involving extensive arterial calcification. While arterial calcification is the primary symptom of GACI, Albright et al. also observed extensive calcifications in other tissues of the model mouse, including heart, aorta, coronary arteries, and the soft tissues of the kidney, where heavy calcifications were centered in the outer medulla of the kidney, with extension into the renal cortex. The GACI mouse model diverges from human disease at least because renal calcifications are not a feature of human GACI (Albright, et al., 2015, Nature Comm. 10006). Fusion proteins of ENPP1 have also been described to treat diseases of severe tissue calcification (PCT/US2014/015945 and PCT/US2016/033236), and a fusion protein of ENPP1 comprising a bone targeting domain has been described to treat GACI (PCT/US2011/051858).

There is thus a need in the art for novel compositions and methods for preventing, reversing, and/or reducing formation and/or progression of nephrolithiasis in a subject. The present invention fulfills this need.

BRIEF SUMMARY OF THE INVENTION

The invention provides a method of preventing, reversing, and/or reducing formation and/or progression of nephrolithiasis in a human subject. In certain embodiments, the subject is diagnosed with nephrolithiasis. In other embodiments, the subject is prone to developing kidney stones. In yet other embodiments, the subject has a family history of nephrolithiasis. In yet other embodiments, the subject has suffered from nephrolithiasis.

The invention provides a method of preventing, reversing, and/or reducing formation and/or progression of nephrocalcinosis in a human subject. In certain embodiments, the subject is diagnosed with nephrocalcinosis. In other embodiments, the subject is prone to developing nephrocalcinosis. In yet other embodiments, the subject has a family history of nephrocalcinosis. In yet other embodiments, the subject has suffered from nephrocalcinosis. In yet other embodiments, the subject does not suffer from any severe disease of calcification, In yet other embodiments, the subject does not suffer from end-stage renal disease (ESRD). In yet other embodiments, the subject does not suffer from generalized arterial calcification of infancy (GACI). In yet other embodiments, the subject does not suffer from diabetes mellitus II. In yet other embodiments, the subject does not suffer from autosomal-recessive hypophosphatemic rickets. In yet other embodiments, the subject does not suffer from cardiovascular disorder. In yet other embodiments, the subject does not suffer from atherosclerosis. In yet other embodiments, the subject does not suffer from chronic kidney disease (CKD). In yet other embodiments, the subject does not suffer from pseudoxanthoma elasticum (PXE).

In certain embodiments, the method comprises administering to the subject a therapeutically effective amount of a soluble ENPP1 polypeptide, wherein formation and/or progression of nephrolithiasis is prevented, reversed and/or reduced in the subject. In other embodiments, the method comprises administering a therapeutically effective amount of a soluble ENPP3 polypeptide to the subject, wherein formation and/or progression of nephrolithiasis is prevented, reversed and/or reduced in the subject.

In certain embodiments, the soluble ENPP1 polypeptide is fused to a moiety that increases half-life and/or reduces immunogenicity of the soluble ENPP1 polypeptide. In other embodiments, the soluble ENPP3 polypeptide is fused to a moiety that increases half-life and/or reduces immunogenicity of the soluble ENPP3 polypeptide.

In certain embodiments, the moiety is selected from the group consisting of an immunoglobulin (Ig) Fc domain, polyethylene glycol (PEG) and albumin.

In certain embodiments, the soluble ENPP1 polypeptide is fused to a bone targeting domain. In other embodiments, the soluble ENPP1 polypeptide is not fused to a bone targeting domain. In yet other embodiments, the soluble ENPP3 polypeptide is fused to a bone targeting domain. In yet other embodiments, the soluble ENPP3 polypeptide is not fused to a bone targeting domain.

In certain embodiments, the soluble ENPP1 polypeptide is a secreted product of a precursor polypeptide comprising a signal sequence fused to the soluble ENPP1 polypeptide, wherein the signal sequence is selected from the group consisting of ENPP2 signal sequence, ENPP5 signal sequence and ENPP7 signal sequence.

In certain embodiments, the soluble ENPP3 polypeptide is a secreted product of a precursor polypeptide comprising a signal sequence fused to the soluble ENPP3 polypeptide, wherein the signal sequence is selected from the group consisting of ENPP2 signal sequence, ENPP5 signal sequence and ENPP7 signal sequence.

In certain embodiments, the nephrolithiasis is selected from the group consisting of calcium stone disease, cystinuria, uric acid stone disease, struvite stone disease, hypercalcinuria, and hyperoxaluria. In other embodiments, the nephrolithiasis is calcium stone disease. In yet other embodiments, the nephrolithiasis is selected from the group consisting of cystinuria, uric acid stone disease, struvite stone disease, hypercalcinuria, and hyperoxaluria.

In certain embodiments, the subject is administered the soluble ENPP1 polypeptide via a route selected from the group consisting of local, regional, parenteral and systemic. In other embodiments, the subject is administered the soluble ENPP3 polypeptide via a route selected from the group consisting of local, regional, parenteral and systemic.

BRIEF DESCRIPTION OF THE DRAWINGS

The following detailed description of illustrative embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

DETAILED DESCRIPTION OF THE INVENTION

Figure 1:
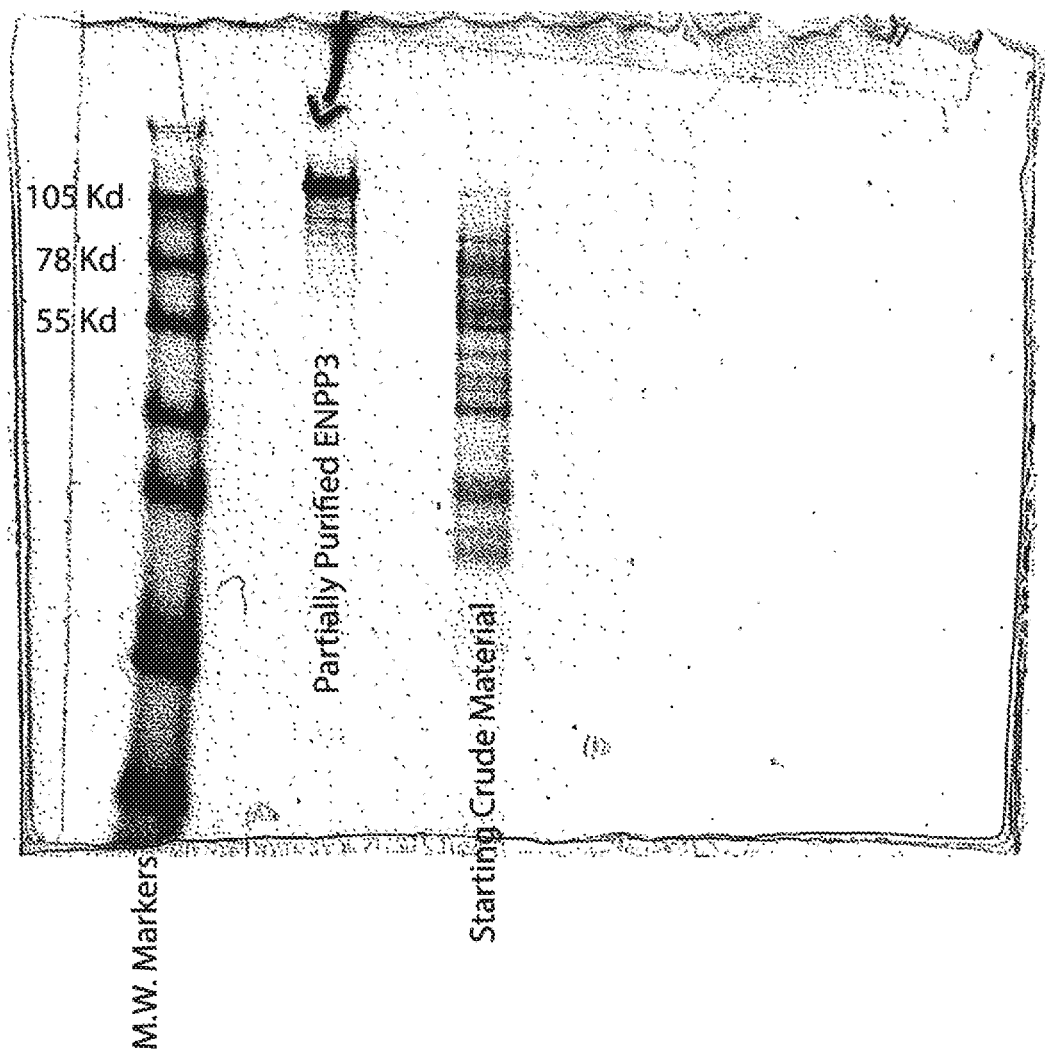
FIG. 1 illustrates a protein gel showing non-limiting expression and purification of a ENPP3 polypeptide.

The present invention relates, in one aspect, to the discovery that polypeptides comprising certain ENPP1 polypeptides or ENPP3 polypeptides, mutants, or mutant fragments thereof, can be used to prevent, reverse, and/or reduce formation and/or progression of nephrolithiasis in a subject.

Certain ENPP1 polypeptides or ENPP3 polypeptides, mutants, or mutant fragments thereof, have been previously disclosed in PCT Application Publication No. WO 2014/126965 and PCT Application Publication No. WO/2016/187408, all of which are incorporated by reference in their entireties herein.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, illustrative methods and materials are described. As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The following notation conventions are applied to the present disclosure for the sake of clarity. In any case, any teaching herein that does not follow this convention is still part of the present disclosure, and can be fully understood in view of the context in which the teaching is disclosed. Protein symbols are disclosed in non-italicized capital letters. As non-limiting examples, 'ENPP1' or 'ENPP7' refer to the corresponding proteins. In certain embodiments, if the protein is a human protein, an 'h' is used before the protein symbol. In other embodiments, if the protein is a mouse protein, an 'm' is used before the symbol. Hence, human ENPP1 is referred to as 'hENPP1', and mouse ENPP1 is referred to as 'mENPP1'. Human gene symbols are disclosed in italicized capital letters. As a non-limiting example, the human gene corresponding to the protein hENPP1 is ENPP1. Mouse gene symbols are disclosed with the first letter in upper case and the remaining letters in lower case; further, the mouse gene symbol is italicized. As a non-limiting example, the mouse gene that makes the protein mEnpp1 is Enpp1. Notations about gens mutations are shown as uppercase text. For example, a transgenic mouse with a mutation in the gene Enpp1 that is associated with stiffened joints is called an 'asj' mutation and is annotated as Enpp1$^{asj/asj}$ to denote the gene and phenotype associated with the mutation.

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

As used herein, the term "ALB" refers to a serum albumin protein. In certain embodiments, albumin refers to human serum albumin. Usage of other albumins, such as bovine serum albumin, equine serum album and porcine serum albumin, are also contemplated within the invention.

A disease or disorder is "alleviated" if the severity of a symptom of the disease or disorder, the frequency with which such a symptom is experienced by a patient, or both, is reduced.

As used herein the terms "alteration," "defect," "variation" or "mutation" refer to a mutation in a gene in a cell that affects the function, activity, expression (transcription or translation) or conformation of the polypeptide it encodes, including missense and nonsense mutations, insertions, deletions, frameshifts and premature terminations.

The term "antibody," as used herein, refers to an immunoglobulin molecule that is able to specifically bind to a specific epitope on an antigen. Antibodies can be intact immunoglobulins derived from natural sources or from recombinant sources and can be immunoreactive portions of intact immunoglobulins.

As used herein, the term "Ap3P" refers to adenosine-5'-triphospho-5'-adenosine or a salt thereof.

As used herein, "calcium stone disease" is a form of nephrolithiasis and represents about 70% of all cases of stone-forming disease of stones that form in kidney tubules.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

As used herein, "cysteine stones" refers to kidney stones that are formed due to "cystinuria", a rare genetic disorder resulting in the defective transport of cysteine causing excess of cysteine in the urine, thereby leading to formation of stones.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, "family history" refers to the occurrence of nephrolithiasis or common kidney stones in a subject's mother or father, or grandparents, or a subject's siblings. "Family history" can also refer to a genealogical family history of genetic mutations associated with nephrolithiasis, and the occurrence of one or more of those same mutations in the subject.

As used herein, the term "Fc" refers to a human IgG (immunoglobulin) Fc domain. Subtypes of IgG such as IgG1, IgG2, IgG3, and IgG4 are contemplated for usage as Fc domains.

As used herein, the term "fragment," as applied to a nucleic acid, refers to a subsequence of a larger nucleic acid. A "fragment" of a nucleic acid can be at least about 15, 50-100, 100-500, 500-1000, 1000-1500 nucleotides, 1500-2500, or 2500 nucleotides (and any integer value in between). As used herein, the term "fragment," as applied to a protein or peptide, refers to a subsequence of a larger protein or peptide, and can be at least about 20, 50, 100, 200, 300 or 400 amino acids in length (and any integer value in between).

As used herein, "hydroxyapatite stones" refer to kidney stones containing hydroxyapatite and which may result from diet-induced renal calcification.

As used herein, "hypercalcinuria" refers to the condition of elevated calcium in the urine. Chronic hypercalcinuria may lead to nephrocalcinosis, impairment of renal function, and renal insufficiency.

As used herein, "hypophosphatemia" refers to an electrolyte imbalance wherein there is an abnormally low level of phosphate in the blood. A decrease in phosphate in the blood is sometimes associated with an increase in phosphate in the urine leading to phosphaturia.

"Instructional material," as that term is used herein, includes a publication, a recording, a diagram, or any other medium of expression that can be used to communicate the usefulness of the nucleic acid, peptide, and/or compound of the invention in the kit for identifying or alleviating or treating the various diseases or disorders recited herein.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

"Nephrocalcinosis" refers to deposition of calcium salts (in the form of calcium phosphate and/or calcium oxalate) in the soft tissue of the kidney. The soft tissues of the kidney include the renal medulla and renal cortext, and do not include the renal tubules (nephrons). The disorder may be symmetric or, in anatomic disorders such as medullary sponge kidney, involve only a single kidney. Soft tissue calcifications may be in the size range of 0.0005-0.002 $\mu m^2$ (calcification size=mineralization area/number of calcifications). The degree of calcifications within a given soft tissue area can range from 0.2%-1.0% (% calcifications=100*mineralization area/tissue area). Nephrocalcinosis occurs in severe diseases of calcification such as end-stage renal disease (ESRD), generalized arterial calcification of infancy (GACI), diabetes mellitus II, autosomal-recessive hypophosphatemic rickets, cardiovascular disorder, atherosclerosis, chronic kidney disease (CKD), and/or pseudoxanthoma elasticum (PXE).

"Nephrolithiasis" refers to formation of kidney stones in a kidney tubule. The disease involves formation of calculi (stones) within the renal pelvis and tubular lumens. The stones form from crystals that precipitate (separate) out of the urine. As used herein, nephrolithiasis does not include end-stage renal disease (ESRD), generalized arterial calcification of infancy (GACI), diabetes mellitus II, autosomal-recessive hypophosphatemic rickets, cardiovascular disorder, atherosclerosis, chronic kidney disease (CKD), and/or pseudoxanthoma elasticum (PXE).

As used herein, the term "NPP" or "ENPP" refers to ectonucleotide pyrophosphatase/phosphodiesterase.

An "oligonucleotide" or "polynucleotide" is a nucleic acid ranging from at least 2, in certain embodiments at least 8, 15 or 25 nucleotides in length, but may be up to 50, 100, 1000, or 5000 nucleotides long or a compound that specifically hybridizes to a polynucleotide.

As used herein, the term "patient," "individual" or "subject" refers to a human.

As used herein, the term "pharmaceutical composition" or "composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid.

As used herein, "phosphaturia" is a condition wherein excess of phosphates are present in the urine, which may look milky or cloudy in appearance.

As used herein the term "plasma pyrophosphate (PPi) levels" refers to the amount of pyrophosphate present in plasma of animals. In certain embodiments, animals include rat, mouse, cat, dog, human, cow and horse. It is necessary to measure PPi in plasma rather than serum because of release from platelets. There are several ways to measure PPi, one of which is by enzymatic assay using uridine-diphosphoglucose (UDPG) pyrophosphorylase (Lust & Seegmiller, 1976, Clin. Chim. Acta 66:241-249; Cheung & Suhadolnik, 1977, Anal. Biochem. 83:61-63) with modifications.

As used herein, the term "polypeptide" refers to a polymer composed of amino acid residues, related naturally occurring structural variants, and synthetic non-naturally occurring analogs thereof linked via peptide bonds.

As used herein, the term "PPi" refers to pyrophosphate.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "reduce formation of" kidney stone refers to the ability to minimize or reverse formation of an existing kidney stone in a subject, and can take place where kidney stones already exist, or where no kidney stones have been formed or detected but the subject has a family history of renal calcification or any other predisposition to renal calcifications. In other embodiments, the reduction in formation of kidney stone is detected within a kidney tubule; in other embodiments, detection of kidney stones, fewer stones, or smaller stones is in the urine of a subject before and after treatment.

As used herein, the term "reduce progression of" kidney stones or kidney stone formation refers to the ability to reduce the size (or cease, hamper or reverse growth in size) of an existing kidney stones, and/or to reduce the number (or cease, hamper or reverse growth in number) of kidney stones.

As used herein, "renal stone" or "kidney stone" refers to a larger mineral deposit formed in the kidney, which may be visible to the eye and can range from 2-50 mm in diameter. Size is not a limiting factor to define a kidney stone, but rather its location in the kidney tubule. Common compositions present in renal stones include calcium, oxalate, phosphate, uric acid, and cysteine. In certain embodiments, formation of a renal stone is initiated by formation of an initial calcification bud (nidus), around which the renal stone forms and grows.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, "substantially purified" refers to being essentially free of other components. For example, a substantially purified polypeptide is a polypeptide that has been separated from other components with which it is normally associated in its naturally occurring state. Non-limiting embodiments include 95% purity, 99% purity, 99.5% purity, 99.9% purity and 100% purity.

As used herein, "struvite stone" refers to an infection stone or triple phosphate stone, develops when a urinary tract infection (e.g., bladder infection) affects the chemical balance of the urine. Bacteria in the urinary tract release chemicals that neutralize urinary acid, which enables bacteria to grow more quickly and promotes struvite stone development.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder (such as, for example, renal stones in the kidney tubules), a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, "uric acid stone" refer to a kidney stone formed when products of purine metabolism such as 2- or 8-dihydroxyadenine, adenine, xanthine, and uric acid precipitate under low urinary pH conditions.

As used herein, the term "wild-type" refers to a gene or gene product isolated from a naturally occurring source. A wild-type gene is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. Naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates, in one aspect, to the discovery that certain ENPP1 polypeptides or ENPP3 polypeptides, mutants, or mutant fragments thereof can be used to prevent, reverse, and/or reduce formation and/or progression of nephrolithiasis in a human subject.

Compositions

In certain embodiments, the invention provides an ENPP1 (also referred to as NPP1) polypeptide. In other embodiments, the invention provides an ENPP3 (also referred to as NPP3) polypeptide.

In certain embodiments, the compositions of the invention comprises at least one compound of formula (I), or a solvate or salt (such as a pharmaceutically acceptable salt) thereof:

$$\text{PROTEIN-}Z\text{-DOMAIN-}X\text{-}Y \tag{I},$$

wherein:

PROTEIN is at least one selected from the group consisting of ENPP1 (SEQ ID NO:1), ENPP121 (SEQ ID NO:15), ENPP71 (SEQ ID NO:17), ENPP71 lacking ENPP1 N-terminus GLK (SEQ ID NO:19), ENPP51 (SEQ ID NO:24), and A-B-SEQ ID NO:32;

A is a protein export sequence;

B is absent or a sequence corresponding to residues $Xaa_p$-$Xaa_{17}$ in SEQ ID NO:33, wherein p is an integer ranging from 1 to 17;

DOMAIN is absent or at least one selected from the group consisting of a human IgG Fc domain (Fc) (such as but not limited to IgG1, IgG2, IgG3 and/or IgG4), human serum albumin protein (ALB) and a fragment thereof;

X and Z are independently absent or a polypeptide comprising 1-20 amino acids; and, Y is absent or a sequence selected from the "bone targeting" sequence group consisting of: $D_m$ (SEQ ID NO:3), $(DSS)_n$ (SEQ ID NO:4), $(ESS)_n$ (SEQ ID NO:5), $(RQQ)_n$ (SEQ ID NO:6), $(KR)_n$ (SEQ ID NO:7), $R_m$ (SEQ ID NO:8), DSSSEEKFLRRIGRFG (SEQ ID NO:9), EEEEEEEPRGDT (SEQ ID NO:10), APWHLSSQYSRT (SEQ ID NO:11), STLPIPHEFSRE (SEQ ID NO:12), VTKHLNQ-ISQSY (SEQ ID NO:13), and $E_m$ (SEQ ID NO:14), wherein m is an integer ranging from 1 to 15, and wherein n is an integer ranging from 1 to 10.

In certain embodiments, A is selected from the group consisting of SEQ ID NOs:34-39.

In certain embodiments, B is absent or selected from the group consisting of SEQ ID NOs:40-55.

In certain embodiments, DOMAIN comprises a human IgG Fc domain or fragment thereof. In other embodiments, DOMAIN consists essentially of a human IgG Fc domain or fragment thereof. In yet other embodiments, DOMAIN consists of a human IgG Fc domain or fragment thereof.

In certain embodiments, DOMAIN comprises a human serum albumin protein or a fragment thereof. In other embodiments, DOMAIN consists essentially of a human serum albumin protein or a fragment thereof. In yet other embodiments, DOMAIN consists of a human serum albumin protein or a fragment thereof. In yet other embodiments, DOMAIN is absent.

In certain embodiments, Y is a negatively-charged bone-targeting sequence. In certain embodiments, Y is absent. In certain embodiments, Y is absent and the compound of formula (I) lacks a negatively-charged bone-targeting sequence. In yet other embodiments, a polyaspartic acid domain and SEQ ID NOs:3-14 are non-limiting examples of a negatively-charged bone-targeting sequence. In yet other embodiments, the soluble ENPP1 polypeptide lacks a negatively-charged bone-targeting domain.

In certain embodiments, the PROTEIN or mutant thereof is truncated to remove the nuclease domain. In yet other embodiments, the PROTEIN or mutant thereof is truncated to remove the nuclease domain from about residue 524 to about residue 885 relative to SEQ ID NO:1, leaving only the catalytic domain from about residue 186 to about residue 586 relative to SEQ ID NO:1, which serves to preserve the catalytic activity of the protein.

In certain embodiments, PROTEIN-Z-DOMAIN comprises (SEQ ID NO:15)-Z-(Fc or fragment thereof). In other embodiments, Z is a tripeptide. In yet other embodiments, Z is L I N. In yet other embodiments, PROTEIN-Z-DOMAIN comprises SEQ ID NO:16.

In certain embodiments, PROTEIN-Z-DOMAIN comprises (SEQ ID NO:17)-Z-(Fc or fragment thereof). In other embodiments, Z is a tripeptide. In yet other embodiments, Z is L I N. In yet other embodiments, PROTEIN-Z-DOMAIN comprises SEQ ID NO:18.

In certain embodiments, PROTEIN-Z-DOMAIN comprises (SEQ ID NO:19)-Z-(Fc or fragment thereof). In other embodiments, Z is a tripeptide. In yet other embodiments, Z is L I N. In yet other embodiments, PROTEIN-Z-DOMAIN comprises SEQ ID NO:20.

In certain embodiments, PROTEIN-Z-DOMAIN comprises (SEQ ID NO:24)-Z-(Fc or fragment thereof). In other embodiments, Z is a tripeptide. In yet other embodiments, Z is L I N. In yet other embodiments, PROTEIN-Z-DOMAIN comprises (SEQ ID NO:24)-Z-(SEQ ID NO:26).

In certain embodiments, PROTEIN-Z-DOMAIN comprises (SEQ ID NO:15)-Z-(ALB or fragment thereof). In other embodiments, Z is a tripeptide. In yet other embodiments, Z is one selected from the group consisting of SEQ ID NOs:28-30. In yet other embodiments, PROTEIN-Z-DOMAIN comprises SEQ ID NO:21.

In certain embodiments, PROTEIN-Z-DOMAIN comprises (SEQ ID NO:17)-Z-(ALB or fragment thereof). In other embodiments, Z is a tripeptide. In yet other embodiments, Z is one selected from the group consisting of SEQ ID NOs:28-30. In yet other embodiments, PROTEIN-Z-DOMAIN comprises (SEQ ID NO:17)-Z-(SEQ ID NO:27), wherein Z is one selected from the group consisting of SEQ ID NOs:28-30.

In certain embodiments, PROTEIN-Z-DOMAIN comprises (SEQ ID NO:19)-Z-(ALB or fragment thereof). In other embodiments, Z is a tripeptide. In yet other embodiments, Z is one selected from the group consisting of SEQ ID NOs:28-30. In yet other embodiments, PROTEIN-Z-DOMAIN comprises SEQ ID NO:22.

In certain embodiments, PROTEIN-Z-DOMAIN comprises (SEQ ID NO:24)-Z-(ALB or fragment thereof). In other embodiments, Z is a tripeptide. In yet other embodiments, Z is one selected from the group consisting of SEQ ID NOs:28-30. In yet other embodiments, PROTEIN-Z-DOMAIN comprises SEQ ID NO:25.

In certain embodiments, X and Z are independently absent or a polypeptide comprising 1-18 amino acids. In other embodiments, X and Z are independently absent or a polypeptide comprising 1-16 amino acids. In yet other embodiments, X and Z are independently absent or a polypeptide comprising 1-14 amino acids. In yet other embodiments, X and Z are independently absent or a polypeptide comprising 1-12 amino acids. In yet other embodiments, X and Z are independently absent or a polypeptide comprising 1-10 amino acids. In yet other embodiments, X and Z are independently absent or a polypeptide comprising 1-8 amino acids. In yet other embodiments, X and Z are independently absent or a polypeptide comprising 1-6 amino acids. In yet other embodiments, X and Z are independently absent or a polypeptide comprising 1-5 amino acids. In yet other embodiments, X and Z are independently absent or a polypeptide comprising 1-4 amino acids. In yet other embodiments, X and Z are independently absent or a polypeptide comprising 1-3 amino acids. In yet other embodiments, X and Z are independently absent or a polypeptide comprising 1-2 amino acids. In yet other embodiments, X and Z are independently absent or a single amino acid.

In certain embodiments, m is 1. In other embodiments, m is 2. In yet other embodiments, m is 3. In yet other embodiments, m is 4. In yet other embodiments, m is 5. In yet other embodiments, m is 6. In yet other embodiments, m is 7. In yet other embodiments, m is 8. In yet other embodiments, m is 9. In yet other embodiments, m is 10. In yet other embodiments, m is 11. In yet other embodiments, m is 12. In yet other embodiments, m is 13. In yet other embodiments, m is 14. In yet other embodiments, m is 15. In yet other embodiments, each occurrence of m is independently selected from the group consisting of an integer ranging from 1 to 15, from 2 to 15, from 3 to 15, from 4 to 15, from 5 to 15, from 6 to 15, from 7 to 15, from 8 to 15, from 9 to 15, from 10 to 15, from 11 to 15, from 12 to 15, from 13 to 15, from 14 to 15, from 1 to 14, from 2 to 14, from 3 to 14, from 4 to 14, from 5 to 14, from 6 to 14, from 7 to 14, from 8 to 14, from 9 to 14, from 10 to 14, from 11 to 14, from 12 to 14, from 13 to 14, from 1 to 13, from 2 to 13, from 3 to 13, from 4 to 13, from 5 to 13, from 6 to 13, from 7 to 13, from 8 to 13, from 9 to 13, from 10 to 13, from 11 to 13, from 12 to 13, from 1 to 12, from 2 to 12, from 3 to 12, from 4 to 12, from 5 to 12, from 6 to 12, from 7 to 12, from 8 to 12, from 9 to 12, from 10 to 12, from 11 to 12, from 1 to 11, from 2 to 11, from 3 to 11, from 4 to 11, from 5 to 11, from 6 to 11, from 7 to 11, from 8 to 11, from 9 to 11, from 10 to 11, from 1 to 10, from 2 to 10, from 3 to 10, from 4 to 10, from 5 to 10, from 6 to 10, from 7 to 10, from 8 to 10, from 9 to 10, from 1 to 9, from 2 to 9, from 3 to 9, from 4 to 9, from 5 to 9, from 6 to 9, from 7 to 9, from 8 to 9, from 1 to 8, from 2 to 8, from 3 to 8, from 4 to 8, from 5 to 8, from 6 to 8, from 7 to 8, from 1 to 7, from 2 to 7, from 3 to 7, from 4 to 7, from 5 to 7, from 6 to 7, from 1 to 6, from 2 to 6, from 3 to 6, from 4 to 6, from 5 to 6, from 1 to 5, from 2 to 5, from 3 to 5, from 4 to 5, from 1 to 4, from 2 to 4, from 3 to 4, from 1 to 3, from 2 to 3, and from 1 to 2.

In certain embodiments, n is 1, n is 2, n is 3, n is 4, n is 5, n is 6, n is 7, n is 8, n is 9, or n is 10. In yet other embodiments, each occurrence of n is independently selected from the group consisting of an integer ranging from 1 to 10, from 2 to 10, from 3 to 10, from 4 to 10, from 5 to 10, from 6 to 10, from 7 to 10, from 8 to 10, from 9 to 10, from 1 to 9, from 2 to 9, from 3 to 9, from 4 to 9, from 5 to 9, from 6 to 9, from 7 to 9, from 8 to 9, from 1 to 8, from 2 to 8, from 3 to 8, from 4 to 8, from 5 to 8, from 6 to 8, from 7 to 8, from 1 to 7, from 2 to 7, from 3 to 7, from 4 to 7, from 5 to 7, from 6 to 7, from 1 to 6, from 2 to 6, from 3 to 6, from 4 to 6, from 5 to 6, from 1 to 5, from 2 to 5, from 3 to 5, from 4 to 5, from 1 to 4, from 2 to 4, from 3 to 4, from 1 to 3, from 2 to 3, and from 1 to 2.

In certain embodiments, the PROTEIN or mutant thereof is modified with a segment of the extracellular region of ENPP1 or ENPP3 containing a furin cleavage site between the transmembrane and extracellular domain, as compared to SEQ ID NO:1. In other embodiments, the PROTEIN or mutant thereof is not modified with a segment of the extracellular region of ENPP1 or ENPP3 containing a furin cleavage site between the transmembrane and extracellular domain, as compared to SEQ ID NO:1.

In certain embodiments, the PROTEIN or mutant thereof is modified with a segment of the extracellular region of ENPP2 containing a signal peptidase cleavage site, as compared to SEQ ID NO:1. In other embodiments, the PROTEIN or mutant thereof is not modified with a segment of the extracellular region of ENPP2 containing a signal peptidase cleavage site, as compared to SEQ ID NO:1.

In certain embodiments, the compound of the invention is soluble. In other embodiments, the compound of the invention is a recombinant polypeptide. In yet other embodiments, the compound of the invention includes an ENPP1 or ENPP3 polypeptide or mutant thereof that lacks the ENPP1 or ENPP3 transmembrane domain. In yet other embodiments, the compound includes an ENPP1 or ENPP3 polypeptide or mutant thereof, wherein the ENPP1 or ENPP3 transmembrane domain or mutant thereof has been removed (and/or truncated) and replaced with the transmembrane domain of another polypeptide, such as, by way of non-limiting example, ENPP2.

In other embodiments, the soluble ENPP1 polypeptide is a secreted product of a precursor polypeptide expressed in a mammalian cell, wherein the precursor polypeptide comprises an ENPP2 signal sequence, which is fused to the N-terminus of an ENPP1 polypeptide, wherein the precursor polypeptide undergoes proteolytic processing to the soluble ENPP1 polypeptide. In yet other embodiments, the soluble ENPP1 polypeptide is a secreted product of a precursor polypeptide expressed in a mammalian cell, wherein the precursor polypeptide comprises residues 1-76 of ENPP1 (SEQ ID NO: 1), residues 12-30 of NPP2 (NCBI accession no. NP_001124335, SEQ ID NO: 2), and residues 96-925 of ENPP1 (SEQ ID NO: 1), wherein the precursor polypeptide undergoes proteolytic processing to the soluble ENPP1 polypeptide. In yet other embodiments, the soluble ENPP1 polypeptide is a secreted product of a precursor polypeptide expressed in a cell, wherein the precursor polypeptide lacks residues 77-98 of the ENPP1 transmembrane domain and comprises a signal sequence, wherein the precursor polypeptide undergoes proteolytic processing to the soluble ENPP1 polypeptide. In yet other embodiments, the soluble ENPP1 polypeptide lacks a polyaspartic acid domain.

In certain embodiments, the soluble ENPP1 polypeptide is a secreted product of a precursor polypeptide expressed in a mammalian cell, wherein the precursor polypeptide comprises a signal peptide selected from the group consisting of an ectonucleotide pyrophosphatase/phosphodiesterase-5 (ENPP5) signal peptide and an ectonucleotide pyrophosphatase/phosphodiesterase-7 (ENPP7) signal peptide, an ENPP1 polypeptide, and a stability domain, wherein the ENPP1 precursor polypeptide fusion is proteolytically processed upon secretion from the cell to yield a soluble enzymatically active ENPP1 polypeptide fusion comprising the stability domain. In other embodiments, the stability domain is selected from the group consisting of albumin and IgG Fc. In yet other embodiments, the ENPP7 signal peptide comprises residues 1-22 of ENPP7 (SEQ ID NO: 17). In yet other embodiments, the ENPP5 signal peptide comprises residues 1-24 of ENPP5 (SEQ ID NO: 24). In yet other embodiments, the soluble enzymatically active ENPP1 polypeptide fusion comprises residues 96-925 of human ENPP1 (SEQ ID NO: 1). In yet other embodiments, the ENPP1 precursor polypeptide fusion lacks residues 77-98 of human ENPP1 (SEQ ID NO: 1). In yet other embodiments, the ENPP1 precursor polypeptide fusion comprises residues 1-76 of human ENPP1 (SEQ ID NO: 1) and residues 96-925 of human ENPP1 (SEQ ID NO: 1).

In certain embodiments, the compound of the invention comprises an ENPP1 or ENPP3 polypeptide or mutant thereof further comprising more than one transmembrane domain.

In certain embodiments, ENPP1 or ENPP3 is C-terminally fused to the Fc domain of human immunoglobulin 1 (IgG1), human immunoglobulin 2 (IgG2), human immunoglobulin 3 (IgG3), and/or human immunoglobulin 4 (IgG4).

In certain embodiments, ENPP1 or ENPP3 is C-terminally fused to human serum albumin.

In certain embodiments, a fragment and/or variant of ENPP1 or ENPP3 is fused with human serum albumin or variants and/or fragments thereof. Human serum albumin may be conjugated to ENPP1 or ENPP3 protein through a chemical linker, including but not limited to naturally occurring or engineered disulfide bonds, or by genetic fusion to ENPP1 or ENPP3, or a fragment and/or variant thereof.

In certain embodiment, the compound of the invention comprises an ENPP1 or ENPP3 polypeptide or mutant thereof comprising transmembrane domains of ENPP1 or ENPP3 and another polypeptide, such as, by way of non-limiting example, ENPP2. In other embodiments, the ENPP1 or ENPP3 polypeptide comprises a cleavage product of a precursor ENPP1 or ENPP3 polypeptide comprising an ENPP2 transmembrane domain. In yet other embodiments, the ENPP2 transmembrane domain comprises residues 12-30 of NCBI accession no. NP_001124335 (SEQ ID NO:2), which corresponds to IISLFTFAVGVNICLGFTA (SEQ ID NO:23).

In certain embodiments, the compound of the invention has a sequence selected from the group consisting of SEQ ID NOs:21, 22 and 25.

In certain embodiments, the compound of the invention has a sequence selected from the group consisting of SEQ ID NOs:21, 22, 25 and (SEQ ID NO:17)-Z-(SEQ ID NO:27).

In certain embodiments, the compound of the invention has a sequence selected from the group consisting of SEQ ID NOs:16, 18, 20 and (SEQ ID NO:24)-Z-(SEQ ID NO:26).

In certain embodiments, the compounds of the invention have more than one transmembrane domain. In other embodiments, the compounds of the invention are further pegylated (fused with a poly(ethylene glycol) chain). In yet other embodiments, the compounds of the invention have more than one transmembrane domain and are further pegylated.

In certain embodiments, the compound of the invention has a $k_{cat}$ value greater than or equal to about 3.4 ($\pm$0.4) s$^{-1}$ enzyme$^{-1}$, wherein the $k_{cat}$ is determined by measuring the rate of hydrolysis of ATP for the compound.

In certain embodiments, the compound of the invention has a $K_M$ value less than or equal to about 2 µM, wherein the $K_M$ is determined by measuring the rate of hydrolysis of ATP for the compound.

In certain embodiments, the compound of the invention is formulated as a liquid formulation. In other embodiments, the invention provides a dry product form of a pharmaceutical composition comprising a therapeutic amount of a compound of the invention, whereby the dry product is reconstitutable to a solution of the compound in liquid form.

The invention provides a kit comprising at least one compound of the invention, or a salt or solvate thereof, and instructions for using the compound within the methods of the invention.

ENPP1 and ENPP3

ENPP1 (also known as PC-1) is a type 2 extracellular membrane-bound glycoprotein located on the mineral-depositing matrix vesicles of osteoblasts and chondrocytes, and hydrolyzes extracellular nucleotides (principally ATP) into AMP and PPi (Bollen, et al., 2000, Crit. Rev. Biochem. Mol. Biol. 35:393-432; Terkeltaub, 2006, Purinergic Signaling 2:371-377). PPi functions as a potent inhibitor of ectopic tissue mineralization by binding to nascent hydroxyapatite (HA) crystals, thereby preventing the future growth of these crystals (Terkeltaub, 2006, Purinergic signaling 2:371-377; Addison, et al., 2007, J. Biol. Chem. 282:15872-15873). ENPP1 generates PPi via the hydrolysis of nucleotide triphosphates (NTPs), ANK transports intracellular PPi into the extracellular space, and TNAP removes PPi via the direct hydrolysis of PPi into Pi (US 2015/0359858 A1, the contents of which are herein incorporated by reference in their entirety).

In certain embodiments, the ENPP1 polypeptide is soluble. In other embodiments, the ENPP1 polypeptide is a recombinant ENPP1 polypeptide. In yet other embodiments, the polypeptide of the invention comprises a ENPP1 polypeptide lacking the ENPP1 transmembrane domain. In yet other embodiments, the polypeptide of the invention comprises a ENPP1 polypeptide wherein the ENPP1 transmembrane domain has been removed and replaced with the transmembrane domain of another polypeptide, such as, by way of non-limiting example, ENPP2, ENPP5 or ENPP7.

In certain embodiments, the polypeptide of the invention comprises an IgG Fc domain. In other embodiments, the polypeptide of the invention comprises or lacks a polyaspartic acid domain, from about 2 to about 20 or more sequential aspartic acid residues. In yet other embodiments, the polypeptide of the invention comprises an IgG Fc domain and a polyaspartic acid domain comprising from about 2 to about 20 or more sequential aspartic acid residues. In yet other embodiments, the ENPP1 polypeptide is truncated and lacks a nuclease domain. In yet other embodiments, the ENPP1 polypeptide is truncated and lacks the nuclease domain from about residue 524 to about residue 885 relative to SEQ ID NO:1, leaving only a catalytic domain from about residue 186 to about residue 586 relative to SEQ ID NO:1, which preserves the catalytic activity of the protein.

In certain embodiments, the polypeptide of the invention comprises albumin or a portion thereof (an albumin domain). In other embodiments, the albumin domain is located at the C terminal region of the ENPP1 polypeptide. In other embodiments, the IgG Fc domain is located at the C terminal region of the ENPP1 polypeptide. In yet embodiments, the presence of IgFc domain or albumin domain improves half-life, solubility, reduces immunogenicity and increases the activity of the ENPP1 polypeptide.

In certain embodiments, the polypeptide of the invention comprises a signal peptide resulting in the secretion of a precursor of the ENPP1 polypeptide, which undergoes proteolytic processing to yield the ENPP1 polypeptide. In other embodiments, the signal peptide is selected from the group consisting of signal peptides of ENPP2, ENPP5 and ENPP7. In yet other embodiments, the signal peptide is selected from the group consisting of SEQ ID NOs:37-39.

In certain embodiments, the IgG Fc domain or the albumin domain is connected to the C terminal region of the ENPP1 polypeptide by a linker region. In other embodiments, the linker is selected from SEQ ID NOs:3-14, where n is an integer ranging from 1-20.

ENPP3 is a potent ATP hydrolase, capable of generating PPi and AMP from ATP. ENPP3 has an ATP hydrolase activity that is comparable to that of ENPP1. ENPP3 catalyzes the hydrolysis of ATP to PPi with nearly the same Michaelis-Menton kinetics as ENPP1, which is another member of the ENPP family of enzymes.

In certain embodiments, the ENPP3 polypeptide is soluble. In other embodiments, the ENPP3 polypeptide is a recombinant ENPP3 polypeptide. In yet other embodiments, the polypeptide of the invention includes a ENPP3 polypeptide that lacks the ENPP3 transmembrane domain. In another embodiment, the polypeptide of the invention includes a ENPP3 polypeptide wherein the ENPP3 transmembrane domain has been removed and replaced with the transmembrane domain of another polypeptide, such as, by way of non-limiting example, ENPP2, ENPP5 or ENPP7.

In some embodiments, the polypeptide of the invention comprises an IgG Fc domain. In other embodiments, the polypeptide of the invention comprises or lacks a polyaspartic acid domain, from about 2 to about 20 or more sequential aspartic acid residues or 2 to about 20 sequential glutamic acid residues. In yet other embodiments, the polypeptide of the invention comprises an IgG Fc domain and a polyaspartic acid domain comprising from about 2 to about 20 or more sequential aspartic acid residues.

In certain embodiments, the polypeptide of the invention comprises an albumin domain. In other embodiments, the albumin domain is located at the C terminal region of the ENPP3 polypeptide. In yet other embodiments, the IgG Fc domain is located at the C terminal region of the ENPP3 polypeptide. In yet other embodiments, the presence of IgG Fc domain or albumin domain improves half-life, solubility, reduces immunogenicity and increases the activity of the ENPP3 polypeptide.

In certain embodiments, the polypeptide of the invention comprises a signal peptide resulting in the secretion of a precursor of the ENPP3 polypeptide, which undergoes proteolytic processing to yield the ENPP3 polypeptide. In other embodiments, the signal peptide is selected from the group consisting of signal peptides of ENPP2, ENPP5 and ENPP7. In yet other embodiments, the signal peptide is selected from the group consisting of SEQ ID NOs:37-39.

In certain embodiments, the IgG Fc domain or the albumin domain is connected to the C terminal region of the ENPP3 polypeptide by a linker region. In other embodiments, the linker is selected from SEQ ID NOs:3-14, where n is an integer ranging from 1-20.

Cloning and Expression of ENPP1

ENPP1, or a ENPP1 polypeptide, is prepared as described in US 2015/0359858 A1, which is incorporated herein in its entirety by reference. ENPP1 is a transmembrane protein localized to the cell surface with distinct intramembrane domains. In order to express ENPP1 as a soluble extracellular protein, the transmembrane domain of ENPP1 may be swapped for the transmembrane domain of ENPP2, which results in the accumulation of soluble, recombinant ENPP1 in the extracellular fluid of the baculovirus cultures.

Signal sequences of any other known proteins may be used to target the extracellular domain of ENPP1 for secretion as well, such as but not limited to the signal sequence of the immunoglobulin kappa and lambda light chain proteins. Further, the invention should not be construed to be limited to the constructs described herein, but also includes constructs comprising any enzymatically active truncation of the ENPP1 extracellular domain.

Figure 2:
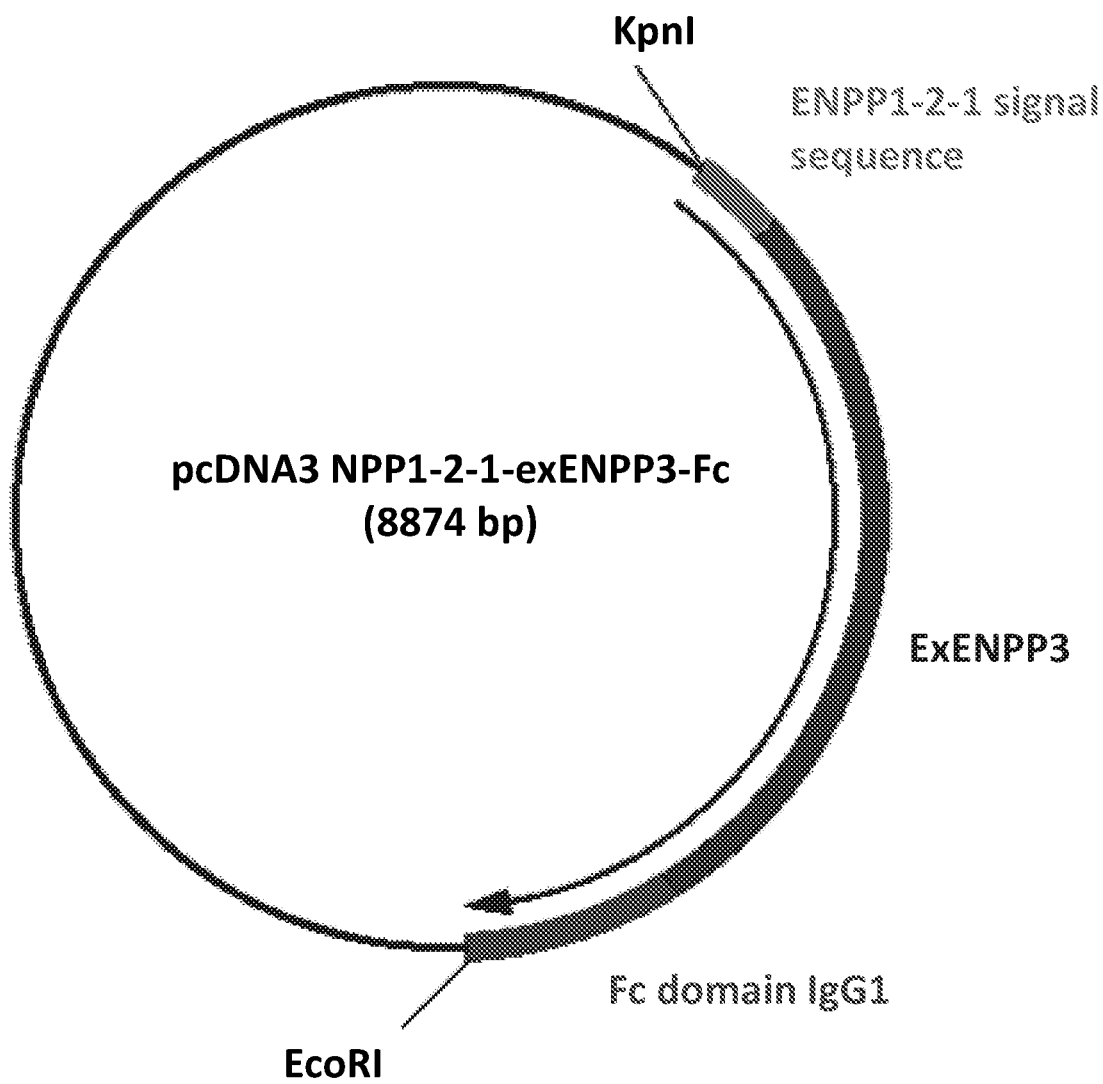
FIG. 2 illustrates a plasmid map of a non-limiting ENPP3 construct contemplated within the invention.
Figure 3:
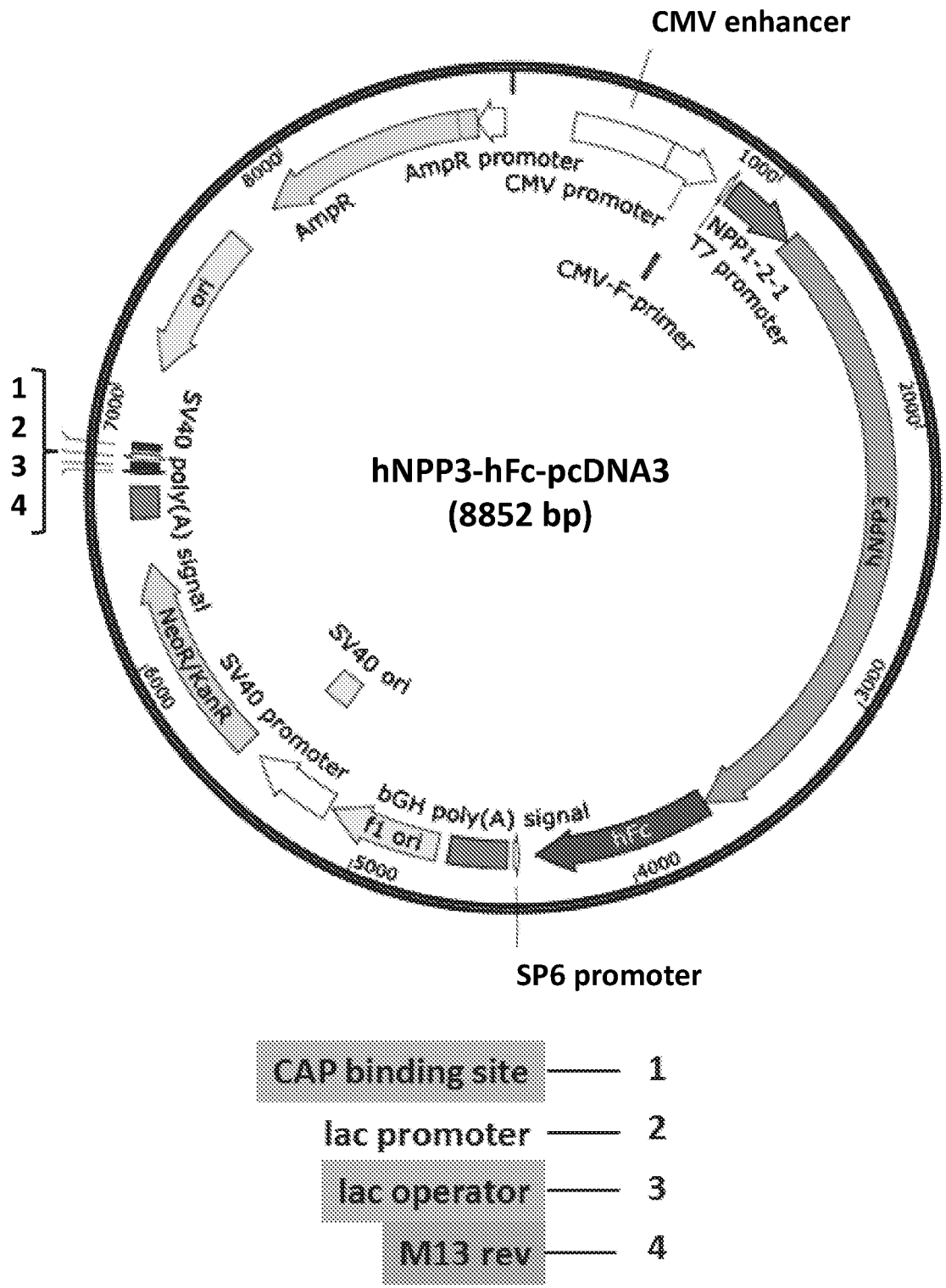
FIG. 3 illustrates a plasmid map of a non-limiting ENPP3-Fc construct contemplated within the invention.
Figure 4:
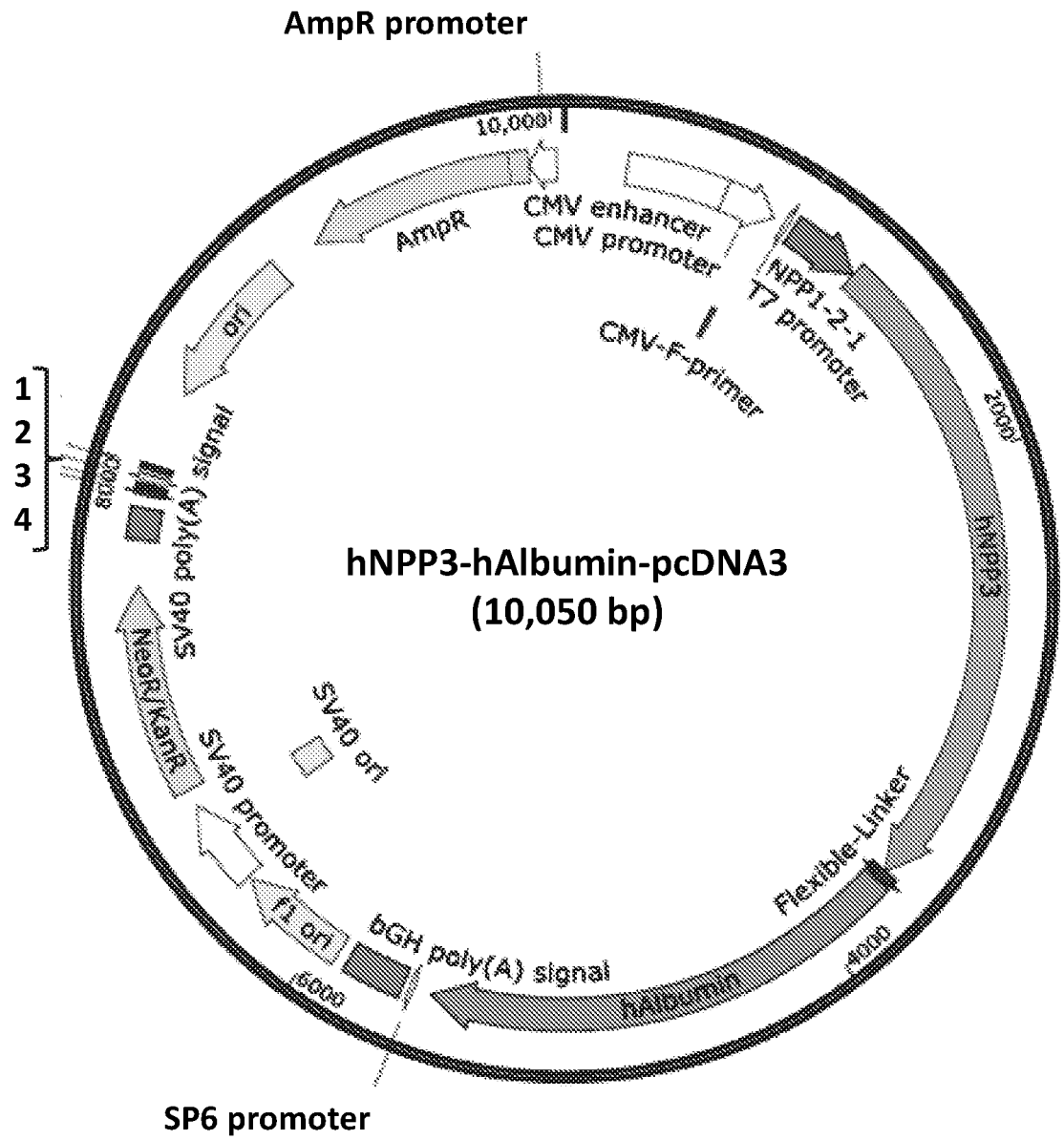
FIG. 4 illustrates a plasmid map of a non-limiting ENPP3-Albumin construct contemplated within the invention.
Figure 4:
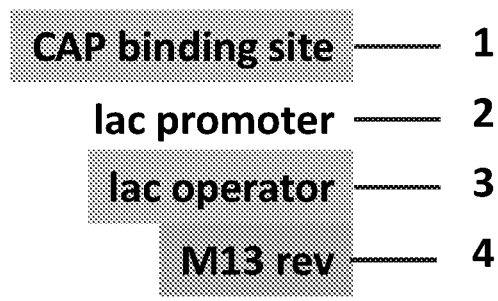

ENPP1 is made soluble by omitting the transmembrane domain. Human ENPP1 (NCBI accession NP 006199) was modified to express a soluble, recombinant protein by replacing its transmembrane region (e.g., residues 77-98) with the corresponding subdomain of human ENPP2 (NCBI accession NP_001124335, e.g., residues 12-30). The modified ENPP1 sequence was cloned into a modified pFastbac FIT vector possessing a TEV protease cleavage site followed by a C-terminus 9-F1IS tag, and cloned and expressed in insect cells, and both proteins were expressed in a baculovirus system as described previously (Albright, et al., 2012, Blood 120:4432-4440; Saunders, et al., 2011, J. Biol. Chem. 18:994-1004; Saunders, et al., 2008, Mol. Cancer Ther. 7:3352-3362), resulting in the accumulation of soluble, recombinant protein in the extracellular fluid (FIGS. 2-3).

Production and Purification of ENPP1 and ENPP1 Fusion Proteins

In certain embodiments, a soluble ENPP1 polypeptide, as well as soluble fusion constructs of ENPP1, including albumin fusion constructs thereof and/or IgG Fc domain constructs thereof, and/or including a bone targeting domain, such as 2-20 consecutive polyaspartic acid residues or 2-20 consecutive polyglutamic acid residues, are efficacious in treating, reducing, and/or preventing progression of renal stones. In other embodiments, the soluble ENPP1 polypeptide does not include a bone targeting domain, such as 2-20 consecutive polyaspartic acid residues or 2-20 consecutive polyglutamic acid residues.

Figure 5:
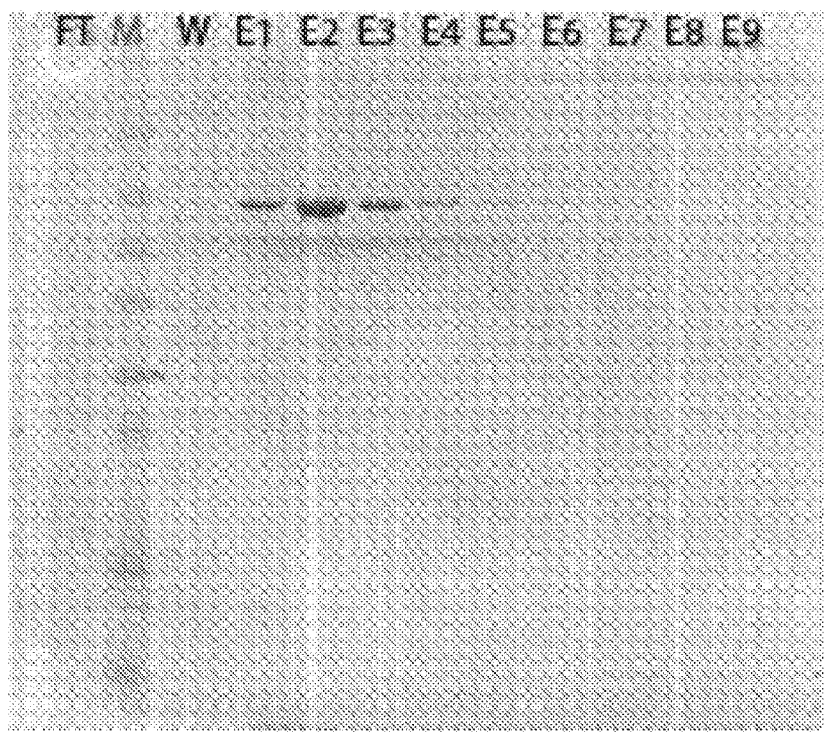
FIG. 5 illustrates a protein gel showing non-limiting expression and purification of a ENPP1 polypeptide.
Figure 6:
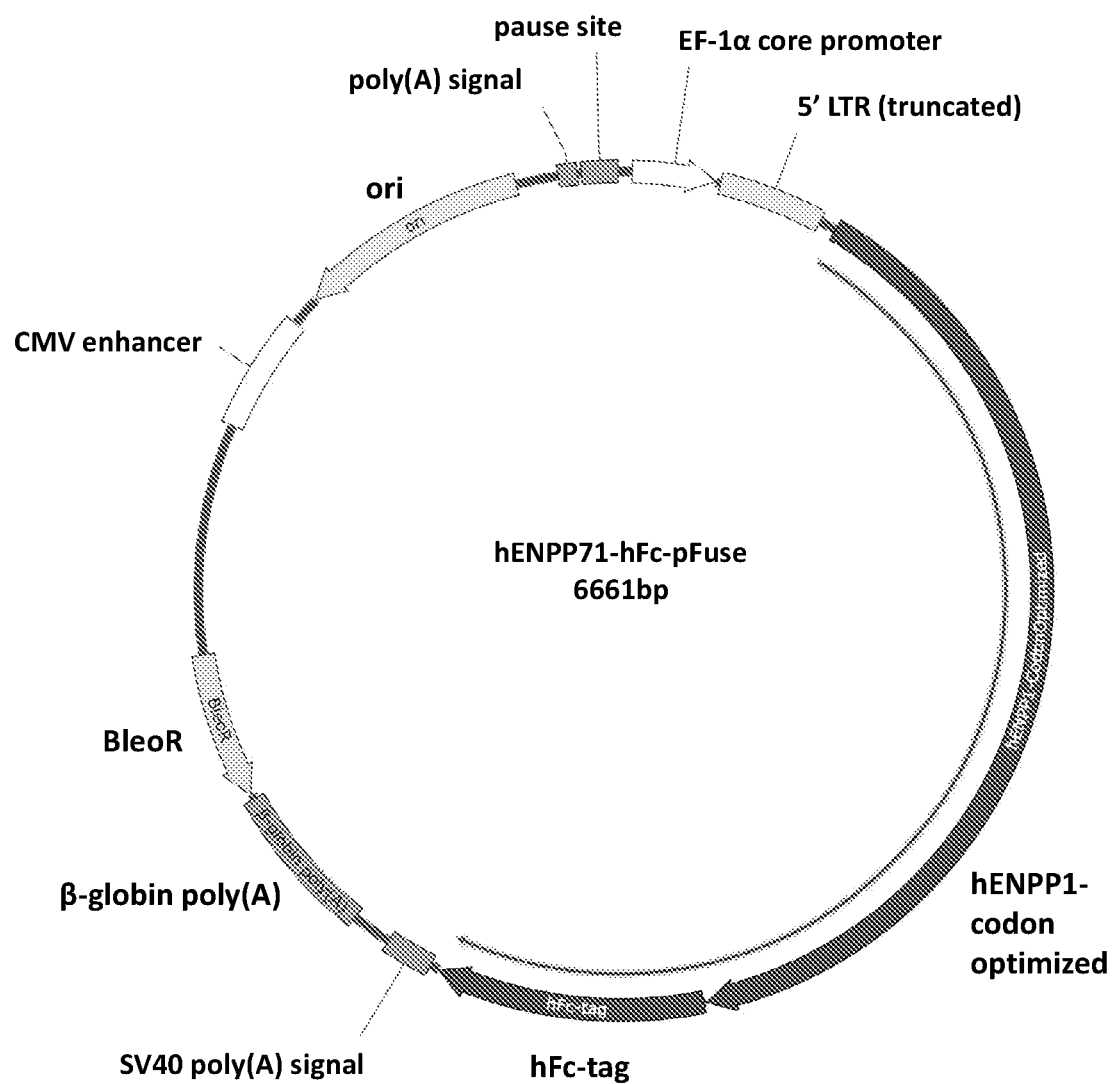
FIG. 6 illustrates a plasmid map of a non-limiting ENPP71-Fc construct contemplated within the invention.
Figure 7:
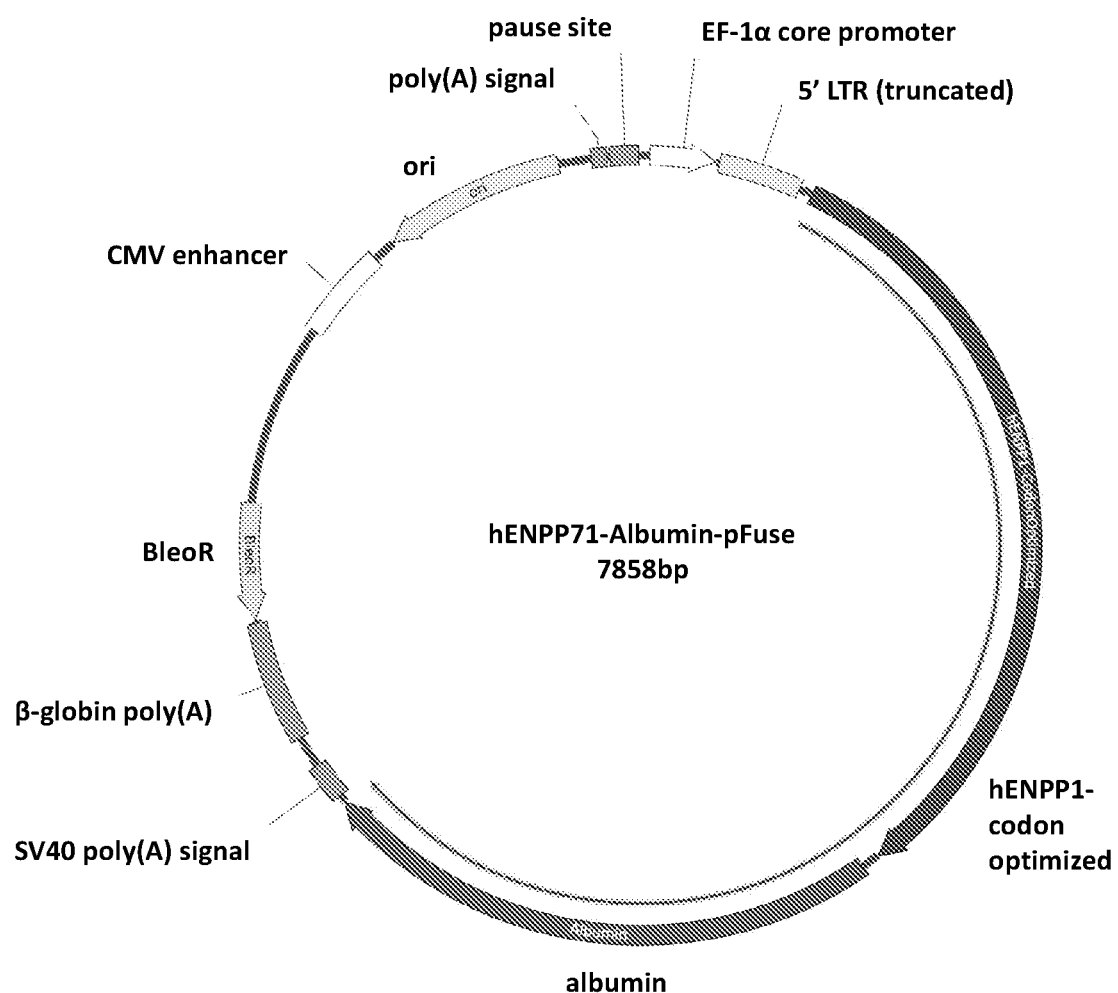
FIG. 7 illustrates a plasmid map of a non-limiting ENPP71-Albumin construct contemplated within the invention.

To produce soluble, recombinant ENPP1 for in vitro use, ENPP1 was fused to the Fc domain of IgG (referred to as "NPP1-Fc") and the fusion protein was expressed in stable mammalian cell lines (HEK293). The protein can also be expressed from Baculovirus insect cell system or Yeast Pichia expression system using suitable vectors. The protein can be produced in either adherent or suspension cells. To establish stable cell lines the nucleic acid sequence encoding ENPP1 fusion proteins (FIGS. 5-7; and sequences recited elsewhere herein) are cloned into an appropriate vector for large scale protein production.

Many expression systems are known can be used for the production of ENPP1 fusion protein, including bacteria (for example *E. coli* and *Bacillus subtilis*), yeasts (for example *Saccharomyces cerevisiae, Kluyveronmyces lactis* and *Pichia pastoris*), filamentous fungi (for example *Aspergillus*), plant cells, animal cells and insect cells. The desired protein can be produced in conventional ways, for example from a coding sequence inserted in the host chromosome or on a free plasmid.

The yeasts can be transformed with a coding sequence for the desired protein in any of the usual ways, for example electroporation. Methods for transformation of yeast by electroporation are disclosed in Becker & Guarente, 1990, Methods Enzymol. 194: 182. Successfully transformed cells, i.e., cells that contain a DNA construct of the present invention, can be identified by well-known techniques. For example, cells resulting from the introduction of an expression construct can be grown to produce the desired polypeptide. Cells can be harvested and lysed and their DNA content examined for the presence of the DNA using a method, such as that described by Southern, 1975, J. Mol. Biol, 98:503 and/or Berent, et al., 1985, Biotech 3:208. Alternatively, the presence of the protein in the supernatant can be detected using antibodies.

Useful yeast plasmid vectors include pRS403-406 and pRS413-416 and are generally available fron1 Strat:1.gene Cloning Systems, La Jolla, CA, USA Plasmids pRS403, pRS404, pRS405 and pRS406 are Yeast Integrating plasmids (Y1ps) and incorporate the yeast selectable markers I-11S3, TRP1, LEU2 and IJRA3. Plasmids pRS413-416 are Yeast Centromere plasmids (YCps).

A variety of methods have been developed to operably link DNA to vectors via complementary cohesive termini. For instance, complementary homopolymer tract can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase I, which are enzymes that remove protruding, 3'-single-stranded termini with their 3'-5'-exonucleolytic activities, and fill in recessed 3'-ends with their polymerizing activities.

The combination of these activities thus generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Clones of single, stably transfected cells are then established and screened for high expressing clones of the desired fusion protein. Screening of the single cell clones for ENPP3 protein expression can be accomplished in a high-throughput manner in 96 well plates using the synthetic enzymatic substrate pNP-TMP as previously described (Albright, et al., 2015, Nat. Commun. 6:10006). Upon identification of high expressing clones through screening, protein production can be accomplished in shaking flasks or bio-reactors are previously described in Albright, et al., 2015, Nat. Commun. 6:10006.

Purification of ENPP1 can be accomplished using a combination of standard purification techniques known in the art. Examples of which are described above in production of ENPP3 protein. Following purification, ENPP1-Fc was dialyzed into PBS supplemented with $Zn^{2+}$ and $Mg^{2+}$ (PBSplus) concentrated to between 5 and 7 mg/ml, and frozen at −80° C. in aliquots of 200-500 µl. Aliquots were thawed immediately prior to use and the specific activity of the solution was adjusted to 31.25 au/ml (or about 0.7 mg/ml depending on the preparation) by dilution in PBSplus.

Cloning and Expression of ENPP3

Soluble ENPP3 polypeptides, as well as soluble fusion constructs of ENPP3, including albumin fusion constructs thereof and/or IgG Fc domain constructs thereof, and/or including a bone targeting domain, such as 2-20 consecutive polyaspartic acid residues or 2-20 consecutive polyglutamic acid residues, are efficacious within the methods of the invention. In certain embodiments, soluble ENPP3 does not include a bone targeting domain, such as 2-20 consecutive polyaspartic acid residues or 2-20 consecutive polyglutamic acid residues.

NPP3 is poorly exported to the cell surface. Soluble ENPP3 protein is constructed by replacing the signal sequence of ENPP3 with the native signal sequence of other ENPPs. Soluble ENPP3 constructs are prepared by using the signal export signal sequence of other ENPP enzymes, such as but not limited to ENPP7 and/or ENPP5. Soluble ENPP3 constructs are prepared using a signal sequence comprised of a combination of the signal sequences of ENPP1 and ENPP2 ("NPP1-2-1" or "NPP121" hereinafter). Signal sequences of any other known proteins may be used to target the extracellular domain of ENPP3 for secretion as well, such as but not limited to the signal sequence of the immunoglobulin kappa and lambda light chain proteins. Further, the invention should not be construed to be limited to the constructs described herein, but also includes constructs comprising any enzymatically active truncation of the ENPP3 extracellular domain.

Production and Purification of ENPP3 and ENPP3 Fusion Proteins:

ENPP3 is produced by establishing stable transfections in either CHO or HEK293 mammalian cells. The protein may be produced in either adherent or suspension cells. To establish stable cell lines the nucleic acid sequence encoding ENPP3 fusion proteins (such as sequences disclosed elsewhere herein) into an appropriate vector for large scale protein production. There are a variety of these vectors available from commercial sources and any of those may be used.

For example, FIG. 3 shows a plasmid map of ENPP121-exNPP3-Fc cloned into the pcDNA3 plasmid with appropriate endonuclease restriction sites. The protein subdomains are color coded to illustrate the signal sequence, extracellular domain of ENPP3, and Fc domains of the fusion protein. The amino acid sequence of the cloned protein is also displayed below the plasmid map and also color coded to illustrate the domains of the fusion protein. The pcDNA3 plasmid containing the desired protein constructs can be stably transfected into expression plasmid using established techniques such as electroporation or lipofectamine, and the cells can be grown under antibiotic selection to enhance for stably transfected cells.

Clones of single, stably transfected cells are then established and screened for high expressing clones of the desired fusion protein. Screening of the single cell clones for ENPP3 protein expression can be accomplished in a high-throughput manner in 96 well plates using the synthetic enzymatic substrate pNP-TMP as previously described for ENPP1 (Saunders, et al., 2008, Mol. Cancer Ther. 7(10):3352-62; Albright, et al., 2015, Nat Commun. 6:10006).

Upon identification of high expressing clones through screening, protein production can be accomplished in shaking flasks or bio-reactors are previously described for ENPP1 (Albright, et al., 2015, Nat Commun. 6:10006).

Purification of ENPP3 can be accomplished using a combination of standard purification techniques known in the art. These techniques are well known in the art and are selected from techniques such as column chromatograph, ultracentrifugation, filtration, and precipitation. Column chromatographic purification is accomplished using affinity chromatography such as protein-A and protein-G resins, metal affinity resins such as nickel or copper, hydrophobic exchange chromatography, and reverse-phase high-pressure chromatography (HPLC) using C8-C14 resins. Ion exchange may also be employed such as anion and cation exchange chromatography using commercially available resins such as Q-sepharose (anion exchange) and SP-sepharose (cation exchange), blue sepharose resin and blue-sephadex resin, and hydroxyapatite resins. Size exclusion chromatography using commercially available S-75 and 5200 Superdex resins may also be employed, as known in the art. Buffers used to solubilize the protein, and provide the selection media for the above described chromatographic steps, are standard biological buffers known to practitioners of the art and science of protein chemistry.

Some examples of buffers that are used in preparation include citrate, phosphate, acetate, tris(hydroxymethyl)aminomethane, saline buffers, glycine-HCL buffers, cacodylate buffers, and sodium barbital buffers which are well known in the art. Using a single techniques or a series of techniques in combination and the appropriate buffer systems adjusted to the appropriate pH one can purify the fusion proteins described to greater than 99% purity from crude material, as demonstrated in FIG. 1. This figure compares partially purified ENPP3 and the crude starting material side by side on a Coomasie stained polyacrylamide gel after a single purification step.

As demonstrated in FIG. 1, a protein of molecular weight slightly greater than 105 kD corresponding to the appropriate molecular weight of ENPP3 is enriched from the crude starting material displayed in the right lane after a single purification step. This material may then be additionally purified using additional techniques and/or chromatographic steps as described above, to reach substantially higher purity such as ~99% purity.

Expression and Purification of ENPP1-Albumin and ENPP3-Albumin Fusion Proteins

Human ENPP1 or ENPP3 protein is fused to human serum albumin (HSA) by sub cloning into pFUSE plasmids (InvivoGen, San Diego CA). Stable transfections of the ENPP1-ALB or ENPP3-ALB are established in HEK293 cells under zeocin selection, and adherent HEK293 cells can be adapted for suspension growth. Adapted cells are used to seed liquid culture growths in FreeStyle medium (Gibco #12338-018) in shaker flasks at 37° C. and 5% $CO_2$, agitated at 120 RPM with high humidity. The culture is gradually expanded to the desired target volume and then maintained for another days to accumulate extracellular protein. During the maintenance phase, cultures are supplemented with CD EfficientFeed CAGI (Gibco #A13275-05) to enhance protein production. Cells are propagated in a 10 liter bioreactor equipped with dissolved oxygen and pH control. Dissolved oxygen is kept at 40% air saturation by supplying the culture with mixture of air and oxygen not exceeding 3 liter per minute at an agitation rate of 80 RPM. pH is controlled at 7.4 by sparging $CO_2$ when the pH is higher than 7.4. Culture growth is followed by measuring cell number, cell viability, glucose and lactate concentrations.

The liquid cultures are centrifuged at 4300×g for 15 min and the supernatants are filtered through a 0.2 µm membrane and concentrated via tangential flow using a Pellicon®3 0.11 m² Ultracell 30 kD cassette (Millipore, Billerica MA). The concentrated supernatant is loaded onto a protein-AG column and can be eluted with a buffer comprising 50 mM Sodium Citrate, 150 mM, NaCl, 3 mM $ZnCl_2$, 3 mM $CaCl_2$, pH=35. Fractions containing enzymatic activity are pooled and dialyzed against IX PBS buffer pH 7.4, 11 µM $ZnCl_2$, 20 µM $CaCl_2$, then concentrated to 6 mg/ml, distributed into small aliquots and stored at −80° C. The resulting protein samples are tested with Pierce LAL Chromogenic Endotoxin Quantitation Kit (cat 88282) to verify that all are free of endotoxin.

The ENPP-albumin fusion protein after purification is characterized following the experimental protocols discussed above and described elsewhere (for example, PCT/2014/015945, and PCT/2016/033236).

Animal Models

The invention contemplates treatment and/or prevention of nephrolithiasis in a patient. Nephrolithiasis commonly involves crystals comprising oxalate, urate, cystine, hydroxyurea, and/or calcium phosphate. In certain non-limiting embodiments, the present invention contemplates treatment of forms of nephrolithiasis such as cystinuria, uric acid stone disease, struvite stone disease, hypercalcinuria, calcium stone disease, and hyperoxaluria, as well as compositions of kidney stone, including oxalate, urate, cystine, hydroxyurea, and/or calcium phosphate.

Animal models can be used to test for treatment of nephrolithiasis according to the invention, for example, the following mouse models: (a) Npt2a$^{-/-}$, (b) the double mutant Npt2a$^{-/-}$/Enpp1$^{asj/asj}$, and (c) a C57BL/6 mouse (Jackson Labs) that has been subject to diet-induced formation of renal stones, the diet being a high calcium, low magnesium diet (such as Teklad Labs diet TD.00042, Harlan Labs, Madison, WI).

Npt2a$^{-/-}$ mice show kidney stone formation when fed using normal chow starting at weaning age and persist at least until 10 weeks of age. Conversely double mutant Npt2a$^{-/-}$/Enpp1$^{asj/asj}$ mice present twice the levels of kidney stone formation when compared with Npt2a$^{-/-}$ mice when fed a normal chow. Npt2a$^{-/-}$ mice, and Enpp1$^{asj/asj}$ mice are commercially obtained from Jackson laboratory, ME. Double mutant mice (Npt2a$^{-/-}$/Enpp$^{asj/asj}$) are created by cross breeding Npt2a$^{-/-}$ mice and Enpp1$^{asj/asj}$ mice following standard protocols known in the art (Jackson Laboratory Recourse Manual, (2007, 1-29). The Npt2a$^{-/-}$ or Npt2a$^{-/-}$/Enpp1$^{asj/asj}$ double mutant mouse models for renal stone related disease can be used to test the efficacy of treatment according to the invention (Khan & Canales, 2011, J. Urol. 186(3):1107-13; Wu, 2015, Urolithiasis 43 (Suppl 1):65-76). Oxalate stone-forming rodent models, i.e., ethylene glycol, hydroxyl purine-fed mice or rats, or intraperitoneal injection of sodium oxalate of mice and rats (Khan & Glenton, J. Urology 184:1189-1196), urate stone forming (Wu, et al., 1994, Proc. Natl. Acad. Sci. USA 91(2):742-6) and cystinuria mouse models (Zee, et al., 2017, Nat. Med. 23(3):288-290; Sahota, et al., 2014, Urology 84(5):1249 e9-15) can also be tested.

Experimental details on enzymatic activity, quantification of plasma PPi, micro-CT scans, quantification of plasma PPi uptake are described in detail in the patent application and publications of PCT/US2016/33236, WO2014/126965 and US 2015/0359858, all of which are herein incorporated in their entirety.

Identification of Kidney Stones or Formation of Kidney Stones

Tests for kidney stones can include: blood tests (to check calcium, phosphorus, uric acid, and electrolyte levels); kidney function tests; urine tests (to look for crystals and/or red blood cells); and examination of the stone to determine its type, composition and morphology.

Kidney stones or a kidney tubule blockage can be seen using one of the following methods: abdominal CT scan; abdominal/kidney MRI; abdominal x-rays; intravenous pyelogram (IVP); kidney ultrasound; and retrograde pyelogram.

```
SEQUENCES
ENPP1 Amino Acid Sequence (NCBI accession NP_006199)
                                                         (SEQ ID NO: 1)
MERDGCAGGGSRGGEGGRAPREGPAGNGRDRGRSHAAEAPGDPQAAASLLAPMDVGEEPLEK

AARARTAKDPNTYKVLSLVLSVCVLTTILGCIFGLKPSCAKEVKSCKGRCFERTFGNCRCDA

ACVELGNCCLDYQETCIEPEHIWTCNKFRCGEKRLTRSLCACSDDCKDKGDCCINYSSVCQG

EKSWVEEPCESINEPQCPAGFETPPILLFSLDGFRAEYLHTWGGLLPVISKLKKCGTYTKNM

RPVYPTKTFPNHYSIVTGLYPESHGIIDNKMYDPKMNASFSLKSKEKFNPEWYKGEPIWVTA

KYQGLKSGTFFWPGSDVEINGIFPDIYKMYNGSVPFEERILAVLQWLQLPKDERPHFYTLYL

EEPDSSGHSYGPVSSEVIKALQRVDGMVGMLMDGLKELNLHRCLNLILISDHGMEQGSCKKY

IYLNKYLGDVKNIKVIYGPAARLRPSDVPDKYYSFNYEGIARNLSCREPNQHFKPYLKHFLP

KRLHFAKSDRIEPLTFYLDPQWQLALNPSERKYCGSGFHGSDNVFSNMQALFVGYGPGFKHG

IEADTFENIEVYNLMCDLLNLTPAPNNGTHGSLNHLLKNPVYTPKHPKEVHPLVQCPFTRNP

RDNLGCSCNPSILPIEDFQTQFNLTVAEEKIIKHETLPYGRPRVLQKENTICLLSQHQFMSG

YSQDILMPLWTSYTVDRNDSFSTEDFSNCLYQDFRIPLSPVHKCSFYKNNTKVSYGFLSPPQ

LNKNSSGIYSEALLTTNIVPMYQSFQVIWRYFHDTLLRKYAEERNGVNVVSGPVFDFDYDGR

CDSLENLRQKRRVIRNQEILIPTHFFIVLTSCKDTSQTPLHCENLDTLAFILPHRTDNSESC

VHGKHDSSWVEELLMLHRARITDVEHITGLSFYQQRKEPVSDILKLKTHLPTFSQED

ENPP2 Amino Acid Sequence (NCBI accession NP_001124335)
                                                         (SEQ ID NO: 2)
MARRSSFQSCQIISLFTFAVGVNICLGFTAHRIKRAEGWEEGPPTVLSDSPWTNISGSCKGR

CFELQEAGPPDCRCDNLCKSYTSCCHDFDELCLKTARGWECTKDRCGEVRNEENACHCSEDC
```

-continued

LARGDCCTNYQVVCKGESHWVDDDCEEIKAAECPAGFVRPPLIIFSVDGFRASYMKKGSKVM
PNIEKLRSCGTHSPYMRPVYPTKTFPNLYTLATGLYPESHGIVGNSMYDPVFDATFHLRGRE
KFNHRWWGGQPLWITATKQGVKAGTFFWSVVIPHERRILTILQWLTLPDHERPSVYAFYSEQ
PDFSGHKYGPFGPEMTNPLREIDKIVGQLMDGLKQLKLHRCVNVIFVGDHGMEDVICDRTEF
LSNYLINVDDITLVPGTLGRIRSKFSNNAKYDPKAIIANLICKKPDQHFKPYLKQHLPKRLH
YANNRRIEDIHLLVERRWHVARKPLDVYKKPSGKCFFQGDHGFDNKVNSMQTVFVGYGSTFK
YKTKVPPFENIELYNVMCDLLGLKPAPNNGTHGSLNHLLRINTFRPTMPEEVIRPNYPGIMY
LQSDFDLGCTCDDKVEPKNKLDELNKRLHTKGSTEAETRKFRGSRNENKENINGNFEPRKER
HLLYGRPAVLYRTRYDILYHTDFESGYSEIFLMPLWTSYTVSKQAEVSSVPDHLTSCVRPDV
RVSPSFSQNCLAYKNDKQMSYGFLFPPYLSSSPEAKYDAFLVTNMVPMYPAFKRVWNYFQRV
LVKKYASERNGVNVISGPIFDYDYDGLHDTEDKIKQYVEGSSIPVPTHYYSITTSCLDFTQP
ADKCDGPLSVSSFILPHRPDNEESCNSSEDESKWVEELMKMHTARVRDIEHLTSLDFFRKTS
RSYPEILTLKTYLHTYESEI

Sequence (SEQ ID NO: 3)

$D_m$ wherein m is an integer ranging from 1 to 15

Sequence (SEQ ID NO: 4)

$(DSS)_n$ wherein n is an integer ranging from 1 to 10

Sequence (SEQ ID NO: 5)

$(ESS)_n$ wherein n is an integer ranging from 1 to 10

Sequence (SEQ ID NO: 6)

$(RQQ)_n$ wherein n is an integer ranging from 1 to 10

Sequence (SEQ ID NO: 7)

$(KR)_n$ wherein n is an integer ranging from 1 to 10

Sequence (SEQ ID NO: 8)

$R_m$ wherein m is an integer ranging from 1 to 15

Sequence (SEQ ID NO: 9)

DSSSEEKFLRRIGRFG

Sequence (SEQ ID NO: 10)

EEEEEEPRGDT

Sequence (SEQ ID NO: 11)

APWHLSSQYSRT

Sequence (SEQ ID NO: 12)

STLPIPHEFSRE

Sequence (SEQ ID NO: 13)

VTKHLNQISQSY

Sequence (SEQ ID NO: 14)

$E_m$ wherein m is an integer ranging from 1 to 15

ENPP121 Amino Acid Sequence (SEQ ID NO: 15)

```
  1 M E R D G C A G G G S R G G E G G R A P
 21 R E G P A G N G R D R G R S H A A E A P
 41 G D P Q A A A S L L A P M D V G E E P L
 61 E K A A R A R T A K D P N T Y K I I S L
 81 F T A V G V N I C L G**F T A G L K P S
101 C A K E V K S C K G R C F E R T F G N C
121 R C D A A C V E L G N C C L D Y Q E T C
141 I E P E H I W T C N K F R C G E K R L T
161 R S L C A C S D D C K D K G D C C I N Y
181 S S V C Q G E K S W V E E P C E S I N E
201 P Q C P A G F E T P P T L L F S L D G F
221 R A E Y L H T W G G L L P V I S K L K K
241 C G T Y T K N M R P V Y P T K T F P N H
261 Y S I V T G L Y P E S H G I I D N K M Y
281 D P K M N A S F S L K S E K F N P E W
301 Y K G E P I W V T A K Y Q G L K S G T F
321 F W P G S D V E I N G I F P D I Y K M Y
341 N G S V P F E E R I L A V L Q W L Q L P
361 K D E R P H F Y T L Y L E E P D S S G H
381 S Y G P V S S E V I K A L Q R V D G M V
401 G M L M D G L K E L N L H R C L N L I L
421 I S D H G M E Q G S C K K Y I Y L N K Y
441 L G D V K N I K V I Y G P A A R L R P S
461 D V P D K Y Y S F N Y E G I A R N L S C
481 R E P N Q H F K P Y L K H F L P K R L H
501 F A K S D R I E P L I E Y L D P Q W Q L
521 A L N P S E R K Y C G S G F H G S D N V
541 F S N M Q A L F V G Y G P G F K H G I E
561 A D T F E N I E V Y N L M C D L L N L T
581 P A P N N G T H G S L N H L L K N P V Y
601 T P K H P K E V H P L V Q C P F T R N P
621 R D N L G C S C N P S I L P I E D F Q T
641 Q F N L T V A E E K I I K H E T L P Y G
661 R P R V L Q K E N T I C L L S Q H Q F M
```

-continued

```
681 S G Y S Q D I L M P L W T S Y T V D R N
701 D S F S T E D F S N C L Y Q D F R I P L
721 S P V H K C S F Y K N N T K V S Y G F L
741 S P P Q L N K N S S G I Y S E A L L T T
761 N I V P M Y Q S F Q V I W R Y F H D T L
781 L R K Y A E E R N G V N V V S G P V F D
801 F D Y D G R C D S L E N L R Q K R R V I
821 R N Q E I L I P T H E E I V L T S C K D
841 T S Q T P L H C E N L D T L A F I L P H
861 R T D N S E S C V H G K H D S S W V E E
881 L L M L H R A R I T D V E H I T G L S F
901 Y Q Q R K E P V S D I L K L K T H L P T
921 F S Q E D
```

Singly Underlined: residues swapped with ENPP2 residues 1-27 to afford cleavage at transition position (**);

Doubly Underlined: ENPP1 protein (beginning and end).

ENPP121-Fc Amino Acid Sequence
(SEQ ID NO: 16)

```
  1 M E R D G C A G G G S R G G E G G R A P
 21 R E G P A G N G R D R G R S H A A E A P
 41 G D P Q A A A S L L A P M D V G E E P L
 61 E K A A R A R T A K D P N T Y K I I S L
 81 F T F A V G V N I C L G**F T A G L K P S
101 C A K E V S C K G R C F E R T F G N C
121 R C D A A C V E L G N C C L D Y Q E T C
141 I E P E H I W T C N K F R C G E K R L T
161 R S L C A C S D D C K D K G D C C I N Y
181 S S V C Q G E K S W V E E P C E S I N E
201 P Q C P A G F E T P P T L L F S L D G F
221 R A E Y L H T W G G L L P V I S K L K K
241 C G T Y T K N M R P V Y P T K T F P N H
261 Y S I V T G L Y P E S H G I I D N K M Y
281 D P K M N A S F S L K S E K F N P E W
301 Y K G E P I W V T A K Y Q G L K S G T F
321 F W P G S D V E I N G I F P D I Y K M Y
341 N G S V P F E E R I L A V L Q W L Q L P
361 K D E R P H F Y T L Y L E E P D S S G H
381 S Y G P V S S E V I K A L Q R V D G M V
401 G M L M D G L K E L N L H R C L N L I L
421 I S D H G M E Q G S C K K Y I Y L N K Y
441 L G D V K N I K V I Y G P A A R L R P S
461 D V P D K Y Y S F N Y E G I A R N L S C
```

```
481 R E P N Q H F K P Y L K H F L P K R L H
501 F A K S D R I E P L T F Y L D P Q W Q L
521 A L N P S E R K Y C G S G F H G S D N V
541 F S N M Q A L F V G Y G P G F K H G I E
561 A D T F E N I E V Y N L M C D L L N L T
581 P A P N N G T H G S L N H L L K N P V Y
601 T P K H P K E V H P L V Q C P F T R N P
621 R D N L G C S C N P S I L P I E D F Q T
641 Q F N L T V A E E K I K H E T L P Y G
661 R P R V L Q K E N T I C L L S Q H Q F M
681 S G Y S Q D I L M P L W T S Y T V D R N
701 D S F S T E D F S N C L Y Q D F R I P L
721 S P V H K C S F Y K N N T K V S Y G F L
741 S P P Q L N K N S S G I Y S E A L L T T
761 N I V P M Y Q S F Q V I W R Y F H D T L
781 L R K Y A E E R N G V N V V S G P V F D
801 F D Y D G R C D S L E N L R Q K R R V I
821 R N Q E I L I P T H E E I V L T S C K D
841 T S Q T P L H C E N L D T L A F I L P H
861 R T D N S E S C V H G K H D S S W V E E
881 L L M L H R A R I T D V E H I T G L S F
901 Y Q Q R K E P V S D I L K L K T H L P T
921 F S Q E D L I N D K T H T C P P C P A P
941 E L L G G P S V F L F P P K P K D T L M
961 I S R T P E V T C V V V D V S H E D P E
981 V K F N W Y V D G V E V H N A K T K P R
1001 E E Q Y N S T Y R V V S V L T V L H Q D
1021 W L N G K E Y K C K V S N K A L P A P I
1041 E K T I S K A K G Q P R E P Q V Y T L P
1061 P S R E E M T K N Q V S L T C L V K G E
1081 Y P S D I A V E W E S N G Q P E N N Y K
1101 T T P P V L D S D G S F F L Y S K L T V
1121 D K S R W Q Q G N V F S C S V M H E A L
1141 H N H Y T Q K S L S L S P G K
```

Singly Underlined: residues swapped with ENPP2 residues 1-27 to afford cleavage at transition position (**); Doubly Underlined: ENPP1 protein (beginning and end); Bold: hIgG1 (Fc)

ENPP71 Amino Acid Sequence (SEQ ID NO: 17)

```
  1 MRGPAVLLTV ALATLLAPGA GAGLKPSCAK EVKSCKGRCF ERTFGNCRCD
 51 AACVELGNCC LDYQETCIEP EHIWTCNKFR CGEKRLTRSL CACSDDCKDK
101 GDCCINYSSV CQGEKSWVEE PCESINEPQC PAGFETPPTL LFSLDGFRAE
151 YLHTWGGLLP VISKLKKCGT YTKNMRPVYP TKTFPNHYSI VTGLYPESHG
201 IIDNKMYDPK MNASFSLKSK EKFNPEWYKG EPIWVTAKYQ GLKSGTFFWP
251 GSDVEINGIF PDIYKMYNGS VPFEERILAV LQWLQLPKDE RPHFYTLYLE
301 EPDSSGHSYG PVSSEVIKAL QRVDGMVGML MDGLKELNLH RCLNLILISD
351 HGMEQGSCKK YIYLNKYLGD VKNIKVIYGP AARLRPSDVP DKYYSFNYEG
401 IARNLSCREP NQHFKPYLKH FLPKRLHFAK SDRIEPLTFY LDPQWQLALN
451 PSERKYCGSG FHGSDNVFSN MQALFVGYGP GFKHGIEADT FENIEVYNLM
501 CDLLNLTPAP NNGTHGSLNH LLKNPVYTPK HPKEVHPLVQ CPFTRNPRDN
551 LGCSCNPSIL PIEDFQTQFN LTVAEEKIIK HETLPYGRPR VLQKENTICL
601 LSQHQFMSGY SQDILMPLWT SYTVDRNDSF STEDFSNCLY QDFRIPLSPV
651 HKCSFYKNNT KVSYGFLSPP QLNKNSSGIY SEALLTTNIV PMYQSFQVIW
701 RYFHDTLLRK YAEERNGVNV VSGPVFDFDY DGRCDSLENL RQKRRVIRNQ
751 EILIPTHFFI VLTSCKDTSQ TPLHCENLDT LAFILPHRTD NSESCVHGKH
801 DSSWVEELLM LHRARITDVE HITGLSFYQQ RKEPVSDILK LKTHLPTFSQ
851 ED
```

Singly Underlined: ENPP7; Doubly Underlined: ENPP1 protein (beginning and end).

ENPP71-Fc Amino Acid Sequence (SEQ ID NO: 18)

```
  1 MRGPAVLLTV ALATLLAPGA GAGLKPSCAK EVKSCKGRCF ERTFGNCRCD
 51 AACVELGNCC LDYQETCIEP EHIWTCNKFR CGEKRLTRSL CACSDDCKDK
101 GDCCINYSSV CQGEKSWVEE PCESINEPQC PAGFETPPTL LFSLDGFRAE
151 YLHTWGGLLP VISKLKKCGT YTKNMRPVYP TKTFPNHYSI VTGLYPESHG
201 IIDNKMYDPK MNASFSLKSK EKFNPEWYKG EPIWVTAKYQ GLKSGTFFWP
251 GSDVEINGIF PDIYKMYNGS VPFEERILAV LQWLQLPKDE RPHFYTLYLE
301 EPDSSGHSYG PVSSEVIKAL QRVDGMVGML MDGLKELNLH RCLNLILISD
351 HGMEQGSCKK YIYLNKYLGD VKNIKVIYGP AARLRPSDVP DKYYSFNYEG
401 IARNLSCREP NQHFKPYLKH FLPKRLHFAK SDRIEPLTFY LDPQWQLALN
451 PSERKYCGSG FHGSDNVFSN MQALFVGYGP GFKHGIEADT FENIEVYNLM
501 CDLLNLTPAP NNGTHGSLNH LLKNPVYTPK HPKEVHPLVQ CPFTRNPRDN
551 LGCSCNPSIL PIEDFQTQFN LTVAEEKIIK HETLPYGRPR VLQKENTICL
601 LSQHQFMSGY SQDILMPLWT SYTVDRNDSF STEDFSNCLY QDFRIPLSPV
651 HKCSFYKNNT KVSYGFLSPP QLNKNSSGIY SEALLTTNIV PMYQSFQVIW
701 RYFHDTLLRK YAEERNGVNV VSGPVFDFDY DGRCDSLENL RQKRRVIRNQ
751 EILIPTHFFI VLTSCKDTSQ TPLHCENLDT LAFILPHRTD NSESCVHGKH
801 DSSWVEELLM LHRARITDVE HITGLSFYQQ RKEPVSDILK LKTHLPTFSQ
851 EDLINDKTHT CPPCPAPELL GGPSVFLFPP KPKDTLMISR TPEVTCVVVD
```

```
 901 VSHEDPEVKF NWYVDGVEVH NAKTKPREEQ YNSTYRVVSV LTVLHQDWLN

951 GKEYKCKVSN KALPAPIEKT ISKAKGQPRE PQVYTLPPSR EEMTKNQVSL

1001 TCLVKGFYPS DIAVEWESNG QPENNYKTTP PVLDSDGSFF LYSKLTVDKS

1051 RWQQGNVFSC SVMHEALHNH YTQKSLSLSP GK
```

Singly Underlined: ENPP7; Doubly Underlined: ENPP1 protein (beginning and end); Bold: hIgG1 (Fc).

(ENPP71 lacking ENPP1 N-Terminus GLK) Amino Acid Sequence
(SEQ ID NO: 19)

```
   1 MRGPAVLLTV ALATLLAPGA GA    PSCAK EVKSCKGRCF ERTFGNCRCD

51 AACVELGNCC LDYQETCIEP EHIWTCNKFR CGEKRLTRSL CACSDDCKDK

101 GDCCINYSSV CQGEKSWVEE PCESINEPQC PAGFETPPTL LFSLDGFRAE

151 YLHTWGGLLP VISKLKKCGT YTKNMRPVYP TKTFPNHYSI VTGLYPESHG

201 IIDNKMYDPK MNASFSLKSK EKFNPEWYKG EPIWVTAKYQ GLKSGTFFWP

251 GSDVEINGIF PDIYKMYNGS VPFEERILAV LQWLQLPKDE RPHFYTLYLE

301 EPDSSGHSYG PVSSEVIKAL QRVDGMVGML MDGLKELNLH RCLNLILISD

351 HGMEQGSCKK YIYLNKYLGD VKNIKVIYGP AARLRPSDVP DKYYSFNYEG

401 IARNLSCREP NQHFKPYLKH FLPKRLHFAK SDRIEPLTFY LDPQWQLALN

451 PSERKYCGSG FHGSDNVFSN MQALFVGYGP GFKHGIEADT FENIEVYNLM

501 CDLLNLTPAP NNGTHGSLNH LLKNPVYTPK HPKEVHPLVQ CPFTRNPRDN

551 LGCSCNPSIL PIEDFQTQFN LTVAEEKIIK HETLPYGRPR VLQKENTICL

601 LSQHQFMSGY SQDILMPLWT SYTVDRNDSF STEDFSNCLY QDFRIPLSPV

651 HKCSFYKNNT KVSYGFLSPP QLNKNSSGIY SEALLTTNIV PMYQSFQVIW

701 RYFHDTLLRK YAEERNGVNV VSGPVFDFDY DGRCDSLENL RQKRRVIRNQ

751 EILIPTHFFI VLTSCKDTSQ TPLHCENLDT LAFILPHRTD NSESCVHGKH

801 DSSWVEELLM LHRARITDVE HITGLSFYQQ RKEPVSDILK LKTHLPIFSQ

851 ED
```

Singly Underlined: ENPP7; Doubly Underlined: ENPP1 protein (beginning and end) (first 3-amino acids at the N-terminus of ENPP1, GLK, are omitted).

(ENPP71 lacking ENPP1 N-Terminus GLK)-Fc Amino Acid Sequence
(SEQ ID NO: 20)

```
   1 MRGPAVLLTV ALATLLAPGA GA    PSCAK EVKSCKGRCF ERTFGNCRCD

51 AACVELGNCC LDYQETCIEP EHIWTCNKFR CGEKRLTRSL CACSDDCKDK

101 GDCCINYSSV CQGEKSWVEE PCESINEPQC PAGFETPPTL LFSLDGFRAE

151 YLHTWGGLLP VISKLKKCGT YTKNMRPVYP TKTFPNHYSI VTGLYPESHG

201 IIDNKMYDPK MNASFSLKSK EKFNPEWYKG EPIWVTAKYQ GLKSGTFFWP

251 GSDVEINGIF PDIYKMYNGS VPFEERILAV LQWLQLPKDE RPHFYTLYLE

301 EPDSSGHSYG PVSSEVIKAL QRVDGMVGML MDGLKELNLH RCLNLILISD

351 HGMEQGSCKK YIYLNKYLGD VKNIKVIYGP AARLRPSDVP DKYYSFNYEG

401 IARNLSCREP NQHFKPYLKH FLPKRLHFAK SDRIEPLTFY LDPQWQLALN

451 PSERKYCGSG FHGSDNVFSN MQALFVGYGP GFKHGIEADT FENIEVYNLM

501 CDLLNLTPAP NNGTHGSLNH LLKNPVYTPK HPKEVHPLVQ CPFTRNPRDN
```

-continued

```
 551 LGCSCNPSIL PIEDFQTQFN LTVAEEKIIK HETLPYGRPR VLQKENTICL

601 LSQHQFMSGY SQDILMPLWT SYTVDRNDSF STEDFSNCLY QDFRIPLSPV

651 HKCSFYKNNT KVSYGFLSPP QLNKNSSGIY SEALLTTNIV PMYQSFQVIW

701 RYFHDTLLRK YAEERNGVNV VSGPVFDFDY DGRCDSLENL RQKRRVIRNQ

751 EILIPTHFFI VLTSCKDTSQ TPLHCENLDT LAFILPHRTD NSESCVHGKH

801 DSSWVEELLM LHRARITDVE HITGLSFYQQ RKEPVSDILK LKTHLPIFSQ

851 EDLINDKTHT CPPCPAPELL GGPSVFLFPP KPKDTLMISR TPEVTCVVVD

901 VSHEDPEVKF NWYVDGVEVH NAKTKPREEQ YNSTYRVVSV LTVLHQDWLN

951 GKEYKCKVSN KALPAPIEKT ISKAKGQPRE PQVYTLPPSR EEMTKNQVSL

1001 TCLVKGFYPS DIAVEWESNG QPENNYKTTP PVLDSDGSFF LYSKLTVDKS

1051 RWQQGNVFSC SVMHEALHNH YTQKSLSLSP GK
```

Singly Underlined: ENPP7; Doubly Underlined: ENPP1 protein (beginning and end) (first 3-amino acids at the N-terminus of ENPP1 are omitted); Bold: hIgG1 (Fc).

ENPP121-ALB Amino Acid Sequence (SEQ ID NO: 21)

*MERDGCAGGGSRGGEGGRAPREGPAGNGRDRGRSHAAEAPGDPQAAASLLAPMDVGEEPLEK*

*AARARTAKDPNTYKIIS*LFTFAVGVNICLGFTAGLKPSCAKEVKSCKGRCFERTFGNCRC

DAACVELGNCCLDYQETCIEPEHIWTCNKFRCGEKRLTRSLCACSDDCKDKGDCCINYSSVC

QGEKSWVEEPCESINEPQCPAGFETPPTLLFSLDGFRAEYLHTWGGLLPVISKLKKCGTYTK

NMRPVYPIKTFPNHYSIVTGLYPESHGIIDNKMYDPKMNASFSLKSKEKFNPEWYKGEPIWV

TAKYQGLKSGTFFWPGSDVEINGIFPDIYKMYNGSVPFEERILAVLQWLQLPKDERPHFYTL

YLEEPDSSGHSYGPVSSEVIKALQRVDGMVGMLMDGLKELNLHRCLNLILISDHGMEQGSCK

KYTYLNKYLGDVKNIKVIYGPAARLRPSDVPDKYYSFNYEGIARNLSCREPNQHFKPYLKHF

LPKRLHFAKSDRIEPLTFYLDPQWQLALNPSERKYCGSGFHGSDNVFSNMQALFVGYGPGFK

HGIEADTFENIEVYNLMCDLLNLTPAPNNGTHGSLNHLLKNPVYTPKHPKEVHPLVQCPFTR

NPRDNLGCSCNPSILPIEDFQTQFNLTVAEEKIIKHETLPYGRPRVLQKENTICLLSQHQFM

SGYSQDILMPLWTSYTVDRNDSFSTEDFSNCLYQDFRIPLSPVHKCSFYKNNTKVSYGFLSP

PQLNKNSSGIYSEALLTTNIVPMYQSFQVIWRYFHDTLLRKYAEERNGVNVVSGPVFDFDYD

GRCDSLENLRQKRRVIRNQEILIPTHFFIVLTSCKDTSQTPLHCENLDTLAFILPHRTDNSE

SCVHGKHDSSWVEELLMLHRARITDVEHITGLSFYQQRKEPVSDILKLKTHLPTFSQEDRSG

SGGSMKWVTFLLLLFVSGSAFSRGVFRREAHKSEIAHRYNDLGEQHFKGLVLIAFSQYLQKC

SYDEHAKLVQEVTDFAKTCVADESAANCDKSLHTLFGDKLCAIPNLRENYGELADCCTKQEP

ERNECFLQHKDDNPSLPPFERPEAEAMCTSFKENPTTFMGHYLHEVARRHPYFYAPELLYYA

EQYNEILTQCCAEADKESCLTPKLDGVKEKALVSSVRQRMKCSSMQKFGERAFKAWAVARLS

QTFPNADFAEITKLATDLTKVNKECCHGDLLECADDRAELAKYMCENQATISSKLQTCCDKP

LLKKAHCLSEVEHDTMPADLPAIAADFVEDQEVCKNYAEAEDVFLGTFLYEYSRRHPDYSVS

LLLRLAKKYEATLEKCCAEANPPACYGTVLAEFQPLVEEPKNLVKTNCDLYEKLGEYGFQNA

ILVRYTQKAPQVSTPTLVEAARNLGRVGTKCCTLPEDQRLPCVEDYLSAILNRVCLLHEKTP

VSEHVTKCCSGSLVERRPCFSALTVDETYVPKEFKAETFTFHSDICTLPEKEKQIKKQTALA

ELVKHKPKATAEQLKTVMDDFAQFLDTCCKAADKDTCFSTEGPNLVTRCKDALARSWSHPQF

EK

Bold Italics: ENPP1 cytoplasmic and transmembrane;

Singly Underlined: Swapped residues with ENPP2 residues 1-27 to give cleavage at transition position (**); Doubly Underlined: ENPP1 transmembrane; Plain:

ENPP1 Extracellular Domain; Bold Underlined: Linker;

Bold: Albumin (ENPP71 lacking ENPP1 N-Terminus GLK)-ALB Amino Acid
Sequence
(SEQ ID NO: 22)

MRGPAVLLTVALATLLAPGAGAPSCAKEVKSCKGRCFERTFGNCRCDAACVELGNCCLDYQE

TCIEPEHIWTCNKFRCGEKRLTRSLCACSDDCKDKGDCCINYSSVCQGEKSWVEEPCESINE

PQCPAGFETPPILLFSLDGFRAEYLHTWGGLLPVISKLKKCGTYTKNMRPVYPTKTFPNHYS

IVTGLYPESHGIIDNKMYDPKMNASFSLKSKEKFNPEWYKGEPIWVTAKYQGLKSGTFFWPG

SDVEINGIFPDIYKMYNGSVPFEERILAVLQWLQLPKDERPHFYTLYLEEPDSSGHSYGPVS

SEVIKALQRVDGMVGMLMDGLKELNLHRCLNLILISDHGMEQGSCKKYIYLNKYLGDVKNIK

VIYGPAARLRPSDVPDKYYSFNYEGIARNLSCREPNQHFKPYLKHFLPKRLHFAKSDRIEPL

TFYLDPQWQLALNPSERKYCGSGFHGSDNVFSNMQALFVGYGPGFKHGIEADTFENIEVYNL

MCDLLNLTPAPNNGTHGSLNHLLKNPVYTPKHPKEVHPLVQCPFTRNPRDNLGCSCNPSILP

IEDFQTQFNLTVAEEKIIKHETLPYGRPRVLQKENTICLLSQHQFMSGYSQDILMPLWTSYT

VDRNDSFSTEDFSNCLYQDFRIPLSPVHKCSFYKNNTKVSYGFLSPPQLNKNSSGIYSEALL

TTNIVPMYQSFQVIWRYFHDTLLRKYAEERNGVNVVSGPVFDFDYDGRCDSLENLRQKRRVI

RNQEILIPTHFFIVLTSCKDTSQTPLHCENLDTLAFILPHRTDNSESCVHGKHDSSWVEELL

MLHRARITDVEHITGLSFYQQRKEPVSDILKLKTHLPTFSQEDRSGSGGSMKWVTFLLLLFV

SGSAFSRGVFRREAHKSEIAHRYNDLGEQHFKGLVLIAFSQYLQKCSYDEHAKLVQEVTDFA

KTCVADESAANCDKSLHTLFGDKLCAIPNLRENYGELADCCTKQEPERNECFLQHKDDNPSL

PPFERPEAEAMCTSFKENPTTFMGHYLHEVARRHPYFYAPELLYYAEQYNEILTQCCAEADK

ESCLTPKLDGVKEKALVSSVRQRMKCSSMQKFGERAFKAWAVARLSQTFPNADFAEITKLAT

DLTKVNKECCHGDLLECADDRAELAKYMCENQATISSKLQTCCDKPLLKKAHCLSEVEHDTM

PADLPAIAADFVEDQEVCKNYAEAKDVFLGTFLYEYSRRHPDYSVSLLLRLAKKYEATLEKC

CAEANPPACYGTVLAEFQPLVEEPKNLVKTNCDLYEKLGEYGFQNAILVRYTQKAPQVSTPT

LVEAARNLGRVGTKCCTLPEDQRLPCVEDYLSAILNRVCLLHEKTPVSEHVTKCCSGSLVER

RPCFSALTVDETYVPKEFKAETFTFHSDICTLPEKEKQIKKQTALAELVKHKPKATAEQLKT

VMDDFAQFLDTCCKAADKDTCFSTEGPNLVTRCKDALARSWSHPQFEK

Doubly Underlined: ENPP7; Plain Text: ENPP1; Bold:

spacer sequence; Singly Underlined: albumin

Sequence
(SEQ ID NO: 23)
IISLFTFAVGVNICLGFTA

ENPP51 Amino Acid Sequence
(SEQ ID NO: 24)
<u>MTSKFLLVSFILAALSLSTTFSLQ</u>PSCAKEVKSCKGRCFERTFSNCRCDAACVSLGNCCLDF
QETCVEPTHIWTCNKFRCGEKRLSRFVCSCADDCKTHNDCCINYSSVCQDKKSWVEETCESI
DTPECPAEFESPPILLFSLDGFRAEYLHTWGGLLPVISKLKNCGTYTKNMRPMYPTKTFPNH
YSIVTGLYPESHGIIDNKMYDPKMNASFSLKSKEKFNPLWYKGQPIWVTANHQEVKSGTYFW
PGSDVEIDGILPDIYKVYNGSVPFEERILAVLEWLQLPSHERPHFYTLYLEEPDSSGHSGP
VSSEVIKALQKVDRLVGMLMDGLKDLGLDKCLNLILISDHGMEQGSCKKYVYLNKYLGDVNN
VKVVYGPAARLRPTDVPETYYSFNYEALAKNLSCREPNQHFRPYLKPFLPKRLHFAKSDRIE
PLTFYLDPQWQLALNPSERKYCGSGFHGSDNLFSNMQALFIGYGPAFKHGAEVDSFENTEVY
NLMCDLLGLIPAPNNGSHGSLNHLLKKPIYNPSHPKEEGFLSQCPIKSTSNDLGCTCDPWIV
PIKDFEKQLNLTTEDVDDIYHMTVPYGRPRILLKQHRVCLLQQQQFLTGYSLDLLMPLWASY
TFLSNDQFSRDDFSNCLYQDLRIPLSPVHKCSYYKSNSKLSYGFLTPPRLNRVSNHIYSEAL
LTSNIVPMYQSFQVIWHYLHDTLLQRYAHERNGINVVSGPVFDFDYDGRYDSLEILKQNSRV
IRSQEILIPTHFFIVLTSCKQLSETPLECSALESSAYILPHRPDNIESCTHGKRESSWVEEL
LTLHRARVTDVELITGLSFYQDRQESVSELLRLKTHLPIFSQED Underlined: ENPP5; Plain: ENPP1

ENPP51-ALB Amino Acid Sequence
(SEQ ID NO: 25)
<u>MTSKFLLVSFILAALSLSITFSLQ</u>PSCAKEVKSCKGRCFERTFSNCRCDAACVSLGNCCLDF
QETCVEPTHIWTCNKFRCGEKRLSRFVCSCADDCKTHNDCCINYSSVCQDKKSWVEETCESI
DTPECPAEFESPPILLFSLDGFRAEYLHTWGGLLPVISKLKNCGTYTKNMRPMYPTKTFPNH
YSIVTGLYPESHGIIDNKMYDPKMNASFSLKSKEKFNPLWYKGQPIWVTANHQEVKSGTYFW
PGSDVEIDGILPDIYKVYNGSVPFEERILAVLEWLQLPSHERPHFYTLYLEEPDSSGHSGP
VSSEVIKALQKVDRLVGMLMDGLKDLGLDKCLNLILISDHGMEQGSCKKYVYLNKYLGDVNN
VKVVYGPAARLRPTDVPETYYSFNYEALAKNLSCREPNQHFRPYLKPFLPKRLHFAKSDRIE
PLTFYLDPQWQLALNPSERKYCGSGFHGSDNLFSNMQALFIGYGPAFKHGAEVDSFENTEVY
NLMCDLLGLIPAPNNGSHGSLNHLLKKPIYNPSHPKEEGFLSQCPIKSTSNDLGCTCDPWIV
PIKDFEKQLNLTTEDVDDIYHMTVPYGRPRILLKQHRVCLLQQQQFLTGYSLDLLMPLWASY
TFLSNDQFSRDDFSNCLYQDLRIPLSPVHKCSYYKSNSKLSYGFLTPPRLNRVSNHIYSEAL
LTSNIVPMYQSFQVIWHYLHDTLLQRYAHERNGINVVSGPVFDFDYDGRYDSLEILKQNSRV
IRSQEILIPTHFFIVLTSCKQLSETPLECSALESSAYILPHRPDNIESCTHGKRESSWVEEL
LTLHRARVTDVELITGLSFYQDRQESVSELLRLKTHLPIFSQEDGGSGGS<u>MKWVTFLLLLFV
SGSAFSRGVFRREAHKSEIAHRYNDLGEQHFKGLVLIAFSQYLQKCSYDEHAKLVQEVTDFA
KTCVADESAANCDKSLHTLFGDKLCAIPNLRENYGELADCCTKQEPERNECFLQHKDDNPSL
PPFERPEAEAMCTSFKENPTTFMGHYLHEVARRHPYFYAPELLYYAEQYNEILTQCCAEADK
ESCLTPKLDGVKEKALVSSVRQRMKCSSMQKFGERAFKAWAVARLSQTFPNADFAEITKLAT
DLTKVNKECCHGDLLECADDRAELAKYMCENQATISSKLQTCCDKPLLKAHCLSEVEHDTM
PADLPAIAADFVEDQEVCKNYAEAKDVFLGTFLYEYSRRHPDYSVSLLLRLAKKYEATLEKC
CAEANPPACYGTVLAEFQPLVEEPKNLVKINCDLYEKLGEYGFQNAILVRYTQKAPQVSTPT
LVEAARNLGRVGTKCCTLPEDQRLPCVEDYLSAILNRVCLLHEKTPVSEHVTKCCSGSLVER</u>

-continued

<u>RPCFSALTVDETYVPKEFKAETFTFHSDICTLPEKEKQIKKQTALAELVKHKPKATAEQLKT</u>

<u>VMDDFAQFLDTCCKAADKDTCFSTEGPNLVTRCKDALARSWSHPQFEK</u>

Doubly Underlined: ENPP5; Plain: ENPP1; Bold: Spacer; Singly Underlined: Albumin Human IgG Fc domain, Fc
(SEQ ID NO: 26)
DKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK ALB
(SEQ ID NO: 27)
MKWVTFLLLLFVSGSAFSRGVFRREAHKSEIAHRYNDLGEQHFKGLVLIAFSQYLQKCSYDE
HAKLVQEVTDFAKTCVADESAANCDKSLHTLFGDKLCAIPNLRENYGELADCCTKQEPERNE
CFLQHKDDNPSLPPFERPEAEAMCTSFKENPTTFMGHYLHEVARRHPYFYAPELLYYAEQYN
EILTQCCAEADKESCLTPKLDGVKEKALVSSVRQRMKCSSMQKFGERAFKAWAVARLSQTFP
NADFAEITKLATDLTKVNKECCHGDLLECADDRAELAKYMCENQATISSKLQTCCDKPLLKK
AHCLSEVEHDTMPADLPAIAADFVEDQEVCKNYAEAKDVFLGTFLYEYSRRHPDYSVSLLLR
LAKKYEATLEKCCAEANPPACYGTVLAEFQPLVEEPKNLVKTNCDLYEKLGEYGFQNAILVR
YTQKAPQVSTPTLVEAARNLGRVGTKCCTLPEDQRLPCVEDYLSAILNRVCLLHEKTPVSEH
VTKCCSGSLVERRPCFSALTVDETYVPKEFKAETFTFHSDICTLPEKEKQIKKQTALAELVK
HKPKATAEQLKTVMDDFAQFLDTCCKAADKDTCFSTEGPNLVTRCKDALARSWSHPQFEK Sequence
(SEQ ID NO: 28)
LIN Sequence
(SEQ ID NO: 29)
GGSGGS Sequence
(SEQ ID NO: 30)
RSGSGGS ENPP3 Amino Acid Sequence (NCBI accession NP_O14638-1)
(SEQ ID NO: 31)
```
         10         20         30         40         50
MESTLTLATE QPVKKNTLKK YKIACIVLLA LLVIMSLGLG LGLGLRKLEK 60         70         80         90        100
QGSCRKKCFD ASFRGLENCR CDVACKDRGD CCWDFEDTCV ESTRIWMCNK 110        120        130        140        150
FRCGETRLEA SLCSCSDDCL QRKDCCADYK SVCQGETSWL EENCDTAQQS 160        170        180        190        200
QCPEGFDLPP VILFSMDGFR AEYLYTWDTL MPNINKLKTC GIHSKYMRAM 210        220        230        240        250
YPTKTFPNHY TIVTGLYPES HGIIDNNMYD VNLNKNFSLS SKEQNNPAWW 260        270        280        290        300
HGQPMWLTAM YQGLKAATYF WPGSEVAING SFPSIYMPYN GSVPFEERIS 310        320        330        340        350
TLLKWLDLPK AERPRFYTMY FEEPDSSGHA GGPVSARVIK ALQVVDHAFG 360        370        380        390        400
MLMEGLKQRN LHNCVNIILL ADHGMDQTYC NKMEYMTDYF PRINFFYMYE 410        420        430        440        450
GPAPRIRAHN IPHDFFSFNS EEIVRNLSCR KPDQHFKPYL TPDLPKRLHY
```

```
              460        470        480        490        500
       AKNVRIDKVH LFVDQQWLAV RSKSNTNCGG GNHGYNNEFR SMEAIFLAHG 510        520        530        540        550
       PSFKEKTEVE PFENIEVYNL MCDLLRIQPA PNNGTHGSLN HLLKVPFYEP 560        570        580        590        600
       SHAEEVSKFS VCGFANPLPT ESLDCFCPHL QNSTQLEQVN QMLNLTQEEI 610        620        630        640        650
       TATVKVNLPF GRPRVLQKNV DHCLLYHREY VSGFGKAMRM PMWSSYTVPQ 660        670        680        690        700
       LGDTSPLPPT VPDCLRADVR VPPSESQKCS FYLADKNITH GFLYPPASNR 710        720        730        740        750
       TSDSQYDALI TSNLVPMYEE FRKMWDYFHS VLLIKHATER NGVNVVSGPI 760        770        780        790        800
       FDYNYDGHFD APDEITKHLA NTDVPIPTHY FVVLISCKNK SHTPENCPGW 810        820        830        840        850
       LDVLPFIIPH RPTNVESCPE GKPEALWVEE RFTAHIARVR DVELLTGLDF 860        870
       YQDKVQPVSE ILQLKTYLPT FETTI

Extracellular domain of ENPP3
                                                  (SEQ ID NO: 32)
                                  EK 60         70         80         90        100
       QGSCRKKCFD ASFRGLENCR CDVACKDRGD CCWDFEDTCV ESTRIWMCNK 110        120        130        140        150
       FRCGETRLEA SLCSCSDDCL QRKDCCADYK SVCQGETSWL EENCDTAQQS 160        170        180        190        200
       QCPEGFDLPP VILFSMDGFR AEYLYTWDTL MPNINKLKTC GIHSKYMRAM 210        220        230        240        250
       YPTKTFPNHY TIVTGLYPES HGIIDNNMYD VNLNKNFSLS SKEQNNPAWW 260        270        280        290        300
       HGQPMWLTAM YQGLKAATYF WPGSEVAING SFPSIYMPYN GSVPFEERIS 310        320        330        340        350
       TLLKWLDLPK AERPRFYTMY FEEPDSSGHA GGPVSARVIK ALQVVDHAFG 360        370        380        390        400
       MLMEGLKQRN LHNCVNIILL ADHGMDQTYC NKMEYMTDYF PRINFFYMYE 410        420        430        440        450
       GPAPRIRAHN IPHDFFSFNS EEIVRNLSCR KPDQHFKPYL TPDLPKRLHY 460        470        480        490        500
       AKNVRIDKVH LFVDQQWLAV RSKSNTNCGG GNHGYNNEFR SMEAIFLAHG 510        520        530        540        550
       PSFKEKTEVE PFENIEVYNL MCDLLRIQPA PNNGTHGSLN HLLKVPFYEP 560        570        580        590        600
       SHAEEVSKFS VCGFANPLPT ESLDCFCPHL QNSTQLEQVN QMLNLTQEEI 610        620        630        640        650
       TATVKVNLPF GRPRVLQKNV DHCLLYHREY VSGFGKAMRM PMWSSYTVPQ 660        670        680        690        700
       LGDTSPLPPT VPDCLRADVR VPPSESQKCS FYLADKNITH GFLYPPASNR 710        720        730        740        750
       TSDSQYDALI TSNLVPMYEE FRKMWDYFHS VLLIKHATER NGVNVVSGPI 760        770        780        790        800
       FDYNYDGHFD APDEITKHLA NTDVPIPTHY FVVLISCKNK SHTPENCPGW
```

```
              810        820        830        840        850
    LDVLPFIIPH RPTNVESCPE GKPEALWVEE RFTAHIARVR DVELLTGLDF 860        870
    YQDKVQPVSE ILQLKTYLPT FETTI exENPP3 sequence
                                                    (SEQ ID NO: 33)
LLVIMSLGLG LGLGLRK ENPP7 protein export signal sequence
                                                    (SEQ ID NO: 34)
MRGPAVLLTV ALATLLAPGA GA ENPP121GLK protein export signal sequence
                                                    (SEQ ID NO: 35)
*MERDGCAGGGSRGGEGGRAPREGPAGNGRDRGRSHAAEA*

*PGDPQAAASLLAPMDVGEEPLEK*AARARTAKDPNTYKIIS<u>LFTFAVGVNICLG</u>**<u>FTAGLK</u>

Bold Italics: ENPP1 cytoplasmic and transmembrane;

Singly Underlined: Swapped residues with ENPP2 residues 1-27 to give cleavage at transition position (**); Doubly Underlined: ENPP1 transmembrane ENPP121 protein export signal sequence
                                                    (SEQ ID NO: 36)
*MERDGCAGGGSRGGEGGRAPREGPAGNGRDRGRSHAAEAP*

*GDPQAAASLLAPMDVGEEPLEK*AARARTAKDPNTYKIIS<u>LFTFAVGVNICLG</u>**<u>FTA</u>

Bold Italics: ENPP1 cytoplasmic and transmembrane;

Singly Underlined: Swapped residues with ENPP2 residues 1-27 to give cleavage at transition position (**); Doubly Underlined: ENPP1 transmembrane ENPP5 protein export signal sequence
                                                    (SEQ ID NO: 37)
MTSKFLLVSFILAALSLSTIFS-Xaa$_{23}$-Xaa$_{24}$, wherein Xaa$_{23}$ is absent or L; and Xaa$_{24}$ is absent if Xaa$_{23}$ is absent, or Xaa$_{24}$ is absent or Q if Xaa$_{23}$ is L ENPP7 signal sequence
                                                    (SEQ ID NO: 38)
MRGPAVLLTV ALATLLAPGA ENPP7 signal sequence
                                                    (SEQ ID NO: 39)
MRGPAVLLTV ALATLLAPGA GA Sequence
                                                    (SEQ ID NO: 40)
LVIMSLGLGLGLGLRK Sequence
                                                    (SEQ ID NO: 41)
VIMSLGLGLGLGLRK Sequence
                                                    (SEQ ID NO: 42)
IMSLGLGLGLGLRK Sequence
                                                    (SEQ ID NO: 43)
MSLGLGLGLGLRK Sequence
                                                    (SEQ ID NO: 44)
SLGLGLGLGLRK
```

Sequence
(SEQ ID NO: 45)
LGLGLGLGLRK

Sequence
(SEQ ID NO: 46)
GLGLGLGLRK

Sequence
(SEQ ID NO: 47)
LGLGLGLRK

Sequence
(SEQ ID NO: 48)
GLGLGLRK

Sequence
(SEQ ID NO: 49)
LGLGLRK

Sequence
(SEQ ID NO: 50)
GLGLRK

Sequence
(SEQ ID NO: 51)
LGLRK

Sequence
(SEQ ID NO: 52)
GLRK

Sequence
(SEQ ID NO: 53)
LRK

Sequence
(SEQ ID NO: 54)
RK

Sequence
(SEQ ID NO: 55)
K

ENPP121-NPP3-Fc sequence
(SEQ ID NO: 56)
MERDGCAGGG SRGGEGGRAP REGPAGNGRD RGRSHAAEAP GDPQAAASLL APMDVGEEPL

EKAARARTAK DPNTYKIISL FTFAVGVNIC LGFTAKQGSC RKKCFDASFR GLENCRCDVA

CKDRGDCCWD FEDTCVESTR IWMCNKFRCG ERLEASLCSC SDDCLQRKDC CADYKSVCQG

ETSWLEENCD TAQQSQCPEG FDLPPVILFS MDGFRAEYLY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NLSCRKPDQH

FKPYLTPDLP KRLHYAKNVR IDKVHLFVDQ QWLAVRSKSN TNCGGGNHGY NNEFRSMEAI

FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TQEEITATVK VNLPFGRPRV

LQKNVDHCLL YHREYVSGFG KAMRMPMWSS YTVPQLGDTS PLPPTVPDCL RADVRVPPSE

SQKCSFYLAD KNITHGFLYP PASNRTSDSQ YDALITSNLV PMYEEFRKMW DYFHSVLLIK

HATERNGVNV VSGPIFDYNY DGHFDAPDEI TKHLANTDVP IPTHYFVVLT SCKNKSHTPE

-continued

NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
<u>CVVVDVSHED PEVKFNWYVD GVEVHNAKTK PREEQYNSTY RVVSVLTVLH QDWLNGKEYK</u>
<u>CKVSNKALPA PIEKTISKAK GQPREPQVYT LPPSREEMTK NQVSLTCLVK GFYPSDIAVE</u>
<u>WESNGQPENN YKTTPPVLDS DGSFFLYSKL TVDKSRWQQG NVFSCSVMHE ALHNHYTQKS</u>
<u>LSLSPGK</u>

Bold residues: sequence from ENPP1. Single underlined residues: signal peptide sequence from ENPP2. Double underlined residues: sequence of IgG Fc domain, which can be from any of the sub classes IgG1, IgG2, IgG3 and IgG4. Alternatively instead of Fc domain, albumin domain can be used. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

ENPP7-ENPP3-Fc sequence (SEQ ID NO: 57)

<u>MRGPAVLLTV ALATLLAPGA</u> KQGSC RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
<u>CVVVDVSHED PEVKFNWYVD GVEVHNAKTK PREEQYNSTY RVVSVLTVLH QDWLNGKEYK</u>
<u>CKVSNKALPA PIEKTISKAK GQPREPQVYT LPPSREEMTK NQVSLTCLVK GFYPSDIAVE</u>
<u>WESNGQPENN YKTTPPVLDS DGSFFLYSKL TVDKSRWQQG NVFSCSVMHE ALHNHYTQKS</u>
<u>LSLSPGK</u>

Single underlined: signal peptide sequence from ENPP7. Double underlined: sequence of IgG Fc domain, which can be from any of the sub classes IgG1, IgG2, IgG3 and -continued IgG4. Alternatively instead of Fc domain, albumin domain can be used. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

ENPP5-ENPP3-Fc sequence
(SEQ ID NO: 58)

<u>MTSKFLLVSF ILAALSLSTT FSKQGSC</u> RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
<u>CVVVDVSHED PEVKFNWYVD GVEVHNAKTK PREEQYNSTY RVVSVLTVLH QDWLNGKEYK</u>
<u>CKVSNKALPA PIEKTISKAK GQPREPQVYT LPPSREEMTK NQVSLTCLVK GFYPSDIAVE</u>
<u>WESNGQPENN YKTTPPVLDS DGSFFLYSKL TVDKSRWQQG NVFSCSVMHE ALHNHYTQKS</u>
<u>LSLSPGK</u>

Single underlined: signal peptide sequence from ENPP5.
Double underlined: sequence of IgG Fc domain, which can be from any of the sub classes IgG1, IgG2, IgG3 and IgG4. Alternatively instead of Fc domain, albumin domain can be used. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

Albumin sequence
(SEQ ID NO: 59)
GGGGSGGGGSGGGGSMKWVTFLLLLFVSGSAFSRGVFRREAHKSEIAHRYNDLGEQHFKGLV
LIAFSQYLQKCSYDEHAKLVQEVTDFAKTCVADESAANCDKSLHTLFGDKLCAIPNLRENYG
ELADCCTKQEPERNECFLQHKDDNPSLPPFERPEAEAMCTSFKENPTTFMGHYLHEVARRHP

```
YFYAPELLYYAEQYNEILTQCCAEADKESCLTPKLDGVKEKALVSSVRQRMKCSSMQKFGER

AFKAWAVARLSQTFPNADFAEITKLATDLTKVNKECCHGDLLECADDRAELAKYMCENQATI

SSKLQTCCDKPLLKKAHCLSEVEHDTMPADLPAIAADFVEDQEVCKNYAEAKDVFLGTFLYE

YSRRHPDYSVSLLLRLAKKYEATLEKCCAEANPPACYGTVLAEFQPLVEEPKNLVKTNCDLY

EKLGEYGFQNAILVRYTQKAPQVSTPTLVEAARNLGRVGTKCCTLPEDQRLPCVEDYLSAIL

NRVCLLHEKTPVSEHVTKCCSGSLVERRPCFSALTVDETYVPKEFKAETFTFHSDICTLPEK

EKQIKKQTALAELVKHKPKATAEQLKTVMDDFAQFLDTCCKAADKDTCFSTEGPNLVTRCKD

ALA
```

ENPP121-ENPP3-Albumin sequence (SEQ ID NO: 60)

MERDGCAGGG SRGGEGGRAP REGPAGNGRD RGRSHAAEAP GDPQAAASLL APMDVGEEPL

EKAARARTAK DPNTYKIISL FTEAVGVNIC LGFTAKQGSC RKKCEDASFR GLENCPCDVA

CKDRGDCCWD FEDTCVESTR TWMCNKFRCG ERLEASLCSC SDDCLQRKDC CADYKSVCQG

ETSWLEENCD TAQQSQCPEG FDLPPVILFS MDGFRAEYIY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NISCRKPDQH

FKPYLTPDLP KRLHYAKNVR IDKVHLFVBQ QWLAVRSKSN TNCGGGNHGY NNEFRSMEAI

FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TOEEITATVK VNLPFGRPRV

LQKNVDHCLL YHREYVSGFG KAMRMPMWSS YTVPOLGDTS PLPPTVPDCL RADVRVPPSE

SQKCSFYIAD KNITHGFLYP PASNRTSDSQ YDALITSNIV PMYEEFRKMW DYFHSVLLIK

HATERNGVNV VSGPIFDYNY DGHFDAPDEI TKHLANTDVP IPTHYFVVLT SCKNKSHTPE

NCPGWLDVLP FIIPHRPTNV ESCPEGEPEA LWVEERFTAH IARVRDVELL TGLDFYODKV

OPVSEILQLK TYLPTFETTI DKTHTCPPCP APELLGGPSV FLFPPKPKDT LMISRTPEVT

<u>GGGSGGGGSG GGGSMKWVTF LLLLFVSGSA FSRGVFRREA HKSEIAHRYN DLGEQHFKGL</u>

<u>VLIAFSQYLQ KCSYDEHAKL VIEVTDFAKT CVADESAANC DKSLHTLFGD KLCAIPNLRE</u>

<u>NYGSLADCCT KQEPERNECF LQHKDDNPSL PPFERPSAEA MCTSFK5NPT TFMGHYLHEV</u>

<u>ARPHPYFYAP ELLYYAEQYN SILTQCCAEA DKESCLTPKL PGVKEKALVS SVRQRMKCSS</u>

<u>MQKFGERAFK AWAVARLSQT FPNADFAEIT KLATDLTKVN KECCHGDLLE CADDRAELAK</u>

<u>YMCENQATIS SKLQTCCDKP LLKKABCLSE VEHDTMPADL PAIAADFVED QEVCKNYAEA</u>

<u>KDVFLGTFLY EYSRRHPDYS VELLLRLAKK YEATLEKCCA EANPPACYGT VLAEFQPLVE</u>

<u>EPKNLVKTNC DLYEKLGEYG FQNAILVRYT QKAPQVSTPT LVEAARNLGR VGTKCCTLPE</u>

<u>DQRLPCVEDY LSAILNRVCL LHEKTPVSEH VTKCCSGSLV ERRPCFSALT VDETYVPKEF</u>

<u>KAETFTERSD ICTLPEKEKQ IKKQTALAEL VKHKPKATAE OLKTVMDDFA QFLDTCCKAA</u>

<u>DKDTCFSTEG PNLVTRCKDA LA</u>

Bold residues: sequence from ENPP1. Single underlined: signal peptide sequences from ENPP2. Double underlined: sequence of albumin domain. In certain embodiments, the ENPP3 C-terminal region and the Fc domain are connected -continued by a flexible linker. In other embodiments, the flexible linker comprises at least two amino acids. In yet other embodiments, the flexible linker comprises synthetic linkers such PEG chains or multicarbon chains.

ENPP7-ENPP3-Albumin sequence
(SEQ ID NO: 61)

<u>MRGPAVLLTV ALATLLAPGA</u> KQGSC RKKCFDASFR GLENCRCDVA

CKDRGDCCWD FEDTCVESTR IWMCNKFRCG ERLEASLCSC SDDCLQRKDC CADYKSVCQG

ETSWLEENCD TAQQSQCPEG FDLPPVILFS MDGFRAEYLY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NLSCRKPDQH

FKPYLTPDLP KRLHYAKNVR IDKVHLFVDQ QWLAVRSKSN TNCGGGNHGY NNEFRSMEAI

FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TQEEITATVK VNLPFGRPRV

LQKNVDHCLL YHREYVSGFG KAMRMPMWSS YTVPQLGDTS PLPPTVPDCL RADVRVPPSE

SQKCSFYLAD KNITHGFLYP PASNRTSDSQ YDALITSNLV PMYEEFRKMW DYFHSVLLIK

HATERNGVNV VSGPIFDYNY DGHFDAPDEI TKHLANTDVP IPTHYFVVLT SCKNKSHTPE

NCPGWLDVLP FIIPHRPTNV ESCPEGKPEA LWVEERFTAH IARVRDVELL TGLDFYQDKV

QPVSEILQLK TYLPTFETTI DKTHTCPPCP APELLGGPSV FLFPPKPKDT LMISRTPEVT

<u>GGGSGGGGSG GGGSMKWVTF LLLLFVSGSA FSRGVFRREA HKSEIAHRYN DLGEQHFKGL</u>

<u>VLIAFSQYLQ KCSYDEHAKL VQEVTDFAKT CVADESAANC DKSLHTLFGD KLCAIPNLRE</u>

<u>NYGELADCCT KQEPERNECF LQHKDDNPSL PPFERPEAEA MCTSFKENPT TFMGHYLHEV</u>

<u>ARRHPYFYAP ELLYYAEQYN EILTQCCAEA DKESCLTPKL DGVKEKALVS SVRQRMKCSS</u>

<u>MQKFGERAFK AWAVARLSQT FPNADFAEIT KLATDLTKVN KECCHGDLLE CADDRAELAK</u>

<u>YMCENQATIS SKLQTCCDKP LLKKAHCLSE VEHDTMPADL PAIAADFVED QEVCKNYAEA</u>

<u>KDVFLGTFLY EYSRRHPDYS VSLLLRLAKK YEATLEKCCA EANPPACYGT VLAEFQPLVE</u>

<u>EPKNLVKTNC DLYEKLGEYG FQNAILVRYT QKAPQVSTPT LVEAARNLGR VGTKCCTLPE</u>

<u>DQRLPCVEDY LSAILNRVCL LHEKTPVSEH VTKCCSGSLV ERRPCFSALT VDETYVPKEF</u>

<u>KAETFTFHSD ICTLPEKEKQ IKKQTALAEL VKHKPKATAE QLKTVMDDFA QFLDTCCKAA</u>

<u>DKDTCFSTEG PNLVTRCKDA LA</u>

Single underlined: signal peptide sequence from ENPP7. Double underlined: sequence of albumin domain. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

ENPP5-ENPP3-albumin sequence
(SEQ ID NO: 62)

<u>MTSKFLLVSF ILAALSLSTT</u> FSKQGSC RKKCFDASFR GLENCRCDVA

CKDRGDCCWD FEDTCVESTR IWMCNKFRCG ERLEASLCSC SDDCLQRKDC CADYKSVCQG

-continued

```
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI DKTHTCPPCP APELLGGPSV FLFPPKPKDT LMISRTPEVT
GGGSGGGGSG GGGSMKWVTF LLLLFVSGSA FSRGVFRREA HKSEIAHRYN DLGEQHFKGL
VLIAFSQYLQ KCSYDEHAKL VQEVTDFAKT CVADESAANC DKSLHTLFGD KLCAIPNLRE
NYGELADCCT KQEPERNECF LQHKDDNPSL PPFERPEAEA MCTSFKENPT TFMGHYLHEV
ARRHPYFYAP ELLYYAEQYN EILTQCCAEA DKESCLTPKL DGVKEKALVS SVRQRMKCSS
MQKFGERAFK AWAVARLSQT FPNADFAEIT KLATDLTKVN KECCHGDLLE CADDRAELAK
YMCENQATIS SKLQTCCDKP LLKKAHCLSE VEHDTMPADL PAIAADFVED QEVCKNYAEA
KDVFLGTFLY EYSRRHPDYS VSLLLRLAKK YEATLEKCCA EANPPACYGT VLAEFQPLVE
EPKNLVKTNC DLYEKLGEYG FQNAILVRYT QKAPQVSTPT LVEAARNLGR VGTKCCTLPE
DQRLPCVEDY LSAILNRVCL LHEKTPVSEH VTKCCSGSLV ERRPCFSALT VDETYVPKEF
KAETFTFHSD ICTLPEKEKQ IKKQTALAEL VKHKPKATAE QLKTVMDDFA QFLDTCCKAA
DKDTCFSTEG PNLVTRCKDA LA
```

Single underlined: signal peptide sequence from ENPP5.
Double underlined: sequence of albumin domain. In certain embodiments, the ENPP3 C-terminal region and the Fc domain are connected by a flexible linker. In other embodiments, the flexible linker comprises at least two amino acids. In yet other embodiments, the flexible linker comprises synthetic linkers such PEG chains or multicarbon chains.

Nucleotide sequence of ENPP121-ENPP3-Fc
(SEQ ID NO: 63)

```
ATGGAAAGGGACGGATGCGCCGGTGGTGGATCTCGCGGAGGCGAAGGTGGAAGGGCCCCTAG
GGAAGGACCTGCCGGAAACGGAAGGGACAGGGGACGCTCTCACGCCGCTGAAGCTCCAGGCG
ACCCTCAGGCCGCTGCCTCTCTGCTGGCTCCTATGGACGTCGGAGAAGAACCCCTGGAAAAG
GCCGCCAGGGCCAGGACTGCCAAGGACCCCAACACCTACAAGATCATCTCCCTCTTCACTTT
CGCCGTCGGAGTCAACATCTGCCTGGGATTCACCGCCGAAAAGCAAGGCAGCTGCAGGAAGA
AGTGCTTTGATGCATCATTTAGAGGACTGGAGAACTGCCGGTGTGATGTGGCATGTAAAGAC
CGAGGTGATTGCTGCTGGGATTTTGAAGACACCTGTGTGGAATCAACTCGAATATGGATGTG
CAATAAATTTCGTTGTGGAGAGACCAGATTAGAGGCCAGCCTTTGCTCTTGTTCAGATGACT
```

-continued

```
GTTTGCAGAGGAAAGATTGCTGTGCTGACTATAAGAGTGTTTGCCAAGGAGAAACCTCATGG
CTGGAAGAAAACTGTGACACAGCCCAGCAGTCTCAGTGCCCAGAAGGGTTTGACCTGCCACC
AGTTATCTTGTTTTCTATGGATGGATTTAGAGCTGAATATTTATACACATGGGATACTTTAA
TGCCAAATATCAATAAACTGAAAACATGTGGAATTCATTCAAAATACATGAGAGCTATGTAT
CCTACCAAAACCTTCCCAAATCATTACACCATTGTCACGGGCTTGTATCCAGAGTCACATGG
CATCATTGACAATAATATGTATGATGTAAATCTCAACAAGAATTTTTCACTTTCTTCAAAGG
AACAAAATAATCCAGCCTGGTGGCATGGGCAACCAATGTGGCTGACAGCAATGTATCAAGGT
TTAAAAGCCGCTACCTACTTTTGGCCCGGATCAGAAGTGGCTATAAATGGCTCCTTTCCTTC
CATATACATGCCTTACAACGGAAGTGTCCCATTTGAAGAGAGGATTTCTACACTGTTAAAAT
GGCTGGACCTGCCCAAAGCTGAAAGACCCAGGTTTTATACCATGTATTTTGAAGAACCTGAT
TCCTCTGGACATGCAGGTGGACCAGTCAGTGCCAGAGTAATTAAAGCCTTACAGGTAGTAGA
TCATGCTTTTGGGATGTTGATGGAAGGCCTGAAGCAGCGGAATTTGCACAACTGTGTCAATA
TCATCCTTCTGGCTGACCATGGAATGGACCAGACTTATTGTAACAAGATGGAATACATGACT
GATTATTTTCCCAGAATAAACTTCTTCTACATGTACGAAGGGCCTGCCCCCCGCATCCGAGC
TCATAATATACCTCATGACTTTTTTAGTTTTAATTCTGAGGAAATTGTTAGAAACCTCAGTT
GCCGAAAACCTGATCAGCATTTCAAGCCCTATTTGACTCCTGATTTGCCAAAGCGACTGCAC
TATGCCAAGAACGTCAGAATCGACAAAGTTCATCTCTTTGTGGATCAACAGTGGCTGGCTGT
TAGGAGTAAATCAAATACAAATTGTGGAGGAGGCAACCATGGTTATAACAATGAGTTTAGGA
GCATGGAGGCTATCTTTCTGGCACATGGACCCAGTTTTAAAGAGAAGACTGAAGTTGAACCA
TTTGAAAATATTGAAGTCTATAACCTAATGTGTGATCTTCTACGCATTCAACCAGCACCAAA
CAATGGAACCCATGGTAGTTTAAACCATCTTCTGAAGGTGCCTTTTTATGAGCCATCCCATG
CAGAGGAGGTGTCAAAGTTTTCTGTTTGTGGCTTTGCTAATCCATTGCCCACAGAGTCTCTT
GACTGTTTCTGCCCTCACCTACAAAATAGTACTCAGCTGGAACAAGTGAATCAGATGCTAAA
TCTCACCCAAGAAGAAATAACAGCAACAGTGAAAGTAAATTTGCCATTTGGGAGGCCTAGGG
TACTGCAGAAGAACGTGGACCACTGTCTCCTTTACCACAGGGAATATGTCAGTGGATTTGGA
AAAGCTATGAGGATGCCCATGTGGAGTTCATACACAGTCCCCAGTTGGGAGACACATCGCC
TCTGCCTCCCACTGTCCCAGACTGTCTGCGGGCTGATGTCAGGGTTCCTCCTTCTGAGAGCC
AAAAATGTTCCTTCTATTTAGCAGACAAGAATATCACCCACGGCTTCCTCTATCCTCCTGCC
AGCAATAGAACATCAGATAGCCAATATGATGCTTTAATTACTAGCAATTTGGTACCTATGTA
TGAAGAATTCAGAAAAATGTGGGACTACTTCCACAGTGTTCTTCTTATAAAACATGCCACAG
AAAGAAATGGAGTAAATGTGGTTAGTGGACCAATATTTGATTATAATTATGATGGCCATTTT
GATGCTCCAGATGAAATTACCAAACATTTAGCCAACACTGATGTTCCCATCCCAACACACTA
CTTTGTGGTGCTGACCAGTTGTAAAAACAAGAGCCACACACCGGAAAACTGCCCTGGGTGGC
TGGATGTCCTACCCTTTATCATCCCTCACCGACCTACCAACGTGGAGAGCTGTCCTGAAGGT
AAACCAGAAGCTCTTTGGGTTGAAGAAAGATTTACAGCTCACATTGCCCGGGTCCGTGATGT
AGAACTTCTCACTGGGCTTGACTTCTATCAGGATAAAGTGCAGCCTGTCTCTGAAATTTTGC
AACTAAAGACATATTTACCAACATTTGAAACCACTATTGACAAAACTCACACATGCCCACCG
TGCCCAGCACCTGAACTCCTGGGGGGACCGTCAGTCTTCCTCTTCCCCCCAAAACCCAAGGA
CACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAG
CCGCGGGAGGAGCAGTACAACAGCACGTACCGTGTGGTCAGCGTCCTCACCGTCCTGCACCA
```

-continued

```
GGACTGGCTGAATGGCAAGGAGTACAAGTGCAAGGTCTCCAACAAAGCCCTCCCAGCCCCCA

TCGAGAAAACCATCTCCAAAGCCAAAGGGCAGCCCCGAGAACCACAGGTGTACACCCTGCCC

CCATCCCGGGAGGAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACCA

CGCCTCCCGTGCTGGACTCCGACGGCTCCTTCTTCCTCTATAGCAAGCTCACCGTGGACAAG

AGCAGGTGGCAGCAGGGGAACGTCTTCTCATGCTCCGTGATGCATGAGGCTCTGCACAACCA

CTACACGCAGAAGAGCCTCTCCCTGTCCCCGGGTAAA
```

Nucleotide sequence of ENPP121-ENPP3-Albumin
(SEQ ID NO: 64)

```
ATGGAAAGGGACGGATGCGCCGGTGGTGGATCTCGCGGAGGCGAAGGTGGAAGGGCCCCTAG

GGAAGGACCTGCCGGAAACGGAAGGGACAGGGGACGCTCTCACGCCGCTGAAGCTCCAGGCG

ACCCTCAGGCCGCTGCCTCTCTGCTGGCTCCTATGGACGTCGGAGAAGLACCCCTGGAAAAG

GCCGCCAGGGCCAGGACTGCCAAGGACCCCAACACCTACAAGATCATCTCCCTCTTCACTTT

CGCCGTCGGAGTCAACATCTGCCTGGGATTCACCGCCGAAAAGCAAGGCAGCTGCAGGAAGA

AGTGCTTTGATGCATCATTTAGAGGACTGGAGAACTGCCGGTGTGATGTGGCATGTAAAGAC

CGAGGTGATTGCTGCTGGGATTTTGAAGACACCTGTGTGGAATCAACTCGAATATGGATGTG

CAATAAATTTCGTTGTGGAGAGACCAGATTAGAGGCCAGCCTTTGCTCTTGTTCAGATGACT

GTTTGCAGAGGAAAGATTGCTGTGCTGACTATAAGAGTGTTTGCCAAGGAGAAACCTCATGG

CTGGAAGAAAACTGTGACACAGCCCAGCAGTCTCAGTGCCCAGAAGGGTTTGACCTGCCACC

AGTTATCTTGTTTTCTATGGATGGATTTAGAGCTGAATATTTATACACATGGGATACTTTAA

TGCCAAATATCAATAAACTGAAAACATGTGGAATTCATTCAAAATACATGAGAGCTATGTAT

CCTACCAAAACCTTCCCAAATCATTACACCATTGTCACGGGCTTGTATCCAGAGTCACATGG

CATCATTGACAATAATATGTATGATGTAAATCTCAACAAGAATTTTTCACTTTCTTCAAAGG

AACAAAATAATCCAGCCTGGTGGCATGGGCAACCAATGTGGCTGACAGCAATGTATCAAGGT

TTAAAAGCCGCTACCTACTTTTGGCCCGGATCAGAAGTGGCTATAAATGGCTCCTTTCCTTC

CATATACATGCCTTACAACGGAAGTGTCCCATTTGAAGAGAGGATTTCTACACTGTTAAAAT

GGCTGGACCTGCCCAAAGCTGAAAGACCCAGGTTTTATACCATGTATTTTGAAGAACCTGAT

TCCTCTGGACATGCAGGTGGACCAGTCAGTGCCAGAGTAATTAAAGCCTTACAGGTAGTAGA

TCATGCTTTTGGGATGTTGATGGAAGGCCTGAAGCAGCGGAATTTGCACAACTGTGTCAATA

TCATCCTTCTGGCTGACCATGGAATGGACCAGACTTATTGTAACAAGATGGAATACATGACT

GATTATTTTCCCAGAATAAACTTCTTCTACATGTACGAAGGGCTGCCCCCCGCATCCGAGC

TCATAATATACCTCATGACTTTTTTAGTTTTAATTCTGAGGAAATTGTTAGAAACCTCAGTT

GCCGAAAACCTGATCAGCATTTCAAGCCCTATTTGACTCCTGATTTGCCAAAGCGACTGCAC

TATGCCAAGAACGTCAGAATCGACAAAGTTCATCTCTTTGTGGATCAACAGTGGCTGGCTGT

TAGGAGTAAATCAAATACAAATTGTGGAGGAGGCAACCATGGTTATAACAATGAGTTTAGGA

GCATGGAGGCTATCTTTCTGGCACATGGACCCAGTTTTAAAGAGAAGACTGAAGTTGAACCA

TTTGAAAATATTGAAGTCTATAACCTAATGTGTGATCTTCTACGCATTCAACCAGCACCAAA

CAATGGAACCCATGGTAGTTTAAACCATCTTCTGAAGGTGCCTTTTTATGAGCCATCCCATG

CAGAGGAGGTGTCAAAGTTTTCTGTTTGTGGCTTTGCTAATCCATTGCCCACAGAGTCTCTT

GACTGTTTCTGCCCTCACCTACAAAATAGTACTCAGCTGGAACAAGTGAATCAGATGCTAAA

TCTCACCCAAGAAGAAATAACAGCAACAGTGAAAGTAAATTTGCCATTTGGGAGGCCTAGGG
```

-continued

```
TACTGCAGAAGAACGTGGACCACTGTCTCCTTTACCACAGGGAATATGTCAGTGGATTTGGA

AAAGCTATGAGGATGCCCATGTGGAGTTCATACACAGTCCCCCAGTTGGGAGACACATCGCC

TCTGCCTCCCACTGTCCCAGACTGTCTGCGGGCTGATGTCAGGGTTCCTCCTTCTGAGAGCC

AAAAATGTTCCTTCTATTTAGCAGACAAGAATATCACCCACGGCTTCCTCTATCCTCCTGCC

AGCAATAGAACATCAGATAGCCAATATGATGCTTTAATTACTAGCAATTTGGTACCTATGTA

TGAAGAATTCAGAAAAATGTGGGACTACTTCCACAGTGTTCTTCTTATAAAACATGCCACAG

AAAGAAATGGAGTAAATGTGGTTAGTGGACCAATATTTGATTATAATTATGATGGCCATTTT

GATGCTCCAGATGAAATTACCAAACATTTAGCCAACACTGATGTTCCCATCCCAACACACTA

CTTTGTGGTGCTGACCAGTTGTAAAAACAAGAGCCACACACCGGAAAACTGCCCTGGGTGGC

TGGATGTCCTACCCTTTATCATCCCTCACCGACCTACCAACGTGGAGAGCTGTCCTGAAGGT

AAACCAGAAGCTCTTTGGGTTGAAGAAAGATTTACAGCTCACATTGCCCGGGTCCGTGATGT

AGAACTTCTCACTGGGCTTGACTTCTATCAGGATAAAGTGCAGCCTGTCTCTGAAATTTTGC

AACTAAAGACATATTTACCAACATTTGAAACCACTATTGGTGGAGGAGGCTCTGGTGGAGGC

GGTAGCGGAGGCGGAGGGTCGATGAAGTGGGTAACCTTTATTTCCCTTCTTTTTCTCTTTAG

CTCGGCTTATTCCAGGGGTGTGTTTCGTCGAGATGCACACAAGAGTGAGGTTGCTCATCGGT

TTAAAGATTTGGGAGAAGAAAATTTCAAAGCCTTGGTGTTGATTGCCTTTGCTCAGTATCTT

CAGCAGTGTCCATTTGAAGATCATGTAAAATTAGTGAATGAAGTAACTGAATTTGCAAAAAC

ATGTGTTGCTGATGAGTCAGCTGAAAATTGTGACAAATCACTTCATACCCTTTTTGGAGACA

AATTATGCACAGTTGCAACTCTTCGTGAAACCTATGGTGAAATGGCTGACTGCTGTGCAAAA

CAAGAACCTGAGAGAAATGAATGCTTCTTGCAACACAAAGATGACAACCCAAACCTCCCCCG

ATTGGTGAGACCAGAGGTTGATGTGATGTGCACTGCTTTTCATGACAATGAAGAGACATTTT

TGAAAAAATACTTATATGAAATTGCCAGAAGACATCCTTACTTTTATGCCCCGGAACTCCTT

TTCTTTGCTAAAAGGTATAAAGCTGCTTTTACAGAATGTTGCCAAGCTGCTGATAAAGCTGC

CTGCCTGTTGCCAAAGCTCGATGAACTTCGGGATGAAGGGAAGGCTTCGTCTGCCAAACAGA

GACTCAAGTGTGCCAGTCTCCAAAAATTTGGAGAAAGAGCTTTCAAAGCATGGGCAGTAGCT

CGCCTGAGCCAGAGATTTCCCAAAGCTGAGTTTGCAGAAGTTTCCAAGTTAGTGACAGATCT

TACCAAAGTCCACACGGAATGCTGCCATGGAGATCTGCTTGAATGTGCTGATGACAGGGCGG

ACCTTGCCAAGTATATCTGTGAAAATCAAGATTCGATCTCCAGTAAACTGAAGGAATGCTGT

GAAAAACCTCTGTTGGAAAAATCCCACTGCATTGCCGAAGTGGAAAATGATGAGATGCCTGC

TGACTTGCCTTCATTAGCTGCTGATTTTGTTGAAAGTAAGGATGTTTGCAAAAACTATGCTG

AGGCAAAGGATGTCTTCCTGGGCATGTTTTTGTATGAATATGCAAGAAGGCATCCTGATTAC

TCTGTCGTGCTGCTGCTGAGACTTGCCAAGACATATGAAACCACTCTAGAGAAGTGCTGTGC

CGCTGCAGATCCTCATGAATGCTATGCCAAAGTGTTCGATGAATTTAAACCTCTTGTGGAAG

AGCCTCAGAATTTAATCAAACAAAATTGTGAGCTTTTTGAGCAGCTTGGAGAGTACAAATTC

CAGAATGCGCTATTAGTTCGTTACACCAAGAAAGTACCCCAAGTGTCAACTCCAACTCTTGT

AGAGGTCTCAAGAAACCTAGGAAAAGTGGGCAGCAAATGTTGTAAACATCCTGAAGCAAAAA

GAATGCCCTGTGCAGAAGACTATCTATCCGTGGTCCTGAACCAGTTATGTGTGTTGCATGAG

AAAACGCCAGTAAGTGACAGAGTCACCAAATGCTGCACAGAATCCTTGGTGAACAGGCGACC

ATGCTTTTCAGCTCTGGAAGTCGATGAAACATACGTTCCCAAAGAGTTTAATGCTGAAACAT

TCACCTTCCATGCAGATATATGCACACTTTCTGAAGGAGAGACAAATCAAGAAACAAACT

GCACTTGTTGAGCTCGTGAAACACAAGCCCAAGGCAACAAAAGAGCAACTGAAAGCTGTTAT
```

-continued

```
GGATGATTTCGCAGCTTTTGTAGAGAAGTGCTGCAAGGCTGACGATAAGGAGACCTGCTTTG

CCGAGGAGGGTAAAAAACTTGTTGCTGCAAGTCAAGCTGCCTTAGGCTTA
```

Nucleotide sequence of hNPP3-hFc-pcDNA3

(SEQ ID NO: 65)

```
GACGGATCGGGAGATCTCCCGATCCCCTATGGTCGACTCTCAGTACAATCTGCTCTGATGCC

GCATAGTTAAGCCAGTATCTGCTCCCTGCTTGTGTGTTGGAGGTCGCTGAGTAGTGCGCGAG

CAAAATTTAAGCTACAACAAGGCAAGGCTTGACCGACAATTGCATGAAGAATCTGCTTAGGG

TTAGGCGTTTTGCGCTGCTTCGCGATGTACGGGCCAGATATACGCGTTGACATTGATTATTG

ACTAGTTATTAATAGTAATCAATTAGGGGGTCATTAGTTCATAGCCCATATATGGAGTTCCG

CGTTACATAACTTACGGTAAATGGCCCGCCTGGCTGACCGCCCAACGACCCCCGCCCATTGA

CGTCAATAATGACGTATGTTCCCATAGTAACGCCAATAGGGACTTTCCATTGACGTCAATGG

GTGGACTATTTACGGTAAACTGCCCACTTGGCAGTACATCAAGTGTATCATATGCCAAGTAC

GCCCCCTATTGACGTCAATGACGGTAAATGGCCCGCCTGGCATTATGCCCAGTACATGACCT

TATGGGACTTTCCTACTTGGCAGTACATCTACGTATTAGTCATCGCTATTACCATGGTGATG

CGGTTTTGGCAGTACATCAATGGGCGTGGATAGCGGTTTGACTCACGGGGATTTCCAAGTCT

CCACCCCATTGACGTCAATGGGAGTTTGTTTTGGCACCAAAATCAACGGGACTTTCCAAAAT

GTCGTAACAACTCCGCCCCATTGACGCAAATGGGCGGTAGGCGTGTACGGTGGGAGGTCTAT

ATAAGCAGAGCTCTCTGGCTAACTAGAGAACCCACTGCTTACTGGCTTATCGAAATTAATAC

GACTCACTATAGGGAGACCCAAGCTTATGGAAAGGGACGGATGCGCCGGTGGTGGATCTCGC

GGAGGCGAAGGTGGAAGGGCCCCTAGGGAAGGACCTGCCGGAAACGGAAGGGACAGGGGACG

CTCTCACGCCGCTGAAGCTCCAGGCGACCCTCAGGCCGCTGCCTCTCTGCTGGCTCCTATGG

ACGTCGGAGAAGAACCCCTGGAAAAGGCCGCCAGGGCCAGGACTGCCAAGGACCCCAACACC

TACAAGATCATCTCCCTCTTCACTTTCGCCGTCGGAGTCAACATCTGCCTGGGATTCACCGC

CGAAAAGCAAGGCAGCTGCAGGAAGAAGTGCTTTGATGCATCATTTAGAGGACTGGAGAACT

GCCGGTGTGATGTGGCATGTAAAGACCGAGGTGATTGCTGCTGGGATTTTGAAGACACCTGT

GTGGAATCAACTCGAATATGGATGTGCAATAAATTTCGTTGTGGAGAGACCAGATTAGAGGC

CAGCCTTTGCTCTTGTTCAGATGACTGTTTGCAGAGGAAAGATTGCTGTGCTGACTATAAGA

GTGTTTGCCAAGGAGAAACCTCATGGCTGGAAGAAAACTGTGACACAGCCCAGCAGTCTCAG

TGCCCAGAAGGGTTTGACCTGCCACCAGTTATCTTGTTTTCTATGGATGGATTTAGAGCTGA

ATATTTATACACATGGGATACTTTAATGCCAAATATCAATAAACTGAAAACATGTGGAATTC

ATTCAAAATACATGAGAGCTATGTATCCTACCAAAACCTTCCCAAATCATTACACCATTGTC

ACGGGCTTGTATCCAGAGTCACATGGCATCATTGACAATAATATGTATGATGTAAATCTCAA

CAAGAATTTTTCACTTTCTTCAAAGGAACAAAATAATCCAGCCTGGTGGCATGGGCAACCAA

TGTGGCTGACAGCAATGTATCAAGGTTTAAAAGCCGCTACCTACTTTTGGCCCCGGATCAGAA

GTGGCTATAAATGGCTCCTTTCCTTCCATATACATGCCTTACAACGGAAGTGTCCCATTTGA

AGAGAGGATTTCTACACTGTTAAAATGGCTGGACCTGCCCAAAGCTGAAAGACCCAGGTTTT

ATACCATGTATTTTGAAGAACCTGATTCCTCTGGACATGCAGGTGGACCAGTCAGTGCCAGA

GTAATTAAAGCCTTACAGGTAGTAGATCATGCTTTTGGGATGTTGATGGAAGGCCTGAAGCA

GCGGAATTTGCACAACTGTGTCAATATCATCCTTCTGGCTGACCATGGAATGGACCAGACTT

ATTGTAACAAGATGGAATACATGACTGATTATTTTCCCAGAATAAACTTCTTCTACATGTAC

GAAGGGCCTGCCCCCCGCATCCGAGCTCATAATATACCTGATGACTTTTTTAGTTTTAATTC
```

-continued

```
TGAGGAAATTGTTAGAAACCTCAGTTGCCGAAAACCTGATCAGCATTTCAAGCCCTATTTGA

CTCCTGATTTGCCAAAGCGACTGCACTATGCCAAGAACGTCAGAATCGACAAAGTTCATCTC

TTTGTGGATCAACAGTGGCTGGCTGTTAGGAGTAAATCAAATACAAATTGTGGAGGAGGCAA

CCATGGTTATAACAATGAGTTTAGGAGCATGGAGGCTATCTTTCTGGCACATGGACCCAGTT

TTAAAGAGAAGACTGAAGTTGAACCATTTGAAAATATTGAAGTCTATAACCTAATGTGTGAT

CTTCTACGCATTCAACCAGCACCAAACAATGGAACCCATGGTAGTTTAAACCATCTTCTGAA

GGTGCCTTTTTATGAGCCATCCCATGCAGAGGAGGTGTCAAAGTTTTCTGTTTGTGGCTTTG

CTAATCCATTGCCCACAGAGTCTCTTGACTGTTTCTGCCCTCACCTACAAAATAGTACTCAG

CTGGAACAAGTGAATCAGATGCTAAATCTCACCCAAGAAGAAATAACAGCAACAGTGAAAGT

AAATTTGCCATTTGGGAGGCCTAGGGTACTGCAGAAGAACGTGGACCACTGTCTCCTTTACC

ACAGGGAATATGTCAGTGGATTTGGAAAAGCTATGAGGATGCCCATGTGGAGTTCATACACA

GTCCCCCAGTTGGGAGACACATCGCCTCTGCCTCCCACTGTCCCAGACTGTCTGCGGGCTGA

TGTCAGGGTTCCTCCTTCTGAGAGCCAAAAATGTTCCTTCTATTTAGCAGACAAGAATATCA

CCCACGGCTTCCTCTATCCTCCTGCCAGCAATAGAACATCAGATAGCCAATATGATGCTTTA

ATTACTAGCAATTTGGTACCTATGTATGAAGAATTCAGAAAAATGTGGGACTACTTCCACAG

TGTTCTTCTTATAAAACATGCCACAGAAAGAAATGGAGTAAATGTGGTTAGTGGACCAATAT

TTGATTATAATTATGATGGCCATTTTGATGCTCCAGATGAAATTACCAAACATTTAGCCAAC

ACTGATGTTCCCATCCCAACACACTACTTTGTGGTGCTGACCAGTTGTAAAAACAAGAGCCA

CACACCGGAAAACTGCCCTGGGTGGCTGGATGTCCTACCCTTTATCATCCCTCACCGACCTA

CCAACGTGGAGAGCTGTCCTGAAGGTAAACCAGAAGCTCTTTGGGTTGAAGAAAGATTTACA

GCTCACATTGCCCGGGTCCGTGATGTAGAACTTCTCACTGGGCTTGACTTCTATCAGGATAA

AGTGCAGCCTGTCTCTGAAATTTTGCAACTAAAGACATATTTACCAACATTTGAAACCACTA

TTGACAAAACTCACACATGCCCACCGTGCCCAGCACCTGAACTCCTGGGGGGACCGTCAGTC

TTCCTCTTCCCCCCAAAACCCAAGGACACCCTCATGATCTCCCGGACCCCTGAGGTCACATG

CGTGGTGGTGGACGTGAGCCACGAAGACCCTGAGGTCAAGTTCAACTGGTACGTGGACGGCG

TGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCAAAGGGCAGCCCC

GAGAACCACAGGTGTACACCCTGCCCCCATCCCGGGAGGAGATGACCAAGAACCAGGTCAGC

CTGACCTGCCTGGTCAAAGGCTTCTATCCCAGCGACATCGCCGTGGAGTGGGAGAGCAATGG

GCAGCCGGAGAACAACTACAAGACCACGCCTCCCGTGCTGGACTCCGACGGCTCCTTCTTCC

TCTATAGCAAGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCCCCGGGTAA

ATGAAATTCTGCAGATATCCATCACACTGGCGGCCGCTCGAGCATGCATCTAGAGGGCCCTA

TTCTATAGTGTCACCTAAATGCTAGAGCTCGCTGATCAGCCTCGACTGTGCCTTCTAGTTGC

CAGCCATCTGTTGTTTGCCCCTCCCCCGTGCCTTCCTTGACCCTGGAAGGTGCCACTCCCAC

TGTCCTTTCCTAATAAAATGAGGAAATTGCATCGCATTGTCTGAGTAGGTGTCATTCTATTC

TGGGGGGTGGGGTGGGGCAGGACAGCAAGGGGGAGGATTGGGAAGACAATAGCAGGCATGCT

GGGGATGCGGTGGGCTCTATGGCTTCTGAGGCGGAAAGAACCAGCTGGGGCTCTAGGGGGTA

TCCCCACGCGCCCTGTAGCGGCGCATTAAGCGCGGCGGGTGTGGTGGTTACGCGCAGCGTGA

CCGCTACACTTGCCAGCGCCCTAGCGCCCGCTCCTTTCGCTTTCTTCCCTTCCTTTCTCGCC
```

-continued

```
ACGTTCGCCGGCTTTCCCCGTCAAGCTCTAAATCGGGGCATCCCTTTAGGGTTCCGATTTAG
TGCTTTACGGCACCTCGACCCCAAAAAACTTGATTAGGGTGATGGTTCACGTAGTGGGCCAT
CGCCCTGATAGACGGTTTTTCGCCCTTTGACGTTGGAGTCCACGTTCTTTAATAGTGGACTC
TTGTTCCAAACTGGAACAACACTCAACCCTATCTCGGTCTATTCTTTTGATTTATAAGGGAT
TTTGGGGATTTCGGCCTATTGGTTAAAAAATGAGCTGATTTAACAAAAATTTAACGCGAATT
AATTCTGTGGAATGTGTGTCAGTTAGGGTGTGGAAAGTCCCCAGGCTCCCCAGGCAGGCAGA
AGTATGCAAAGCATGCATCTCAATTAGTCAGCAACCAGGTGTGGAAAGTCCCCAGGCTCCCC
AGCAGGCAGAAGTATGCAAAGCATGCATCTCAATTAGTCAGCAACCATAGTCCCGCCCCTAA
CTCCGCCCATCCCGCCCCTAACTCCGCCCAGTTCCGCCCATTCTCCGCCCCATGGCTGACTA
ATTTTTTTTATTTATGCAGAGGCCGAGGCCGCCTCTGCCTCTGAGCTATTCCAGAAGTAGTG
AGGAGGGTTTTTGGAGGCCTAGGCTTTTGCAAAAAGCTCCCGGGAGCTTGTATATCCATTT
TCGGATCTGATCAAGAGACAGGATGAGGATCGTTTCGCATGATTGAACAAGATGGATTGCAC
GCAGGTTCTCCGGCCGCTTGGGTGGAGAGGCTATTCGGCTATGACTGGGCACAACAGACAAT
CGGCTGCTCTGATGCCGCCGTGTTCCGGCTGTCAGCGCAGGGGCGCCCGGTTCTTTTTGTCA
AGACCGACCTGTCCGGTGCCCTGAATGAACTGCAGGACGAGGCAGCGCGGCTATCGTGGCTG
GCCACGACGGGCGTTCCTTGCGCAGCTGTGCTCGACGTTGTCACTGAAGCGGGAAGGGACTG
GCTGCTATTGGGCGAAGTGCCGGGGCAGGATCTCCTGTCATCTCACCTTGCTCCTGCCGAGA
AAGTATCCATCATGGCTGATGCAATGCGGCGGCTGCATACGCTTGATCCGGCTACCTGCCCA
TTCGACCACCAAGCGAAACATCGCATCGAGCGAGCACGTACTCGGATGGAAGCCGGTCTTGT
CGATCAGGATGATCTGGACGAAGAGCATCAGGGGCTCGCGCCAGCCGAACTGTTCGCCAGGC
TCAAGGCGCGCATGCCCGACGGCGAGGATCTCGTCGTGACCCATGGCGATGCCTGCTTGCCG
AATATCATGGTGGAAAATGGCCGCTTTTCTGGATTCATCGACTGTGGCCGGCTGGGTGTGGC
GGACCGCTATCAGGACATAGCGTTGGCTACCCGTGATATTGCTGAAGAGCTTGGCGGCGAAT
GGGCTGACCGCTTCCTCGTGCTTTACGGTATCGCCGCTCCCGATTCGCAGCGCATCGCCTTC
TATCGCCTTCTTGACGAGTTCTTCTGAGCGGGACTCTGGGGTTCGAAATGACCGACCAAGCG
ACGCCCAACCTGCCATCACGAGATTTCGATTCCACCGCCGCCTTCTATGAAAGGTTGGGCTT
CGGAATCGTTTTCCGGGACGCCGGCTGGATGATCCTCCAGCGCGGGGATCTCATGCTGGAGT
TCTTCGCCCACCCCAACTTGTTTATTGCAGCTTATAATGGTTACAAATAAAGCAATAGCATC
ACAAATTTCACAAATAAAGCATTTTTTTCACTGCATTCTAGTTGTGGTTTGTCCAAACTCAT
CAATGTATCTTATCATGTCTGTATACCGTCGACCTCTAGCTAGAGCTTGGCGTAATCATGGT
CATAGCTGTTTCCTGTGTGAAATTGTTATCCGCTCACAATTCCACACAACATACGAGCCGGA
AGCATAAAGTGTAAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTCACTGACTCGCTG
CGCTCGGTCGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAAAGGCCAGGA
ACCGTAAAAAGGCCGCGTTGCTGGCGTTTTTCCATAGGCTCCGCCCCCCTGAXGAGCATCAC
AAAAATCGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATACCTGT
CCGCCTTTCTCCCTTCGGGAAGCGTGGCGCTTTCTCAATGCTCACGCTGTAGGTATCTCAGT
```

-continued

```
TCGGTGTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGTTC
TTGAAGTGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGGAACAAACCACCGCTG
GTAGCGGTGGTTTTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGATCAAGGCGAGTT
ACATGATCCCCCATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATAATTCTCTTACTG
TCATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGCAAAAA
GGGAATAAGGGCGACACGGAAATGTTGAATACTCATACTCTTCCTTTTTCAATATTATTGAA
GCATTTATCAGGGTTATTGTCTCATGAGCGGATACATATTTGAATGTATTTAGAAAAATAAA
CAAATAGGGGTTCCGCGCACATTTCCCCGAAAAGTGCCACCTGACGTC
```

ENPP121-Fc Amino acid sequence
(SEQ ID NO: 66)
MERDGCAGGGSRGGEGGRAPREGPAGNGRDRGRSHAAEAPGDPQAAASLLAPMDVGEEPLEK

AARARTAKDPNTYKIISLFTFAVGVNICLG**FTAGLKPSCAKEVKSCKGRCFERTFGNCRC

DAACVELGNCCLDYQETCIEPEHIWTCNKFRCGEKRLTRSLCACSDDCKDKGDCCINYSSVC

QGEKSWVEEPCESINEPQCPAGFETPPILLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPIWV

TAKYQGLKSGTFFWPGSDVEINGIFPDIYKMYNGSVPFEERILAVLQWLQLPKDERPHFYTL

YLEEPDSSGHSYGPVSSEVIKALQRVDGMVGMLMDGLKELNLHRCLNLILISDHGMEQGSCK

KYIYLNKYLGDVKNIKVIYGPAARLRPSDVPDKYYSFNYEGIARNLSCREPNQHFKPYLKHF

LPKRLHFAKSDRIEPLTFYLDPQWQLALNPSERKYCGSGFHGSDNVFSNMQALFVGYGPGFK

HGIEADTFENIEVYNLMCDLLNLTPAPNNGTHGSLNHLLKNPVYTPKHPKEVHPLVQCPFIR

NPRDNLGCSCNPSILPIEDFQTQFNLTVAEEKIIKHETLPYGRPRVLQKENTICLLSQHQFM

SGYSQDILMPLWTSYTVDRNDSFSTEDFSNCLYQDFRIPLSPVHKCSFYKNNTKVSYGFLSP

PQLNKNSSGIYSEALLTTNIVPMYQSFQVIWRYFHDTLLRKYAEERNGVNVVSGPVFDFDYD

GRCDSLENLRQKRRVIRNQEILPTHFFIVLTSCKDTSQTPLHCENLDTLAFILPHRTDNSE

SCVHGKHOSSWVEELLMLHRARITDVEHITGLSFYQQRKEPVSDILKLKTHLPTFSQEDDKT

HTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Singly underlined: residues swapped with ENPP2 residues
to afford cleavage at transition position (**), Doubly
underlined: connote the beginning and the end of ENPP1
residues. Bold residues indicate residues of IgG Fc
domain.

ENPP71-Fc Amino acid sequence
(SEQ ID NO: 67)

<u>MRGPAVLLTVALATLLAPGA</u>GLKPSCAKEVKSCKGRCFERTFGNCRCDAACVELGNCCLDYQ
ETCIEPEHIWTCNKFRCGEKRLTRSLCACSDDCKDKGDCCINYSSVCQGEKSWVEEPCESIN
EPQCPAGFETPPILLFSLDGFRAEYLHTWGGLLPVISKLKKCGTYTKNMRPVYPTKTFPNHY
SIVTGLYPESHGIIDNKMYDPKMNASFSLKSKEKFNPEWYKGEPIWVTAKYQGLKSGTFFWP
GSDVEINGIFPDIYKMYNGSVPFEERILAVLQWLQLPKDERPHFYTLYLEEPDSSGHSYGPV
SSEVIKALQRVDGMVGMLMDGLKELNLHRCLNLILISDHGMEQGSCKKYIYLNKYLGDVKNI
KVIYGPAARLRPSDVPDKYYSFNYEGIARNLSCREPNQHFKPYLKHFLPKRLHFAKSDRIEP
LTFYLDPQWQLALNPSERKYCGSGFHGSDNVFSNMQALFVGYGPGFKHGIEADTFENIEVYN
LMCDLLNLTPAPNNGTHGSLNHLLKNPVYTPKHPKEVHPLVQCPFTRNPRDNLGCSCNPSIL
PIEDFQTQFNLTVAEEKIIKHETLPYGRPRVLQKENTICLLSQHQFMSGYSQDILMPLWTSY
TVDRNDSFSTEDFSNCLYQDFRIPLSPVHKCSFYKNNTKVSYGFLSPPQLNKNSSGIYSEAL
LTTNIVPMYQSFQVIWRYFHDTLLRKYAEERNGVNVVSGPVFDFDYDGRCDSLENLRQKRRV
IRNQEILIPTHFFIVLTSCKDTSQTPLHCENLDTLAFILPHRTDNSESCVHGKHOSSWVEEL
LMLHRARITDVEHITGLSFYQQRKEPVSDILKLKTHLPTFS<u>QED</u>DKTHTCPPCPAPELLGGP
SVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNVFS
CSVMHEALHNHYTQKSLSLSPGK

Singly underlined: ENPP7 residues. Doubly underlined:
beginning and end of ENPP1 residues. Bold: residues
of IgG Fc domain ENPP51-Fc Amino acid sequence
(SEQ ID NO: 68)

<u>MTSKFLLVSFILAALSLSITFS</u>GLKPSCAKEVKSCKGRCFERTFGNCRCDAACVELGNCCLD
YQETCIEPEHIWTCNKFRCGEKRLTRSLCACSDDCKDKGDCCINYSSVCQGEKSWVEEPCES
INEPQCPAGFETPPTLLFSLDGFRAEYLHTWGGLLPVISKLKKCGTYTKNMRPVYPTKTFPN
HYSIVTGLYPESHGIIDNKMYDPKMNASFSLKSKEKFNPEWYKGEPIWVTAKYQGLKSGTFF
WPGSDVEINGIFPDIYKMYNGSVPFEERILAVLQWLQLPKDERPHFYTLYLEEPDSSGHSYG
PVSSEVIKALQRVDGMVGMLMDGLKELNLHRCLNLILISDHGMEQGSCKKYIYLNKYLGDVK
NIKVIYGPAARLRPSDVPDKYYSFNYEGIARNLSCREPNQHFKPYLKHFLPKRLHFAKSDRI
EPLTFYLDPQWQLALNPSERKYCGSGFHGSDNVFSNMQALFVGYGPGFKHGIEADTFENIEV

-continued

YNLMCDLLNLTPAPNNGTHGSLNHLLKNPVYTPKHPKEVHPLVQCPFTRNPRDNLGCSCNPS

ILPIEDFQTQFNLTVAEEKIIKHETLPYGRPRVLQKENTICLLSQHQFMSGYSQDILMPLWT

SYTVDRNDSFSTEDFSNCLYQDFRIPLSPVHKCSFYKNNTKVSYGFLSPPQLNKNSSGIYSE

ALLTTNIVPMYQSFQVIWRYFHDTLLRKYAEERNGVNVVSGPVFDFDYDGRCDSLENLRQKR

RVIRNQEILIPTHFFIVLTSCKDTSQTPLHCENLDTLAFILPHRTDNSESCVHGKHOSSWVE

ELLMLHRARITDVEHITGLSFYQQRKEPVSDILKLKTHLPTFSQEDDKTHTCPPCPAPELLG

GPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKLTVDKSRWQQGNV

FSCSVMHEALHNHYTQKSLSLSPGK

Singly underlined: ENPP5 residues. Doubly underlined:

beginning and end of ENPP1 residues. Bold: residues of IgG Fc domain

ENPP121-ALB Amino acid sequence (SEQ ID NO: 69)

MERDGCAGGGSRGGEGGRAPREGPAGNGRDRGRSHAAEAPGDPQAAASLLAPMDVGEEPLEK

AARARTAKDPNTYKIIS<u>LFTFAVGVNICLG**FTA</u>G<u>LKP</u>SCAKEVKSCKGRCFERTFGNCRC

DAACVELGNCCLDYQETCIEPEHIWTCNKFRCGEKRLTRSLCACSDDCKDKGDCCINYSSVC

QGEKSWVEEPCESINEPQCPAGFETPPILLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPIWV

TAKYQGLKSGTFFWPGSDVEINGIFPDIYKMYNGSVPFEERILAVLQWLQLPKDERPHFYTL

YLEEPDSSGHSYGPVSSEVIKALQRVDGMVGMLMDGLKELNLHRCLNLILISDHGMEQGSCK

KYIYLNKYLGDVKNIKVIYGPAARLRPSDVPDKYYSFNYEGIARNLSCREPNQHFKPYLKHF

LPKRLHFAKSDRIEPLTFYLDPQWQLALNPSERKYCGSGFHGSDNVFSNMQALFVGYGPGFK

HGTEADTFENIEVYNLMCDLLNLTPAPNNGTHGSLNHLLKNPVYTPKHPKEVHPLVQCPFIR

NPRDNLGCSCNPSILPIEDFQTQFNLTVAEEKIIKHETLPYGRPRVLQKENTICLLSQHQFM

SGYSQDILMPLWTSYTVDRNDSFSTEDFSNCLYQDFRIPLSPVHKCSFYKNNTKVSYGFLSP

PQLNKNSSGIYSEALLTTNIVPMYQSFQVIWRYFHDTLLRKYAEERNGVNVVSGPVFDFDYD

GRCDSLENLRQKRRVIRNQEILIPTHFFIVLTSCKDTSQTPLHCENLDTLAFILPHRTDNSE

SCVHGKHDSSWVEELLMLHRARITDVEHITGLSFYQQRKEPVSDILKLKTHLPTFSQEDRSG

SGGSMKWVTFLLLLFVSGSAFSRGVFRREAHKSEIAHRYNDLGEQHFKGLVLIAFSQYLQKC

SYDEHAKLVQEVTDFAKTCVADESAANCDKSLHTLFGDKLCAIPNLRENYGELADCCTKQEP

ERNECFLQHKDDNPSLPPFERPEAEAMCTSFKENPTTFMGHYLHEVARRHPYFYAPELLYYA

EQYNEILTQCCAEADKESCLTPKLDGVKEKALVSSVRQRMKCSSMQKFGERAFKAWAVARLS

QTFPNADFAEITKLATDLTKVNKECCHGDLLECADDRAELAKYMCENQATISSKLQTCCDKP

LLKKAHCLSEVEHDTMPADLPAIAADFVEDQEVCKNYAEAKDVFLGTFLYEYSRRHPDYSVS

LLLRLAKKYEATLEKCCAEANPPACYGTVLAEFQPLVEEPKNLVKTNCDLYEKLGEYGFQNA

ILVRYTQKAPQVSTPTLVEAARNLGRVGTKCCTLPEDQRLPCVEDYLSAILNRVCLLHEKTP

VSEHVTKCCSGSLVERRPCFSALTVDETYVPKEFKAETFTFHSDICTL

Singly underlined: residues swapped with ENPP2 residues to afford cleavage at transition position (**), Doubly underlined: connote the beginning and the end of ENPP1 residues. Bold: residues of Albumin. Bold underlined: linker region.

NPP71-ALB Amino acid sequence
(SEQ ID NO: 70)

<u>MRGPAVLLTVALATLLAPGA</u>GLKPSCAKEVKSCKGRCFERTFGNCRCDAACVELGNCCLDYQ
ETCIEPEHIWTCNKFRCGEKRLTRSLCACSDDCKDKGDCCINYSSVCQGEKSWVEEPCESIN
EPQCPAGFETPPILLFSLDGFRAEYLHTWGGLLPVISKLKKCGTYTKNMRPVYPTKTFPNHY
SIVTGLYPESHGIIDNKMYDPKMNASFSLKSKEKFNPEWYKGEPIWVTAKYQGLKSGTFFWP
GSDVEINGIFPDIYKMYNGSVPFEERILAVLQWLQLPKDERPHFYTLYLEEPDSSGHSYGPV
SSEVIKALQRVDGMVGMLMDGLKELNLHRCLNLILISDHGMEQGSCKKYIYLNKYLGDVKNI
KVIYGPAARLRPSDVPDKYYSFNYEGIARNLSCREPNQHFKPYLKHFLPKRLHFAKSDRIEP
LTFYLDPQWQLALNPSERKYCGSGFHGSDNVFSNMQALFVGYGPGFKHGIEADTFENIEVYN
LMCDLLNLTPAPNNGTHGSLNHLLKNPVYTPKHPKEVHPLVQCPFTRNPRDNLGCSCNPSIL
PIEDFQTQFNLTVAEEKIIKHETLPYGRPRVLQKENTICLLSQHQFMSGYSQDILMPLWTSY
TVDRNDSFSTEDFSNCLYQDFRIPLSPVHKCSFYKNNTKVSYGFLSPPQLNKNSSGIYSEAL
LTTNIVPMYQSFQVIWRYFHDTLLRKYAEERNGVNVVSGPVFDFDYDGRCDSLENLRQKRRV
IRNQEILIPTHFFIVLTSCKDTSQTPLHCENLDTLAFILPHRTDNSESCVHGKHOSSWVEEL
LMLHRARITDVEHITGLSFYQQRKEPVSDILKLKTHLPTFS<u>QED</u>GGSGGSMKWVTFLLLLFV
SGSAFSRGVFRREAHKSEIAHRYNDLGEQHFKGLVLIAFSQYLQKCSYDEHAKLVQEVTDFA
KTCVADESAANCDKSLHTLFGDKLCAIPNLRENYGELADCCTKQEPERNECFLQHKDDNPSL
PPFERPEAEAMCTSFKENPTTFMGHYLHEVARRHPYFYAPELLYYAEQYNEILTQCCAEADK
ESCLTPKLDGVKEKALVSSVRQRMKCSSMQKFGERAFKAWAVARLSQTFPNADFAEITKLAT
DLTKVNKECCHGDLLECADDRAELAKYMCENQATISSKLQTCCDKPLLKKAHCLSEVEHDTM
PADLPAIAADFVEDQEVCKNYAEAKDVFLGTFLYEYSRRHPDYSVSLLLRLAKKYEATLEKC
CAEANPPACYGTVLAEFQPLVEEPKNLVKTNCDLYEKLGEYGFQNAILVRYTQKAPQVSTPT
LVEAARNLGRVGTKCCTLPEDQRLPCVEDYLSAILNRVCLLHEKTPVSEHVTKCCSGSLVER
RPCFSALTVDETYVPKEFKAETFTFHSDICTL

Singly underlined: ENPP7 residues. Doubly underlined: beginning and end of ENPP1 residues. Bold: residues of Albumin. Bold underline: linker region.

Nucleotide sequence of ENPP121-Fc
(SEQ ID NO: 71)
ATGGAAAGGGACGGATGCGCCGGTGGTGGATCTCGCGGAGGCGAAGGTGGAAGGGCCCCTAG
GGAAGGACCTGCCGGAAACGGAAGGGACAGGGGACGCTCTCACGCCGCTGAAGCTCCAGGCG
ACCCTCAGGCCGCTGCCTCTCTGCTGGCTCCTATGGACGTCGGAGAAGAACCCCTGGAAAAG
GCCGCCAGGGCCAGGACTGCCAAGGACCCCAACACCTACAAGATCATCTCCCTCTTCACTTT
CGCCGTCGGAGTCAACATCTGCCTGGATTCACCGCCGGACTGAAGcccagCTGCGCCAAAG
AAGTGAAGTCCTGCAAGGGCCGGTGCTTCGAGCGGACCTTCGGCAACTGCAGATGCGACGCC
GCCTGTGTGGAACTGGGCAACTGCTGCCTGGACTACCAGGAAACCTGCATCGAGCCCGAGCA -continued

```
CATCTGGACCTGCAACAAGTTCAGATGCGGCGAGAAGCGGCTGACCAGATCCCTGTGTGCCT
GCAGCGACGACTGCAAGGACAAGGGCGACTGCTGCATCAACTACAGCAGCGTGTGCCAGGGC
GAGAAGTCCTGGGTGGAAGAACCCTGCGAGAGCATCAACGAGCCCCAGTGCCCTGCCGGCTT
CGAGACACCTCCTACCCTGCTGTTCAGCCTGGACGGCTTTCGGGCCGAGTACCTGCACACAT
GGGGAGGCCTGCTGCCCGTGATCAGCAAGCTGAAGAAGTGCGGCACCTACACCAAGAACATG
CGGCCCGTGTACCCCACCAAGACCTTCCCCAACCACTACTCCATCGTGACCGGCCTGTACCC
CGAGAGCCACGGCATCATCGACAACAAGATGTACGACCCCAAGATGAACGCCAGCTTCAGCC
TGAAGTCCAAAGAGAAGTTCAACCCCGAGTGGTATAAGGGCGAGCCCATCTGGGTCACCGCC
AAGTACCAGGGCCTGAAAAGCGGCACATTCTTTTGGCCCGGCAGCGACGTGGAAATCAACGG
CATCTTCCCCGACATCTATAAGATGTACAACGGCAGCGTGCCCTTCGAGGAACGGATCCTGG
CTGTGCTGCAGTGGCTGCAGCTGCCCAAGGATGAGCGGCCCCACTTCTACACCCTGTACCTG
GAAGAACCTGACAGCAGCGGCCACAGCTACGGCCCTGTGTCCAGCGAAGTGATCAAGGCCCT
GCAGCGGGTGGACGGCATGGTGGGAATGCTGATGGACGGCCTGAAAGAGCTGAACCTGCACA
GATGCCTGAACCTGATCCTGATCAGCGACCACGGCATGGAACAGGGATCCTGCAAGAAGTAC
ATCTACCTGAACAAGTACCTGGGCGACGTGAAGAACATCAAAGTGATCTACGGCCCAGCCGC
CAGACTGAGGCCTAGCGACGTGCCCGACAAGTACTACAGCTTCAACTACGAGGGAATCGCCC
GGAACCTGAGCTGCAGAGAGCCCAACCAGCACTTCAAGCCCTACCTGAAGCACTTCCTGCCC
AAGCGGCTGCACTTCGCCAAGAGCGACAGAATCGAGCCCCTGACCTTCTACCTGGACCCCCA
GTGGCAGCTGGCCCTGAATCCCAGCGAGAGAAAGTACTGCGGCAGCGGCTTCCACGGCTCCG
ACAACGTGTTCAGCAACATGCAGGCCCTGTTCGTGGGCTACGGACCCGGCTTTAAGCACGGC
ATCGAGGCCGACACCTTCGAGAACATCGAGGTGTACAATCTGATGTGCGACCTGCTGAATCT
GACCCCTGCCCCCAACAATGGCACCCACGGCAGCCTGAACCATCTGCTGAAGAACCCCGTGT
ACACCCCTAAGCACCCCAAAGAGGTGCACCCCCTGGTGCAGTGCCCCTTCACCAGAAACCCC
AGAGACAACCTGGGCTGTAGCTGCAACCCCAGCATCCTGCCCATCGAGGACTTCCAGACCCA
GTTCAACCTGACCGTGGCCGAGGAAAAGATCATCAAGCACGAGACACTGCCCTACGGCAGAC
CCCGGGTGCTGCAGAAAGAGAACACCATCTGCCTGCTGAGCCAGCACCAGTTCATGAGCGGC
TACTCCCAGGACATCCTGATGCCCCTGTGGACCAGCTACACCGTGGACCGGAACGACAGCTT
CTCCACCGAGGATTTCAGCAACTGCCTGTACCAGGATTTCCGGATCCCCCTGAGCCCCGTGC
ACAAGTGCAGCTTCTACAAGAACAACACCAAGGTGTCCTACGGCTTCCTGAGCCCTCCCCAG
CTGAACAAGAACAGCTCCGGCATCTACAGCGAGGCCCTGCTGACTACCAACATCGTGCCCAT
GTACCAGAGCTTCCAAGTGATCTGGCGGTACTTCCACGACACCCTGCTGCGGAAGTACGCCG
AAGAACGGAACGGCGTGAACGTGGTGTCCGGCCCAGTGTTCGACTTCGACTACGACGGCAGA
TGTGACAGCCTGGAAAATCTGCGGCAGAAAAGAAGAGTGATCCGGAACCAGGAAATTCTGAT
CCCTACCCACTTCTTTATCGTGCTGACAAGCTGCAAGGATACCAGCCAGACCCCCCTGCACT
GCGAGAACCTGGATACCCTGGCCTTCATCCTGCCTCACCGGACCGACAACAGCGAGAGCTGT
GTGCACGGCAAGCACGACAGCTCTTGGGTGGAAGAACTGCTGATGCTGCACCGGGCCAGAAT
CACCGATGTGGAACACATCACCGGCCTGAGCTTTTACCAGCAGCGGAAAGAACCCGTGTCCG
ATATCCTGAAGCTGAAAACCCATCTGCCCACCTTCAGCCAGGAAGATGACAAGACCCACACT
TGCCCCCCCTGCCCAGCTCCTGAACTGCTGGGAGGACCCTCTGTGTTCCTGTTCCCCCCAAA
GCCCAAGGACACCCTGATGATCTCTAGGACCCCCGAAGTCACTTGCGTCGTCGTCGACGTGT
CCCACGAGGACCCTGAAGTCAAGTTCAACTGGTACGTCGACGGTGTCGAAGTCCACAACGCC
```

-continued

AAGACCAAGCCCAGGGAAGAACAGTACAACTCTACCTACCGCGTCGTCAGCGTCCTGACCGT

CCTGCACCAGGACTGGCTGAACGGAAAGGAATACAAGTGCAAGGTGTCCAACAAGGCCCTGC

CTGCCCCCATCGAAAAGACCATCTCTAAGGCCAAGGGACAGCCCCGCGAACCCCAGGTCTAC

ACCCTGCCACCCTCTAGGGAAGAAATGACCAAGAACCAGGTGTCCCTGACCTGCCTGGTCAA

GGGATTCTACCCCTCTGACATCGCCGTCGAATGGGAATCTAACGGACAGCCCGAAAACAACT

ACAAGACCACCCCCCCTGTCCTGGACTCTGACGGATCATTCTTCCTGTACTCTAAGCTGACT

GTCGACAAGTCTAGGTGGCAGCAGGGAAACGTGTTCTCTTGCTCTGTCATGCACGAAGCCCT

GCACAACCACTACACCCAGAAGTCTCTGTCTCTGTCCCCCGGAAAG

Nucleotide sequence of ENPP121-Albumin (SEQ ID NO: 72)

ATGGAAAGGGACGGATGCGCCGGTGGTGGATCTCGCGGAGGCGAAGGTGGAAGGGCCCCTAG

GGAAGGACCTGCCGGAAACGGAAGGGACAGGGGACGCTCTCACGCCGCTGAAGCTCCAGGCG

ACCCTCAGGCCGCTGCCTCTCTGCTGGCTCCTATGGACGTCGGAGAAGAACCCCTGGAAAAG

GCCGCCAGGGCCAGGACTGCCAAGGACCCCAACACCTACAAGATCATCTCCCTCTTCACTTT

CGCCGTCGGAGTCAACATCTGCCTGGGATTCACCGCCGGACTGAAGcccagCTGCGCCAAAG

AAGTGAAGTCCTGCAAGGGCCGGTGCTTCGAGCGGACCTTCGGCAACTGCAGATGCGACGCC

GCCTGTGTGGAACTGGGCAACTGCTGCCTGGACTACCAGGAAACCTGCATCGAGCCCGAGCA

CATCTGGACCTGCAACAAGTTCAGATGCGGCGAGAAGCGGCTGACCAGATCCCTGTGTGCCT

GCAGCGACGACTGCAAGGACAAGGGCGACTGCTGCATCAACTACAGCAGCGTGTGCCAGGGC

GAGAAGTCCTGGGTGGAAGAACCCTGCGAGAGCATCAACGAGCCCCAGTGCCCTGCCGGCTT

CGAGACACCTCCTACCCTGCTGTTCAGCCTGGACGGCTTTCGGGCCGAGTACCTGCACACAT

GGGGAGGCCTGCTGCCCGTGATCAGCAAGCTGAAGAAGTGCGGCACCTACACCAAGAACATG

CGGCCCGTGTACCCCACCAAGACCTTCCCCAACCACTACTCCATCGTGACCGGCCTGTACCC

CGAGAGCCACGGCATCATCGACAACAAGATGTACGACCCCAAGATGAACGCCAGCTTCAGCC

TGAAGTCCAAAGAGAAGTTCAACCCCGAGTGGTATAAGGGCGAGCCCATCTGGGTCACCGCC

AAGTACCAGGGCCTGAAAAGCGGCACATTCTTTTGGCCCGGCAGCGACGTGGAAATCAACGG

CATCTTCCCCGACATCTATAAGATGTACAACGGCAGCGTGCCCTTCGAGGAACGGATCCTGG

CTGTGCTGCAGTGGCTGCAGCTGCCCAAGGATGAGCGGCCCCACTTCTACACCCTGTACCTG

GAAGAACCTGACAGCAGCGGCCACAGCTACGGCCCTGTGTCCAGCGAAGTGATCAAGGCCCT

GCAGCGGGTGGACGGCATGGTGGGAATGCTGATGGACGGCCTGAAAGAGCTGAACCTGCACA

GATGCCTGAACCTGATCCTGATCAGCGACCACGGCATGGAACAGGGATCCTGCAAGAAGTAC

ATCTACCTGAACAAGTACCTGGGCGACGTGAAGAACATCAAAGTGATCTACGGCCCAGCCGC

CAGACTGAGGCCTAGCGACGTGCCCGACAAGTACTACAGCTTCAACTACGAGGGAATCGCCC

GGAACCTGAGCTGCAGAGAGCCCAACCAGCACTTCAAGCCCTACCTGAAGCACTTCCTGCCC

AAGCGGCTGCACTTCGCCAAGAGCGACAGAATCGAGCCCCTGACCTTCTACCTGGACCCCCA

GTGGCAGCTGGCCCTGAATCCCAGCGAGAGAAAGTACTGCGGCAGCGGCTTCCACGGCTCCG

ACAACGTGTTCAGCAACATGCAGGCCCTGTTCGTGGGCTACGGACCCGGCTTTAAGCACGGC

ATCGAGGCCGACACCTTCGAGAACATCGAGGTGTACAATCTGATGTGCGACCTGCTGAATCT

GACCCCTGCCCCCAACAATGGCACCCACGGCAGCCTGAACCATCTGCTGAAGAACCCCGTGT

ACACCCCTAAGCACCCCAAAGAGGTGCACCCCCTGGTGCAGTGCCCCTTCACCAGAAACCCC

AGAGACAACCTGGGCTGTAGCTGCAACCCCAGCATCCTGCCCATCGAGGACTTCCAGACCCA

-continued

```
GTTCAACCTGACCGTGGCCGAGGAAAAGATCATCAAGCACGAGACACTGCCCTACGGCAGAC
CCCGGGTGCTGCAGAAAGAGAACACCATCTGCCTGCTGAGCCAGCACCAGTTCATGAGCGGC
TACTCCCAGGACATCCTGATGCCCCTGTGGACCAGCTACACCGTGGACCGGAACGACAGCTT
CTCCACCGAGGATTTCAGCAACTGCCTGTACCAGGATTTCCGGATCCCCCTGAGCCCCGTGC
ACAAGTGCAGCTTCTACAAGAACAACACCAAGGTGTCCTACGGCTTCCTGAGCCCTCCCCAG
CTGAACAAGAACAGCTCCGGCATCTACAGCGAGGCCCTGCTGACTACCAACATCGTGCCCAT
GTACCAGAGCTTCCAAGTGATCTGGCGGTACTTCCACGACACCCTGCTGCGGAAGTACGCCG
AAGAACGGAACGGCGTGAACGTGGTGTCCGGCCCAGTGTTCGACTTCGACTACGACGGCAGA
TGTGACAGCCTGGAAAATCTGCGGCAGAAAGAAGAGTGATCCGGAACCAGGAAATTCTGAT
CCCTACCCACTTCTTTATCGTGCTGACAAGCTGCAAGGATACCAGCCAGACCCCCCTGCACT
GCGAGAACCTGGATACCCTGGCCTTCATCCTGCCTCACCGGACCGACAACAGCGAGAGCTGT
GTGCACGGCAAGCACGACAGCTCTTGGGTGGAAGAACTGCTGATGCTGCACCGGGCCAGAAT
CACCGATGTGGAACACATCACCGGCCTGAGCTTTTACCAGCAGCGGAAAGAACCCGTGTCCG
ATATCCTGAAGCTGAAAACCCATCTGCCCACCTTCAGCCAGGAAGATGGTGGAGGAGGCTCT
GGTGGAGGCGGTAGCGGAGGCGGAGGGTCGGGAGGTTCTGGATCAATGAAGTGGGTAACCTT
TATTTCCCTTCTTTTTCTCTTTAGCTCGGCTTATTCCAGGGGTGTGTTTCGTCGAGATGCAC
ACAAGAGTGAGGTTGCTCATCGGTTTAAAGATTTGGGAGAAGAAAATTTCAAAGCCTTGGTG
TTGATTGCCTTTGCTCAGTATCTTCAGCAGTGTCCATTTGAAGATCATGTAAAATTAGTGAA
TGAAGTAACTGAATTTGCAAAAACATGTGTTGCTGATGAGTCAGCTGAAAATTGTGACAAAT
CACTTCATACCCTTTTTGGAGACAAATTATGCACAGTTGCAACTCTTCGTGAAACCTATGGT
GAAATGGCTGACTGCTGTGCAAAACAAGAACCTGAGAGAAATGAATGCTTCTTGCAACACAA
AGATGACAACCCAAACCTCCCCCGATTGGTGAGACCAGAGGTTGATGTGATGTGCACTGCTT
TTCATGACAATGAAGAGACATTTTTGAAAAAATACTTATATGAAATTGCCAGAAGACATCCT
TACTTTTATGCCCCGGAACTCCTTTTCTTTGCTAAAAGGTATAAAGCTGCTTTTACAGAATG
TTGCCAAGCTGCTGATAAAGCTGCCTGCCTGTTGCCAAAGCTCGATGAACTTCGGGATGAAG
GGAAGGCTTCGTCTGCCAAACAGAGACTCAAGTGTGCCAGTCTCCAAAAATTTGGAGAAAGA
GCTTTCAAAGCATGGGCAGTAGCTCGCCTGAGCCAGAGATTTCCCAAAGCTGAGTTTGCAGA
AGTTTCCAAGTTAGTGACAGATCTTACCAAAGTCCACACGGAATGCTGCCATGGAGATCTGC
TTGAATGTGCTGATGACAGGGCGGACCTTGCCAAGTATATCTGTGAAAATCAAGATTCGATC
TCCAGTAAACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTTGAAAGTA
AGGATGTTTGCAAAAACTATGCTGAGGCAAAGGATGTCTTCCTGGGCATGTTTTTGTATGAA
TATGCAAGAAGGCATCCTGATTACTCTGTCGTGCTGCTGCTGAGACTTGCCAAGACATATGA
AACCACTCTAGAGAAGTGCTGTGCCGCTGCAGATCCTCATGAATGCTATGCCAAAGTGTTCG
ATGAATTTAAACCTCTTGTGGAAGAGCCTCAGAATTTAATCAAACAAAATTGTGAGCTTTTT
GAGCAGCTTGGAGAGTACAAATTCCAGAATGCGCTATTAGTTCGTTACACCAAGAAAGTACC
CCAAGTGTCAACTCCAACTCTTGTAGAGGTCTCAAGAAACCTAGGAAAAGTGGGCAGCAAAT
GTTGTAAACATCCTGAAGCAAAAAGAATGCCCTGTGCAGAAGACTATCTATCCGTGGTCCTG
AACCAGTTATGTGTGTTGCATGAGAAAACGCCAGTAAGTGACAGAGTCACCAAATGCTGCAC
AGAATCCTTGGTGAACAGGCGACCATGCTTTTCAGCTCTGGAAGTCGATGAAACATACGTTC
CCAAAGAGTTTAATGCTGAAACATTCACCTTCCATGCAGATATATGCACACTTTCTGAGAAG
```

-continued

```
GAGAGACAAATCAAGAAACAAACTGCACTTGTTGAGCTCGTGAAACACAAGCCCAAGGCAAC

AAAAGAGCAACTGAAAGCTGTTATGGATGATTTCGCAGCTTTTGTAGAGAAGTGCTGCAAGG

CTGACGATAAGGAGACCTGCTTTGCCGAGGAGGGTAAAAAACTTGTTGCTGCAAGTCAAGCT

GCCTTAGGCTTA
```

Nucleotide sequence of ENPP7-1-Fc (SEQ ID NO: 73)
```
ATGAGAGGACCTGCCGTCCTGCTGACCGTCGCCCTGGCTACCTTGCTGGCCCCTGGTGCTGG TGCAcccagCTGCGCCAAAGAAGTGAAGTCCTGCAAGGGCCGGTGCTTCGAGCGGACCTTCG

GCAACTGCAGATGCGACGCCGCCTGTGTGGAACTGGGCAACTGCTGCCTGGACTACCAGGAA

ACCTGCATCGAGCCCGAGCACATCTGGACCTGCAACAAGTTCAGATGCGGCGAGAAGCGGCT

GACCAGATCCCTGTGTGCCTGCAGCGACGACTGCAAGGACAAGGGCGACTGCTGCATCAACT

ACAGCAGCGTGTGCCAGGGCGAGAAGTCCTGGGTGGAAGAACCCTGCGAGAGCATCAACGAG

CCCCAGTGCCCTGCCGGCTTCGAGACACCTCCTACCCTGCTGTTCAGCCTGGACGGCTTTCG

GGCCGAGTACCTGCACACATGGGGAGGCCTGCTGCCCGTGATCAGCAAGCTGAAGAAGTGCG

GCACCTACACCAAGAACATGCGGCCCGTGTACCCCACCAAGACCTTCCCCAACCACTACTCC

ATCGTGACCGGCCTGTACCCCGAGAGCCACGGCATCATCGACAACAAGATGTACGACCCCAA

GATGAACGCCAGCTTCAGCCTGAAGTCCAAAGAGAAGTTCAACCCCGAGTGGTATAAGGGCG

AGCCCATCTGGGTCACCGCCAAGTACCAGGGCCTGAAAAGCGGCACATTCTTTTGGCCCGGC

AGCGACGTGGAAATCAACGGCATCTTCCCCGACATCTATAAGATGTACAACGGCAGCGTGCC

CTTCGAGGAACGGATCCTGGCTGTGCTGCAGTGGCTGCAGCTGCCCAAGGATGAGCGGCCCC

ACTTCTACACCCTGTACCTGGAAGAACCTGACAGCAGCGGCCACAGCTACGGCCCTGTGTCC

AGCGAAGTGATCAAGGCCCTGCAGCGGGTGGACGGCATGGTGGGAATGCTGATGGACGGCCT

GAAAGAGCTGAACCTGCACAGATGCCTGAACCTGATCCTGATCAGCGACCACGGCATGGAAC

AGGGATCCTGCAAGAAGTACATCTACCTGAACAAGTACCTGGGCGACGTGAAGAACATCAAA

GTGATCTACGGCCCAGCCGCCAGACTGAGGCCTAGCGACGTGCCCGACAAGTACTACAGCTT

CAACTACGAGGGAATCGCCCGGAACCTGAGCTGCAGAGAGCCCAACCAGCACTTCAAGCCCT

ACCTGAAGCACTTCCTGCCCAAGCGGCTGCACTTCGCCAAGAGCGACAGAATCGAGCCCCTG

ACCTTCTACCTGGACCCCCAGTGGCAGCTGGCCCTGAATCCCAGCGAGAGAAAGTACTGCGG

CAGCGGCTTCCACGGCTCCGACAACGTGTTCAGCAACATGCAGGCCCTGTTCGTGGGCTACG

GACCCGGCTTTAAGCACGGCATCGAGGCCGACACCTTCGAGAACATCGAGGTGTACAATCTG

ATGTGCGACCTGCTGAATCTGACCCCTGCCCCCAACAATGGCACCCACGGCAGCCTGAACCA

TCTGCTGAAGAACCCCGTGTACACCCCTAAGCACCCCAAAGAGGTGCACCCCCTGGTGCAGT

GCCCCTTCACCAGAAACCCCAGAGACAACCTGGGCTGTAGCTGCAACCCCAGCATCCTGCCC

ATCGAGGACTTCCAGACCCAGTTCAACCTGACCGTGGCCGAGGAAAGATCATCAAGCACGA

GACACTGCCCTACGGCAGACCCCGGGTGCTGCAGAAAGAGAACACCATCTGCCTGCTGAGCC

AGCACCAGTTCATGAGCGGCTACTCCCAGGACATCCTGATGCCCCTGTGGACCAGCTACACC

GTGGACCGGAACGACAGCTTCTCCACCGAGGATTTCAGCAACTGCCTGTACCAGGATTTCCG

GATCCCCCTGAGCCCCGTGCACAAGTGCAGCTTCTACAAGAACAACACCAAGGTGTCCTACG

GCTTCCTGAGCCCTCCCCAGCTGAACAAGAACAGCTCCGGCATCTACAGCGAGGCCCTGCTG

ACTACCAACATCGTGCCCATGTACCAGAGCTTCCAAGTGATCTGGCGGTACTTCCACGACAC

CCTGCTGCGGAAGTACGCCGAAGAACGGAACGGCGTGAACGTGGTGTCCGGCCCAGTGTTCG
```

-continued

ACTTCGACTACGACGGCAGATGTGACAGCCTGGAAAATCTGCGGCAGAAAAGAAGAGTGATC

CGGAACCAGGAAATTCTGATCCCTACCCACTTCTTTATCGTGCTGACAAGCTGCAAGGATAC

CAGCCAGACCCCCCTGCACTGCGAGAACCTGGATACCCTGGCCTTCATCCTGCCTCACCGGA

CCGACAACAGCGAGAGCTGTGTGCACGGCAAGCACGACAGCTCTTGGGTGGAAGAACTGCTG

ATGCTGCACCGGGCCAGAATCACCGATGTGGAACACATCACCGGCCTGAGCTTTTACCAGCA

GCGGAAAGAACCCGTGTCCGATATCCTGAAGCTGAAAACCCATCTGCCCACCTTCAGCCAGG

AAGATGACAAGACCCACACTTGCCCCCCCTGCCCAGCTCCTGAACTGCTGGGAGGACCCTCT

GTGTTCCTGTTCCCCCCAAAGCCCAAGGACACCCTGATGATCTCTAGGACCCCCGAAGTCAC

TTGCGTCGTCGTCGACGTGTCCCACGAGGACCCTGAAGTCAAGTTCAACTGGTACGTCGACG

GTGTCGAAGTCCACAACGCCAAGACCAAGCCCAGGGAAGAACAGTACAACTCTACCTACCGC

GTCGTCAGCGTCCTGACCGTCCTGCACCAGGACTGGCTGAACGGAAAGGAATACAAGTGCAA

GGTGTCCAACAAGGCCCTGCCTGCCCCCATCGAAAAGACCATCTCTAAGGCCAAGGGACAGC

CCCGCGAACCCCAGGTCTACACCCTGCCCACCCTCTAGGGAAGAAATGACCAAGAACCAGGTG

TCCCTGACCTGCCTGGTCAAGGGATTCTACCCCTCTGACATCGCCGTCGAATGGGAATCTAA

CGGACAGCCCGAAAACAACTACAAGACCACCCCCCCTGTCCTGGACTCTGACGGATCATTCT

TCCTGTACTCTAAGCTGACTGTCGACAAGTCTAGGTGGCAGCAGGGAAACGTGTTCTCTTGC

TCTGTCATGCACGAAGCCCTGCACAACCACTACACCCAGAAGTCTCTGTCTCTGTCCCCCGG

AAAG

Nucleotide sequence of ENPP7-NPP1-Albumin
(SEQ ID NO: 74)
ATGAGAGGACCTGCCGTCCTGCTGACCGTCGCCCTGGCTACCTTGCTGGCCCCTGGTGCTGG TGCAcccagCTGCGCCAAAGAAGTGAAGTCCTGCAAGGGCCGGTGCTTCGAGCGGACCTTCG

GCAACTGCAGATGCGACGCCGCCTGTGTGGAACTGGGCAACTGCTGCCTGGACTACCAGGAA

ACCTGCATCGAGCCCGAGCACATCTGGACCTGCAACAAGTTCAGATGCGGCGAGAAGCGGCT

GACCAGATCCCTGTGTGCCTGCAGCGACGACTGCAAGGACAAGGGCGACTGCTGCATCAACT

ACAGCAGCGTGTGCCAGGGCGAGAAGTCCTGGGTGGAAGAACCCTGCGAGAGCATCAACGAG

CCCCAGTGCCCTGCCGGCTTCGAGACACCTCCTACCCTGCTGTTCAGCCTGGACGGCTTTCG

GGCCGAGTACCTGCACACATGGGGAGGCCTGCTGCCCGTGATCAGCAAGCTGAAGAAGTGCG

GCACCTACACCAAGAACATGCGGCCCGTGTACCCCACCAAGACCTTCCCCAACCACTACTCC

ATCGTGACCGGCCTGTACCCCGAGAGCCACGGCATCATCGACAACAAGATGTACGACCCCAA

GATGAACGCCAGCTTCAGCCTGAAGTCCAAAGAGAAGTTCAACCCCGAGTGGTATAAGGGCG

AGCCCATCTGGGTCACCGCCAAGTACCAGGGCCTGAAAAGCGGCACATTCTTTTGGCCCGGC

AGCGACGTGGAAATCAACGGCATCTTCCCCGACATCTATAAGATGTACAACGGCAGCGTGCC

CTTCGAGGAACGGATCCTGGCTGTGCTGCAGTGGCTGCAGCTGCCCAAGGATGAGCGGCCCC

ACTTCTACACCCTGTACCTGGAAGAACCTGACAGCAGCGGCCACAGCTACGGCCCTGTGTCC

AGCGAAGTGATCAAGGCCCTGCAGCGGGTGGACGGCATGGTGGGAATGCTGATGGACGGCCT

GAAAGAGCTGAACCTGCACAGATGCCTGAACCTGATCCTGATCAGCGACCACGGCATGGAAC

AGGGATCCTGCAAGAAGTACATCTACCTGAACAAGTACCTGGGCGACGTGAAGAACATCAAA

GTGATCTACGGCCCAGCCGCCAGACTGAGGCCTAGCGACGTGCCCGACAAGTACTACAGCTT

CAACTACGAGGGAATCGCCCGGAACCTGAGCTGCAGAGAGCCCAACCAGCACTTCAAGCCCT

ACCTGAAGCACTTCCTGCCCAAGCGGCTGCACTTCGCCAAGAGCGACAGAATCGAGCCCCTG

ACCTTCTACCTGGACCCCCAGTGGCAGCTGGCCCTGAATCCCAGCGAGAGAAAGTACTGCGG

-continued

```
CAGCGGCTTCCACGGCTCCGACAACGTGTTCAGCAACATGCAGGCCCTGTTCGTGGGCTACG
GACCCGGCTTTAAGCACGGCATCGAGGCCGACACCTTCGAGAACATCGAGGTGTACAATCTG
ATGTGCGACCTGCTGAATCTGACCCCTGCCCCCAACAATGGCACCCACGGCAGCCTGAACCA
TCTGCTGAAGAACCCCGTGTACACCCCTAAGCACCCCAAAGAGGTGCACCCCCTGGTGCAGT
GCCCCTTCACCAGAAACCCCAGAGACAACCTGGGCTGTAGCTGCAACCCCAGCATCCTGCCC
ATCGAGGACTTCCAGACCCAGTTCAACCTGACCGTGGCCGAGGAAAAGATCATCAAGCACGA
GACACTGCCCTACGGCAGACCCCGGGTGCTGCAGAAAGAGAACACCATCTGCCTGCTGAGCC
AGCACCAGTTCATGAGCGGCTACTCCCAGGACATCCTGATGCCCCTGTGGACCAGCTACACC
GTGGACCGGAACGACAGCTTCTCCACCGAGGATTTCAGCAACTGCCTGTACCAGGATTTCCG
GATCCCCCTGAGCCCCGTGCACAAGTGCAGCTTCTACAAGAACAACACCAAGGTGTCCTACG
GCTTCCTGAGCCCTCCCCAGCTGAACAAGAACAGCTCCGGCATCTACAGCGAGGCCCTGCTG
ACTACCAACATCGTGCCCATGTACCAGAGCTTCCAAGTGATCTGGCGGTACTTCCACGACAC
CCTGCTGCGGAAGTACGCCAAGAACGGAACGGCGTGAACGTGGTGTCCGGCCCAGTGTTCG
ACTTCGACTACGACGGCAGATGTGACAGCCTGGAAAATCTGCGGCAGAAAAGAAGAGTGATC
CGGAACCAGGAAATTCTGATCCCTACCCACTTCTTTATCGTGCTGACAAGCTGCAAGGATAC
CAGCCAGACCCCCCTGCACTGCGAGAACCTGGATACCCTGGCCTTCATCCTGCCTCACCGGA
CCGACAACAGCGAGAGCTGTGTGCACGGCAAGCACGACAGCTCTTGGGTGGAAGAACTGCTG
ATGCTGCACCGGGCCAGAATCACCGATGTGGAACACATCACCGGCCTGAGCTTTTACCAGCA
GCGGAAAGAACCCGTGTCCGATATCCTGAAGCTGAAAACCCATCTGCCCACCTTCAGCCAGG
AAGATGGTGGAGGAGGCTCTGGTGGAGGCGGTAGCGGAGGCGGAGGGTCGGGAGGTTCTGGA
TCAATGAAGTGGGTAACCTTTATTTCCCTTCTTTTTCTCTTTAGCTCGGCTTATTCCAGGGG
TGTGTTTCGTCGAGATGCACACAAGAGTGAGGTTGCTCATCGGTTTAAAGATTTGGGAGAAG
AAAATTTCAAAGCCTTGGTGTTGATTGCCTTTGCTCAGTATCTTCAGCAGTGTCCATTTGAA
GATCATGTAAAATTAGTGAATGAAGTAACTGAATTTGCAAAAACATGTGTTGCTGATGAGTC
AGCTGAAAATTGTGACAAATCACTTCATACCCTTTTTGGAGACAAATTATGCACAGTTGCAA
CTCTTCGTGAAACCTATGGTGAAATGGCTGACTGCTGTGCAAAACAAGAACCTGAGAGAAAT
GAATGCTTCTTGCAACACAAAGATGACAACCCAAACCTCCCCCGATTGGTGAGACCAGAGGT
TGATGTGATGTGCACTGCTTTTCATGACAATGAAGAGACATTTTTGAAAAAATACTTATATG
AAAATTGCCAGAAGACATCCTTACTTTTATGCCCCGGAACTCCTTTTCTTTGCTAAAAGGTAT
AAAGCTGCTTTTACAGAATGTTGCCAAGCTGCTGATAAAGCTGCCTGCCTGTTGCCAAAGCT
CGATGAACTTCGGGATGAAGGGAAGGCTTCGTCTGCCAAACAGAGACTCAAGTGTGCCAGTC
TCCAAAAATTTGGAGAAAGAGCTTTCAAAGCATGGGCAGTAGCTCGCCTGAGCCAGAGATTT
CCCAAAGCTGAGTTTGCAGAAGTTTCCAAGTTAGTGACAGATCTTACCAAAGTCCACACGGA
ATGCTGCCATGGAGATCTGCTTGAATGTGCTGATGACAGGGCGGACCTTGCCAAGTATATCT
GTGAAAATCAAGATTCGATCTCCAGTAAACTGAAGGAATGCTGTGAAAAACCTCTGTTGGAA
AAATCCCACTGCATTGCCGAAGTGGAAAATGATGAGATGCCTGCTGACTTGCCTTCATTAGC
TGCTGATTTTGTTGAAAGTAAGGATGTTTGCAAAAACTATGCTGAGGCAAAGGATGTCTTCC
TGGGCATGTTTTTGTATGAATATGCAAGAAGGCATCCTGATTACTCTGTCGTGCTGCTGCTG
AGACTTGCCAAGACATATGAAACCACTCTAGAGAAGTGCTGTGCCGCTGCAGATCCTCATGA
ATGCTATGCCAAAGTGTTCGATGAATTTAAACCTCTTGTGGAAGAGCCTCAGAATTTAATCA
```

-continued

```
AACAAAATTGTGAGCTTTTTGAGCAGCTTGGAGAGTACAAATTCCAGAATGCGCTATTAGTT
CGTTACACCAAGAAAGTACCCCAAGTGTCAACTCCAACTCTTGTAGAGGTCTCAAGAAACCT
AGGAAAAGTGGGCAGCAAATGTTGTAAACATCCTGAAGCAAAAGAATGCCCTGTGCAGAAG
ACTATCTATCCGTGGTCCTGAACCAGTTATGTGTGTTGCATGAGAAAACGCCAGTAAGTGAC
AGAGTCACCAAATGCTGCACAGAATCCTTGGTGAACAGGCGACCATGCTTTTCAGCTCTGGA
AGTCGATGAAACATACGTTCCCAAAGAGTTTAATGCTGAAACATTCACCTTCCATGCAGATA
TATGCACACTTTCTGAGAAGGAGAGACAAATCAAGAAACAAACTGCACTTGTTGAGCTCGTG
AAACACAAGCCCAAGGCAACAAAAGAGCAACTGAAAGCTGTTATGGATGATTTCGCAGCTTT
TGTAGAGAAGTGCTGCAAGGCTGACGATAAGGAGACCTGCTTTGCCGAGGAGGGTAAAAAAC
TTGTTGCTGCAAGTCAAGCTGCCTTAGGCTTA
```

Nucleotide sequence of ENPP3
(SEQ ID NO: 75)
```
ATGGAATCTACGTTGACTTTAGCAACGGAACAACCTGTTAAGAAGAACACTCTTAAGAAATA
TAAAATAGCTTGCATTGTTCTTCTTGCTTTGCTGGTGATCATGTCACTTGGATTAGGCCTGG
GGCTTGGACTCAGGAAACTGGAAAAGCAAGGCAGCTGCAGGAAGAAGTGCTTTGATGCATCA
TTTAGAGGACTGGAGAACTGCCGGTGTGATGTGGCATGTAAAGACCGAGGTGATTGCTGCTG
GGATTTTGAAGACACCTGTGTGGAATCAACTCGAATATGGATGTGCAATAAATTTCGTTGTG
GAGAGACCAGATTAGAGGCCAGCCTTTGCTCTTGTTCAGATGACTGTTTGCAGAGGAAAGAT
TGCTGTGCTGACTATAAGAGTGTTTGCCAAGGAGAAACCTCATGGCTGGAAGAAAACTGTGA
CACAGCCCAGCAGTCTCAGTGCCCAGAAGGGTTTGACCTGCCACCAGTTATCTTGTTTTCTA
TGGATGGATTTAGAGCTGAATATTTATACACATGGGATACTTTAATGCCAAATATCAATAAA
CTGAAAACATGTGGAATTCATTCAAAATACATGAGAGCTATGTATCCTACCAAAACCTTCCC
AAATCATTACACCATTGTCACGGGCTTGTATCCAGAGTCACATGGCATCATTGACAATAATA
TGTATGATGTAAATCTCAACAAGAATTTTTCACTTTCTTCAAAGGAACAAAATAATCCAGCC
TGGTGGCATGGGCAACCAATGTGGCTGACAGCAATGTATCAAGGTTTAAAAGCCGCTACCTA
CTTTTGGCCCGGATCAGAAGTGGCTATAAATGGCTCCTTTCCTTCCATATACATGCCTTACA
ACGGAAGTGTCCCATTTGAAGAGAGGATTTCTACACTGTTAAAATGGCTGGACCTGCCCAAA
GCTGAAAGACCCAGGTTTTATACCATGTATTTTGAAGAACCTGATTCCTCTGGACATGCAGG
TGGACCAGTCAGTGCCAGAGTAATTAAAGCCTTACAGGTAGTAGATCATGCTTTTGGGATGT
TGATGGAAGGCCTGAAGCAGCGGAATTTGCACAACTGTGTCAATATCATCCTTCTGGCTGAC
CATGGAATGGACCAGACTTATTGTAACAAGATGGAATACATGACTGATTATTTTCCCAGAAT
AAACTTCTTCTACATGTACGAAGGGCCTGCCCCCCGCATCCGAGCTCATAATATACCTCATG
ACTTTTTTAGTTTTAATTCTGAGGAAATTGTTAGAAACCTCAGTTGCCGAAAACCTGATCAG
CATTTCAAGCCCTATTTGACTCCTGATTTGCCAAAGCGACTGCACTATGCCAAGAACGTCAG
AATCGACAAAGTTCATCTCTTTGTGGATCAACAGTGGCTGGCTGTTAGGAGTAAATCAAATA
CAAATTGTGGAGGAGGCAACCATGGTTATAACAATGAGTTTAGGAGCATGGAGGCTATCTTT
CTGGCACATGGACCCAGTTTTAAAGAGAAGACTGAAGTTGAACCATTTGAAAATATTGAAGT
CTATAACCTAATGTGTGATCTTCTACGCATTCAACCAGCACCAAACAATGGAACCCATGGTA
GTTTAAACCATCTTCTGAAGGTGCCTTTTTATGAGCCATCCCATGCAGAGGAGGTGTCAAAG
TTTTCTGTTTGTGGCTTTGCTAATCCATTGCCCACAGAGTCTCTTGACTGTTTCTGCCCTCA
CCTACAAAATAGTACTCAGCTGGAACAAGTGAATCAGATGCTAAATCTCACCCAAGAAGAAA
TAACAGCAACAGTGAAAGTAAATTTGCCATTTGGGAGGCCTAGGGTACTGCAGAAGAACGTG
```

-continued

```
GACCACTGTCTCCTTTACCACAGGGAATATGTCAGTGGATTTGGAAAAGCTATGAGGATGCC

CATGTGGAGTTCATACACAGTCCCCCAGTTGGGAGACACATCGCCTCTGCCTCCCACTGTCC

CAGACTGTCTGCGGGCTGATGTCAGGGTTCCTCCTTCTGAGAGCCAAAAATGTTCCTTCTAT

TTAGCAGACAAGAATATCACCCACGGCTTCCTCTATCCTCCTGCCAGCAATAGAACATCAGA

TAGCCAATATGATGCTTTAATTACTAGCAATTTGGTACCTATGTATGAAGAATTCAGAAAAA

TGTGGGACTACTTCCACAGTGTTCTTCTTATAAAACATGCCACAGAAAGAAATGGAGTAAAT

GTGGTTAGTGGACCAATATTTGATTATAATTATGATGGCCATTTTGATGCTCCAGATGAAAT

TACCAAACATTTAGCCAACACTGATGTTCCCATCCCAACACACTACTTTGTGGTGCTGACCA

GTTGTAAAAACAAGAGCCACACACCGGAAAACTGCCCTGGGTGGCTGGATGTCCTACCCTTT

ATCATCCCTCACCGACCTACCAACGTGGAGAGCTGTCCTGAAGGTAAACCAGAAGCTCTTTG

GGTTGAAGAAAGATTTACAGCTCACATTGCCCGGGTCCGTGATGTAGAACTTCTCACTGGGC

TTGACTTCTATCAGGATAAAGTGCAGCCTGTCTCTGAAATTTTGCAACTAAAGACATATTTA

CCAACATTTGAAACCACTATT
```

Nucleotide sequence of ENPP1

(SEQ ID NO: 76)

```
ATGGAACGGGACGGCTGTGCCGGCGGAGGATCAAGAGGCGGAGAAGGCGGCAGAGCCCCTAG

AGAAGGACCTGCCGGCAACGGCAGAGACAGAGGCAGATCTCATGCCGCCGAAGCCCCTGGCG

ATCCTCAGGCTGCTGCTTCTCTGCTGGCCCCATGGATGTGGGCGAGGAACCTCTGGAAAAG

GCCGCCAGAGCCAGAACCGCCAAGGACCCCAACACCTACAAGGTGCTGAGCCTGGTGCTGTC

CGTGTGCGTGCTGACCACCATCCTGGGCTGCATCTTCGGCCTGAAGCCCAGCTGCGCCAAAG

AAGTGAAGTCCTGCAAGGGCCGGTGCTTCGAGCGGACCTTCGGCAACTGCAGATGCGACGCC

GCCTGTGTGGAACTGGGCAACTGCTGCCTGGACTACCAGGAAACCTGCATCGAGCCCGAGCA

CATCTGGACCTGCAACAAGTTCAGATGCGGCGAGAAGCGGCTGACCAGATCCCTGTGTGCCT

GCAGCGACGACTGCAAGGACAAGGGCGACTGCTGCATCAACTACAGCAGCGTGTGCCAGGGC

GAGAAGTCCTGGGTGGAAGAACCCTGCGAGAGCATCAACGAGCCCCAGTGCCCTGCCGGCTT

CGAGACACCTCCTACCCTGCTGTTCAGCCTGGACGGCTTTCGGGCCGAGTACCTGCACACAT

GGGGAGGCCTGCTGCCCGTGATCAGCAAGCTGAAGAAGTGCGGCACCTACACCAAGAACATG

CGGCCCGTGTACCCCACCAAGACCTTCCCCAACCACTACTCCATCGTGACCGGCCTGTACCC

CGAGAGCCACGGCATCATCGACAACAAGATGTACGACCCCAAGATGAACGCCAGCTTCAGCC

TGAAGTCCAAAGAGAAGTTCAACCCCGAGTGGTATAAGGGCGAGCCCATCTGGGTCACCGCC

AAGTACCAGGGCCTGAAAAGCGGCACATTCTTTTGGCCCGGCAGCGACGTGGAAATCAACGG

CATCTTCCCCGACATCTATAAGATGTACAACGGCAGCGTGCCCTTCGAGGAACGGATCCTGG

CTGTGCTGCAGTGGCTGCAGCTGCCCAAGGATGAGCGGCCCCACTTCTACACCCTGTACCTG

GAAGAACCTGACAGCAGCGGCCACAGCTACGGCCCTGTGTCCAGCGAAGTGATCAAGGCCCT

GCAGCGGGTGGACGGCATGGTGGGAATGCTGATGGACGGCCTGAAAGAGCTGAACCTGCACA

GATGCCTGAACCTGATCCTGATCAGCGACCACGGCATGGAACAGGGATCCTGCAAGAAGTAC

ATCTACCTGAACAAGTACCTGGGCGACGTGAAGAACATCAAAGTGATCTACGGCCCAGCCGC

CAGACTGAGGCCTAGCGACGTGCCCGACAAGTACTACAGCTTCAACTACGAGGGAATCGCCC

GGAACCTGAGCTGCAGAGAGCCCAACCAGCACTTCAAGCCCTACCTGAAGCACTTCCTGCCC

AAGCGGCTGCACTTCGCCAAGAGCGACAGAATCGAGCCCCTGACCTTCTACCTGGACCCCCA

GTGGCAGCTGGCCCTGAATCCCAGCGAGAGAAAGTACTGCGGCAGCGGCTTCCACGGCTCCG
```

-continued

```
ACAACGTGTTCAGCAACATGCAGGCCCTGTTCGTGGGCTACGGACCCGGCTTTAAGCACGGC

ATCGAGGCCGACACCTTCGAGAACATCGAGGTGTACAATCTGATGTGCGACCTGCTGAATCT

GACCCCTGCCCCCAACAATGGCACCCACGGCAGCCTGAACCATCTGCTGAAGAACCCCGTGT

ACACCCCTAAGCACCCCAAAGAGGTGCACCCCCTGGTGCAGTGCCCCTTCACCAGAAACCCC

AGAGACAACCTGGGCTGTAGCTGCAACCCCAGCATCCTGCCCATCGAGGACTTCCAGACCCA

GTTCAACCTGACCGTGGCCGAGGAAAAGATCATCAAGCACGAGACACTGCCCTACGGCAGAC

CCCGGGTGCTGCAGAAAGAGAACACCATCTGCCTGCTGAGCCAGCACCAGTTCATGAGCGGC

TACTCCCAGGACATCCTGATGCCCCTGTGGACCAGCTACACCGTGGACCGGAACGACAGCTT

CTCCACCGAGGATTTCAGCAACTGCCTGTACCAGGATTTCCGGATCCCCCTGAGCCCCGTGC

ACAAGTGCAGCTTCTACAAGAACAACACCAAGGTGTCCTACGGCTTCCTGAGCCCTCCCCAG

CTGAACAAGAACAGCTCCGGCATCTACAGCGAGGCCCTGCTGACTACCAACATCGTGCCCAT

GTACCAGAGCTTCCAAGTGATCTGGCGGTACTTCCACGACACCCTGCTGCGGAAGTACGCCG

AAGAACGGAACGGCGTGAACGTGGTGTCCGGCCCAGTGTTCGACTTCGACTACGACGGCAGA

TGTGACAGCCTGGAAAATCTGCGGCAGAAAAGAAGAGTGATCCGGAACCAGGAAATTCTGAT

CCCTACCCACTTCTTTATCGTGCTGACAAGCTGCAAGGATACCAGCCAGACCCCCCTGCACT

GCGAGAACCTGGATACCCTGGCCTTCATCCTGCCTCACCGGACCGACAACAGCGAGAGCTGT

GTGCACGGCAAGCACGACAGCTCTTGGGTGGAAGAACTGCTGATGCTGCACCGGGCCAGAAT

CACCGATGTGGAACACATCACCGGCCTGAGCTTTTACCAGCAGCGGAAAGAACCCGTGTCCG

ATATCCTGAAGCTGAAAACCCATCTGCCCACCTTCAGCCAGGAAGAT
```

Methods

The invention includes a method of preventing, reversing, and/or reducing formation and/or progression of kidney stones in a subject in need thereof. In certain embodiments, the method comprises administering to the subject a therapeutically effective amount of a polypeptide comprising a ENPP1 polypeptide and/or a ENPP3 polypeptide, mutant, or mutant fragment thereof, the polypeptide having similar ATP hydrolytic activity to the native protein. In other embodiments, the subject is diagnosed with nephrolithiasis. In yet other embodiments, the subject is a mammal. In yet other embodiments, the mammal is human.

The invention further includes a method of preventing, reversing, and/or reducing formation and/or progression of nephrocalcinosis in a human subject. In certain embodiments, the subject is diagnosed with nephrocalcinosis. In other embodiments, the subject is prone to developing nephrocalcinosis. In yet other embodiments, the subject has a family history of nephrocalcinosis. In yet other embodiments, the subject has suffered from nephrocalcinosis. In yet other embodiments, the subject does not suffer from any severe disease of calcification, In yet other embodiments, the subject does not suffer from end-stage renal disease (ESRD). In yet other embodiments, the subject does not suffer from generalized arterial calcification of infancy (GACI). In yet other embodiments, the subject does not suffer from diabetes mellitus II. In yet other embodiments, the subject does not suffer from autosomal-recessive hypophosphatemic rickets. In yet other embodiments, the subject does not suffer from cardiovascular disorder. In yet other embodiments, the subject does not suffer from atherosclerosis. In yet other embodiments, the subject does not suffer from chronic kidney disease (CKD). In yet other embodiments, the subject does not suffer from pseudoxanthoma elasticum (PXE).

In yet other embodiments, the subject suffers from end-stage renal disease (ESRD). In yet other embodiments, the subject suffers from generalized arterial calcification of infancy (GACI). In yet other embodiments, the subject suffers from diabetes mellitus II. In yet other embodiments, the subject suffers from autosomal-recessive hypophosphatemic rickets. In yet other embodiments, the subject suffers from cardiovascular disorder. In yet other embodiments, the subject suffers from atherosclerosis. In yet other embodiments, the subject suffers from chronic kidney disease (CKD). In yet other embodiments, the subject suffers from pseudoxanthoma elasticum (PXE).

Nephrolithiasis involves formation or progression of a kidney stone in a kidney tubule. In certain embodiments, the nephrolithiasis is cystine stones. In other embodiments, the nephrolithiasis is calcium stone disease (in certain embodiments, caused by idiopathic hypercalciuria). In yet other embodiments, the nephrolithiasis is uric acid stone disease (in certain embodiments, caused by gout). In yet other embodiments, the nephrolithiasis is struvite stone disease (in certain embodiments, caused by urinary tract infections). In yet other embodiments, the nephrolithiasis is oxalate stone disease (in certain embodiments, caused by hyperoxaluria). In yet other embodiments, the nephrolithiasis is hypercalcinuria.

Nephrolithiasis does not comprise, or correspond to, calcification in a renal parenchyma and/or renal soft tissue. In certain embodiments, the subject does not suffer from GACI (generalized arterial calcification of infancy).

In certain embodiments, the subject had kidney stones, has had kidney stones, has renal stones, or has a family history of renal stones. In other embodiments, the subject has a high likelihood of developing renal stones. In yet other embodiments, the subject has predisposition to developing renal stones.

In certain embodiments, the subject is Npt2a$^{-/-}$. In other embodiments, the subject is Npt2a$^{-/-}$. In yet other embodiments, the subject is Npt2c$^{-/-}$. In yet other embodiments, the subject is Npt2c$^{-/-}$.

In certain embodiments, the subject is homozygous for a gene causing renal calcifications. In other embodiments, the subject is heterozygous for a gene causing renal calcifications.

In certain embodiments, the ENPP1 polypeptide or ENPP3 polypeptide, mutant, or mutant fragment thereof is administered as a precursor molecule that is cleaved to provide a soluble ENPP1 or ENPP3 protein, respectively. In certain embodiments, the ENPP1 polypeptide or ENPP3 polypeptide, mutant, or mutant fragment thereof is administered as a soluble ENPP1 or ENPP3 protein itself. In yet other embodiments, the ENPP1 polypeptide or ENPP3 polypeptide, mutant, or mutant fragment thereof is administered as a soluble ENPP1 or ENPP3 protein fused to a moiety that increases half-life and/or reduces immunogenicity of the ENPP1 or ENPP3 soluble protein. Such moieties include, for example, Ig Fc domain, PEG and/or albumin. In yet other embodiments, the soluble ENPP1 or ENPP3 polypeptide, or the precursor thereof, comprises a ENPP2, ENPP5 and/or ENPP7 signal sequence fused to a ENPP1 or ENPP3 polypeptide, respectively.

In certain embodiments, the soluble ENPP1 polypeptide comprises residues 96-925 of human ENPP1 [NCBI #006199, SEQ ID NO: I]. In other embodiments, the soluble ENPP1 polypeptide is a secreted product of a precursor polypeptide expressed in a mammalian cell, wherein the precursor polypeptide comprises a signal sequence and ENPP1, wherein the precursor polypeptide undergoes proteolytic processing to the soluble ENPP1 polypeptide.

It will be understood that the use of a ENPP1 polypeptide or ENPP3 polypeptide according to the invention includes not only the native human proteins, but also any fragment, derivative, fusion, conjugate or mutant thereof having ATP hydrolytic activity of the native protein. As used herein in this disclosure, the phrase "a ENPP1 polypeptide and/or a ENPP3 polypeptide, mutant, or mutant fragment thereof" also includes any compound or polypeptide (such as, but not limited to, a fusion protein) comprising a ENPP1 polypeptide and/or a ENPP3 polypeptide, mutant, or mutant fragment thereof. Fusion proteins according to the invention are considered biological equivalents of ENPP1 and ENPP3, but are intended to provide longer half-life.

In certain embodiments, the polypeptide of the invention, or its precursor, is administered by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary and topical. In other embodiments, the polypeptide of the invention, or its precursor, is administered to the subject as a pharmaceutical composition further comprising at least one pharmaceutically acceptable carrier.

In certain embodiments, the polypeptide of the invention is administered acutely or chronically to the subject. In other embodiments, the polypeptide of the invention is administered locally, regionally or systemically to the subject. In yet another embodiment, the polypeptide of the invention or its precursor is delivered on an encoded vector, wherein the vector encodes the protein and it is transcribed and translated from the vector upon administration of the vector to the subject.

It will be appreciated by one of skill in the art, when armed with the present disclosure including the methods detailed herein, that the invention is not limited to treatment of a disease or disorder once it is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit.

Thus, the present invention, as described more fully herein, includes a method for preventing diseases and disorders in a subject, in that a compound of the invention, as discussed elsewhere herein, can be administered to a subject prior to the onset of the disease or disorder, thereby preventing the disease or disorder from developing. Particularly, where the symptoms of renal calcifications have not manifested to the point of detriment to the subject; indeed, renal calcifications need not be detected in a subject before treatment is administered. That is, significant pathology from renal calcifications does not have to occur before the present invention may provide benefit. Therefore, the present invention includes methods for preventing or delaying onset, or reducing progression or growth, of renal calcifications in a subject, in that a compound of the invention can be administered to a subject prior to detection of renal calcifications. In certain embodiments, the compound of the invention is administered to a subject with a strong family history of renal calcifications, thereby preventing or delaying onset or the progression of or the formation of renal calcifications.

Armed with the disclosure herein, one skilled in the art would thus appreciate that the prevention of a disease or disorder in a subject encompasses administering to a subject a compound of the invention as a preventative measure against renal stone formation and/or growth.

Pharmaceutical Compositions and Formulations

The invention provides pharmaceutical compositions comprising a compound of the invention within the methods described herein.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between about 0.1% and about 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Administration/Dosing

The regimen of administration may affect what constitutes an effective amount. For example, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation. In certain embodiments, administration of the compound of the invention to a subject elevates the subject's plasma PPi to a level of about 2.5 µM.

Administration of the compositions of the present invention to a patient, such as a mammal, such as a human, may be carried out using known procedures, at dosages and for periods of time effective to treat a disease or disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an patient as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the patient.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. The frequency of administration of the various combination compositions of the invention varies from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. The formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Single unit dosage forms suitable for oral administration, such as tablets, capsules, gelcaps, and caplets, which are adapted for controlled-release are encompassed by the present invention.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form. For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation. In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and preparation conditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Methods and Materials
Animals

A C57BL/6 mouse (Jackson Labs), which undergoes diet-induced formation of renal stones, is used as a model for nephrolithiasis. Kidney stone formation is induced by feeding the model mouse with a high calcium, low magnesium diet (such as Teklad Labs diet TD.00042, Harlan Labs, Madison, WI).

Male and female C57BL/6 mice are obtained from Charles River Laboratory, MA. Male and female Npt2a$^{-/-}$ mice (B6.129S2-Slc34a1$^{tm1Hten}$/J, Stock No: 004802), and Enpp1$^{asj/asj}$ mice (C57BL/6J-Enpp1$^{asj}$/GrsJ Stock No: 012810) are purchased from The Jackson Laboratory, ME. The Enpp1$^{asj}$ allele is leaky and shows approximately 15% level of Enpp1 activity compared to wild-type controls (Li, et al., 2013, Dis. Model Mech. 6:1227-1235). Mice are genotyped by PCR amplification of genomic DNA extracted from tail clippings and amplified by polymerase chain reaction (PCR) as described (Albright, et al., 2015, Nat. Commun. 6:10006). Mice are weaned at 3 weeks of age and allowed free access to water and regular chow (1.0% calcium, 0.7% phosphorus, of which 0.3% phosphorus is readily available for absorption, Harlan Teklad TD.2018S). Mice are sacrificed at 4 weeks after daily intraperitoneal (i.p.) injection of Hanks Buffered Saline (Gibco, Life Sciences) or sodium pyrophosphate in HBSS for two weeks (160 micromol/Kg/day) according to O'Neill, et al., 2011, Kidney Int. 79:512-517. To determine whether kidney stones persist beyond weaning age mice are sacrificed at 10 weeks of age after overnight fast and approximately 18-24 hours following the last i.p. injection as described (Caballero, et al., 2016, Am. J. Physiol. Renal Physiol. ajprenal 0036702016). The background of all mouse lines is C57BL/6, use of littermates for controls further reduced bias based on genetic background. No difference in renal stones was observed between sexes as previously reported (Caballero, et al., 2016, Am. J. Physiol. Renal Physiol. ajprenal 0036702016) and thus both genders were combined here.

Blood and Urine Parameters

Biochemical analyses are done on blood samples collected by orbital exsanguination and spot urines following an overnight fast at the same time of day between 10 AM and 2 PM. Following deproteinization of heparinized plasma by filtration (NanoSep 300 K, Pall Corp., Ann Arbor, MI), plasma and urinary total pyrophosphate (PPi) concentrations are determined using a fluorometric probe (AB112155, ABCAM, Cambridge, MA). Urine PPi is corrected for urine creatinine, which is measured by LC-MS/MS or by ELISA using appropriate controls to adjust for inter-assay variability.

Kidney Histology

Left kidneys are fixed in 4% formalin/PBS at 4° C. for 12 h and then dehydrated with increasing concentration of ethanol and xylene, followed by paraffin embedding. Mineral deposits are determined on 10 μm von Kossa stained sections counterstained with 1% methyl green. Hematoxyline/eosin is used as counterstain for morphological evaluation. Histomorphometric evaluation of one saggital kidney section that includes cortex, medulla and pelvis per animal is performed blinded by two independent observers using an Osteomeasure System (Osteometrics, Atlanta, GA). Mineralization size was determined using the formula: calc. size=calcified area/number of observed calcified areas per section.

For transmission electron microscopy, a 1 mm$^3$ block of the left kidney was fixed in 2.5% glutaraldehyde and 2% paraformaldehyde in phosphate buffered saline for 2 hours, followed by post-fixation in 1% osmium liquid for 2 hours. Dehydration is carried out using a series of ethanol concentrations (50% to 100%). Renal tissue is embedded in epoxy resin, and polymerization is carried out at 60° C. for overnight. After preparing a thin section (50 nm), the tissues are double stained with uranium and lead and observed using a Tecnai Biotwin (LaB6, 80 kV) (FEI, Thermo Fisher, Hillsboro, OR) at the Yale Center for Cellular and Molecular Imaging (YCCMI).

Renal Gene Expression Analysis

Right kidneys are used for preparation of total RNA using Trizol (Thermo Fisher Sci, Inc., Waltham, MA). qRT-PCR (Omniscript, QuantiTect, Qiagen, Valencia, CA) is performed in an ABI-Step One Plus Cycler (Fisher, life technologies, Waltham, MA) using the mouse beta actin forward primer: GGCTGTATTCCCCTCCATCG (SEQ ID NO:77), and reverse primer: CCAGTTGGTAACAATGCCATGT (SEQ ID NO:78), the mouse Enpp1 forward primer: CTGGTTTTGTCAGTATGTGTGCT (SEQ ID NO:79) and reverse primer: CTCACCGCACCTGAATTTGTT (SEQ ID NO:80), the mouse Entpd5 forward primer: CCAAAGACTCGATCCCCAGAA (SEQ ID NO:81) and reverse primer: TGTTAGAAAGTTCACGGTAACCC (SEQ ID NO: 82), the mouse Ank forward primer: TACGGGCTGGCGTATTCTTTG (SEQ ID NO:83) and reverse primer: CACTGTAGGCTATCAGGGTGT (SEQ ID NO:84), and the mouse Tnsalp forward primer CCAACTCTTTTGTGCCAGAGA (SEQ ID NO:85) and reverse primer: GGCTACATTGGTGTTGAGCTTTT (SEQ ID NO:86).

Statistical Analysis

Data are expressed as means±SEM and analyzed in Microsoft Excel 2010 or Graphpad Prism 6.0. Differences were considered significant, if p-values using an unpaired, two-tailed Student's t-test or one-way ANOVA using Tukey's adjustment for multiple comparisons were smaller than 0.05.

Example 1: Treatment of Nephrolithiasis Using ENPP1 Polypeptide

The invention contemplates the administration of a soluble ENPP1 polypeptide to a mouse model of nephrolithiasis, in order to reduce renal tubule stone formation. In certain embodiments, the soluble ENPP1 polypeptide reduces the size and/or number of kidney stones and/or prevents and/or reverses formation of kidney stones in the mouse model.

Intraperitoneal injection of ENPP1 at a dosage of 5-40 mg/kg to the model mouse is performed every day for a period of 4 weeks, starting at 2 weeks of age. After the completion of 4 weeks, the mice are sacrificed and the kidneys are analyzed to identify the presence of kidney stones in order to determine the effect of ENPP1 administration. In certain embodiments, administration of a ENPP1 polypeptide reduces the size and/or the amount of kidney stones by at least about 10%, 25%, 30%, 40%, or 50%, or more, when compared with untreated mutant mice.

Untreated model mice exhibit intratubular stones on light microscopy, using transmission electron microscopy (TEM; Khan, et al., 2011, J. Urol 0.186:1107-1113). In certain embodiments, administration of a ENPP1 polypeptide results in significantly reduced kidney stones and/or stone formation. In other embodiments, similar results are obtained by administering any ENPP1 polypeptide or fusion variants thereof, such as ENPP1-Fc or ENPP1-Albumin fusion proteins.

Example 2: Treatment of Renal Stones Using ENPP3

The invention contemplates the administration of a soluble ENPP3 polypeptide to a mouse model of nephrolithiasis, in order to reduce renal tubule stone formation. In certain embodiments, the soluble ENPP3 polypeptide reduces the size and/or number of kidney stones and/or prevents and/or reverses formation of kidney stones in the mouse model.

Intraperitoneal injection of ENPP3 at a dosage of 5-40 mg/kg to the model mouse is performed every day for a period of 4 weeks, starting at 2 weeks of age. After the completion of 4 weeks, the mice are sacrificed and the kidneys are analyzed to identify the presence of kidney stones in order to determine the effect of ENPP3 administration. In certain embodiments, administration of a ENPP3 polypeptide reduces the size and/or the amount of kidney stones by at least about 10%, 25%, 30%, 40%, or 50%, or more, when compared with untreated mutant mice.

Untreated model mice exhibit intratubular stones on light microscopy, using transmission electron microscopy (TEM; Khan, et al., 2011, J. Urol 0.186:1107-1113). In certain embodiments, administration of a ENPP3 polypeptide results in significantly reduced kidney stones and/or stone formation. In other embodiments, similar results are obtained by administering any ENPP3 polypeptide or fusion variants thereof, such as ENPP1-Fc or ENPP1-Albumin fusion proteins.

ENUMERATED EMBODIMENTS

The following exemplary embodiments are provided, the numbering of which is not to be construed as designating levels of importance:

Embodiment 1 provides a method of reducing progression of nephrolithiasis in a human subject diagnosed with nephrolithiasis, the method comprising administering a therapeutically effective amount of a soluble ENPP1 polypeptide to the subject, wherein progression of the nephrolithiasis is reduced in the subject.

Embodiment 2 provides the method of Embodiment 1, wherein the soluble ENPP1 polypeptide is fused to a moiety that increases half-life and/or reduces immunogenicity of the soluble ENPP1 polypeptide.

Embodiment 3 provides the method of Embodiment 2, wherein the moiety is selected from the group consisting of an immunoglobulin (Ig) Fc domain, polyethylene glycol (PEG) and albumin.

Embodiment 4 provides the method of any of Embodiments 1-3, wherein the soluble ENPP1 polypeptide is fused to a bone targeting domain.

Embodiment 5 provides the method of any of Embodiments 1-4, wherein the soluble ENPP1 polypeptide is a secreted product of a precursor polypeptide comprising a signal sequence fused to the soluble ENPP1 polypeptide, wherein the signal sequence is selected from the group consisting of ENPP2 signal sequence, ENPP5 signal sequence, and ENPP7 signal sequence.

Embodiment 6 provides the method of any of Embodiments 1-5, wherein the nephrolithiasis is selected from the group consisting of cystinuria, uric acid stone disease, struvite stone disease, hypercalcinuria, calcium stone disease, and hyperoxaluria.

Embodiment 7 provides the method of any of Embodiments 1-6, wherein the nephrolithiasis is calcium stone disease.

Embodiment 8 provides the method of any of Embodiments 1-7, wherein the nephrolithiasis comprises at least one kidney stone containing a mineral selected from the group consisting of oxalate, urate, cystine, hydroxyurea, and calcium phosphate.

Embodiment 9 provides the method of any of Embodiments 1-8, wherein the subject is administered the soluble ENPP1 polypeptide via a route selected from the group consisting of local, regional, parenteral and systemic.

Embodiment 10 provides a method of reducing progression of nephrolithiasis in a subject diagnosed with nephrolithiasis, the method comprising administering a therapeutically effective amount of a soluble ENPP3 polypeptide to the subject, wherein progression of the nephrolithiasis is reduced in the subject.

Embodiment 11 provides the method of Embodiment 10, wherein the soluble ENPP3 polypeptide is fused to a moiety that increases half-life and/or reduces immunogenicity of the soluble ENPP3 polypeptide.

Embodiment 12 provides the method of Embodiment 11, wherein the moiety is selected from the group consisting of an immunoglobulin (Ig) Fc domain, polyethylene glycol (PEG) and albumin.

Embodiment 13 provides the method of any of Embodiments 10-12, wherein the soluble ENPP3 polypeptide is fused to a bone targeting domain.

Embodiment 14 provides the method of any of Embodiments 10-13, wherein the soluble ENPP3 polypeptide is a secreted product of a precursor polypeptide comprising a signal sequence fused to the soluble ENPP3 polypeptide, wherein the signal sequence is selected from the group consisting of ENPP2 signal sequence, ENPP5 signal sequence and ENPP7 signal sequence.

Embodiment 15 provides the method of any of Embodiments 10-14, wherein the nephrolithiasis is selected from the group consisting of cystinuria, uric acid stone disease, struvite stone disease, hypercalcinuria, calcium stone disease, and hyperoxaluria.

Embodiment 16 provides the method of any of Embodiments 10-15, wherein the nephrolithiasis is calcium stone disease.

Embodiment 17 provides the method of any of Embodiments 10-16, wherein the nephrolithiasis comprises at least one kidney stone containing a mineral selected from the group consisting of oxalate, urate, cystine, hydroxyurea, and calcium phosphate.

Embodiment 18 provides the method of any of Embodiments 10-17, wherein the subject is administered the soluble ENPP3 polypeptide via a route selected from the group consisting of local, regional, parenteral and systemic.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of reducing progression of nephrolithiasis in a subject diagnosed with nephrolithiasis,
the method comprising administering a therapeutically effective amount of a soluble EctoNucleotide Pyrophosphatase/Phosphodiesterase 3 (ENPP3) polypeptide to the subject, wherein progression of the nephrolithiasis is reduced in the subject.

2. The method of claim 1, wherein the soluble ENPP3 polypeptide is further fused to a moiety that increases half-life or reduces immunogenicity of the soluble ENPP3 polypeptide relative to the soluble ENPP3 polypeptide lacking the moiety.

3. The method of claim 2, wherein the moiety is selected from the group consisting of an immunoglobulin (Ig) Fc domain, polyethylene glycol (PEG), and albumin.

4. The method of claim 1, wherein the soluble ENPP3 polypeptide is further fused to a bone targeting domain.

5. The method of claim 1, wherein the soluble ENPP3 polypeptide is a secreted product of a precursor polypeptide comprising a signal sequence fused to the soluble ENPP3 polypeptide, wherein the signal sequence is selected from the group consisting of ENPP2 signal sequence, ENPP5 signal sequence and ENPP7 signal sequence.

6. The method of claim 1, wherein the nephrolithiasis is selected from the group consisting of cystinuria, uric acid stone disease, struvite stone disease, hypercalcinuria, calcium stone disease, and hyperoxaluria.

7. The method of claim 6, wherein the nephrolithiasis is calcium stone disease.

8. The method of claim 1, wherein the nephrolithiasis comprises at least one kidney stone containing a mineral selected from the group consisting of oxalate, urate, cystine, hydroxyurea, and calcium phosphate.

9. The method of claim 1, wherein the subject is administered the soluble ENPP3 polypeptide via a route selected from the group consisting of local, regional, parenteral, and systemic.

* * * * *

SEQUENCE LISTING

```
<160> NUMBER OF SEQ ID NOS: 86

<210> SEQ ID NO 1
<211> LENGTH: 925
<212> TYPE: PRT
<213> ORGANISM: Homo sapiens

<400> SEQUENCE: 1

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Val Leu Ser Leu
65                  70                  75                  80

Val Leu Ser Val Cys Val Leu Thr Thr Ile Leu Gly Cys Ile Phe Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270
```

```
Gly Ile Ile Asp Asn Lys Met Tyr Asp Pro Lys Met Asn Ala Ser Phe
            275                 280                 285

Ser Leu Lys Ser Lys Glu Lys Phe Asn Pro Glu Trp Tyr Lys Gly Glu
        290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
        370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
        450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
                500                 505                 510

Tyr Leu Asp Pro Gln Trp Gln Leu Ala Leu Asn Pro Ser Glu Arg Lys
            515                 520                 525

Tyr Cys Gly Ser Gly Phe His Gly Ser Asp Asn Val Phe Ser Asn Met
        530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
        610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685
```

```
Met Pro Leu Trp Thr Ser Tyr Thr Val Asp Arg Asn Asp Ser Phe Ser
    690             695                 700             705?

-wait
```

```
Met Pro Leu Trp Thr Ser Tyr Thr Val Asp Arg Asn Asp Ser Phe Ser
    690             695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
                740                 745                 750

Tyr Ser Glu Ala Leu Leu Thr Thr Asn Ile Val Pro Met Tyr Gln Ser
            755                 760                 765

Phe Gln Val Ile Trp Arg Tyr Phe His Asp Thr Leu Leu Arg Lys Tyr
770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
                820                 825                 830

Ile Val Leu Thr Ser Cys Lys Asp Thr Ser Gln Thr Pro Leu His Cys
            835                 840                 845

Glu Asn Leu Asp Thr Leu Ala Phe Ile Leu Pro His Arg Thr Asp Asn
850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
                900                 905                 910

Lys Leu Lys Thr His Leu Pro Thr Phe Ser Gln Glu Asp
            915                 920                 925

<210> SEQ ID NO 2
<211> LENGTH: 888
<212> TYPE: PRT
<213> ORGANISM: Homo sapiens

<400> SEQUENCE: 2

Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140
```

-continued

```
Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
            165                 170                 175

Ser Tyr Met Lys Lys Gly Ser Lys Val Met Pro Asn Ile Glu Lys Leu
        180                 185                 190

Arg Ser Cys Gly Thr His Ser Pro Tyr Met Arg Pro Val Tyr Pro Thr
    195                 200                 205

Lys Thr Phe Pro Asn Leu Tyr Thr Leu Ala Thr Gly Leu Tyr Pro Glu
210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
            245                 250                 255

Gly Gln Pro Leu Trp Ile Thr Ala Thr Lys Gln Gly Val Lys Ala Gly
        260                 265                 270

Thr Phe Phe Trp Ser Val Val Ile Pro His Glu Arg Ile Leu Thr
    275                 280                 285

Ile Leu Gln Trp Leu Thr Leu Pro Asp His Glu Arg Pro Ser Val Tyr
290                 295                 300

Ala Phe Tyr Ser Glu Gln Pro Asp Phe Ser Gly His Lys Tyr Gly Pro
305                 310                 315                 320

Phe Gly Pro Glu Met Thr Asn Pro Leu Arg Glu Ile Asp Lys Ile Val
            325                 330                 335

Gly Gln Leu Met Asp Gly Leu Lys Gln Leu Lys Leu His Arg Cys Val
        340                 345                 350

Asn Val Ile Phe Val Gly Asp His Gly Met Glu Asp Val Thr Cys Asp
    355                 360                 365

Arg Thr Glu Phe Leu Ser Asn Tyr Leu Thr Asn Val Asp Asp Ile Thr
370                 375                 380

Leu Val Pro Gly Thr Leu Gly Arg Ile Arg Ser Lys Phe Ser Asn Asn
385                 390                 395                 400

Ala Lys Tyr Asp Pro Lys Ala Ile Ile Ala Asn Leu Thr Cys Lys Lys
            405                 410                 415

Pro Asp Gln His Phe Lys Pro Tyr Leu Lys Gln His Leu Pro Lys Arg
        420                 425                 430

Leu His Tyr Ala Asn Asn Arg Arg Ile Glu Asp Ile His Leu Leu Val
    435                 440                 445

Glu Arg Arg Trp His Val Ala Arg Lys Pro Leu Asp Val Tyr Lys Lys
450                 455                 460

Pro Ser Gly Lys Cys Phe Phe Gln Gly Asp His Gly Phe Asp Asn Lys
465                 470                 475                 480

Val Asn Ser Met Gln Thr Val Phe Val Gly Tyr Gly Ser Thr Phe Lys
            485                 490                 495

Tyr Lys Thr Lys Val Pro Pro Phe Glu Asn Ile Glu Leu Tyr Asn Val
        500                 505                 510

Met Cys Asp Leu Leu Gly Leu Lys Pro Ala Pro Asn Asn Gly Thr His
    515                 520                 525

Gly Ser Leu Asn His Leu Leu Arg Thr Asn Thr Phe Arg Pro Thr Met
530                 535                 540

Pro Glu Glu Val Thr Arg Pro Asn Tyr Pro Gly Ile Met Tyr Leu Gln
545                 550                 555                 560
```

```
Ser Asp Phe Asp Leu Gly Cys Thr Cys Asp Asp Lys Val Glu Pro Lys
            565                 570                 575

Asn Lys Leu Asp Glu Leu Asn Lys Arg Leu His Thr Lys Gly Ser Thr
        580                 585                 590

Glu Ala Glu Thr Arg Lys Phe Arg Gly Ser Arg Asn Glu Asn Lys Glu
    595                 600                 605

Asn Ile Asn Gly Asn Phe Glu Pro Arg Lys Glu Arg His Leu Leu Tyr
610                 615                 620

Gly Arg Pro Ala Val Leu Tyr Arg Thr Arg Tyr Asp Ile Leu Tyr His
625                 630                 635                 640

Thr Asp Phe Glu Ser Gly Tyr Ser Glu Ile Phe Leu Met Pro Leu Trp
            645                 650                 655

Thr Ser Tyr Thr Val Ser Lys Gln Ala Glu Val Ser Ser Val Pro Asp
            660                 665                 670

His Leu Thr Ser Cys Val Arg Pro Asp Val Arg Val Ser Pro Ser Phe
            675                 680                 685

Ser Gln Asn Cys Leu Ala Tyr Lys Asn Asp Lys Gln Met Ser Tyr Gly
        690                 695                 700

Phe Leu Phe Pro Pro Tyr Leu Ser Ser Ser Pro Glu Ala Lys Tyr Asp
705                 710                 715                 720

Ala Phe Leu Val Thr Asn Met Val Pro Met Tyr Pro Ala Phe Lys Arg
                725                 730                 735

Val Trp Asn Tyr Phe Gln Arg Val Leu Val Lys Lys Tyr Ala Ser Glu
                740                 745                 750

Arg Asn Gly Val Asn Val Ile Ser Gly Pro Ile Phe Asp Tyr Asp Tyr
                755                 760                 765

Asp Gly Leu His Asp Thr Glu Asp Lys Ile Lys Gln Tyr Val Glu Gly
            770                 775                 780

Ser Ser Ile Pro Val Pro Thr His Tyr Tyr Ser Ile Ile Thr Ser Cys
785                 790                 795                 800

Leu Asp Phe Thr Gln Pro Ala Asp Lys Cys Asp Gly Pro Leu Ser Val
                805                 810                 815

Ser Ser Phe Ile Leu Pro His Arg Pro Asp Asn Glu Glu Ser Cys Asn
                820                 825                 830

Ser Ser Glu Asp Glu Ser Lys Trp Val Glu Glu Leu Met Lys Met His
            835                 840                 845

Thr Ala Arg Val Arg Asp Ile Glu His Leu Thr Ser Leu Asp Phe Phe
        850                 855                 860

Arg Lys Thr Ser Arg Ser Tyr Pro Glu Ile Leu Thr Leu Lys Thr Tyr
865                 870                 875                 880

Leu His Thr Tyr Glu Ser Glu Ile
                885

<210> SEQ ID NO 3
<211> LENGTH: 1
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(1)
<223> OTHER INFORMATION: sequence can be repeated 1-15 times

<400> SEQUENCE: 3

Asp
1
```

```
<210> SEQ ID NO 4
<211> LENGTH: 3
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(3)
<223> OTHER INFORMATION: sequence can be repeated 1-10 times

<400> SEQUENCE: 4

Asp Ser Ser
1

<210> SEQ ID NO 5
<211> LENGTH: 3
<212> TYPE: PRT
<213> ORGANISM: Artificial Sequence
<220> FEATURE:
<223> OTHER INFORMATION: chemically synsthesized
<220> FEATURE:
<221> NAME/KEY: REPEAT
<222> LOCATION: (1)..(3)
<223> OTHER INFORMATION: sequence can be repeated 1-10 times

<400> SEQUENCE: 5

Glu Ser Ser
1

<210> SEQ ID NO 6
<211> LENGTH: 3
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(3)
<223> OTHER INFORMATION: sequence can be repeated 1-10 times

<400> SEQUENCE: 6

Arg Gln Gln
1

<210> SEQ ID NO 7
<211> LENGTH: 2
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(2)
<223> OTHER INFORMATION: sequence can be repeated 1-10 times

<400> SEQUENCE: 7

Lys Arg
1

<210> SEQ ID NO 8
<211> LENGTH: 1
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(1)
```

```
<223> OTHER INFORMATION: sequence can be repeated 1-15 times

<400> SEQUENCE: 8

Arg
1

<210> SEQ ID NO 9
<211> LENGTH: 16
<212> TYPE: PRT
<213> ORGANISM: Artificial Sequence
<220> FEATURE:
<223> OTHER INFORMATION: chemically synthesized

<400> SEQUENCE: 9

Asp Ser Ser Ser Glu Glu Lys Phe Leu Arg Arg Ile Gly Arg Phe Gly
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: chemically synthesized

<400> SEQUENCE: 10

Glu Glu Glu Glu Glu Glu Glu Pro Arg Gly Asp Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: chemically synthesized

<400> SEQUENCE: 11

Ala Pro Trp His Leu Ser Ser Gln Tyr Ser Arg Thr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: chemically synthesized

<400> SEQUENCE: 12

Ser Thr Leu Pro Ile Pro His Glu Phe Ser Arg Glu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: chemically synthesized

<400> SEQUENCE: 13

Val Thr Lys His Leu Asn Gln Ile Ser Gln Ser Tyr
1               5                   10

<210> SEQ ID NO 14
<211> LENGTH: 1
<212> TYPE: PRT
<213> ORGANISM: Artificial Sequence
<220> FEATURE:
<223> OTHER INFORMATION: chemically synthesized
```

```
<220> FEATURE:
<221> NAME/KEY: REPEAT
<222> LOCATION: (1)..(1)
<223> OTHER INFORMATION: sequence can be repeated 1-15 times

<400> SEQUENCE: 14

Glu
1

<210> SEQ ID NO 15
<211> LENGTH: 925
<212> TYPE: PRT
<213> ORGANISM: Artificial Sequence
<220> FEATURE:
<223> OTHER INFORMATION: ENPP121

<400> SEQUENCE: 15
```

Met Glu Arg Asp Gly Cys Ala Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

-continued

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Arg Ile Leu Ala
            340                 345                 350

Val Leu Gln Trp Leu Gln Leu Pro Lys Asp Glu Arg Pro His Phe Tyr
            355                 360                 365

Thr Leu Tyr Leu Glu Glu Pro Asp Ser Ser Gly His Ser Tyr Gly Pro
        370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
                420                 425                 430

Lys Tyr Ile Tyr Leu Asn Lys Tyr Leu Gly Asp Val Lys Asn Ile Lys
            435                 440                 445

Val Ile Tyr Gly Pro Ala Ala Arg Leu Arg Pro Ser Asp Val Pro Asp
        450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
        530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
            595                 600                 605

His Pro Leu Val Gln Cys Pro Phe Thr Arg Asn Pro Arg Asp Asn Leu
        610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
        690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

-continued

```
Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
        915                 920                 925

<210> SEQ ID NO 16
<211> LENGTH: 1155
<212> TYPE: PRT
<213> ORGANISM: Artificial Sequence
<220> FEATURE:
<223> OTHER INFORMATION: ENPP121 Fc

<400> SEQUENCE: 16

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175
```

```
Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
```

-continued

```
               595                 600                 605
His Pro Leu Val Gln Cys Pro Phe Thr Arg Asn Pro Arg Asp Asn Leu
610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
                660                 665                 670

Leu Leu Ser Gln His Gln Phe Met Ser Gly Tyr Ser Gln Asp Ile Leu
                675                 680                 685

Met Pro Leu Trp Thr Ser Tyr Thr Val Asp Arg Asn Asp Ser Phe Ser
690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
                740                 745                 750

Tyr Ser Glu Ala Leu Leu Thr Thr Asn Ile Val Pro Met Tyr Gln Ser
                755                 760                 765

Phe Gln Val Ile Trp Arg Tyr Phe His Asp Thr Leu Leu Arg Lys Tyr
                770                 775                 780

Ala Glu Arg Asn Gly Val Asn Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
                820                 825                 830

Ile Val Leu Thr Ser Cys Lys Asp Thr Ser Gln Thr Pro Leu His Cys
                835                 840                 845

Glu Asn Leu Asp Thr Leu Ala Phe Ile Leu Pro His Arg Thr Asp Asn
850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
                900                 905                 910

Lys Leu Lys Thr His Leu Pro Thr Phe Ser Gln Glu Asp Leu Ile Asn
                915                 920                 925

Asp Lys Thr His Thr Cys Pro Pro Cys Pro Ala Pro Glu Leu Leu Gly
                930                 935                 940

Gly Pro Ser Val Phe Leu Phe Pro Pro Lys Pro Lys Asp Thr Leu Met
945                 950                 955                 960

Ile Ser Arg Thr Pro Glu Val Thr Cys Val Val Val Asp Val Ser His
                965                 970                 975

Glu Asp Pro Glu Val Lys Phe Asn Trp Tyr Val Asp Gly Val Glu Val
                980                 985                 990

His Asn Ala Lys Thr Lys Pro Arg Glu Glu Gln Tyr Asn Ser Thr Tyr
                995                 1000                1005

Arg Val Val Ser Val Leu Thr Val Leu His Gln Asp Trp Leu Asn
                1010                1015                1020
```

```
Gly Lys Glu Tyr Lys Cys Lys Val Ser Asn Lys Ala Leu Pro Ala
    1025                1030                1035

Pro Ile Glu Lys Thr Ile Ser Lys Ala Lys Gly Gln Pro Arg Glu
    1040                1045                1050

Pro Gln Val Tyr Thr Leu Pro Pro Ser Arg Glu Glu Met Thr Lys
    1055                1060                1065

Asn Gln Val Ser Leu Thr Cys Leu Val Lys Gly Phe Tyr Pro Ser
    1070                1075                1080

Asp Ile Ala Val Glu Trp Glu Ser Asn Gly Gln Pro Glu Asn Asn
    1085                1090                1095

Tyr Lys Thr Thr Pro Pro Val Leu Asp Ser Asp Gly Ser Phe Phe
    1100                1105                1110

Leu Tyr Ser Lys Leu Thr Val Asp Lys Ser Arg Trp Gln Gln Gly
    1115                1120                1125

Asn Val Phe Ser Cys Ser Val Met His Glu Ala Leu His Asn His
    1130                1135                1140

Tyr Thr Gln Lys Ser Leu Ser Leu Ser Pro Gly Lys
    1145                1150                1155

<210> SEQ ID NO 17
<211> LENGTH: 852
<212> TYPE: PRT
<213> ORGANISM: Artificial Sequence
<220> FEATURE:
<223> OTHER INFORMATION: ENNP71

<400> SEQUENCE: 17

Met Arg Gly Pro Ala Val Leu Leu Thr Val Ala Leu Ala Thr Leu Leu
1               5                   10                  15

Ala Pro Gly Ala Gly Ala Gly Leu Lys Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140

Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
        195                 200                 205

Pro Lys Met Asn Ala Ser Phe Ser Leu Lys Ser Lys Glu Lys Phe Asn
    210                 215                 220
```

```
Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
                260                 265                 270

Phe Glu Glu Arg Ile Leu Ala Val Leu Gln Trp Leu Gln Leu Pro Lys
                275                 280                 285

Asp Glu Arg Pro His Phe Tyr Thr Leu Tyr Leu Glu Glu Pro Asp Ser
                290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
                340                 345                 350

Met Glu Gln Gly Ser Cys Lys Lys Tyr Ile Tyr Leu Asn Lys Tyr Leu
                355                 360                 365

Gly Asp Val Lys Asn Ile Lys Val Ile Tyr Gly Pro Ala Ala Arg Leu
370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
                420                 425                 430

Arg Ile Glu Pro Leu Thr Phe Tyr Leu Asp Pro Gln Trp Gln Leu Ala
                435                 440                 445

Leu Asn Pro Ser Glu Arg Lys Tyr Cys Gly Ser Gly Phe His Gly Ser
450                 455                 460

Asp Asn Val Phe Ser Asn Met Gln Ala Leu Phe Val Gly Tyr Gly Pro
465                 470                 475                 480

Gly Phe Lys His Gly Ile Glu Ala Asp Thr Phe Glu Asn Ile Glu Val
                485                 490                 495

Tyr Asn Leu Met Cys Asp Leu Leu Asn Leu Thr Pro Ala Pro Asn Asn
                500                 505                 510

Gly Thr His Gly Ser Leu Asn His Leu Leu Lys Asn Pro Val Tyr Thr
                515                 520                 525

Pro Lys His Pro Lys Glu Val His Pro Leu Val Gln Cys Pro Phe Thr
                530                 535                 540

Arg Asn Pro Arg Asp Asn Leu Gly Cys Ser Cys Asn Pro Ser Ile Leu
545                 550                 555                 560

Pro Ile Glu Asp Phe Gln Thr Gln Phe Asn Leu Thr Val Ala Glu Glu
                565                 570                 575

Lys Ile Ile Lys His Glu Thr Leu Pro Tyr Gly Arg Pro Arg Val Leu
                580                 585                 590

Gln Lys Glu Asn Thr Ile Cys Leu Leu Ser Gln His Gln Phe Met Ser
                595                 600                 605

Gly Tyr Ser Gln Asp Ile Leu Met Pro Leu Trp Thr Ser Tyr Thr Val
                610                 615                 620

Asp Arg Asn Asp Ser Phe Ser Thr Glu Asp Phe Ser Asn Cys Leu Tyr
625                 630                 635                 640
```

```
Gln Asp Phe Arg Ile Pro Leu Ser Pro Val His Lys Cys Ser Phe Tyr
                645                 650                 655

Lys Asn Asn Thr Lys Val Ser Tyr Gly Phe Leu Ser Pro Pro Gln Leu
            660                 665                 670

Asn Lys Asn Ser Ser Gly Ile Tyr Ser Glu Ala Leu Leu Thr Thr Asn
        675                 680                 685

Ile Val Pro Met Tyr Gln Ser Phe Gln Val Ile Trp Arg Tyr Phe His
    690                 695                 700

Asp Thr Leu Leu Arg Lys Tyr Ala Glu Glu Arg Asn Gly Val Asn Val
705                 710                 715                 720

Val Ser Gly Pro Val Phe Asp Phe Asp Tyr Asp Gly Arg Cys Asp Ser
                725                 730                 735

Leu Glu Asn Leu Arg Gln Lys Arg Val Ile Arg Asn Gln Glu Ile
            740                 745                 750

Leu Ile Pro Thr His Phe Phe Ile Val Leu Thr Ser Cys Lys Asp Thr
        755                 760                 765

Ser Gln Thr Pro Leu His Cys Glu Asn Leu Asp Thr Leu Ala Phe Ile
    770                 775                 780

Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
                805                 810                 815

Thr Asp Val Glu His Ile Thr Gly Leu Ser Phe Tyr Gln Gln Arg Lys
            820                 825                 830

Glu Pro Val Ser Asp Ile Leu Lys Leu Lys Thr His Leu Pro Thr Phe
        835                 840                 845

Ser Gln Glu Asp
    850

<210> SEQ ID NO 18
<211> LENGTH: 1082
<212> TYPE: PRT
<213> ORGANISM: Artificial Sequence
<220> FEATURE:
<223> OTHER INFORMATION: ENPP71 Fc

<400> SEQUENCE: 18

Met Arg Gly Pro Ala Val Leu Leu Thr Val Ala Leu Ala Thr Leu Leu
1               5                   10                  15

Ala Pro Gly Ala Gly Ala Gly Leu Lys Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140
```

```
Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
            165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
            195                 200                 205

Pro Lys Met Asn Ala Ser Phe Ser Leu Lys Ser Lys Glu Lys Phe Asn
        210                 215                 220

Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270

Phe Glu Glu Arg Ile Leu Ala Val Leu Gln Trp Leu Gln Leu Pro Lys
        275                 280                 285

Asp Glu Arg Pro His Phe Tyr Thr Leu Tyr Leu Glu Glu Pro Asp Ser
290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350

Met Glu Gln Gly Ser Cys Lys Lys Tyr Ile Tyr Leu Asn Lys Tyr Leu
        355                 360                 365

Gly Asp Val Lys Asn Ile Lys Val Ile Tyr Gly Pro Ala Ala Arg Leu
            370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
            420                 425                 430

Arg Ile Glu Pro Leu Thr Phe Tyr Leu Asp Pro Gln Trp Gln Leu Ala
            435                 440                 445

Leu Asn Pro Ser Glu Arg Lys Tyr Cys Gly Ser Gly Phe His Gly Ser
    450                 455                 460

Asp Asn Val Phe Ser Asn Met Gln Ala Leu Phe Val Gly Tyr Gly Pro
465                 470                 475                 480

Gly Phe Lys His Gly Ile Glu Ala Asp Thr Phe Glu Asn Ile Glu Val
                485                 490                 495

Tyr Asn Leu Met Cys Asp Leu Leu Asn Leu Thr Pro Ala Pro Asn Asn
            500                 505                 510

Gly Thr His Gly Ser Leu Asn His Leu Leu Lys Asn Pro Val Tyr Thr
        515                 520                 525

Pro Lys His Pro Lys Glu Val His Pro Leu Val Gln Cys Pro Phe Thr
    530                 535                 540

Arg Asn Pro Arg Asp Asn Leu Gly Cys Ser Cys Asn Pro Ser Ile Leu
545                 550                 555                 560

Pro Ile Glu Asp Phe Gln Thr Gln Phe Asn Leu Thr Val Ala Glu Glu
```

```
               565                 570                 575
Lys Ile Ile Lys His Glu Thr Leu Pro Tyr Gly Arg Pro Arg Val Leu
            580                 585                 590
Gln Lys Glu Asn Thr Ile Cys Leu Leu Ser Gln His Gln Phe Met Ser
            595                 600                 605
Gly Tyr Ser Gln Asp Ile Leu Met Pro Leu Trp Thr Ser Tyr Thr Val
610                 615                 620
Asp Arg Asn Asp Ser Phe Ser Thr Glu Asp Phe Ser Asn Cys Leu Tyr
625                 630                 635                 640
Gln Asp Phe Arg Ile Pro Leu Ser Pro Val His Lys Cys Ser Phe Tyr
            645                 650                 655
Lys Asn Asn Thr Lys Val Ser Tyr Gly Phe Leu Ser Pro Pro Gln Leu
            660                 665                 670
Asn Lys Asn Ser Ser Gly Ile Tyr Ser Glu Ala Leu Leu Thr Thr Asn
            675                 680                 685
Ile Val Pro Met Tyr Gln Ser Phe Gln Val Ile Trp Arg Tyr Phe His
            690                 695                 700
Asp Thr Leu Leu Arg Lys Tyr Ala Glu Glu Arg Asn Gly Val Asn Val
705                 710                 715                 720
Val Ser Gly Pro Val Phe Asp Phe Asp Tyr Asp Gly Arg Cys Asp Ser
                725                 730                 735
Leu Glu Asn Leu Arg Gln Lys Arg Arg Val Ile Arg Asn Gln Glu Ile
            740                 745                 750
Leu Ile Pro Thr His Phe Phe Ile Val Leu Thr Ser Cys Lys Asp Thr
            755                 760                 765
Ser Gln Thr Pro Leu His Cys Glu Asn Leu Asp Thr Leu Ala Phe Ile
770                 775                 780
Leu Pro His Arg Thr Asp Asn Ser Glu Ser Cys Val His Gly Lys His
785                 790                 795                 800
Asp Ser Ser Trp Val Glu Glu Leu Leu Met Leu His Arg Ala Arg Ile
                805                 810                 815
Thr Asp Val Glu His Ile Thr Gly Leu Ser Phe Tyr Gln Gln Arg Lys
            820                 825                 830
Glu Pro Val Ser Asp Ile Leu Lys Leu Lys Thr His Leu Pro Thr Phe
            835                 840                 845
Ser Gln Glu Asp Leu Ile Asn Asp Lys Thr His Thr Cys Pro Pro Cys
            850                 855                 860
Pro Ala Pro Glu Leu Leu Gly Gly Pro Ser Val Phe Leu Phe Pro Pro
865                 870                 875                 880
Lys Pro Lys Asp Thr Leu Met Ile Ser Arg Thr Pro Glu Val Thr Cys
                885                 890                 895
Val Val Val Asp Val Ser His Glu Asp Pro Glu Val Lys Phe Asn Trp
                900                 905                 910
Tyr Val Asp Gly Val Glu Val His Asn Ala Lys Thr Lys Pro Arg Glu
            915                 920                 925
Glu Gln Tyr Asn Ser Thr Tyr Arg Val Val Ser Val Leu Thr Val Leu
            930                 935                 940
His Gln Asp Trp Leu Asn Gly Lys Glu Tyr Lys Cys Lys Val Ser Asn
945                 950                 955                 960
Lys Ala Leu Pro Ala Pro Ile Glu Lys Thr Ile Ser Lys Ala Lys Gly
                965                 970                 975
Gln Pro Arg Glu Pro Gln Val Tyr Thr Leu Pro Pro Ser Arg Glu Glu
            980                 985                 990
```

```
Met Thr Lys Asn Gln Val Ser Leu Thr Cys Leu Val Lys Gly Phe Tyr
        995                 1000                1005

Pro Ser Asp Ile Ala Val Glu Trp Glu Ser Asn Gly Gln Pro Glu
        1010                1015                1020

Asn Asn Tyr Lys Thr Thr Pro Val Leu Asp Ser Asp Gly Ser
        1025                1030                1035

Phe Phe Leu Tyr Ser Lys Leu Thr Val Asp Lys Ser Arg Trp Gln
        1040                1045                1050

Gln Gly Asn Val Phe Ser Cys Ser Val Met His Glu Ala Leu His
        1055                1060                1065

Asn His Tyr Thr Gln Lys Ser Leu Ser Leu Ser Pro Gly Lys
        1070                1075                1080

<210> SEQ ID NO 19
<211> LENGTH: 849
<212> TYPE: PRT
<213> ORGANISM: Artificial Sequence
<220> FEATURE:
<223> OTHER INFORMATION: ENPP71 lacking ENPP1 N-Terminus GLK

<400> SEQUENCE: 19

Met Arg Gly Pro Ala Val Leu Leu Thr Val Ala Leu Ala Thr Leu Leu
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

Ala Cys Val Glu Leu Gly Asn Cys Cys Leu Asp Tyr Gln Glu Thr Cys
    50                  55                  60

Ile Glu Pro Glu His Ile Trp Thr Cys Asn Lys Phe Arg Cys Gly Glu
65                  70                  75                  80

Lys Arg Leu Thr Arg Ser Leu Cys Ala Cys Ser Asp Asp Cys Lys Asp
                85                  90                  95

Lys Gly Asp Cys Cys Ile Asn Tyr Ser Ser Val Cys Gln Gly Glu Lys
            100                 105                 110

Ser Trp Val Glu Glu Pro Cys Glu Ser Ile Asn Glu Pro Gln Cys Pro
        115                 120                 125

Ala Gly Phe Glu Thr Pro Pro Thr Leu Leu Phe Ser Leu Asp Gly Phe
    130                 135                 140

Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
            180                 185                 190

Pro Glu Ser His Gly Ile Ile Asp Asn Lys Met Tyr Asp Pro Lys Met
        195                 200                 205

Asn Ala Ser Phe Ser Leu Lys Ser Lys Glu Lys Phe Asn Pro Glu Trp
    210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270
```

```
Arg Ile Leu Ala Val Leu Gln Trp Leu Gln Leu Pro Lys Asp Glu Arg
        275                 280                 285
Pro His Phe Tyr Thr Leu Tyr Leu Glu Glu Pro Asp Ser Ser Gly His
        290                 295                 300
Ser Tyr Gly Pro Val Ser Ser Glu Val Ile Lys Ala Leu Gln Arg Val
305                 310                 315                 320
Asp Gly Met Val Gly Met Leu Met Asp Gly Lys Glu Leu Asn Leu
                    325                 330                 335
His Arg Cys Leu Asn Leu Ile Leu Ile Ser Asp His Gly Met Glu Gln
            340                 345                 350
Gly Ser Cys Lys Lys Tyr Ile Tyr Leu Asn Lys Tyr Leu Gly Asp Val
            355                 360                 365
Lys Asn Ile Lys Val Ile Tyr Gly Pro Ala Ala Arg Leu Arg Pro Ser
370                 375                 380
Asp Val Pro Asp Lys Tyr Tyr Ser Phe Asn Tyr Glu Gly Ile Ala Arg
385                 390                 395                 400
Asn Leu Ser Cys Arg Glu Pro Asn Gln His Phe Lys Pro Tyr Leu Lys
                    405                 410                 415
His Phe Leu Pro Lys Arg Leu His Phe Ala Lys Ser Arg Ile Glu
                420                 425                 430
Pro Leu Thr Phe Tyr Leu Asp Pro Gln Trp Gln Leu Ala Leu Asn Pro
            435                 440                 445
Ser Glu Arg Lys Tyr Cys Gly Ser Gly Phe His Gly Ser Asp Asn Val
    450                 455                 460
Phe Ser Asn Met Gln Ala Leu Phe Val Gly Tyr Gly Pro Gly Phe Lys
465                 470                 475                 480
His Gly Ile Glu Ala Asp Thr Phe Glu Asn Ile Glu Val Tyr Asn Leu
                    485                 490                 495
Met Cys Asp Leu Leu Asn Leu Thr Pro Ala Pro Asn Asn Gly Thr His
            500                 505                 510
Gly Ser Leu Asn His Leu Leu Lys Asn Pro Val Tyr Thr Pro Lys His
            515                 520                 525
Pro Lys Glu Val His Pro Leu Val Gln Cys Pro Phe Thr Arg Asn Pro
            530                 535                 540
Arg Asp Asn Leu Gly Cys Ser Cys Asn Pro Ser Ile Leu Pro Ile Glu
545                 550                 555                 560
Asp Phe Gln Thr Gln Phe Asn Leu Thr Val Ala Glu Glu Lys Ile Ile
                565                 570                 575
Lys His Glu Thr Leu Pro Tyr Gly Arg Pro Arg Val Leu Gln Lys Glu
                580                 585                 590
Asn Thr Ile Cys Leu Leu Ser Gln His Gln Phe Met Ser Gly Tyr Ser
            595                 600                 605
Gln Asp Ile Leu Met Pro Leu Trp Thr Ser Tyr Thr Val Asp Arg Asn
610                 615                 620
Asp Ser Phe Ser Thr Glu Asp Phe Ser Asn Cys Leu Tyr Gln Asp Phe
625                 630                 635                 640
Arg Ile Pro Leu Ser Pro Val His Lys Cys Ser Phe Tyr Lys Asn Asn
                645                 650                 655
Thr Lys Val Ser Tyr Gly Phe Leu Ser Pro Pro Gln Leu Asn Lys Asn
            660                 665                 670
Ser Ser Gly Ile Tyr Ser Glu Ala Leu Leu Thr Thr Asn Ile Val Pro
            675                 680                 685
```

Met Tyr Gln Ser Phe Gln Val Ile Trp Arg Tyr Phe His Asp Thr Leu
    690             695                 700
Leu Arg Lys Tyr Ala Glu Glu Arg Asn Gly Val Asn Val Val Ser Gly
705                 710                 715                 720
Pro Val Phe Asp Phe Asp Tyr Asp Gly Arg Cys Asp Ser Leu Glu Asn
                725                 730                 735
Leu Arg Gln Lys Arg Val Ile Arg Asn Gln Glu Ile Leu Ile Pro
            740                 745                 750
Thr His Phe Phe Ile Val Leu Thr Ser Cys Lys Asp Thr Ser Gln Thr
                755                 760                 765
Pro Leu His Cys Glu Asn Leu Asp Thr Leu Ala Phe Ile Leu Pro His
770                 775                 780
Arg Thr Asp Asn Ser Glu Ser Cys Val His Gly Lys His Asp Ser Ser
785                 790                 795                 800
Trp Val Glu Glu Leu Leu Met Leu His Arg Ala Arg Ile Thr Asp Val
                805                 810                 815
Glu His Ile Thr Gly Leu Ser Phe Tyr Gln Gln Arg Lys Glu Pro Val
                820                 825                 830
Ser Asp Ile Leu Lys Leu Lys Thr His Leu Pro Thr Phe Ser Gln Glu
            835                 840                 845
Asp

<210> SEQ ID NO 20
<211> LENGTH: 1079
<212> TYPE: PRT
<213> ORGANISM: Artificial Sequence
<220> FEATURE:
<223> OTHER INFORMATION: (ENPP71 lacking ENPP1 N-Terminus GLK)-Fc

<400> SEQUENCE: 20

Met Arg Gly Pro Ala Val Leu Leu Thr Val Ala Leu Ala Thr Leu Leu
1               5                   10                  15
Ala Pro Gly Ala Gly Ala Pro Ser Cys Ala Lys Glu Val Lys Ser Cys
                20                  25                  30
Lys Gly Arg Cys Phe Glu Arg Thr Phe Gly Asn Cys Arg Cys Asp Ala
            35                  40                  45
Ala Cys Val Glu Leu Gly Asn Cys Cys Leu Asp Tyr Gln Glu Thr Cys
50                  55                  60
Ile Glu Pro Glu His Ile Trp Thr Cys Asn Lys Phe Arg Cys Gly Glu
65                  70                  75                  80
Lys Arg Leu Thr Arg Ser Leu Cys Ala Cys Ser Asp Asp Cys Lys Asp
                85                  90                  95
Lys Gly Asp Cys Cys Ile Asn Tyr Ser Ser Val Cys Gln Gly Glu Lys
                100                 105                 110
Ser Trp Val Glu Glu Pro Cys Glu Ser Ile Asn Glu Pro Gln Cys Pro
            115                 120                 125
Ala Gly Phe Glu Thr Pro Thr Leu Leu Phe Ser Leu Asp Gly Phe
            130                 135                 140
Arg Ala Glu Tyr Leu His Thr Trp Gly Gly Leu Leu Pro Val Ile Ser
145                 150                 155                 160
Lys Leu Lys Lys Cys Gly Thr Tyr Thr Lys Asn Met Arg Pro Val Tyr
                165                 170                 175
Pro Thr Lys Thr Phe Pro Asn His Tyr Ser Ile Val Thr Gly Leu Tyr
            180                 185                 190
Pro Glu Ser His Gly Ile Ile Asp Asn Lys Met Tyr Asp Pro Lys Met

-continued

```
                195                 200                 205
Asn Ala Ser Phe Ser Leu Lys Ser Lys Glu Lys Phe Asn Pro Glu Trp
210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270

Arg Ile Leu Ala Val Leu Gln Trp Leu Gln Leu Pro Lys Asp Glu Arg
        275                 280                 285

Pro His Phe Tyr Thr Leu Tyr Leu Glu Glu Pro Asp Ser Ser Gly His
    290                 295                 300

Ser Tyr Gly Pro Val Ser Ser Glu Val Ile Lys Ala Leu Gln Arg Val
305                 310                 315                 320

Asp Gly Met Val Gly Met Leu Met Asp Gly Leu Lys Glu Leu Asn Leu
                325                 330                 335

His Arg Cys Leu Asn Leu Ile Leu Ile Ser Asp His Gly Met Glu Gln
            340                 345                 350

Gly Ser Cys Lys Lys Tyr Ile Tyr Leu Asn Lys Tyr Leu Gly Asp Val
        355                 360                 365

Lys Asn Ile Lys Val Ile Tyr Gly Pro Ala Ala Arg Leu Arg Pro Ser
370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
                405                 410                 415

His Phe Leu Pro Lys Arg Leu His Phe Ala Lys Ser Asp Arg Ile Glu
            420                 425                 430

Pro Leu Thr Phe Tyr Leu Asp Pro Gln Trp Gln Leu Ala Leu Asn Pro
        435                 440                 445

Ser Glu Arg Lys Tyr Cys Gly Ser Gly Phe His Gly Ser Asp Asn Val
    450                 455                 460

Phe Ser Asn Met Gln Ala Leu Phe Val Gly Tyr Gly Pro Gly Phe Lys
465                 470                 475                 480

His Gly Ile Glu Ala Asp Thr Phe Glu Asn Ile Glu Val Tyr Asn Leu
                485                 490                 495

Met Cys Asp Leu Leu Asn Leu Thr Pro Ala Pro Asn Asn Gly Thr His
            500                 505                 510

Gly Ser Leu Asn His Leu Leu Lys Asn Pro Val Tyr Thr Pro Lys His
        515                 520                 525

Pro Lys Glu Val His Pro Leu Val Gln Cys Pro Phe Thr Arg Asn Pro
    530                 535                 540

Arg Asp Asn Leu Gly Cys Ser Cys Asn Pro Ser Ile Leu Pro Ile Glu
545                 550                 555                 560

Asp Phe Gln Thr Gln Phe Asn Leu Thr Val Ala Glu Glu Lys Ile Ile
                565                 570                 575

Lys His Glu Thr Leu Pro Tyr Gly Arg Pro Arg Val Leu Gln Lys Glu
            580                 585                 590

Asn Thr Ile Cys Leu Leu Ser Gln His Gln Phe Met Ser Gly Tyr Ser
        595                 600                 605

Gln Asp Ile Leu Met Pro Leu Trp Thr Ser Tyr Thr Val Asp Arg Asn
    610                 615                 620
```

```
Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
            645                 650                 655

Thr Lys Val Ser Tyr Gly Phe Leu Ser Pro Pro Gln Leu Asn Lys Asn
        660                 665                 670

Ser Ser Gly Ile Tyr Ser Glu Ala Leu Leu Thr Thr Asn Ile Val Pro
            675                 680                 685

Met Tyr Gln Ser Phe Gln Val Ile Trp Arg Tyr Phe His Asp Thr Leu
        690                 695                 700

Leu Arg Lys Tyr Ala Glu Glu Arg Asn Gly Val Asn Val Val Ser Gly
705                 710                 715                 720

Pro Val Phe Asp Phe Asp Tyr Asp Gly Arg Cys Asp Ser Leu Glu Asn
                725                 730                 735

Leu Arg Gln Lys Arg Arg Val Ile Arg Asn Gln Glu Ile Leu Ile Pro
            740                 745                 750

Thr His Phe Phe Ile Val Leu Thr Ser Cys Lys Asp Thr Ser Gln Thr
        755                 760                 765

Pro Leu His Cys Glu Asn Leu Asp Thr Leu Ala Phe Ile Leu Pro His
    770                 775                 780

Arg Thr Asp Asn Ser Glu Ser Cys Val His Gly Lys His Asp Ser Ser
785                 790                 795                 800

Trp Val Glu Glu Leu Leu Met Leu His Arg Ala Arg Ile Thr Asp Val
                805                 810                 815

Glu His Ile Thr Gly Leu Ser Phe Tyr Gln Gln Arg Lys Glu Pro Val
            820                 825                 830

Ser Asp Ile Leu Lys Leu Lys Thr His Leu Pro Thr Phe Ser Gln Glu
        835                 840                 845

Asp Leu Ile Asn Asp Lys Thr His Thr Cys Pro Pro Cys Pro Ala Pro
    850                 855                 860

Glu Leu Leu Gly Gly Pro Ser Val Phe Leu Phe Pro Pro Lys Pro Lys
865                 870                 875                 880

Asp Thr Leu Met Ile Ser Arg Thr Pro Glu Val Thr Cys Val Val Val
                885                 890                 895

Asp Val Ser His Glu Asp Pro Glu Val Lys Phe Asn Trp Tyr Val Asp
            900                 905                 910

Gly Val Glu Val His Asn Ala Lys Thr Lys Pro Arg Glu Glu Gln Tyr
        915                 920                 925

Asn Ser Thr Tyr Arg Val Val Ser Val Leu Thr Val Leu His Gln Asp
    930                 935                 940

Trp Leu Asn Gly Lys Glu Tyr Lys Cys Lys Val Ser Asn Lys Ala Leu
945                 950                 955                 960

Pro Ala Pro Ile Glu Lys Thr Ile Ser Lys Ala Lys Gly Gln Pro Arg
                965                 970                 975

Glu Pro Gln Val Tyr Thr Leu Pro Pro Ser Arg Glu Glu Met Thr Lys
            980                 985                 990

Asn Gln Val Ser Leu Thr Cys Leu Val Lys Gly Phe Tyr Pro Ser Asp
        995                1000                1005

Ile Ala Val Glu Trp Glu Ser Asn Gly Gln Pro Glu Asn Asn Tyr
    1010                1015                1020

Lys Thr Thr Pro Pro Val Leu Asp Ser Asp Gly Ser Phe Phe Leu
    1025                1030                1035
```

```
Tyr Ser Lys Leu Thr Val Asp Lys Ser Arg Trp Gln Gln Gly Asn
    1040                1045                1050

Val Phe Ser Cys Ser Val Met His Glu Ala Leu His Asn His Tyr
    1055                1060                1065

Thr Gln Lys Ser Leu Ser Leu Ser Pro Gly Lys
    1070                1075

<210> SEQ ID NO 21
<211> LENGTH: 1550
<212> TYPE: PRT
<213> ORGANISM: Artificial Sequence
<220> FEATURE:
<223> OTHER INFORMATION: ENPP121-ALB

<400> SEQUENCE: 21

Met Glu Arg Asp Gly Cys Ala Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320
```

```
Phe Trp Pro Gly Ser Asp Val Glu Ile Asn Gly Ile Phe Pro Asp Ile
            325                 330                 335

Tyr Lys Met Tyr Asn Gly Ser Val Pro Phe Glu Glu Arg Ile Leu Ala
        340                 345                 350

Val Leu Gln Trp Leu Gln Leu Pro Lys Asp Glu Arg Pro His Phe Tyr
            355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
            405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
            485                 490                 495

Lys Arg Leu His Phe Ala Lys Ser Asp Arg Ile Glu Pro Leu Thr Phe
        500                 505                 510

Tyr Leu Asp Pro Gln Trp Gln Leu Ala Leu Asn Pro Ser Glu Arg Lys
    515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
            565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
            645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
            725                 730                 735

Tyr Gly Phe Leu Ser Pro Pro Gln Leu Asn Lys Asn Ser Ser Gly Ile
```

```
            740                 745                 750
Tyr Ser Glu Ala Leu Leu Thr Thr Asn Ile Val Pro Met Tyr Gln Ser
            755                 760                 765
Phe Gln Val Ile Trp Arg Tyr Phe His Asp Thr Leu Leu Arg Lys Tyr
            770                 775                 780
Ala Glu Glu Arg Asn Gly Val Asn Val Val Ser Gly Pro Val Phe Asp
785                 790                 795                 800
Phe Asp Tyr Asp Gly Arg Cys Asp Ser Leu Glu Asn Leu Arg Gln Lys
                    805                 810                 815
Arg Arg Val Ile Arg Asn Gln Glu Ile Leu Ile Pro Thr His Phe Phe
            820                 825                 830
Ile Val Leu Thr Ser Cys Lys Asp Thr Ser Gln Thr Pro Leu His Cys
            835                 840                 845
Glu Asn Leu Asp Thr Leu Ala Phe Ile Leu Pro His Arg Thr Asp Asn
            850                 855                 860
Ser Glu Ser Cys Val His Gly Lys His Asp Ser Ser Trp Val Glu Glu
865                 870                 875                 880
Leu Leu Met Leu His Arg Ala Arg Ile Thr Asp Val Glu His Ile Thr
                    885                 890                 895
Gly Leu Ser Phe Tyr Gln Gln Arg Lys Glu Pro Val Ser Asp Ile Leu
            900                 905                 910
Lys Leu Lys Thr His Leu Pro Thr Phe Ser Gln Glu Asp Arg Ser Gly
            915                 920                 925
Ser Gly Gly Ser Met Lys Trp Val Thr Phe Leu Leu Leu Leu Phe Val
            930                 935                 940
Ser Gly Ser Ala Phe Ser Arg Gly Val Phe Arg Arg Glu Ala His Lys
945                 950                 955                 960
Ser Glu Ile Ala His Arg Tyr Asn Asp Leu Gly Glu Gln His Phe Lys
                    965                 970                 975
Gly Leu Val Leu Ile Ala Phe Ser Gln Tyr Leu Gln Lys Cys Ser Tyr
            980                 985                 990
Asp Glu His Ala Lys Leu Val Gln  Glu Val Thr Asp Phe  Ala Lys Thr
            995                 1000                 1005
Cys Val  Ala Asp Glu Ser Ala  Ala Asn Cys Asp Lys   Ser Leu His
    1010                 1015                 1020
Thr Leu  Phe Gly Asp Lys Leu  Cys Ala Ile Pro Asn  Leu Arg Glu
    1025                 1030                 1035
Asn Tyr  Gly Glu Leu Ala Asp  Cys Cys Thr Lys Gln  Glu Pro Glu
    1040                 1045                 1050
Arg Asn  Glu Cys Phe Leu Gln  His Lys Asp Asp Asn  Pro Ser Leu
    1055                 1060                 1065
Pro Pro  Phe Glu Arg Pro Glu  Ala Glu Ala Met Cys   Thr Ser Phe
    1070                 1075                 1080
Lys Glu  Asn Pro Thr Thr Phe  Met Gly His Tyr Leu   His Glu Val
    1085                 1090                 1095
Ala Arg  Arg His Pro Tyr Phe  Tyr Ala Pro Glu Leu  Leu Tyr Tyr
    1100                 1105                 1110
Ala Glu  Gln Tyr Asn Glu Ile  Leu Thr Gln Cys Cys  Ala Glu Ala
    1115                 1120                 1125
Asp Lys  Glu Ser Cys Leu Thr  Pro Lys Leu Asp Gly  Val Lys Glu
    1130                 1135                 1140
Lys Ala  Leu Val Ser Ser Val  Arg Gln Arg Met Lys  Cys Ser Ser
    1145                 1150                 1155
```

-continued

```
Met Gln Lys Phe Gly Glu Arg Ala Phe Lys Ala Trp Ala Val Ala
1160                1165                1170

Arg Leu Ser Gln Thr Phe Pro Asn Ala Asp Phe Ala Glu Ile Thr
1175                1180                1185

Lys Leu Ala Thr Asp Leu Thr Lys Val Asn Lys Glu Cys Cys His
1190                1195                1200

Gly Asp Leu Leu Glu Cys Ala Asp Asp Arg Ala Glu Leu Ala Lys
1205                1210                1215

Tyr Met Cys Glu Asn Gln Ala Thr Ile Ser Ser Lys Leu Gln Thr
1220                1225                1230

Cys Cys Asp Lys Pro Leu Leu Lys Lys Ala His Cys Leu Ser Glu
1235                1240                1245

Val Glu His Asp Thr Met Pro Ala Asp Leu Pro Ala Ile Ala Ala
1250                1255                1260

Asp Phe Val Glu Asp Gln Glu Val Cys Lys Asn Tyr Ala Glu Ala
1265                1270                1275

Lys Asp Val Phe Leu Gly Thr Phe Leu Tyr Glu Tyr Ser Arg Arg
1280                1285                1290

His Pro Asp Tyr Ser Val Ser Leu Leu Leu Arg Leu Ala Lys Lys
1295                1300                1305

Tyr Glu Ala Thr Leu Glu Lys Cys Cys Ala Glu Ala Asn Pro Pro
1310                1315                1320

Ala Cys Tyr Gly Thr Val Leu Ala Glu Phe Gln Pro Leu Val Glu
1325                1330                1335

Glu Pro Lys Asn Leu Val Lys Thr Asn Cys Asp Leu Tyr Glu Lys
1340                1345                1350

Leu Gly Glu Tyr Gly Phe Gln Asn Ala Ile Leu Val Arg Tyr Thr
1355                1360                1365

Gln Lys Ala Pro Gln Val Ser Thr Pro Thr Leu Val Glu Ala Ala
1370                1375                1380

Arg Asn Leu Gly Arg Val Gly Thr Lys Cys Cys Thr Leu Pro Glu
1385                1390                1395

Asp Gln Arg Leu Pro Cys Val Glu Asp Tyr Leu Ser Ala Ile Leu
1400                1405                1410

Asn Arg Val Cys Leu Leu His Glu Lys Thr Pro Val Ser Glu His
1415                1420                1425

Val Thr Lys Cys Cys Ser Gly Ser Leu Val Glu Arg Arg Pro Cys
1430                1435                1440

Phe Ser Ala Leu Thr Val Asp Glu Thr Tyr Val Pro Lys Glu Phe
1445                1450                1455

Lys Ala Glu Thr Phe Thr Phe His Ser Asp Ile Cys Thr Leu Pro
1460                1465                1470

Glu Lys Glu Lys Gln Ile Lys Lys Gln Thr Ala Leu Ala Glu Leu
1475                1480                1485

Val Lys His Lys Pro Lys Ala Thr Ala Glu Gln Leu Lys Thr Val
1490                1495                1500

Met Asp Asp Phe Ala Gln Phe Leu Asp Thr Cys Cys Lys Ala Ala
1505                1510                1515

Asp Lys Asp Thr Cys Phe Ser Thr Glu Gly Pro Asn Leu Val Thr
1520                1525                1530

Arg Cys Lys Asp Ala Leu Ala Arg Ser Trp Ser His Pro Gln Phe
1535                1540                1545
```

Glu Lys
   1550

<210> SEQ ID NO 22
<211> LENGTH: 1474
<212> TYPE: PRT
<213> ORGANISM: Artificial Sequence
<220> FEATURE:
<223> OTHER INFORMATION: (ENPP71 lacking ENPP1 N-Terminus GLK)-ALB

<400> SEQUENCE: 22

Met Arg Gly Pro Ala Val Leu Leu Thr Val Ala Leu Ala Thr Leu Leu
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

Ala Cys Val Glu Leu Gly Asn Cys Cys Leu Asp Tyr Gln Glu Thr Cys
    50                  55                  60

Ile Glu Pro Glu His Ile Trp Thr Cys Asn Lys Phe Arg Cys Gly Glu
65                  70                  75                  80

Lys Arg Leu Thr Arg Ser Leu Cys Ala Cys Ser Asp Asp Cys Lys Asp
                85                  90                  95

Lys Gly Asp Cys Cys Ile Asn Tyr Ser Ser Val Cys Gln Gly Glu Lys
            100                 105                 110

Ser Trp Val Glu Glu Pro Cys Glu Ser Ile Asn Glu Pro Gln Cys Pro
        115                 120                 125

Ala Gly Phe Glu Thr Pro Pro Thr Leu Leu Phe Ser Leu Asp Gly Phe
    130                 135                 140

Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
            180                 185                 190

Pro Glu Ser His Gly Ile Ile Asp Asn Lys Met Tyr Asp Pro Lys Met
        195                 200                 205

Asn Ala Ser Phe Ser Leu Lys Ser Lys Glu Lys Phe Asn Pro Glu Trp
    210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270

Arg Ile Leu Ala Val Leu Gln Trp Leu Gln Leu Pro Lys Asp Glu Arg
        275                 280                 285

Pro His Phe Tyr Thr Leu Tyr Leu Glu Glu Pro Asp Ser Ser Gly His
    290                 295                 300

Ser Tyr Gly Pro Val Ser Ser Glu Val Ile Lys Ala Leu Gln Arg Val
305                 310                 315                 320

Asp Gly Met Val Gly Met Leu Met Asp Gly Leu Lys Glu Leu Asn Leu
                325                 330                 335

His Arg Cys Leu Asn Leu Ile Leu Ile Ser Asp His Gly Met Glu Gln
            340                 345                 350

```
Gly Ser Cys Lys Lys Tyr Ile Tyr Leu Asn Lys Tyr Leu Gly Asp Val
        355                 360                 365

Lys Asn Ile Lys Val Ile Tyr Gly Pro Ala Ala Arg Leu Arg Pro Ser
370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
                405                 410                 415

His Phe Leu Pro Lys Arg Leu His Phe Ala Lys Ser Asp Arg Ile Glu
            420                 425                 430

Pro Leu Thr Phe Tyr Leu Asp Pro Gln Trp Gln Leu Ala Leu Asn Pro
        435                 440                 445

Ser Glu Arg Lys Tyr Cys Gly Ser Gly Phe His Gly Ser Asp Asn Val
    450                 455                 460

Phe Ser Asn Met Gln Ala Leu Phe Val Gly Tyr Gly Pro Gly Phe Lys
465                 470                 475                 480

His Gly Ile Glu Ala Asp Thr Phe Glu Asn Ile Glu Val Tyr Asn Leu
                485                 490                 495

Met Cys Asp Leu Leu Asn Leu Thr Pro Ala Pro Asn Asn Gly Thr His
            500                 505                 510

Gly Ser Leu Asn His Leu Leu Lys Asn Pro Val Tyr Thr Pro Lys His
        515                 520                 525

Pro Lys Glu Val His Pro Leu Val Gln Cys Pro Phe Thr Arg Asn Pro
    530                 535                 540

Arg Asp Asn Leu Gly Cys Ser Cys Asn Pro Ser Ile Leu Pro Ile Glu
545                 550                 555                 560

Asp Phe Gln Thr Gln Phe Asn Leu Thr Val Ala Glu Glu Lys Ile Ile
                565                 570                 575

Lys His Glu Thr Leu Pro Tyr Gly Arg Pro Arg Val Leu Gln Lys Glu
            580                 585                 590

Asn Thr Ile Cys Leu Leu Ser Gln His Gln Phe Met Ser Gly Tyr Ser
        595                 600                 605

Gln Asp Ile Leu Met Pro Leu Trp Thr Ser Tyr Thr Val Asp Arg Asn
    610                 615                 620

Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
                645                 650                 655

Thr Lys Val Ser Tyr Gly Phe Leu Ser Pro Pro Gln Leu Asn Lys Asn
            660                 665                 670

Ser Ser Gly Ile Tyr Ser Glu Ala Leu Leu Thr Thr Asn Ile Val Pro
        675                 680                 685

Met Tyr Gln Ser Phe Gln Val Ile Trp Arg Tyr Phe His Asp Thr Leu
    690                 695                 700

Leu Arg Lys Tyr Ala Glu Glu Arg Asn Gly Val Asn Val Val Ser Gly
705                 710                 715                 720

Pro Val Phe Asp Phe Asp Tyr Asp Gly Arg Cys Asp Ser Leu Glu Asn
                725                 730                 735

Leu Arg Gln Lys Arg Arg Val Ile Arg Asn Gln Glu Ile Leu Ile Pro
            740                 745                 750

Thr His Phe Phe Ile Val Leu Thr Ser Cys Lys Asp Thr Ser Gln Thr
        755                 760                 765

Pro Leu His Cys Glu Asn Leu Asp Thr Leu Ala Phe Ile Leu Pro His
```

```
                770             775             780
Arg Thr Asp Asn Ser Glu Ser Cys Val His Gly Lys His Asp Ser Ser
785             790             795             800

Trp Val Glu Glu Leu Leu Met Leu His Arg Ala Arg Ile Thr Asp Val
                805             810             815

Glu His Ile Thr Gly Leu Ser Phe Tyr Gln Gln Arg Lys Glu Pro Val
                820             825             830

Ser Asp Ile Leu Lys Leu Lys Thr His Leu Pro Thr Phe Ser Gln Glu
            835             840             845

Asp Arg Ser Gly Ser Gly Ser Met Lys Trp Val Thr Phe Leu Leu
850             855             860

Leu Leu Phe Val Ser Gly Ser Ala Phe Ser Arg Gly Val Phe Arg Arg
865             870             875             880

Glu Ala His Lys Ser Glu Ile Ala His Arg Tyr Asn Asp Leu Gly Glu
                885             890             895

Gln His Phe Lys Gly Leu Val Leu Ile Ala Phe Ser Gln Tyr Leu Gln
                900             905             910

Lys Cys Ser Tyr Asp Glu His Ala Lys Leu Val Gln Glu Val Thr Asp
                915             920             925

Phe Ala Lys Thr Cys Val Ala Asp Glu Ser Ala Ala Asn Cys Asp Lys
                930             935             940

Ser Leu His Thr Leu Phe Gly Asp Lys Leu Cys Ala Ile Pro Asn Leu
945             950             955             960

Arg Glu Asn Tyr Gly Glu Leu Ala Asp Cys Cys Thr Lys Gln Glu Pro
                965             970             975

Glu Arg Asn Glu Cys Phe Leu Gln His Lys Asp Asp Asn Pro Ser Leu
                980             985             990

Pro Pro Phe Glu Arg Pro Glu Ala  Glu Ala Met Cys Thr  Ser Phe Lys
                995             1000            1005

Glu Asn  Pro Thr Thr Phe Met  Gly His Tyr Leu His  Glu Val Ala
    1010            1015            1020

Arg Arg  His Pro Tyr Phe Tyr  Ala Pro Glu Leu Leu  Tyr Tyr Ala
    1025            1030            1035

Glu Gln  Tyr Asn Glu Ile Leu  Thr Gln Cys Cys Ala  Glu Ala Asp
    1040            1045            1050

Lys Glu  Ser Cys Leu Thr Pro  Lys Leu Asp Gly Val  Lys Glu Lys
    1055            1060            1065

Ala Leu  Val Ser Ser Val Arg  Gln Arg Met Lys Cys  Ser Ser Met
    1070            1075            1080

Gln Lys  Phe Gly Glu Arg Ala  Phe Lys Ala Trp Ala  Val Ala Arg
    1085            1090            1095

Leu Ser  Gln Thr Phe Pro Asn  Ala Asp Phe Ala Glu  Ile Thr Lys
    1100            1105            1110

Leu Ala  Thr Asp Leu Thr Lys  Val Asn Lys Glu Cys  Cys His Gly
    1115            1120            1125

Asp Leu  Leu Glu Cys Ala Asp  Asp Arg Ala Glu Leu  Ala Lys Tyr
    1130            1135            1140

Met Cys  Glu Asn Gln Ala Thr  Ile Ser Ser Lys Leu  Gln Thr Cys
    1145            1150            1155

Cys Asp  Lys Pro Leu Leu Lys  Lys Ala His Cys Leu  Ser Glu Val
    1160            1165            1170

Glu His  Asp Thr Met Pro Ala  Asp Leu Pro Ala Ile  Ala Ala Asp
    1175            1180            1185
```

```
Phe Val Glu Asp Gln Glu Val Cys Lys Asn Tyr Ala Glu Ala Lys
    1190                1195                1200

Asp Val Phe Leu Gly Thr Phe Leu Tyr Glu Tyr Ser Arg Arg His
    1205                1210                1215

Pro Asp Tyr Ser Val Ser Leu Leu Leu Arg Leu Ala Lys Lys Tyr
    1220                1225                1230

Glu Ala Thr Leu Glu Lys Cys Cys Ala Glu Ala Asn Pro Pro Ala
    1235                1240                1245

Cys Tyr Gly Thr Val Leu Ala Glu Phe Gln Pro Leu Val Glu Glu
    1250                1255                1260

Pro Lys Asn Leu Val Lys Thr Asn Cys Asp Leu Tyr Glu Lys Leu
    1265                1270                1275

Gly Glu Tyr Gly Phe Gln Asn Ala Ile Leu Val Arg Tyr Thr Gln
    1280                1285                1290

Lys Ala Pro Gln Val Ser Thr Pro Thr Leu Val Glu Ala Ala Arg
    1295                1300                1305

Asn Leu Gly Arg Val Gly Thr Lys Cys Cys Thr Leu Pro Glu Asp
    1310                1315                1320

Gln Arg Leu Pro Cys Val Glu Asp Tyr Leu Ser Ala Ile Leu Asn
    1325                1330                1335

Arg Val Cys Leu Leu His Glu Lys Thr Pro Val Ser Glu His Val
    1340                1345                1350

Thr Lys Cys Cys Ser Gly Ser Leu Val Glu Arg Arg Pro Cys Phe
    1355                1360                1365

Ser Ala Leu Thr Val Asp Glu Thr Tyr Val Pro Lys Glu Phe Lys
    1370                1375                1380

Ala Glu Thr Phe Thr Phe His Ser Asp Ile Cys Thr Leu Pro Glu
    1385                1390                1395

Lys Glu Lys Gln Ile Lys Lys Gln Thr Ala Leu Ala Glu Leu Val
    1400                1405                1410

Lys His Lys Pro Lys Ala Thr Ala Glu Gln Leu Lys Thr Val Met
    1415                1420                1425

Asp Asp Phe Ala Gln Phe Leu Asp Thr Cys Cys Lys Ala Ala Asp
    1430                1435                1440

Lys Asp Thr Cys Phe Ser Thr Glu Gly Pro Asn Leu Val Thr Arg
    1445                1450                1455

Cys Lys Asp Ala Leu Ala Arg Ser Trp Ser His Pro Gln Phe Glu
    1460                1465                1470

Lys

<210> SEQ ID NO 23
<211> LENGTH: 19
<212> TYPE: PRT
<213> ORGANISM: Artificial Sequence
<220> FEATURE:
<223> OTHER INFORMATION: chemically synthesized

<400> SEQUENCE: 23

Ile Ile Ser Leu Phe Thr Phe Ala Val Gly Val Asn Ile Cys Leu Gly
1               5                   10                  15

Phe Thr Ala

<210> SEQ ID NO 24
<211> LENGTH: 850
<212> TYPE: PRT
```

-continued

<213> ORGANISM: Artificial Sequence
<220> FEATURE:
<223> OTHER INFORMATION: ENPP51

<400> SEQUENCE: 24

```
Met Thr Ser Lys Phe Leu Leu Val Ser Phe Ile Leu Ala Ala Leu Ser
1               5                   10                  15

Leu Ser Thr Thr Phe Ser Leu Gln Pro Ser Cys Ala Lys Glu Val Lys
            20                  25                  30

Ser Cys Lys Gly Arg Cys Phe Glu Arg Thr Phe Ser Asn Cys Arg Cys
        35                  40                  45

Asp Ala Ala Cys Val Ser Leu Gly Asn Cys Cys Leu Asp Phe Gln Glu
    50                  55                  60

Thr Cys Val Glu Pro Thr His Ile Trp Thr Cys Asn Lys Phe Arg Cys
65                  70                  75                  80

Gly Glu Lys Arg Leu Ser Arg Phe Val Cys Ser Cys Ala Asp Asp Cys
                85                  90                  95

Lys Thr His Asn Asp Cys Cys Ile Asn Tyr Ser Ser Val Cys Gln Asp
            100                 105                 110

Lys Lys Ser Trp Val Glu Glu Thr Cys Glu Ser Ile Asp Thr Pro Glu
        115                 120                 125

Cys Pro Ala Glu Phe Glu Ser Pro Thr Leu Leu Phe Ser Leu Asp
    130                 135                 140

Gly Phe Arg Ala Glu Tyr Leu His Thr Trp Gly Leu Leu Pro Val
145                 150                 155                 160

Ile Ser Lys Leu Lys Asn Cys Gly Thr Tyr Thr Lys Asn Met Arg Pro
                165                 170                 175

Met Tyr Pro Thr Lys Thr Phe Pro Asn His Tyr Ser Ile Val Thr Gly
            180                 185                 190

Leu Tyr Pro Glu Ser His Gly Ile Ile Asp Asn Lys Met Tyr Asp Pro
        195                 200                 205

Lys Met Asn Ala Ser Phe Ser Leu Lys Ser Lys Glu Lys Phe Asn Pro
    210                 215                 220

Leu Trp Tyr Lys Gly Gln Pro Ile Trp Val Thr Ala Asn His Gln Glu
225                 230                 235                 240

Val Lys Ser Gly Thr Tyr Phe Trp Pro Gly Ser Asp Val Glu Ile Asp
                245                 250                 255

Gly Ile Leu Pro Asp Ile Tyr Lys Val Tyr Asn Gly Ser Val Pro Phe
            260                 265                 270

Glu Glu Arg Ile Leu Ala Val Leu Glu Trp Leu Gln Leu Pro Ser His
        275                 280                 285

Glu Arg Pro His Phe Tyr Thr Leu Tyr Leu Glu Glu Pro Asp Ser Ser
    290                 295                 300

Gly His Ser His Gly Pro Val Ser Ser Glu Val Ile Lys Ala Leu Gln
305                 310                 315                 320

Lys Val Asp Arg Leu Val Gly Met Leu Met Asp Gly Leu Lys Asp Leu
                325                 330                 335

Gly Leu Asp Lys Cys Leu Asn Leu Ile Leu Ile Ser Asp His Gly Met
            340                 345                 350

Glu Gln Gly Ser Cys Lys Lys Tyr Val Tyr Leu Asn Lys Tyr Leu Gly
        355                 360                 365

Asp Val Asn Asn Val Lys Val Val Tyr Gly Pro Ala Ala Arg Leu Arg
    370                 375                 380

Pro Thr Asp Val Pro Glu Thr Tyr Tyr Ser Phe Asn Tyr Glu Ala Leu
```

```
            385                 390                 395                 400
Ala Lys Asn Leu Ser Cys Arg Glu Pro Asn Gln His Phe Arg Pro Tyr
                    405                 410                 415

Leu Lys Pro Phe Leu Pro Lys Arg Leu His Phe Ala Lys Ser Asp Arg
                420                 425                 430

Ile Glu Pro Leu Thr Phe Tyr Leu Asp Pro Gln Trp Gln Leu Ala Leu
            435                 440                 445

Asn Pro Ser Glu Arg Lys Tyr Cys Gly Ser Gly Phe His Gly Ser Asp
450                 455                 460

Asn Leu Phe Ser Asn Met Gln Ala Leu Phe Ile Gly Tyr Gly Pro Ala
465                 470                 475                 480

Phe Lys His Gly Ala Glu Val Asp Ser Phe Glu Asn Ile Glu Val Tyr
                    485                 490                 495

Asn Leu Met Cys Asp Leu Leu Gly Leu Ile Pro Ala Pro Asn Asn Gly
                500                 505                 510

Ser His Gly Ser Leu Asn His Leu Leu Lys Pro Ile Tyr Asn Pro
            515                 520                 525

Ser His Pro Lys Glu Glu Gly Phe Leu Ser Gln Cys Pro Ile Lys Ser
        530                 535                 540

Thr Ser Asn Asp Leu Gly Cys Thr Cys Asp Pro Trp Ile Val Pro Ile
545                 550                 555                 560

Lys Asp Phe Glu Lys Gln Leu Asn Leu Thr Thr Glu Asp Val Asp Asp
                    565                 570                 575

Ile Tyr His Met Thr Val Pro Tyr Gly Arg Pro Arg Ile Leu Leu Lys
                580                 585                 590

Gln His Arg Val Cys Leu Leu Gln Gln Gln Phe Leu Thr Gly Tyr
        595                 600                 605

Ser Leu Asp Leu Leu Met Pro Leu Trp Ala Ser Tyr Thr Phe Leu Ser
        610                 615                 620

Asn Asp Gln Phe Ser Arg Asp Asp Phe Ser Asn Cys Leu Tyr Gln Asp
625                 630                 635                 640

Leu Arg Ile Pro Leu Ser Pro Val His Lys Cys Ser Tyr Tyr Lys Ser
                    645                 650                 655

Asn Ser Lys Leu Ser Tyr Gly Phe Leu Thr Pro Arg Leu Asn Arg
                660                 665                 670

Val Ser Asn His Ile Tyr Ser Glu Ala Leu Leu Thr Ser Asn Ile Val
            675                 680                 685

Pro Met Tyr Gln Ser Phe Gln Val Ile Trp His Tyr Leu His Asp Thr
        690                 695                 700

Leu Leu Gln Arg Tyr Ala His Glu Arg Asn Gly Ile Asn Val Val Ser
705                 710                 715                 720

Gly Pro Val Phe Asp Phe Asp Tyr Asp Gly Arg Tyr Asp Ser Leu Glu
                    725                 730                 735

Ile Leu Lys Gln Asn Ser Arg Val Ile Arg Ser Gln Glu Ile Leu Ile
                740                 745                 750

Pro Thr His Phe Phe Ile Val Leu Thr Ser Cys Lys Gln Leu Ser Glu
            755                 760                 765

Thr Pro Leu Glu Cys Ser Ala Leu Glu Ser Ser Ala Tyr Ile Leu Pro
        770                 775                 780

His Arg Pro Asp Asn Ile Glu Ser Cys Thr His Gly Lys Arg Glu Ser
785                 790                 795                 800

Ser Trp Val Glu Glu Leu Leu Thr Leu His Arg Ala Arg Val Thr Asp
                    805                 810                 815
```

```
Val Glu Leu Ile Thr Gly Leu Ser Phe Tyr Gln Asp Arg Gln Glu Ser
            820                 825                 830

Val Ser Glu Leu Leu Arg Leu Lys Thr His Leu Pro Ile Phe Ser Gln
        835                 840                 845

Glu Asp
    850

<210> SEQ ID NO 25
<211> LENGTH: 1474
<212> TYPE: PRT
<213> ORGANISM: Artificial Sequence
<220> FEATURE:
<223> OTHER INFORMATION: ENPP51-ALB

<400> SEQUENCE: 25

Met Thr Ser Lys Phe Leu Leu Val Ser Phe Ile Leu Ala Ala Leu Ser
1               5                   10                  15

Leu Ser Thr Thr Phe Ser Leu Gln Pro Ser Cys Ala Lys Glu Val Lys
            20                  25                  30

Ser Cys Lys Gly Arg Cys Phe Glu Arg Thr Phe Ser Asn Cys Arg Cys
        35                  40                  45

Asp Ala Ala Cys Val Ser Leu Gly Asn Cys Cys Leu Asp Phe Gln Glu
    50                  55                  60

Thr Cys Val Glu Pro Thr His Ile Trp Thr Cys Asn Lys Phe Arg Cys
65                  70                  75                  80

Gly Glu Lys Arg Leu Ser Arg Phe Val Cys Ser Cys Ala Asp Asp Cys
                85                  90                  95

Lys Thr His Asn Asp Cys Cys Ile Asn Tyr Ser Ser Val Cys Gln Asp
            100                 105                 110

Lys Lys Ser Trp Val Glu Glu Thr Cys Glu Ser Ile Asp Thr Pro Glu
        115                 120                 125

Cys Pro Ala Glu Phe Glu Ser Pro Pro Thr Leu Leu Phe Ser Leu Asp
    130                 135                 140

Gly Phe Arg Ala Glu Tyr Leu His Thr Trp Gly Gly Leu Leu Pro Val
145                 150                 155                 160

Ile Ser Lys Leu Lys Asn Cys Gly Thr Tyr Thr Lys Asn Met Arg Pro
                165                 170                 175

Met Tyr Pro Thr Lys Thr Phe Pro Asn His Tyr Ser Ile Val Thr Gly
            180                 185                 190

Leu Tyr Pro Glu Ser His Gly Ile Ile Asp Asn Lys Met Tyr Asp Pro
        195                 200                 205

Lys Met Asn Ala Ser Phe Ser Leu Lys Ser Lys Glu Lys Phe Asn Pro
    210                 215                 220

Leu Trp Tyr Lys Gly Gln Pro Ile Trp Val Thr Ala Asn His Gln Glu
225                 230                 235                 240

Val Lys Ser Gly Thr Tyr Phe Trp Pro Gly Ser Asp Val Glu Ile Asp
                245                 250                 255

Gly Ile Leu Pro Asp Ile Tyr Lys Val Tyr Asn Gly Ser Val Pro Phe
            260                 265                 270

Glu Glu Arg Ile Leu Ala Val Leu Glu Trp Leu Gln Leu Pro Ser His
        275                 280                 285

Glu Arg Pro His Phe Tyr Thr Leu Tyr Leu Glu Glu Pro Asp Ser Ser
    290                 295                 300

Gly His Ser His Gly Pro Val Ser Glu Val Ile Lys Ala Leu Gln
305                 310                 315                 320
```

-continued

Lys Val Asp Arg Leu Val Gly Met Leu Met Asp Gly Leu Lys Asp Leu
                    325                 330                 335

Gly Leu Asp Lys Cys Leu Asn Leu Ile Leu Ile Ser Asp His Gly Met
                340                 345                 350

Glu Gln Gly Ser Cys Lys Lys Tyr Val Tyr Leu Asn Lys Tyr Leu Gly
            355                 360                 365

Asp Val Asn Asn Val Lys Val Val Tyr Gly Pro Ala Ala Arg Leu Arg
        370                 375                 380

Pro Thr Asp Val Pro Glu Thr Tyr Tyr Ser Phe Asn Tyr Glu Ala Leu
385                 390                 395                 400

Ala Lys Asn Leu Ser Cys Arg Glu Pro Asn Gln His Phe Arg Pro Tyr
                405                 410                 415

Leu Lys Pro Phe Leu Pro Lys Arg Leu His Phe Ala Lys Ser Asp Arg
                420                 425                 430

Ile Glu Pro Leu Thr Phe Tyr Leu Asp Pro Gln Trp Gln Leu Ala Leu
            435                 440                 445

Asn Pro Ser Glu Arg Lys Tyr Cys Gly Ser Gly Phe His Gly Ser Asp
        450                 455                 460

Asn Leu Phe Ser Asn Met Gln Ala Leu Phe Ile Gly Tyr Gly Pro Ala
465                 470                 475                 480

Phe Lys His Gly Ala Glu Val Asp Ser Phe Glu Asn Ile Glu Val Tyr
                485                 490                 495

Asn Leu Met Cys Asp Leu Leu Gly Leu Ile Pro Ala Pro Asn Asn Gly
                500                 505                 510

Ser His Gly Ser Leu Asn His Leu Leu Lys Lys Pro Ile Tyr Asn Pro
            515                 520                 525

Ser His Pro Lys Glu Glu Gly Phe Leu Ser Gln Cys Pro Ile Lys Ser
        530                 535                 540

Thr Ser Asn Asp Leu Gly Cys Thr Cys Asp Pro Trp Ile Val Pro Ile
545                 550                 555                 560

Lys Asp Phe Glu Lys Gln Leu Asn Leu Thr Thr Glu Asp Val Asp Asp
                565                 570                 575

Ile Tyr His Met Thr Val Pro Tyr Gly Arg Pro Arg Ile Leu Leu Lys
                580                 585                 590

Gln His Arg Val Cys Leu Leu Gln Gln Gln Phe Leu Thr Gly Tyr
            595                 600                 605

Ser Leu Asp Leu Leu Met Pro Leu Trp Ala Ser Tyr Thr Phe Leu Ser
        610                 615                 620

Asn Asp Gln Phe Ser Arg Asp Asp Phe Ser Asn Cys Leu Tyr Gln Asp
625                 630                 635                 640

Leu Arg Ile Pro Leu Ser Pro Val His Lys Cys Ser Tyr Tyr Lys Ser
                645                 650                 655

Asn Ser Lys Leu Ser Tyr Gly Phe Leu Thr Pro Pro Arg Leu Asn Arg
                660                 665                 670

Val Ser Asn His Ile Tyr Ser Glu Ala Leu Leu Thr Ser Asn Ile Val
            675                 680                 685

Pro Met Tyr Gln Ser Phe Gln Val Ile Trp His Tyr Leu His Asp Thr
        690                 695                 700

Leu Leu Gln Arg Tyr Ala His Glu Arg Asn Gly Ile Asn Val Val Ser
705                 710                 715                 720

Gly Pro Val Phe Asp Phe Asp Tyr Asp Gly Arg Tyr Asp Ser Leu Glu
                725                 730                 735

```
Ile Leu Lys Gln Asn Ser Arg Val Ile Arg Ser Gln Glu Ile Leu Ile
            740                 745                 750

Pro Thr His Phe Phe Ile Val Leu Thr Ser Cys Lys Gln Leu Ser Glu
            755                 760                 765

Thr Pro Leu Glu Cys Ser Ala Leu Glu Ser Ser Ala Tyr Ile Leu Pro
        770                 775                 780

His Arg Pro Asp Asn Ile Glu Ser Cys Thr His Gly Lys Arg Glu Ser
785                 790                 795                 800

Ser Trp Val Glu Glu Leu Leu Thr Leu His Arg Ala Arg Val Thr Asp
                805                 810                 815

Val Glu Leu Ile Thr Gly Leu Ser Phe Tyr Gln Asp Arg Gln Glu Ser
            820                 825                 830

Val Ser Glu Leu Leu Arg Leu Lys Thr His Leu Pro Ile Phe Ser Gln
            835                 840                 845

Glu Asp Gly Gly Ser Gly Gly Ser Met Lys Trp Val Thr Phe Leu Leu
        850                 855                 860

Leu Leu Phe Val Ser Gly Ser Ala Phe Ser Arg Gly Val Phe Arg Arg
865                 870                 875                 880

Glu Ala His Lys Ser Glu Ile Ala His Arg Tyr Asn Asp Leu Gly Glu
                885                 890                 895

Gln His Phe Lys Gly Leu Val Leu Ile Ala Phe Ser Gln Tyr Leu Gln
            900                 905                 910

Lys Cys Ser Tyr Asp Glu His Ala Lys Leu Val Gln Glu Val Thr Asp
            915                 920                 925

Phe Ala Lys Thr Cys Val Ala Asp Glu Ser Ala Ala Asn Cys Asp Lys
        930                 935                 940

Ser Leu His Thr Leu Phe Gly Asp Lys Leu Cys Ala Ile Pro Asn Leu
945                 950                 955                 960

Arg Glu Asn Tyr Gly Glu Leu Ala Asp Cys Cys Thr Lys Gln Glu Pro
                965                 970                 975

Glu Arg Asn Glu Cys Phe Leu Gln His Lys Asp Asp Asn Pro Ser Leu
            980                 985                 990

Pro Pro Phe Glu Arg Pro Glu Ala  Glu Ala Met Cys Thr  Ser Phe Lys
            995                 1000                1005

Glu Asn  Pro Thr Thr Phe Met  Gly His Tyr Leu His  Glu Val Ala
    1010                1015                1020

Arg Arg  His Pro Tyr Phe Tyr  Ala Pro Glu Leu Leu  Tyr Tyr Ala
    1025                1030                1035

Glu Gln  Tyr Asn Glu Ile Leu  Thr Gln Cys Cys Ala  Glu Ala Asp
    1040                1045                1050

Lys Glu  Ser Cys Leu Thr Pro  Lys Leu Asp Gly Val  Lys Glu Lys
    1055                1060                1065

Ala Leu Val Ser Ser Val Arg  Gln Arg Met Lys Cys  Ser Ser Met
    1070                1075                1080

Gln Lys  Phe Gly Glu Arg Ala  Phe Lys Ala Trp Ala  Val Ala Arg
    1085                1090                1095

Leu Ser  Gln Thr Phe Pro Asn  Ala Asp Phe Ala Glu  Ile Thr Lys
    1100                1105                1110

Leu Ala  Thr Asp Leu Thr Lys  Val Asn Lys Glu Cys  Cys His Gly
    1115                1120                1125

Asp Leu  Leu Glu Cys Ala Asp  Arg Ala Glu Leu Ala  Lys Tyr
    1130                1135                1140

Met Cys  Glu Asn Gln Ala Thr  Ile Ser Ser Lys Leu  Gln Thr Cys
```

```
              1145                1150                1155

Cys Asp Lys Pro Leu Leu Lys Lys Ala His Cys Leu Ser Glu Val
     1160                1165                1170

Glu His Asp Thr Met Pro Ala Asp Leu Pro Ala Ile Ala Ala Asp
     1175                1180                1185

Phe Val Glu Asp Gln Glu Val Cys Lys Asn Tyr Ala Glu Ala Lys
     1190                1195                1200

Asp Val Phe Leu Gly Thr Phe Leu Tyr Glu Tyr Ser Arg Arg His
     1205                1210                1215

Pro Asp Tyr Ser Val Ser Leu Leu Leu Arg Leu Ala Lys Lys Tyr
     1220                1225                1230

Glu Ala Thr Leu Glu Lys Cys Cys Ala Glu Ala Asn Pro Pro Ala
     1235                1240                1245

Cys Tyr Gly Thr Val Leu Ala Glu Phe Gln Pro Leu Val Glu Glu
     1250                1255                1260

Pro Lys Asn Leu Val Lys Thr Asn Cys Asp Leu Tyr Glu Lys Leu
     1265                1270                1275

Gly Glu Tyr Gly Phe Gln Asn Ala Ile Leu Val Arg Tyr Thr Gln
     1280                1285                1290

Lys Ala Pro Gln Val Ser Thr Pro Thr Leu Val Glu Ala Ala Arg
     1295                1300                1305

Asn Leu Gly Arg Val Gly Thr Lys Cys Cys Thr Leu Pro Glu Asp
     1310                1315                1320

Gln Arg Leu Pro Cys Val Glu Asp Tyr Leu Ser Ala Ile Leu Asn
     1325                1330                1335

Arg Val Cys Leu Leu His Glu Lys Thr Pro Val Ser Glu His Val
     1340                1345                1350

Thr Lys Cys Cys Ser Gly Ser Leu Val Glu Arg Arg Pro Cys Phe
     1355                1360                1365

Ser Ala Leu Thr Val Asp Glu Thr Tyr Val Pro Lys Glu Phe Lys
     1370                1375                1380

Ala Glu Thr Phe Thr Phe His Ser Asp Ile Cys Thr Leu Pro Glu
     1385                1390                1395

Lys Glu Lys Gln Ile Lys Lys Gln Thr Ala Leu Ala Glu Leu Val
     1400                1405                1410

Lys His Lys Pro Lys Ala Thr Ala Glu Gln Leu Lys Thr Val Met
     1415                1420                1425

Asp Asp Phe Ala Gln Phe Leu Asp Thr Cys Cys Lys Ala Ala Asp
     1430                1435                1440

Lys Asp Thr Cys Phe Ser Thr Glu Gly Pro Asn Leu Val Thr Arg
     1445                1450                1455

Cys Lys Asp Ala Leu Ala Arg Ser Trp Ser His Pro Gln Phe Glu
     1460                1465                1470

Lys

<210> SEQ ID NO 26
<211> LENGTH: 227
<212> TYPE: PRT
<213> ORGANISM: Artificial Sequence
<220> FEATURE:
<223> OTHER INFORMATION: Human IgG Fc domain, Fc

<400> SEQUENCE: 26

Asp Lys Thr His Thr Cys Pro Pro Cys Pro Ala Pro Glu Leu Leu Gly
1               5                   10                  15
```

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 27
<211> LENGTH: 618
<212> TYPE: PRT
<213> ORGANISM: Artificial Sequence
<220> FEATURE:
<223> OTHER INFORMATION: ALB

<400> SEQUENCE: 27

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
 50                  55                  60

Lys Leu Val Gln Glu Val Thr Asp Phe Ala Lys Thr Cys Val Ala Asp
 65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
130                 135                 140

```
Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gln Arg Met Lys Cys
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
    370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
    450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Glu Lys Glu
    530                 535                 540

Lys Gln Ile Lys Lys Gln Thr Ala Leu Ala Glu Leu Val Lys His Lys
545                 550                 555                 560
```

```
Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Asp Ala Leu Ala
        595                 600                 605

Arg Ser Trp Ser His Pro Gln Phe Glu Lys
    610                 615
```

<210> SEQ ID NO 28
<211> LENGTH: 3
<212> TYPE: PRT
<213> ORGANISM: Artificial Sequence
<220> FEATURE:
<223> OTHER INFORMATION: chemically synthesized

<400> SEQUENCE: 28

```
Leu Ile Asn
1
```

<210> SEQ ID NO 29
<211> LENGTH: 6
<212> TYPE: PRT
<213> ORGANISM: Artificial Sequence
<220> FEATURE:
<223> OTHER INFORMATION: chemically synthesized

<400> SEQUENCE: 29

```
Gly Gly Ser Gly Gly Ser
1               5
```

<210> SEQ ID NO 30
<211> LENGTH: 7
<212> TYPE: PRT
<213> ORGANISM: Artificial Sequence
<220> FEATURE:
<223> OTHER INFORMATION: chemically synthesized

<400> SEQUENCE: 30

```
Arg Ser Gly Ser Gly Gly Ser
1               5
```

<210> SEQ ID NO 31
<211> LENGTH: 875
<212> TYPE: PRT
<213> ORGANISM: Homo sapiens

<400> SEQUENCE: 31

```
Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
                20                  25                  30

Val Ile Met Ser Leu Gly Leu Gly Leu Gly Leu Gly Leu Arg Lys Leu
            35                  40                  45

Glu Lys Gln Gly Ser Cys Arg Lys Lys Cys Phe Asp Ala Ser Phe Arg
        50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
                100                 105                 110
```

```
Cys Ser Cys Ser Asp Asp Cys Leu Gln Arg Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
    290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
    370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525
```

Pro Ala Pro Asn Asn Gly Thr His Gly Ser Leu Asn His Leu Leu Lys
530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
                580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
                660                 665                 670

Pro Ser Glu Ser Gln Lys Cys Ser Phe Tyr Leu Ala Asp Lys Asn Ile
            675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
                740                 745                 750

Tyr Asn Tyr Asp Gly His Phe Asp Ala Pro Asp Glu Ile Thr Lys His
            755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
                820                 825                 830

Thr Ala His Ile Ala Arg Val Arg Asp Val Glu Leu Leu Thr Gly Leu
            835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 32
<211> LENGTH: 827
<212> TYPE: PRT
<213> ORGANISM: Artificial Sequence
<220> FEATURE:
<223> OTHER INFORMATION: Extracellular domain of ENPP3

<400> SEQUENCE: 32

Glu Lys Gln Gly Ser Cys Arg Lys Lys Cys Phe Asp Ala Ser Phe Arg
1               5                   10                  15

```
Gly Leu Glu Asn Cys Arg Cys Asp Val Ala Cys Lys Asp Arg Gly Asp
             20                  25                  30

Cys Cys Trp Asp Phe Glu Asp Thr Cys Val Glu Ser Thr Arg Ile Trp
         35                  40                  45

Met Cys Asn Lys Phe Arg Cys Gly Glu Thr Arg Leu Glu Ala Ser Leu
     50                  55                  60

Cys Ser Cys Ser Asp Asp Cys Leu Gln Arg Lys Asp Cys Cys Ala Asp
 65                  70                  75                  80

Tyr Lys Ser Val Cys Gln Gly Glu Thr Ser Trp Leu Glu Glu Asn Cys
                 85                  90                  95

Asp Thr Ala Gln Gln Ser Gln Cys Pro Glu Gly Phe Asp Leu Pro Pro
            100                 105                 110

Val Ile Leu Phe Ser Met Asp Gly Phe Arg Ala Glu Tyr Leu Tyr Thr
            115                 120                 125

Trp Asp Thr Leu Met Pro Asn Ile Asn Lys Leu Lys Thr Cys Gly Ile
    130                 135                 140

His Ser Lys Tyr Met Arg Ala Met Tyr Pro Thr Lys Thr Phe Pro Asn
145                 150                 155                 160

His Tyr Thr Ile Val Thr Gly Leu Tyr Pro Glu Ser His Gly Ile Ile
                165                 170                 175

Asp Asn Asn Met Tyr Asp Val Asn Leu Asn Lys Asn Phe Ser Leu Ser
            180                 185                 190

Ser Lys Glu Gln Asn Asn Pro Ala Trp Trp His Gly Gln Pro Met Trp
    195                 200                 205

Leu Thr Ala Met Tyr Gln Gly Leu Lys Ala Ala Thr Tyr Phe Trp Pro
    210                 215                 220

Gly Ser Glu Val Ala Ile Asn Gly Ser Phe Pro Ser Ile Tyr Met Pro
225                 230                 235                 240

Tyr Asn Gly Ser Val Pro Phe Glu Glu Arg Ile Ser Thr Leu Leu Lys
                245                 250                 255

Trp Leu Asp Leu Pro Lys Ala Glu Arg Pro Arg Phe Tyr Thr Met Tyr
            260                 265                 270

Phe Glu Glu Pro Asp Ser Ser Gly His Ala Gly Gly Pro Val Ser Ala
            275                 280                 285

Arg Val Ile Lys Ala Leu Gln Val Val Asp His Ala Phe Gly Met Leu
    290                 295                 300

Met Glu Gly Leu Lys Gln Arg Asn Leu His Asn Cys Val Asn Ile Ile
305                 310                 315                 320

Leu Leu Ala Asp His Gly Met Asp Gln Thr Tyr Cys Asn Lys Met Glu
                325                 330                 335

Tyr Met Thr Asp Tyr Phe Pro Arg Ile Asn Phe Phe Tyr Met Tyr Glu
            340                 345                 350

Gly Pro Ala Pro Arg Ile Arg Ala His Asn Ile Pro His Asp Phe Phe
            355                 360                 365

Ser Phe Asn Ser Glu Glu Ile Val Arg Asn Leu Ser Cys Arg Lys Pro
    370                 375                 380

Asp Gln His Phe Lys Pro Tyr Leu Thr Pro Asp Leu Pro Lys Arg Leu
385                 390                 395                 400

His Tyr Ala Lys Asn Val Arg Ile Asp Lys Val His Leu Phe Val Asp
                405                 410                 415

Gln Gln Trp Leu Ala Val Arg Ser Lys Ser Asn Thr Asn Cys Gly Gly
            420                 425                 430

Gly Asn His Gly Tyr Asn Asn Glu Phe Arg Ser Met Glu Ala Ile Phe
```

```
                435                 440                 445
Leu Ala His Gly Pro Ser Phe Lys Glu Lys Thr Glu Val Glu Pro Phe
450                 455                 460

Glu Asn Ile Glu Val Tyr Asn Leu Met Cys Asp Leu Leu Arg Ile Gln
465                 470                 475                 480

Pro Ala Pro Asn Asn Gly Thr His Gly Ser Leu Asn His Leu Leu Lys
                485                 490                 495

Val Pro Phe Tyr Glu Pro Ser His Ala Glu Glu Val Ser Lys Phe Ser
                500                 505                 510

Val Cys Gly Phe Ala Asn Pro Leu Pro Thr Glu Ser Leu Asp Cys Phe
                515                 520                 525

Cys Pro His Leu Gln Asn Ser Thr Gln Leu Glu Gln Val Asn Gln Met
                530                 535                 540

Leu Asn Leu Thr Gln Glu Glu Ile Thr Ala Thr Val Lys Val Asn Leu
545                 550                 555                 560

Pro Phe Gly Arg Pro Arg Val Leu Gln Lys Asn Val Asp His Cys Leu
                565                 570                 575

Leu Tyr His Arg Glu Tyr Val Ser Gly Phe Gly Lys Ala Met Arg Met
                580                 585                 590

Pro Met Trp Ser Ser Tyr Thr Val Pro Gln Leu Gly Asp Thr Ser Pro
                595                 600                 605

Leu Pro Pro Thr Val Pro Asp Cys Leu Arg Ala Asp Val Arg Val Pro
610                 615                 620

Pro Ser Glu Ser Gln Lys Cys Ser Phe Tyr Leu Ala Asp Lys Asn Ile
625                 630                 635                 640

Thr His Gly Phe Leu Tyr Pro Pro Ala Ser Asn Arg Thr Ser Asp Ser
                645                 650                 655

Gln Tyr Asp Ala Leu Ile Thr Ser Asn Leu Val Pro Met Tyr Glu Glu
                660                 665                 670

Phe Arg Lys Met Trp Asp Tyr Phe His Ser Val Leu Leu Ile Lys His
                675                 680                 685

Ala Thr Glu Arg Asn Gly Val Asn Val Val Ser Gly Pro Ile Phe Asp
690                 695                 700

Tyr Asn Tyr Asp Gly His Phe Asp Ala Pro Asp Glu Ile Thr Lys His
705                 710                 715                 720

Leu Ala Asn Thr Asp Val Pro Ile Pro Thr His Tyr Phe Val Val Leu
                725                 730                 735

Thr Ser Cys Lys Asn Lys Ser His Thr Pro Glu Asn Cys Pro Gly Trp
                740                 745                 750

Leu Asp Val Leu Pro Phe Ile Ile Pro His Arg Pro Thr Asn Val Glu
                755                 760                 765

Ser Cys Pro Glu Gly Lys Pro Glu Ala Leu Trp Val Glu Glu Arg Phe
                770                 775                 780

Thr Ala His Ile Ala Arg Val Arg Asp Val Glu Leu Leu Thr Gly Leu
785                 790                 795                 800

Asp Phe Tyr Gln Asp Lys Val Gln Pro Val Ser Glu Ile Leu Gln Leu
                805                 810                 815

Lys Thr Tyr Leu Pro Thr Phe Glu Thr Thr Ile
                820                 825

<210> SEQ ID NO 33
<211> LENGTH: 17
<212> TYPE: PRT
<213> ORGANISM: Artificial Sequence
```

```
<220> FEATURE:
<223> OTHER INFORMATION: exENPP3

<400> SEQUENCE: 33

Leu Leu Val Ile Met Ser Leu Gly Leu Gly Leu Gly Leu Gly Leu Arg
1               5                   10                  15

Lys

<210> SEQ ID NO 34
<211> LENGTH: 22
<212> TYPE: PRT
<213> ORGANISM: Artificial Sequence
<220> FEATURE:
<223> OTHER INFORMATION: ENPP7 protein export signal sequence

<400> SEQUENCE: 34

Met Arg Gly Pro Ala Val Leu Leu Thr Val Ala Leu Ala Thr Leu Leu
1               5                   10                  15

Ala Pro Gly Ala Gly Ala
            20

<210> SEQ ID NO 35
<211> LENGTH: 98
<212> TYPE: PRT
<213> ORGANISM: Artificial Sequence
<220> FEATURE:
<223> OTHER INFORMATION: ENPP121GLK protein export signal sequence

<400> SEQUENCE: 35

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
                20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65              70                  75                  80

Phe Thr Phe Ala Val Gly Val Asn Ile Cys Leu Gly Phe Thr Ala Gly
                85                  90                  95

Leu Lys

<210> SEQ ID NO 36
<211> LENGTH: 95
<212> TYPE: PRT
<213> ORGANISM: Artificial Sequence
<220> FEATURE:
<223> OTHER INFORMATION: ENPP121 protein export signal sequence

<400> SEQUENCE: 36

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
                20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
```

```
                65                  70                  75                  80
Phe Thr Phe Ala Val Gly Val Asn Ile Cys Leu Gly Phe Thr Ala
                    85                  90                  95

<210> SEQ ID NO 37
<211> LENGTH: 24
<212> TYPE: PRT
<213> ORGANISM: Artificial Sequence
<220> FEATURE:
<223> OTHER INFORMATION: ENPP5 protein export signal sequence
<220> FEATURE:
<221> NAME/KEY: MOD_RES
<222> LOCATION: (23)..(23)
<223> OTHER INFORMATION: residue can be absent or L
<220> FEATURE:
<221> NAME/KEY: MOD_RES
<222> LOCATION: (24)..(24)
<223> OTHER INFORMATION: if residue 23 is absent, residue 24 is absent;
      if position 23 is L, residue 24 is absent or Q

<400> SEQUENCE: 37

Met Thr Ser Lys Phe Leu Leu Val Ser Phe Ile Leu Ala Ala Leu Ser
1               5                   10                  15

Leu Ser Thr Thr Phe Ser Xaa Xaa
            20

<210> SEQ ID NO 38
<211> LENGTH: 20
<212> TYPE: PRT
<213> ORGANISM: Artificial Sequence
<220> FEATURE:
<223> OTHER INFORMATION: ENPP7 signal sequence

<400> SEQUENCE: 38

Met Arg Gly Pro Ala Val Leu Leu Thr Val Ala Leu Ala Thr Leu Leu
1               5                   10                  15

Ala Pro Gly Ala
            20

<210> SEQ ID NO 39
<211> LENGTH: 22
<212> TYPE: PRT
<213> ORGANISM: Artificial Sequence
<220> FEATURE:
<223> OTHER INFORMATION: ENPP7 signal sequence

<400> SEQUENCE: 39

Met Arg Gly Pro Ala Val Leu Leu Thr Val Ala Leu Ala Thr Leu Leu
1               5                   10                  15

Ala Pro Gly Ala Gly Ala
            20

<210> SEQ ID NO 40
<211> LENGTH: 16
<212> TYPE: PRT
<213> ORGANISM: Artificial Sequence
<220> FEATURE:
<223> OTHER INFORMATION: chemically synthesized

<400> SEQUENCE: 40

Leu Val Ile Met Ser Leu Gly Leu Gly Leu Gly Leu Gly Leu Arg Lys
1               5                   10                  15

<210> SEQ ID NO 41
<211> LENGTH: 15
<212> TYPE: PRT
```

```
<213> ORGANISM: Artificial Sequence
<220> FEATURE:
<223> OTHER INFORMATION: chemically synthesized

<400> SEQUENCE: 41

Val Ile Met Ser Leu Gly Leu Gly Leu Gly Leu Gly Leu Arg Lys
1               5                   10                  15

<210> SEQ ID NO 42
<211> LENGTH: 14
<212> TYPE: PRT
<213> ORGANISM: Artificial Sequence
<220> FEATURE:
<223> OTHER INFORMATION: chemically synthesized

<400> SEQUENCE: 42

Ile Met Ser Leu Gly Leu Gly Leu Gly Leu Gly Leu Arg Lys
1               5                   10

<210> SEQ ID NO 43
<211> LENGTH: 13
<212> TYPE: PRT
<213> ORGANISM: Artificial Sequence
<220> FEATURE:
<223> OTHER INFORMATION: chemically synthesized

<400> SEQUENCE: 43

Met Ser Leu Gly Leu Gly Leu Gly Leu Gly Leu Arg Lys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: chemically synthesized

<400> SEQUENCE: 44

Ser Leu Gly Leu Gly Leu Gly Leu Gly Leu Arg Lys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: chemically synthesized

<400> SEQUENCE: 45

Leu Gly Leu Gly Leu Gly Leu Gly Leu Arg Lys
1               5                   10

<210> SEQ ID NO 46
<211> LENGTH: 10
<212> TYPE: PRT
<213> ORGANISM: Artificial Sequence
<220> FEATURE:
<223> OTHER INFORMATION: chemically synthesized

<400> SEQUENCE: 46

Gly Leu Gly Leu Gly Leu Gly Leu Arg Lys
1               5                   10

<210> SEQ ID NO 47
<211> LENGTH: 9
<212> TYPE: PRT
<213> ORGANISM: Artificial Sequence
```

```
<220> FEATURE:
<223> OTHER INFORMATION: chemically synthesized

<400> SEQUENCE: 47

Leu Gly Leu Gly Leu Gly Leu Arg Lys
1               5

<210> SEQ ID NO 48
<211> LENGTH: 8
<212> TYPE: PRT
<213> ORGANISM: Artificial Sequence
<220> FEATURE:
<223> OTHER INFORMATION: chemically synthesized

<400> SEQUENCE: 48

Gly Leu Gly Leu Gly Leu Arg Lys
1               5

<210> SEQ ID NO 49
<211> LENGTH: 7
<212> TYPE: PRT
<213> ORGANISM: Artificial Sequence
<220> FEATURE:
<223> OTHER INFORMATION: chemically synthesized

<400> SEQUENCE: 49

Leu Gly Leu Gly Leu Arg Lys
1               5

<210> SEQ ID NO 50
<211> LENGTH: 6
<212> TYPE: PRT
<213> ORGANISM: Artificial Sequence
<220> FEATURE:
<223> OTHER INFORMATION: chemically synthesized

<400> SEQUENCE: 50

Gly Leu Gly Leu Arg Lys
1               5

<210> SEQ ID NO 51
<211> LENGTH: 5
<212> TYPE: PRT
<213> ORGANISM: Artificial Sequence
<220> FEATURE:
<223> OTHER INFORMATION: chemically synthesized

<400> SEQUENCE: 51

Leu Gly Leu Arg Lys
1               5

<210> SEQ ID NO 52
<211> LENGTH: 4
<212> TYPE: PRT
<213> ORGANISM: Artificial Sequence
<220> FEATURE:
<223> OTHER INFORMATION: chemically synthesized

<400> SEQUENCE: 52

Gly Leu Arg Lys
1

<210> SEQ ID NO 53
<211> LENGTH: 3
<212> TYPE: PRT
<213> ORGANISM: Artificial Sequence
<220> FEATURE:
```

<223> OTHER INFORMATION: chemically synthesized

<400> SEQUENCE: 53

Leu Arg Lys
1

<210> SEQ ID NO 54
<211> LENGTH: 2
<212> TYPE: PRT
<213> ORGANISM: Artificial Sequence
<220> FEATURE:
<223> OTHER INFORMATION: chemically synthesized

<400> SEQUENCE: 54

Arg Lys
1

<210> SEQ ID NO 55
<211> LENGTH: 1
<212> TYPE: PRT
<213> ORGANISM: Artificial Sequence
<220> FEATURE:
<223> OTHER INFORMATION: chemically synthesized

<400> SEQUENCE: 55

Lys
1

<210> SEQ ID NO 56
<211> LENGTH: 1147
<212> TYPE: PRT
<213> ORGANISM: Artificial Sequence
<220> FEATURE:
<223> OTHER INFORMATION: ENPP121-NPP3-Fc

<400> SEQUENCE: 56

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Lys
                85                  90                  95

Gln Gly Ser Cys Arg Lys Lys Cys Phe Asp Ala Ser Phe Arg Gly Leu
            100                 105                 110

Glu Asn Cys Arg Cys Asp Val Ala Cys Lys Asp Arg Gly Asp Cys Cys
        115                 120                 125

Trp Asp Phe Glu Asp Thr Cys Val Glu Ser Thr Arg Ile Trp Met Cys
    130                 135                 140

Asn Lys Phe Arg Cys Gly Glu Arg Leu Glu Ala Ser Leu Cys Ser Cys
145                 150                 155                 160

Ser Asp Asp Cys Leu Gln Arg Lys Asp Cys Cys Ala Asp Tyr Lys Ser
                165                 170                 175

Val Cys Gln Gly Glu Thr Ser Trp Leu Glu Glu Asn Cys Asp Thr Ala
            180                 185                 190
```

-continued

```
Gln Gln Ser Gln Cys Pro Glu Gly Phe Asp Leu Pro Val Ile Leu
        195                 200                 205
Phe Ser Met Asp Gly Phe Arg Ala Glu Tyr Leu Tyr Thr Trp Asp Thr
210                 215                 220
Leu Met Pro Asn Ile Asn Lys Leu Lys Thr Cys Gly Ile His Ser Lys
225                 230                 235                 240
Tyr Met Arg Ala Met Tyr Pro Thr Lys Thr Phe Pro Asn His Tyr Thr
                245                 250                 255
Ile Val Thr Gly Leu Tyr Pro Glu Ser His Gly Ile Ile Asp Asn Asn
            260                 265                 270
Met Tyr Asp Val Asn Leu Asn Lys Asn Phe Ser Leu Ser Ser Lys Glu
        275                 280                 285
Gln Asn Asn Pro Ala Trp Trp His Gly Gln Pro Met Trp Leu Thr Ala
    290                 295                 300
Met Tyr Gln Gly Leu Lys Ala Ala Thr Tyr Phe Trp Pro Gly Ser Glu
305                 310                 315                 320
Val Ala Ile Asn Gly Ser Phe Pro Ser Ile Tyr Met Pro Tyr Asn Gly
                325                 330                 335
Ser Val Pro Phe Glu Glu Arg Ile Ser Thr Leu Leu Lys Trp Leu Asp
            340                 345                 350
Leu Pro Lys Ala Glu Arg Pro Arg Phe Tyr Thr Met Tyr Phe Glu Glu
        355                 360                 365
Pro Asp Ser Ser Gly His Ala Gly Gly Pro Val Ser Ala Arg Val Ile
    370                 375                 380
Lys Ala Leu Gln Val Val Asp His Ala Phe Gly Met Leu Met Glu Gly
385                 390                 395                 400
Leu Lys Gln Arg Asn Leu His Asn Cys Val Asn Ile Ile Leu Leu Ala
                405                 410                 415
Asp His Gly Met Asp Gln Thr Tyr Cys Asn Lys Met Glu Tyr Met Thr
            420                 425                 430
Asp Tyr Phe Pro Arg Ile Asn Phe Phe Tyr Met Tyr Glu Gly Pro Ala
        435                 440                 445
Pro Arg Ile Arg Ala His Asn Ile Pro His Asp Phe Phe Ser Phe Asn
    450                 455                 460
Ser Glu Glu Ile Val Arg Asn Leu Ser Cys Arg Lys Pro Asp Gln His
465                 470                 475                 480
Phe Lys Pro Tyr Leu Thr Pro Asp Leu Pro Lys Arg Leu His Tyr Ala
                485                 490                 495
Lys Asn Val Arg Ile Asp Lys Val His Leu Phe Val Asp Gln Gln Trp
            500                 505                 510
Leu Ala Val Arg Ser Lys Ser Asn Thr Asn Cys Gly Gly Gly Asn His
        515                 520                 525
Gly Tyr Asn Asn Glu Phe Arg Ser Met Glu Ala Ile Phe Leu Ala His
    530                 535                 540
Gly Pro Ser Phe Lys Glu Lys Thr Glu Val Glu Pro Phe Glu Asn Ile
545                 550                 555                 560
Glu Val Tyr Asn Leu Met Cys Asp Leu Leu Arg Ile Gln Pro Ala Pro
                565                 570                 575
Asn Asn Gly Thr His Gly Ser Leu Asn His Leu Leu Lys Val Pro Phe
            580                 585                 590
Tyr Glu Pro Ser His Ala Glu Glu Val Ser Lys Phe Ser Val Cys Gly
        595                 600                 605
Phe Ala Asn Pro Leu Pro Thr Glu Ser Leu Asp Cys Phe Cys Pro His
```

```
            610             615             620
Leu Gln Asn Ser Thr Gln Leu Glu Gln Val Asn Gln Met Leu Asn Leu
625                 630                 635                 640

Thr Gln Glu Glu Ile Thr Ala Thr Val Lys Val Asn Leu Pro Phe Gly
                645                 650                 655

Arg Pro Arg Val Leu Gln Lys Asn Val Asp His Cys Leu Leu Tyr His
            660                 665                 670

Arg Glu Tyr Val Ser Gly Phe Gly Lys Ala Met Arg Met Pro Met Trp
        675                 680                 685

Ser Ser Tyr Thr Val Pro Gln Leu Gly Asp Thr Ser Pro Leu Pro Pro
    690                 695                 700

Thr Val Pro Asp Cys Leu Arg Ala Asp Val Arg Val Pro Pro Ser Glu
705                 710                 715                 720

Ser Gln Lys Cys Ser Phe Tyr Leu Ala Asp Lys Asn Ile Thr His Gly
                725                 730                 735

Phe Leu Tyr Pro Pro Ala Ser Asn Arg Thr Ser Asp Ser Gln Tyr Asp
                740                 745                 750

Ala Leu Ile Thr Ser Asn Leu Val Pro Met Tyr Glu Glu Phe Arg Lys
            755                 760                 765

Met Trp Asp Tyr Phe His Ser Val Leu Leu Ile Lys His Ala Thr Glu
        770                 775                 780

Arg Asn Gly Val Asn Val Val Ser Gly Pro Ile Phe Asp Tyr Asn Tyr
785                 790                 795                 800

Asp Gly His Phe Asp Ala Pro Asp Glu Ile Thr Lys His Leu Ala Asn
                805                 810                 815

Thr Asp Val Pro Ile Pro Thr His Tyr Phe Val Leu Thr Ser Cys
                820                 825                 830

Lys Asn Lys Ser His Thr Pro Glu Asn Cys Pro Gly Trp Leu Asp Val
            835                 840                 845

Leu Pro Phe Ile Ile Pro His Arg Pro Thr Asn Val Glu Ser Cys Pro
850                 855                 860

Glu Gly Lys Pro Glu Ala Leu Trp Val Glu Glu Arg Phe Thr Ala His
865                 870                 875                 880

Ile Ala Arg Val Arg Asp Val Glu Leu Leu Thr Gly Leu Asp Phe Tyr
                885                 890                 895

Gln Asp Lys Val Gln Pro Val Ser Glu Ile Leu Gln Leu Lys Thr Tyr
            900                 905                 910

Leu Pro Thr Phe Glu Thr Thr Ile Asp Lys Thr His Thr Cys Pro Pro
        915                 920                 925

Cys Pro Ala Pro Glu Leu Leu Gly Gly Pro Ser Val Phe Leu Phe Pro
930                 935                 940

Pro Lys Pro Lys Asp Thr Leu Met Ile Ser Arg Thr Pro Glu Val Thr
945                 950                 955                 960

Cys Val Val Val Asp Val Ser His Glu Asp Pro Glu Val Lys Phe Asn
                965                 970                 975

Trp Tyr Val Asp Gly Val Glu Val His Asn Ala Lys Thr Lys Pro Arg
            980                 985                 990

Glu Glu Gln Tyr Asn Ser Thr Tyr Arg Val Val Ser Val Leu Thr Val
        995                 1000                1005

Leu His Gln Asp Trp Leu Asn Gly Lys Glu Tyr Lys Cys Lys Val
    1010                1015                1020

Ser Asn Lys Ala Leu Pro Ala Pro Ile Glu Lys Thr Ile Ser Lys
    1025                1030                1035
```

```
Ala Lys Gly Gln Pro Arg Glu Pro Gln Val Tyr Thr Leu Pro Pro
    1040                1045                1050

Ser Arg Glu Glu Met Thr Lys Asn Gln Val Ser Leu Thr Cys Leu
    1055                1060                1065

Val Lys Gly Phe Tyr Pro Ser Asp Ile Ala Val Glu Trp Glu Ser
    1070                1075                1080

Asn Gly Gln Pro Glu Asn Asn Tyr Lys Thr Thr Pro Pro Val Leu
    1085                1090                1095

Asp Ser Asp Gly Ser Phe Phe Leu Tyr Ser Lys Leu Thr Val Asp
    1100                1105                1110

Lys Ser Arg Trp Gln Gln Gly Asn Val Phe Ser Cys Ser Val Met
    1115                1120                1125

His Glu Ala Leu His Asn His Tyr Thr Gln Lys Ser Leu Ser Leu
    1130                1135                1140

Ser Pro Gly Lys
    1145

<210> SEQ ID NO 57
<211> LENGTH: 1072
<212> TYPE: PRT
<213> ORGANISM: Artificial Sequence
<220> FEATURE:
<223> OTHER INFORMATION: ENPP7-ENPP3-Fc

<400> SEQUENCE: 57

Met Arg Gly Pro Ala Val Leu Leu Thr Val Ala Leu Ala Thr Leu Leu
1               5                   10                  15

Ala Pro Gly Ala Lys Gln Gly Ser Cys Arg Lys Lys Cys Phe Asp Ala
                20                  25                  30

Ser Phe Arg Gly Leu Glu Asn Cys Arg Cys Asp Val Ala Cys Lys Asp
            35                  40                  45

Arg Gly Asp Cys Cys Trp Asp Phe Glu Asp Thr Cys Val Glu Ser Thr
        50                  55                  60

Arg Ile Trp Met Cys Asn Lys Phe Arg Cys Gly Glu Arg Leu Glu Ala
65                  70                  75                  80

Ser Leu Cys Ser Cys Ser Asp Asp Cys Leu Gln Arg Lys Asp Cys Cys
                85                  90                  95

Ala Asp Tyr Lys Ser Val Cys Gln Gly Glu Thr Ser Trp Leu Glu Glu
                100                 105                 110

Asn Cys Asp Thr Ala Gln Gln Ser Gln Cys Pro Glu Gly Phe Asp Leu
            115                 120                 125

Pro Pro Val Ile Leu Phe Ser Met Asp Gly Phe Arg Ala Glu Tyr Leu
        130                 135                 140

Tyr Thr Trp Asp Thr Leu Met Pro Asn Ile Asn Lys Leu Lys Thr Cys
145                 150                 155                 160

Gly Ile His Ser Lys Tyr Met Arg Ala Met Tyr Pro Thr Lys Thr Phe
                165                 170                 175

Pro Asn His Tyr Thr Ile Val Thr Gly Leu Tyr Pro Glu Ser His Gly
            180                 185                 190

Ile Ile Asp Asn Asn Met Tyr Asp Val Asn Leu Asn Lys Asn Phe Ser
        195                 200                 205

Leu Ser Ser Lys Glu Gln Asn Asn Pro Ala Trp Trp His Gly Gln Pro
        210                 215                 220

Met Trp Leu Thr Ala Met Tyr Gln Gly Leu Lys Ala Ala Thr Tyr Phe
225                 230                 235                 240
```

```
Trp Pro Gly Ser Glu Val Ala Ile Asn Gly Ser Phe Pro Ser Ile Tyr
            245                 250                 255

Met Pro Tyr Asn Gly Ser Val Pro Phe Glu Arg Ile Ser Thr Leu
        260                 265                 270

Leu Lys Trp Leu Asp Leu Pro Lys Ala Glu Arg Pro Arg Phe Tyr Thr
        275                 280                 285

Met Tyr Phe Glu Glu Pro Asp Ser Ser Gly His Ala Gly Gly Pro Val
        290                 295                 300

Ser Ala Arg Val Ile Lys Ala Leu Gln Val Val Asp His Ala Phe Gly
305                 310                 315                 320

Met Leu Met Glu Gly Leu Lys Gln Arg Asn Leu His Asn Cys Val Asn
                325                 330                 335

Ile Ile Leu Leu Ala Asp His Gly Met Asp Gln Thr Tyr Cys Asn Lys
                340                 345                 350

Met Glu Tyr Met Thr Asp Tyr Phe Pro Arg Ile Asn Phe Phe Tyr Met
                355                 360                 365

Tyr Glu Gly Pro Ala Pro Arg Ile Arg Ala His Asn Ile Pro His Asp
        370                 375                 380

Phe Phe Ser Phe Asn Ser Glu Glu Ile Val Arg Asn Leu Ser Cys Arg
385                 390                 395                 400

Lys Pro Asp Gln His Phe Lys Pro Tyr Leu Thr Pro Asp Leu Pro Lys
                405                 410                 415

Arg Leu His Tyr Ala Lys Asn Val Arg Ile Asp Lys Val His Leu Phe
                420                 425                 430

Val Asp Gln Gln Trp Leu Ala Val Arg Ser Lys Ser Asn Thr Asn Cys
        435                 440                 445

Gly Gly Gly Asn His Gly Tyr Asn Asn Glu Phe Arg Ser Met Glu Ala
        450                 455                 460

Ile Phe Leu Ala His Gly Pro Ser Phe Lys Glu Lys Thr Glu Val Glu
465                 470                 475                 480

Pro Phe Glu Asn Ile Glu Val Tyr Asn Leu Met Cys Asp Leu Leu Arg
                485                 490                 495

Ile Gln Pro Ala Pro Asn Asn Gly Thr His Gly Ser Leu Asn His Leu
                500                 505                 510

Leu Lys Val Pro Phe Tyr Glu Pro Ser His Ala Glu Glu Val Ser Lys
        515                 520                 525

Phe Ser Val Cys Gly Phe Ala Asn Pro Leu Pro Thr Glu Ser Leu Asp
530                 535                 540

Cys Phe Cys Pro His Leu Gln Asn Ser Thr Gln Leu Glu Gln Val Asn
545                 550                 555                 560

Gln Met Leu Asn Leu Thr Gln Glu Glu Ile Thr Ala Thr Val Lys Val
                565                 570                 575

Asn Leu Pro Phe Gly Arg Pro Arg Val Leu Gln Lys Asn Val Asp His
                580                 585                 590

Cys Leu Leu Tyr His Arg Glu Tyr Val Ser Gly Phe Gly Lys Ala Met
        595                 600                 605

Arg Met Pro Met Trp Ser Ser Tyr Thr Val Pro Gln Leu Gly Asp Thr
        610                 615                 620

Ser Pro Leu Pro Pro Thr Val Pro Asp Cys Leu Arg Ala Asp Val Arg
625                 630                 635                 640

Val Pro Pro Ser Glu Ser Gln Lys Cys Ser Phe Tyr Leu Ala Asp Lys
                645                 650                 655
```

```
Asn Ile Thr His Gly Phe Leu Tyr Pro Pro Ala Ser Asn Arg Thr Ser
            660                 665                 670

Asp Ser Gln Tyr Asp Ala Leu Ile Thr Ser Asn Leu Val Pro Met Tyr
        675                 680                 685

Glu Glu Phe Arg Lys Met Trp Asp Tyr Phe His Ser Val Leu Leu Ile
    690                 695                 700

Lys His Ala Thr Glu Arg Asn Gly Val Asn Val Ser Gly Pro Ile
705                 710                 715                 720

Phe Asp Tyr Asn Tyr Asp Gly His Phe Asp Ala Pro Asp Glu Ile Thr
                725                 730                 735

Lys His Leu Ala Asn Thr Asp Val Pro Ile Pro Thr His Tyr Phe Val
            740                 745                 750

Val Leu Thr Ser Cys Lys Asn Lys Ser His Thr Pro Glu Asn Cys Pro
        755                 760                 765

Gly Trp Leu Asp Val Leu Pro Phe Ile Ile Pro His Arg Pro Thr Asn
    770                 775                 780

Val Glu Ser Cys Pro Glu Gly Lys Pro Glu Ala Leu Trp Val Glu Glu
785                 790                 795                 800

Arg Phe Thr Ala His Ile Ala Arg Val Arg Asp Val Glu Leu Leu Thr
                805                 810                 815

Gly Leu Asp Phe Tyr Gln Asp Lys Val Gln Pro Val Ser Glu Ile Leu
            820                 825                 830

Gln Leu Lys Thr Tyr Leu Pro Thr Phe Glu Thr Thr Ile Asp Lys Thr
        835                 840                 845

His Thr Cys Pro Pro Cys Pro Ala Pro Glu Leu Leu Gly Gly Pro Ser
    850                 855                 860

Val Phe Leu Phe Pro Pro Lys Pro Lys Asp Thr Leu Met Ile Ser Arg
865                 870                 875                 880

Thr Pro Glu Val Thr Cys Val Val Asp Val Ser His Glu Asp Pro
                885                 890                 895

Glu Val Lys Phe Asn Trp Tyr Val Asp Gly Val Glu Val His Asn Ala
            900                 905                 910

Lys Thr Lys Pro Arg Glu Glu Gln Tyr Asn Ser Thr Tyr Arg Val Val
        915                 920                 925

Ser Val Leu Thr Val Leu His Gln Asp Trp Leu Asn Gly Lys Glu Tyr
    930                 935                 940

Lys Cys Lys Val Ser Asn Lys Ala Leu Pro Ala Pro Ile Glu Lys Thr
945                 950                 955                 960

Ile Ser Lys Ala Lys Gly Gln Pro Arg Glu Pro Gln Val Tyr Thr Leu
                965                 970                 975

Pro Pro Ser Arg Glu Glu Met Thr Lys Asn Gln Val Ser Leu Thr Cys
            980                 985                 990

Leu Val Lys Gly Phe Tyr Pro Ser Asp Ile Ala Val Glu Trp Glu Ser
        995                 1000                1005

Asn Gly Gln Pro Glu Asn Asn Tyr Lys Thr Thr Pro Pro Val Leu
    1010                1015                1020

Asp Ser Asp Gly Ser Phe Phe Leu Tyr Ser Lys Leu Thr Val Asp
    1025                1030                1035

Lys Ser Arg Trp Gln Gln Gly Asn Val Phe Ser Cys Ser Val Met
    1040                1045                1050

His Glu Ala Leu His Asn His Tyr Thr Gln Lys Ser Leu Ser Leu
    1055                1060                1065

Ser Pro Gly Lys
```

```
                1070
```

<210> SEQ ID NO 58
<211> LENGTH: 1074
<212> TYPE: PRT
<213> ORGANISM: Artificial Sequence
<220> FEATURE:
<223> OTHER INFORMATION: ENPP5-ENPP3-Fc

<400> SEQUENCE: 58

```
Met Thr Ser Lys Phe Leu Leu Val Ser Phe Ile Leu Ala Ala Leu Ser
1               5                   10                  15

Leu Ser Thr Thr Phe Ser Lys Gln Gly Ser Cys Arg Lys Lys Cys Phe
            20                  25                  30

Asp Ala Ser Phe Arg Gly Leu Glu Asn Cys Arg Cys Asp Val Ala Cys
        35                  40                  45

Lys Asp Arg Gly Asp Cys Cys Trp Asp Phe Glu Asp Thr Cys Val Glu
    50                  55                  60

Ser Thr Arg Ile Trp Met Cys Asn Lys Phe Arg Cys Gly Glu Arg Leu
65                  70                  75                  80

Glu Ala Ser Leu Cys Ser Cys Ser Asp Asp Cys Leu Gln Arg Lys Asp
                85                  90                  95

Cys Cys Ala Asp Tyr Lys Ser Val Cys Gln Gly Glu Thr Ser Trp Leu
            100                 105                 110

Glu Glu Asn Cys Asp Thr Ala Gln Gln Ser Gln Cys Pro Glu Gly Phe
        115                 120                 125

Asp Leu Pro Pro Val Ile Leu Phe Ser Met Asp Gly Phe Arg Ala Glu
    130                 135                 140

Tyr Leu Tyr Thr Trp Asp Thr Leu Met Pro Asn Ile Asn Lys Leu Lys
145                 150                 155                 160

Thr Cys Gly Ile His Ser Lys Tyr Met Arg Ala Met Tyr Pro Thr Lys
                165                 170                 175

Thr Phe Pro Asn His Tyr Thr Ile Val Thr Gly Leu Tyr Pro Glu Ser
            180                 185                 190

His Gly Ile Ile Asp Asn Asn Met Tyr Asp Val Asn Leu Asn Lys Asn
        195                 200                 205

Phe Ser Leu Ser Ser Lys Glu Gln Asn Asn Pro Ala Trp Trp His Gly
    210                 215                 220

Gln Pro Met Trp Leu Thr Ala Met Tyr Gln Gly Leu Lys Ala Ala Thr
225                 230                 235                 240

Tyr Phe Trp Pro Gly Ser Glu Val Ala Ile Asn Gly Ser Phe Pro Ser
                245                 250                 255

Ile Tyr Met Pro Tyr Asn Gly Ser Val Pro Phe Glu Glu Arg Ile Ser
            260                 265                 270

Thr Leu Leu Lys Trp Leu Asp Leu Pro Lys Ala Glu Arg Pro Arg Phe
        275                 280                 285

Tyr Thr Met Tyr Phe Glu Glu Pro Asp Ser Ser Gly His Ala Gly Gly
    290                 295                 300

Pro Val Ser Ala Arg Val Ile Lys Ala Leu Gln Val Val Asp His Ala
305                 310                 315                 320

Phe Gly Met Leu Met Glu Gly Leu Lys Gln Arg Asn Leu His Asn Cys
                325                 330                 335

Val Asn Ile Ile Leu Leu Ala Asp His Gly Met Asp Gln Thr Tyr Cys
            340                 345                 350

Asn Lys Met Glu Tyr Met Thr Asp Tyr Phe Pro Arg Ile Asn Phe Phe
```

```
            355                 360                 365
Tyr Met Tyr Glu Gly Pro Ala Pro Arg Ile Arg Ala His Asn Ile Pro
    370                 375                 380
His Asp Phe Phe Ser Phe Asn Ser Glu Glu Ile Val Arg Asn Leu Ser
385                 390                 395                 400
Cys Arg Lys Pro Asp Gln His Phe Lys Pro Tyr Leu Thr Pro Asp Leu
                405                 410                 415
Pro Lys Arg Leu His Tyr Ala Lys Asn Val Arg Ile Asp Lys Val His
            420                 425                 430
Leu Phe Val Asp Gln Gln Trp Leu Ala Val Arg Ser Lys Ser Asn Thr
                435                 440                 445
Asn Cys Gly Gly Asn His Gly Tyr Asn Asn Glu Phe Arg Ser Met
            450                 455                 460
Glu Ala Ile Phe Leu Ala His Gly Pro Ser Phe Lys Glu Lys Thr Glu
465                 470                 475                 480
Val Glu Pro Phe Glu Asn Ile Glu Val Tyr Asn Leu Met Cys Asp Leu
                485                 490                 495
Leu Arg Ile Gln Pro Ala Pro Asn Asn Gly Thr His Gly Ser Leu Asn
            500                 505                 510
His Leu Leu Lys Val Pro Phe Tyr Glu Pro Ser His Ala Glu Glu Val
            515                 520                 525
Ser Lys Phe Ser Val Cys Gly Phe Ala Asn Pro Leu Pro Thr Glu Ser
530                 535                 540
Leu Asp Cys Phe Cys Pro His Leu Gln Asn Ser Thr Gln Leu Glu Gln
545                 550                 555                 560
Val Asn Gln Met Leu Asn Leu Thr Gln Glu Glu Ile Thr Ala Thr Val
                565                 570                 575
Lys Val Asn Leu Pro Phe Gly Arg Pro Arg Val Leu Gln Lys Asn Val
            580                 585                 590
Asp His Cys Leu Leu Tyr His Arg Glu Tyr Val Ser Gly Phe Gly Lys
            595                 600                 605
Ala Met Arg Met Pro Met Trp Ser Ser Tyr Thr Val Pro Gln Leu Gly
            610                 615                 620
Asp Thr Ser Pro Leu Pro Pro Thr Val Pro Asp Cys Leu Arg Ala Asp
625                 630                 635                 640
Val Arg Val Pro Pro Ser Glu Ser Gln Lys Cys Ser Phe Tyr Leu Ala
                645                 650                 655
Asp Lys Asn Ile Thr His Gly Phe Leu Tyr Pro Pro Ala Ser Asn Arg
            660                 665                 670
Thr Ser Asp Ser Gln Tyr Asp Ala Leu Ile Thr Ser Asn Leu Val Pro
            675                 680                 685
Met Tyr Glu Glu Phe Arg Lys Met Trp Asp Tyr Phe His Ser Val Leu
            690                 695                 700
Leu Ile Lys His Ala Thr Glu Arg Asn Gly Val Asn Val Val Ser Gly
705                 710                 715                 720
Pro Ile Phe Asp Tyr Asn Tyr Asp Gly His Phe Asp Ala Pro Asp Glu
                725                 730                 735
Ile Thr Lys His Leu Ala Asn Thr Asp Val Pro Ile Pro Thr His Tyr
            740                 745                 750
Phe Val Val Leu Thr Ser Cys Lys Asn Lys Ser His Thr Pro Glu Asn
                755                 760                 765
Cys Pro Gly Trp Leu Asp Val Leu Pro Phe Ile Ile Pro His Arg Pro
            770                 775                 780
```

Thr Asn Val Glu Ser Cys Pro Glu Gly Lys Pro Glu Ala Leu Trp Val
785                 790                 795                 800

Glu Glu Arg Phe Thr Ala His Ile Ala Arg Val Arg Asp Val Glu Leu
            805                 810                 815

Leu Thr Gly Leu Asp Phe Tyr Gln Asp Lys Val Gln Pro Val Ser Glu
        820                 825                 830

Ile Leu Gln Leu Lys Thr Tyr Leu Pro Thr Phe Glu Thr Thr Ile Asp
        835                 840                 845

Lys Thr His Thr Cys Pro Pro Cys Pro Ala Pro Glu Leu Leu Gly Gly
        850                 855                 860

Pro Ser Val Phe Leu Phe Pro Pro Lys Pro Lys Asp Thr Leu Met Ile
865                 870                 875                 880

Ser Arg Thr Pro Glu Val Thr Cys Val Val Asp Val Ser His Glu
                885                 890                 895

Asp Pro Glu Val Lys Phe Asn Trp Tyr Val Asp Gly Val Glu Val His
                900                 905                 910

Asn Ala Lys Thr Lys Pro Arg Glu Glu Gln Tyr Asn Ser Thr Tyr Arg
        915                 920                 925

Val Val Ser Val Leu Thr Val Leu His Gln Asp Trp Leu Asn Gly Lys
930                 935                 940

Glu Tyr Lys Cys Lys Val Ser Asn Lys Ala Leu Pro Ala Pro Ile Glu
945                 950                 955                 960

Lys Thr Ile Ser Lys Ala Lys Gly Gln Pro Arg Glu Pro Gln Val Tyr
            965                 970                 975

Thr Leu Pro Pro Ser Arg Glu Glu Met Thr Lys Asn Gln Val Ser Leu
            980                 985                 990

Thr Cys Leu Val Lys Gly Phe Tyr Pro Ser Asp Ile Ala Val Glu Trp
        995                 1000                1005

Glu Ser Asn Gly Gln Pro Glu Asn Asn Tyr Lys Thr Thr Pro Pro
    1010                1015                1020

Val Leu Asp Ser Asp Gly Ser Phe Phe Leu Tyr Ser Lys Leu Thr
    1025                1030                1035

Val Asp Lys Ser Arg Trp Gln Gln Gly Asn Val Phe Ser Cys Ser
    1040                1045                1050

Val Met His Glu Ala Leu His Asn His Tyr Thr Gln Lys Ser Leu
    1055                1060                1065

Ser Leu Ser Pro Gly Lys
    1070

<210> SEQ ID NO 59
<211> LENGTH: 623
<212> TYPE: PRT
<213> ORGANISM: Homo sapiens

<400> SEQUENCE: 59

Gly Gly Gly Gly Ser Gly Gly Gly Ser Gly Gly Gly Ser Met
1               5                   10                  15

Lys Trp Val Thr Phe Leu Leu Leu Leu Phe Val Ser Gly Ser Ala Phe
            20                  25                  30

Ser Arg Gly Val Phe Arg Arg Glu Ala His Lys Ser Glu Ile Ala His
        35                  40                  45

Arg Tyr Asn Asp Leu Gly Glu Gln His Phe Lys Gly Leu Val Leu Ile
    50                  55                  60

Ala Phe Ser Gln Tyr Leu Gln Lys Cys Ser Tyr Asp Glu His Ala Lys

```
            65                  70                  75                  80
Leu Val Gln Glu Val Thr Asp Phe Ala Lys Thr Cys Val Ala Asp Glu
                    85                  90                  95
Ser Ala Ala Asn Cys Asp Lys Ser Leu His Thr Leu Phe Gly Asp Lys
                    100                 105                 110
Leu Cys Ala Ile Pro Asn Leu Arg Glu Asn Tyr Gly Glu Leu Ala Asp
                    115                 120                 125
Cys Cys Thr Lys Gln Glu Pro Glu Arg Asn Glu Cys Phe Leu Gln His
                    130                 135                 140
Lys Asp Asp Asn Pro Ser Leu Pro Pro Phe Glu Arg Pro Glu Ala Glu
145                 150                 155                 160
Ala Met Cys Thr Ser Phe Lys Glu Asn Pro Thr Thr Phe Met Gly His
                    165                 170                 175
Tyr Leu His Glu Val Ala Arg Arg His Pro Tyr Phe Tyr Ala Pro Glu
                    180                 185                 190
Leu Leu Tyr Tyr Ala Glu Gln Tyr Asn Glu Ile Leu Thr Gln Cys Cys
                    195                 200                 205
Ala Glu Ala Asp Lys Glu Ser Cys Leu Thr Pro Lys Leu Asp Gly Val
                    210                 215                 220
Lys Glu Lys Ala Leu Val Ser Ser Val Arg Gln Arg Met Lys Cys Ser
225                 230                 235                 240
Ser Met Gln Lys Phe Gly Glu Arg Ala Phe Lys Ala Trp Ala Val Ala
                    245                 250                 255
Arg Leu Ser Gln Thr Phe Pro Asn Ala Asp Phe Ala Glu Ile Thr Lys
                    260                 265                 270
Leu Ala Thr Asp Leu Thr Lys Val Asn Lys Glu Cys Cys His Gly Asp
                    275                 280                 285
Leu Leu Glu Cys Ala Asp Asp Arg Ala Glu Leu Ala Lys Tyr Met Cys
                    290                 295                 300
Glu Asn Gln Ala Thr Ile Ser Ser Lys Leu Gln Thr Cys Cys Asp Lys
305                 310                 315                 320
Pro Leu Leu Lys Lys Ala His Cys Leu Ser Glu Val Glu His Asp Thr
                    325                 330                 335
Met Pro Ala Asp Leu Pro Ala Ile Ala Ala Asp Phe Val Glu Asp Gln
                    340                 345                 350
Glu Val Cys Lys Asn Tyr Ala Glu Ala Lys Asp Val Phe Leu Gly Thr
                    355                 360                 365
Phe Leu Tyr Glu Tyr Ser Arg Arg His Pro Asp Tyr Ser Val Ser Leu
                    370                 375                 380
Leu Leu Arg Leu Ala Lys Lys Tyr Glu Ala Thr Leu Glu Lys Cys Cys
385                 390                 395                 400
Ala Glu Ala Asn Pro Pro Ala Cys Tyr Gly Thr Val Leu Ala Glu Phe
                    405                 410                 415
Gln Pro Leu Val Glu Glu Pro Lys Asn Leu Val Lys Thr Asn Cys Asp
                    420                 425                 430
Leu Tyr Glu Lys Leu Gly Glu Tyr Gly Phe Gln Asn Ala Ile Leu Val
                    435                 440                 445
Arg Tyr Thr Gln Lys Ala Pro Gln Val Ser Thr Pro Thr Leu Val Glu
                    450                 455                 460
Ala Ala Arg Asn Leu Gly Arg Val Gly Thr Lys Cys Cys Thr Leu Pro
465                 470                 475                 480
Glu Asp Gln Arg Leu Pro Cys Val Glu Asp Tyr Leu Ser Ala Ile Leu
                    485                 490                 495
```

```
Asn Arg Val Cys Leu Leu His Glu Lys Thr Pro Val Ser Glu His Val
            500                 505                 510

Thr Lys Cys Cys Ser Gly Ser Leu Val Glu Arg Arg Pro Cys Phe Ser
            515                 520                 525

Ala Leu Thr Val Asp Glu Thr Tyr Val Pro Lys Glu Phe Lys Ala Glu
            530                 535                 540

Thr Phe Thr Phe His Ser Asp Ile Cys Thr Leu Pro Glu Lys Glu Lys
545                 550                 555                 560

Gln Ile Lys Lys Gln Thr Ala Leu Ala Glu Leu Val Lys His Lys Pro
                565                 570                 575

Lys Ala Thr Ala Glu Gln Leu Lys Thr Val Met Asp Asp Phe Ala Gln
            580                 585                 590

Phe Leu Asp Thr Cys Cys Lys Ala Ala Asp Lys Asp Thr Cys Phe Ser
            595                 600                 605

Thr Glu Gly Pro Asn Leu Val Thr Arg Cys Lys Asp Ala Leu Ala
            610                 615                 620

<210> SEQ ID NO 60
<211> LENGTH: 1582
<212> TYPE: PRT
<213> ORGANISM: Artificial Sequence
<220> FEATURE:
<223> OTHER INFORMATION: ENPP121-ENPP3-Albumin

<400> SEQUENCE: 60

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
            35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65              70                  75                  80

Phe Thr Phe Ala Val Gly Val Asn Ile Cys Leu Gly Phe Thr Ala Lys
                85                  90                  95

Gln Gly Ser Cys Arg Lys Lys Cys Phe Asp Ala Ser Phe Arg Gly Leu
            100                 105                 110

Glu Asn Cys Arg Cys Asp Val Ala Cys Lys Asp Arg Gly Asp Cys Cys
            115                 120                 125

Trp Asp Phe Glu Asp Thr Cys Val Glu Ser Thr Arg Ile Trp Met Cys
        130                 135                 140

Asn Lys Phe Arg Cys Gly Glu Arg Leu Glu Ala Ser Leu Cys Ser Cys
145                 150                 155                 160

Ser Asp Asp Cys Leu Gln Arg Lys Asp Cys Cys Ala Asp Tyr Lys Ser
                165                 170                 175

Val Cys Gln Gly Glu Thr Ser Trp Leu Glu Glu Asn Cys Asp Thr Ala
            180                 185                 190

Gln Gln Ser Gln Cys Pro Glu Gly Phe Asp Leu Pro Pro Val Ile Leu
            195                 200                 205

Phe Ser Met Asp Gly Phe Arg Ala Glu Tyr Leu Tyr Thr Trp Asp Thr
        210                 215                 220

Leu Met Pro Asn Ile Asn Lys Leu Lys Thr Cys Gly Ile His Ser Lys
225                 230                 235                 240
```

```
Tyr Met Arg Ala Met Tyr Pro Thr Lys Thr Phe Pro Asn His Tyr Thr
            245                 250                 255

Ile Val Thr Gly Leu Tyr Pro Glu Ser His Gly Ile Ile Asp Asn Asn
        260                 265                 270

Met Tyr Asp Val Asn Leu Asn Lys Asn Phe Ser Leu Ser Ser Lys Glu
    275                 280                 285

Gln Asn Asn Pro Ala Trp Trp His Gly Gln Pro Met Trp Leu Thr Ala
290                 295                 300

Met Tyr Gln Gly Leu Lys Ala Ala Thr Tyr Phe Trp Pro Gly Ser Glu
305                 310                 315                 320

Val Ala Ile Asn Gly Ser Phe Pro Ser Ile Tyr Met Pro Tyr Asn Gly
                325                 330                 335

Ser Val Pro Phe Glu Glu Arg Ile Ser Thr Leu Leu Lys Trp Leu Asp
            340                 345                 350

Leu Pro Lys Ala Glu Arg Pro Arg Phe Tyr Thr Met Tyr Phe Glu Glu
        355                 360                 365

Pro Asp Ser Ser Gly His Ala Gly Gly Pro Val Ser Ala Arg Val Ile
    370                 375                 380

Lys Ala Leu Gln Val Val Asp His Ala Phe Gly Met Leu Met Glu Gly
385                 390                 395                 400

Leu Lys Gln Arg Asn Leu His Asn Cys Val Asn Ile Ile Leu Leu Ala
                405                 410                 415

Asp His Gly Met Asp Gln Thr Tyr Cys Asn Lys Met Glu Tyr Met Thr
            420                 425                 430

Asp Tyr Phe Pro Arg Ile Asn Phe Phe Tyr Met Tyr Glu Gly Pro Ala
        435                 440                 445

Pro Arg Ile Arg Ala His Asn Ile Pro His Asp Phe Phe Ser Phe Asn
    450                 455                 460

Ser Glu Glu Ile Val Arg Asn Leu Ser Cys Arg Lys Pro Asp Gln His
465                 470                 475                 480

Phe Lys Pro Tyr Leu Thr Pro Asp Leu Pro Lys Arg Leu His Tyr Ala
                485                 490                 495

Lys Asn Val Arg Ile Asp Lys Val His Leu Phe Val Asp Gln Gln Trp
            500                 505                 510

Leu Ala Val Arg Ser Lys Ser Asn Thr Asn Cys Gly Gly Gly Asn His
        515                 520                 525

Gly Tyr Asn Asn Glu Phe Arg Ser Met Glu Ala Ile Phe Leu Ala His
    530                 535                 540

Gly Pro Ser Phe Lys Glu Lys Thr Glu Val Glu Pro Phe Glu Asn Ile
545                 550                 555                 560

Glu Val Tyr Asn Leu Met Cys Asp Leu Leu Arg Ile Gln Pro Ala Pro
                565                 570                 575

Asn Asn Gly Thr His Gly Ser Leu Asn His Leu Leu Lys Val Pro Phe
            580                 585                 590

Tyr Glu Pro Ser His Ala Glu Glu Val Ser Lys Phe Ser Val Cys Gly
        595                 600                 605

Phe Ala Asn Pro Leu Pro Thr Glu Ser Leu Asp Cys Phe Cys Pro His
    610                 615                 620

Leu Gln Asn Ser Thr Gln Leu Glu Gln Val Asn Gln Met Leu Asn Leu
625                 630                 635                 640

Thr Gln Glu Glu Ile Thr Ala Thr Val Lys Val Asn Leu Pro Phe Gly
                645                 650                 655
```

```
Arg Pro Arg Val Leu Gln Lys Asn Val Asp His Cys Leu Tyr His
            660                 665                 670

Arg Glu Tyr Val Ser Gly Phe Gly Lys Ala Met Arg Met Pro Met Trp
            675                 680                 685

Ser Ser Tyr Thr Val Pro Gln Leu Gly Asp Thr Ser Pro Leu Pro Pro
690                 695                 700

Thr Val Pro Asp Cys Leu Arg Ala Asp Val Arg Val Pro Pro Ser Glu
705                 710                 715                 720

Ser Gln Lys Cys Ser Phe Tyr Leu Ala Asp Lys Asn Ile Thr His Gly
                725                 730                 735

Phe Leu Tyr Pro Pro Ala Ser Asn Arg Thr Ser Asp Ser Gln Tyr Asp
            740                 745                 750

Ala Leu Ile Thr Ser Asn Leu Val Pro Met Tyr Glu Glu Phe Arg Lys
            755                 760                 765

Met Trp Asp Tyr Phe His Ser Val Leu Leu Ile Lys His Ala Thr Glu
            770                 775                 780

Arg Asn Gly Val Asn Val Val Ser Gly Pro Ile Phe Asp Tyr Asn Tyr
785                 790                 795                 800

Asp Gly His Phe Asp Ala Pro Asp Glu Ile Thr Lys His Leu Ala Asn
                805                 810                 815

Thr Asp Val Pro Ile Pro Thr His Tyr Phe Val Val Leu Thr Ser Cys
            820                 825                 830

Lys Asn Lys Ser His Thr Pro Glu Asn Cys Pro Gly Trp Leu Asp Val
                835                 840                 845

Leu Pro Phe Ile Ile Pro His Arg Pro Thr Asn Val Glu Ser Cys Pro
850                 855                 860

Glu Gly Lys Pro Glu Ala Leu Trp Val Glu Glu Arg Phe Thr Ala His
865                 870                 875                 880

Ile Ala Arg Val Arg Asp Val Glu Leu Leu Thr Gly Leu Asp Phe Tyr
                885                 890                 895

Gln Asp Lys Val Gln Pro Val Ser Glu Ile Leu Gln Leu Lys Thr Tyr
            900                 905                 910

Leu Pro Thr Phe Glu Thr Thr Ile Asp Lys Thr His Thr Cys Pro Pro
            915                 920                 925

Cys Pro Ala Pro Glu Leu Leu Gly Gly Pro Ser Val Phe Leu Phe Pro
930                 935                 940

Pro Lys Pro Lys Asp Thr Leu Met Ile Ser Arg Thr Pro Glu Val Thr
945                 950                 955                 960

Gly Gly Gly Ser Gly Gly Gly Ser Gly Gly Gly Ser Met Lys
                965                 970                 975

Trp Val Thr Phe Leu Leu Leu Leu Phe Val Ser Gly Ser Ala Phe Ser
            980                 985                 990

Arg Gly Val Phe Arg Arg Glu Ala His Lys Ser Glu Ile Ala His Arg
            995                 1000                1005

Tyr Asn Asp Leu Gly Glu Gln His Phe Lys Gly Leu Val Leu Ile
            1010                1015                1020

Ala Phe Ser Gln Tyr Leu Gln Lys Cys Ser Tyr Asp Glu His Ala
            1025                1030                1035

Lys Leu Val Gln Glu Val Thr Asp Phe Ala Lys Thr Cys Val Ala
            1040                1045                1050

Asp Glu Ser Ala Ala Asn Cys Asp Lys Ser Leu His Thr Leu Phe
            1055                1060                1065

Gly Asp Lys Leu Cys Ala Ile Pro Asn Leu Arg Glu Asn Tyr Gly
```

-continued

```
                1070                1075                1080
Glu Leu Ala Asp Cys Cys Thr Lys Gln Glu Pro Glu Arg Asn Glu
    1085                1090                1095
Cys Phe Leu Gln His Lys Asp Asp Asn Pro Ser Leu Pro Pro Phe
    1100                1105                1110
Glu Arg Pro Glu Ala Glu Ala Met Cys Thr Ser Phe Lys Glu Asn
    1115                1120                1125
Pro Thr Thr Phe Met Gly His Tyr Leu His Glu Val Ala Arg Arg
    1130                1135                1140
His Pro Tyr Phe Tyr Ala Pro Glu Leu Leu Tyr Tyr Ala Glu Gln
    1145                1150                1155
Tyr Asn Glu Ile Leu Thr Gln Cys Cys Ala Glu Ala Asp Lys Glu
    1160                1165                1170
Ser Cys Leu Thr Pro Lys Leu Asp Gly Val Lys Glu Lys Ala Leu
    1175                1180                1185
Val Ser Ser Val Arg Gln Arg Met Lys Cys Ser Ser Met Gln Lys
    1190                1195                1200
Phe Gly Glu Arg Ala Phe Lys Ala Trp Ala Val Ala Arg Leu Ser
    1205                1210                1215
Gln Thr Phe Pro Asn Ala Asp Phe Ala Glu Ile Thr Lys Leu Ala
    1220                1225                1230
Thr Asp Leu Thr Lys Val Asn Lys Glu Cys Cys His Gly Asp Leu
    1235                1240                1245
Leu Glu Cys Ala Asp Asp Arg Ala Glu Leu Ala Lys Tyr Met Cys
    1250                1255                1260
Glu Asn Gln Ala Thr Ile Ser Ser Lys Leu Gln Thr Cys Cys Asp
    1265                1270                1275
Lys Pro Leu Leu Lys Lys Ala His Cys Leu Ser Glu Val Glu His
    1280                1285                1290
Asp Thr Met Pro Ala Asp Leu Pro Ala Ile Ala Ala Asp Phe Val
    1295                1300                1305
Glu Asp Gln Glu Val Cys Lys Asn Tyr Ala Glu Ala Lys Asp Val
    1310                1315                1320
Phe Leu Gly Thr Phe Leu Tyr Glu Tyr Ser Arg Arg His Pro Asp
    1325                1330                1335
Tyr Ser Val Ser Leu Leu Leu Arg Leu Ala Lys Lys Tyr Glu Ala
    1340                1345                1350
Thr Leu Glu Lys Cys Cys Ala Glu Ala Asn Pro Pro Ala Cys Tyr
    1355                1360                1365
Gly Thr Val Leu Ala Glu Phe Gln Pro Leu Val Glu Glu Pro Lys
    1370                1375                1380
Asn Leu Val Lys Thr Asn Cys Asp Leu Tyr Glu Lys Leu Gly Glu
    1385                1390                1395
Tyr Gly Phe Gln Asn Ala Ile Leu Val Arg Tyr Thr Gln Lys Ala
    1400                1405                1410
Pro Gln Val Ser Thr Pro Thr Leu Val Glu Ala Ala Arg Asn Leu
    1415                1420                1425
Gly Arg Val Gly Thr Lys Cys Cys Thr Leu Pro Glu Asp Gln Arg
    1430                1435                1440
Leu Pro Cys Val Glu Asp Tyr Leu Ser Ala Ile Leu Asn Arg Val
    1445                1450                1455
Cys Leu Leu His Glu Lys Thr Pro Val Ser Glu His Val Thr Lys
    1460                1465                1470
```

```
Cys Cys Ser Gly Ser Leu Val Glu Arg Arg Pro Cys Phe Ser Ala
    1475                1480                1485

Leu Thr Val Asp Glu Thr Tyr Val Pro Lys Glu Phe Lys Ala Glu
    1490                1495                1500

Thr Phe Thr Phe His Ser Asp Ile Cys Thr Leu Pro Glu Lys Glu
    1505                1510                1515

Lys Gln Ile Lys Lys Gln Thr Ala Leu Ala Glu Leu Val Lys His
    1520                1525                1530

Lys Pro Lys Ala Thr Ala Glu Gln Leu Lys Thr Val Met Asp Asp
    1535                1540                1545

Phe Ala Gln Phe Leu Asp Thr Cys Cys Lys Ala Ala Asp Lys Asp
    1550                1555                1560

Thr Cys Phe Ser Thr Glu Gly Pro Asn Leu Val Thr Arg Cys Lys
    1565                1570                1575

Asp Ala Leu Ala
    1580

<210> SEQ ID NO 61
<211> LENGTH: 1507
<212> TYPE: PRT
<213> ORGANISM: Artificial Sequence
<220> FEATURE:
<223> OTHER INFORMATION: ENPP7-ENPP3-Albumin

<400> SEQUENCE: 61

Met Arg Gly Pro Ala Val Leu Leu Thr Val Ala Leu Ala Thr Leu Leu
1               5                   10                  15

Ala Pro Gly Ala Lys Gln Gly Ser Cys Arg Lys Lys Cys Phe Asp Ala
                20                  25                  30

Ser Phe Arg Gly Leu Glu Asn Cys Arg Cys Asp Val Ala Cys Lys Asp
            35                  40                  45

Arg Gly Asp Cys Cys Trp Asp Phe Glu Asp Thr Cys Val Glu Ser Thr
        50                  55                  60

Arg Ile Trp Met Cys Asn Lys Phe Arg Cys Gly Glu Arg Leu Glu Ala
65                  70                  75                  80

Ser Leu Cys Ser Cys Ser Asp Asp Cys Leu Gln Arg Lys Asp Cys Cys
                85                  90                  95

Ala Asp Tyr Lys Ser Val Cys Gln Gly Glu Thr Ser Trp Leu Glu Glu
                100                 105                 110

Asn Cys Asp Thr Ala Gln Gln Ser Gln Cys Pro Glu Gly Phe Asp Leu
            115                 120                 125

Pro Pro Val Ile Leu Phe Ser Met Asp Gly Phe Arg Ala Glu Tyr Leu
        130                 135                 140

Tyr Thr Trp Asp Thr Leu Met Pro Asn Ile Asn Lys Leu Lys Thr Cys
145                 150                 155                 160

Gly Ile His Ser Lys Tyr Met Arg Ala Met Tyr Pro Thr Lys Thr Phe
                165                 170                 175

Pro Asn His Tyr Thr Ile Val Thr Gly Leu Tyr Pro Glu Ser His Gly
            180                 185                 190

Ile Ile Asp Asn Asn Met Tyr Asp Val Asn Leu Asn Lys Asn Phe Ser
        195                 200                 205

Leu Ser Ser Lys Glu Gln Asn Asn Pro Ala Trp Trp His Gly Gln Pro
    210                 215                 220

Met Trp Leu Thr Ala Met Tyr Gln Gly Leu Lys Ala Ala Thr Tyr Phe
225                 230                 235                 240
```

```
Trp Pro Gly Ser Glu Val Ala Ile Asn Gly Ser Phe Pro Ser Ile Tyr
            245                 250                 255

Met Pro Tyr Asn Gly Ser Val Pro Phe Glu Arg Ile Ser Thr Leu
        260                 265                 270

Leu Lys Trp Leu Asp Leu Pro Lys Ala Glu Arg Pro Arg Phe Tyr Thr
        275                 280                 285

Met Tyr Phe Glu Glu Pro Asp Ser Ser Gly His Ala Gly Gly Pro Val
    290                 295                 300

Ser Ala Arg Val Ile Lys Ala Leu Gln Val Val Asp His Ala Phe Gly
305                 310                 315                 320

Met Leu Met Glu Gly Leu Lys Gln Arg Asn Leu His Asn Cys Val Asn
                325                 330                 335

Ile Ile Leu Leu Ala Asp His Gly Met Asp Gln Thr Tyr Cys Asn Lys
            340                 345                 350

Met Glu Tyr Met Thr Asp Tyr Phe Pro Arg Ile Asn Phe Phe Tyr Met
            355                 360                 365

Tyr Glu Gly Pro Ala Pro Arg Ile Arg Ala His Asn Ile Pro His Asp
        370                 375                 380

Phe Phe Ser Phe Asn Ser Glu Glu Ile Val Arg Asn Leu Ser Cys Arg
385                 390                 395                 400

Lys Pro Asp Gln His Phe Lys Pro Tyr Leu Thr Pro Asp Leu Pro Lys
                405                 410                 415

Arg Leu His Tyr Ala Lys Asn Val Arg Ile Asp Lys Val His Leu Phe
                420                 425                 430

Val Asp Gln Gln Trp Leu Ala Val Arg Ser Lys Ser Asn Thr Asn Cys
            435                 440                 445

Gly Gly Gly Asn His Gly Tyr Asn Asn Glu Phe Arg Ser Met Glu Ala
        450                 455                 460

Ile Phe Leu Ala His Gly Pro Ser Phe Lys Glu Lys Thr Glu Val Glu
465                 470                 475                 480

Pro Phe Glu Asn Ile Glu Val Tyr Asn Leu Met Cys Asp Leu Leu Arg
                485                 490                 495

Ile Gln Pro Ala Pro Asn Asn Gly Thr His Gly Ser Leu Asn His Leu
            500                 505                 510

Leu Lys Val Pro Phe Tyr Glu Pro Ser His Ala Glu Glu Val Ser Lys
        515                 520                 525

Phe Ser Val Cys Gly Phe Ala Asn Pro Leu Pro Thr Glu Ser Leu Asp
530                 535                 540

Cys Phe Cys Pro His Leu Gln Asn Ser Thr Gln Leu Glu Gln Val Asn
545                 550                 555                 560

Gln Met Leu Asn Leu Thr Gln Glu Glu Ile Thr Ala Thr Val Lys Val
                565                 570                 575

Asn Leu Pro Phe Gly Arg Pro Arg Val Leu Gln Lys Asn Val Asp His
            580                 585                 590

Cys Leu Leu Tyr His Arg Glu Tyr Val Ser Gly Phe Gly Lys Ala Met
        595                 600                 605

Arg Met Pro Met Trp Ser Ser Tyr Thr Val Pro Gln Leu Gly Asp Thr
    610                 615                 620

Ser Pro Leu Pro Pro Thr Val Pro Asp Cys Leu Arg Ala Asp Val Arg
625                 630                 635                 640

Val Pro Pro Ser Glu Ser Gln Lys Cys Ser Phe Tyr Leu Ala Asp Lys
                645                 650                 655
```

```
Asn Ile Thr His Gly Phe Leu Tyr Pro Pro Ala Ser Asn Arg Thr Ser
            660             665                 670

Asp Ser Gln Tyr Asp Ala Leu Ile Thr Ser Asn Leu Val Pro Met Tyr
        675             680             685

Glu Glu Phe Arg Lys Met Trp Asp Tyr Phe His Ser Val Leu Leu Ile
    690             695             700

Lys His Ala Thr Glu Arg Asn Gly Val Asn Val Ser Gly Pro Ile
705             710             715             720

Phe Asp Tyr Asn Tyr Asp Gly His Phe Asp Ala Pro Asp Glu Ile Thr
            725             730             735

Lys His Leu Ala Asn Thr Asp Val Pro Ile Pro Thr His Tyr Phe Val
        740             745             750

Val Leu Thr Ser Cys Lys Asn Lys Ser His Thr Pro Glu Asn Cys Pro
    755             760             765

Gly Trp Leu Asp Val Leu Pro Phe Ile Ile Pro His Arg Pro Thr Asn
    770             775             780

Val Glu Ser Cys Pro Glu Gly Lys Pro Glu Ala Leu Trp Val Glu Glu
785             790             795             800

Arg Phe Thr Ala His Ile Ala Arg Val Arg Asp Val Glu Leu Leu Thr
            805             810             815

Gly Leu Asp Phe Tyr Gln Asp Lys Val Gln Pro Val Ser Glu Ile Leu
        820             825             830

Gln Leu Lys Thr Tyr Leu Pro Thr Phe Glu Thr Thr Ile Asp Lys Thr
    835             840             845

His Thr Cys Pro Pro Cys Pro Ala Pro Glu Leu Leu Gly Gly Pro Ser
850             855             860

Val Phe Leu Phe Pro Pro Lys Pro Lys Asp Thr Leu Met Ile Ser Arg
865             870             875             880

Thr Pro Glu Val Thr Gly Gly Ser Gly Gly Gly Ser Gly Gly
            885             890             895

Gly Gly Ser Met Lys Trp Val Thr Phe Leu Leu Leu Phe Val Ser
        900             905             910

Gly Ser Ala Phe Ser Arg Gly Val Phe Arg Arg Glu Ala His Lys Ser
    915             920             925

Glu Ile Ala His Arg Tyr Asn Asp Leu Gly Glu Gln His Phe Lys Gly
    930             935             940

Leu Val Leu Ile Ala Phe Ser Gln Tyr Leu Gln Lys Cys Ser Tyr Asp
945             950             955             960

Glu His Ala Lys Leu Val Gln Glu Val Thr Asp Phe Ala Lys Thr Cys
            965             970             975

Val Ala Asp Glu Ser Ala Ala Asn Cys Asp Lys Ser Leu His Thr Leu
        980             985             990

Phe Gly Asp Lys Leu Cys Ala Ile Pro Asn Leu Arg Glu Asn Tyr Gly
    995             1000            1005

Glu Leu Ala Asp Cys Cys Thr Lys Gln Glu Pro Glu Arg Asn Glu
    1010            1015            1020

Cys Phe Leu Gln His Lys Asp Asp Asn Pro Ser Leu Pro Pro Phe
    1025            1030            1035

Glu Arg Pro Glu Ala Glu Ala Met Cys Thr Ser Phe Lys Glu Asn
    1040            1045            1050

Pro Thr Thr Phe Met Gly His Tyr Leu His Glu Val Ala Arg Arg
    1055            1060            1065

His Pro Tyr Phe Tyr Ala Pro Glu Leu Leu Tyr Tyr Ala Glu Gln
```

-continued

```
            1070                1075                1080
Tyr Asn Glu Ile Leu Thr Gln Cys Cys Ala Glu Ala Asp Lys Glu
            1085                1090                1095

Ser Cys Leu Thr Pro Lys Leu Asp Gly Val Lys Glu Lys Ala Leu
            1100                1105                1110

Val Ser Ser Val Arg Gln Arg Met Lys Cys Ser Ser Met Gln Lys
            1115                1120                1125

Phe Gly Glu Arg Ala Phe Lys Ala Trp Ala Val Ala Arg Leu Ser
            1130                1135                1140

Gln Thr Phe Pro Asn Ala Asp Phe Ala Glu Ile Thr Lys Leu Ala
            1145                1150                1155

Thr Asp Leu Thr Lys Val Asn Lys Glu Cys Cys His Gly Asp Leu
            1160                1165                1170

Leu Glu Cys Ala Asp Asp Arg Ala Glu Leu Ala Lys Tyr Met Cys
            1175                1180                1185

Glu Asn Gln Ala Thr Ile Ser Ser Lys Leu Gln Thr Cys Cys Asp
            1190                1195                1200

Lys Pro Leu Leu Lys Lys Ala His Cys Leu Ser Glu Val Glu His
            1205                1210                1215

Asp Thr Met Pro Ala Asp Leu Pro Ala Ile Ala Ala Asp Phe Val
            1220                1225                1230

Glu Asp Gln Glu Val Cys Lys Asn Tyr Ala Glu Ala Lys Asp Val
            1235                1240                1245

Phe Leu Gly Thr Phe Leu Tyr Glu Tyr Ser Arg Arg His Pro Asp
            1250                1255                1260

Tyr Ser Val Ser Leu Leu Leu Arg Leu Ala Lys Lys Tyr Glu Ala
            1265                1270                1275

Thr Leu Glu Lys Cys Cys Ala Glu Ala Asn Pro Pro Ala Cys Tyr
            1280                1285                1290

Gly Thr Val Leu Ala Glu Phe Gln Pro Leu Val Glu Glu Pro Lys
            1295                1300                1305

Asn Leu Val Lys Thr Asn Cys Asp Leu Tyr Glu Lys Leu Gly Glu
            1310                1315                1320

Tyr Gly Phe Gln Asn Ala Ile Leu Val Arg Tyr Thr Gln Lys Ala
            1325                1330                1335

Pro Gln Val Ser Thr Pro Thr Leu Val Glu Ala Ala Arg Asn Leu
            1340                1345                1350

Gly Arg Val Gly Thr Lys Cys Cys Thr Leu Pro Glu Asp Gln Arg
            1355                1360                1365

Leu Pro Cys Val Glu Asp Tyr Leu Ser Ala Ile Leu Asn Arg Val
            1370                1375                1380

Cys Leu Leu His Glu Lys Thr Pro Val Ser Glu His Val Thr Lys
            1385                1390                1395

Cys Cys Ser Gly Ser Leu Val Glu Arg Arg Pro Cys Phe Ser Ala
            1400                1405                1410

Leu Thr Val Asp Glu Thr Tyr Val Pro Lys Glu Phe Lys Ala Glu
            1415                1420                1425

Thr Phe Thr Phe His Ser Asp Ile Cys Thr Leu Pro Glu Lys Glu
            1430                1435                1440

Lys Gln Ile Lys Lys Gln Thr Ala Leu Ala Glu Leu Val Lys His
            1445                1450                1455

Lys Pro Lys Ala Thr Ala Glu Gln Leu Lys Thr Val Met Asp Asp
            1460                1465                1470
```

```
Phe Ala Gln Phe Leu Asp Thr Cys Cys Lys Ala Ala Asp Lys Asp
    1475                1480                1485

Thr Cys Phe Ser Thr Glu Gly Pro Asn Leu Val Thr Arg Cys Lys
    1490                1495                1500

Asp Ala Leu Ala
    1505

<210> SEQ ID NO 62
<211> LENGTH: 1509
<212> TYPE: PRT
<213> ORGANISM: Artificial Sequence
<220> FEATURE:
<223> OTHER INFORMATION: ENPP5-ENPP3-Albumin

<400> SEQUENCE: 62

Met Thr Ser Lys Phe Leu Leu Val Ser Phe Ile Leu Ala Ala Leu Ser
1               5                   10                  15

Leu Ser Thr Thr Phe Ser Lys Gln Gly Ser Cys Arg Lys Lys Cys Phe
            20                  25                  30

Asp Ala Ser Phe Arg Gly Leu Glu Asn Cys Arg Cys Asp Val Ala Cys
        35                  40                  45

Lys Asp Arg Gly Asp Cys Cys Trp Asp Phe Glu Asp Thr Cys Val Glu
    50                  55                  60

Ser Thr Arg Ile Trp Met Cys Asn Lys Phe Arg Cys Gly Glu Arg Leu
65                  70                  75                  80

Glu Ala Ser Leu Cys Ser Cys Ser Asp Asp Cys Leu Gln Arg Lys Asp
                85                  90                  95

Cys Cys Ala Asp Tyr Lys Ser Val Cys Gln Gly Glu Thr Ser Trp Leu
            100                 105                 110

Glu Glu Asn Cys Asp Thr Ala Gln Gln Ser Gln Cys Pro Glu Gly Phe
        115                 120                 125

Asp Leu Pro Pro Val Ile Leu Phe Ser Met Asp Gly Phe Arg Ala Glu
    130                 135                 140

Tyr Leu Tyr Thr Trp Asp Thr Leu Met Pro Asn Ile Asn Lys Leu Lys
145                 150                 155                 160

Thr Cys Gly Ile His Ser Lys Tyr Met Arg Ala Met Tyr Pro Thr Lys
                165                 170                 175

Thr Phe Pro Asn His Tyr Thr Ile Val Thr Gly Leu Tyr Pro Glu Ser
            180                 185                 190

His Gly Ile Ile Asp Asn Asn Met Tyr Asp Val Asn Leu Asn Lys Asn
        195                 200                 205

Phe Ser Leu Ser Ser Lys Glu Gln Asn Asn Pro Ala Trp Trp His Gly
    210                 215                 220

Gln Pro Met Trp Leu Thr Ala Met Tyr Gln Gly Leu Lys Ala Ala Thr
225                 230                 235                 240

Tyr Phe Trp Pro Gly Ser Glu Val Ala Ile Asn Gly Ser Phe Pro Ser
                245                 250                 255

Ile Tyr Met Pro Tyr Asn Gly Ser Val Pro Phe Glu Glu Arg Ile Ser
            260                 265                 270

Thr Leu Leu Lys Trp Leu Asp Leu Pro Lys Ala Glu Arg Pro Arg Phe
        275                 280                 285

Tyr Thr Met Tyr Phe Glu Glu Pro Asp Ser Ser Gly His Ala Gly Gly
    290                 295                 300

Pro Val Ser Ala Arg Val Ile Lys Ala Leu Gln Val Val Asp His Ala
305                 310                 315                 320
```

```
Phe Gly Met Leu Met Glu Gly Leu Lys Gln Arg Asn Leu His Asn Cys
                325                 330                 335

Val Asn Ile Ile Leu Leu Ala Asp His Gly Met Asp Gln Thr Tyr Cys
                340                 345                 350

Asn Lys Met Glu Tyr Met Thr Asp Tyr Phe Pro Arg Ile Asn Phe Phe
                355                 360                 365

Tyr Met Tyr Glu Gly Pro Ala Pro Arg Ile Arg Ala His Asn Ile Pro
                370                 375                 380

His Asp Phe Phe Ser Phe Asn Ser Glu Glu Ile Val Arg Asn Leu Ser
385                 390                 395                 400

Cys Arg Lys Pro Asp Gln His Phe Lys Pro Tyr Leu Thr Pro Asp Leu
                405                 410                 415

Pro Lys Arg Leu His Tyr Ala Lys Asn Val Arg Ile Asp Lys Val His
                420                 425                 430

Leu Phe Val Asp Gln Gln Trp Leu Ala Val Arg Ser Lys Ser Asn Thr
                435                 440                 445

Asn Cys Gly Gly Gly Asn His Gly Tyr Asn Asn Glu Phe Arg Ser Met
                450                 455                 460

Glu Ala Ile Phe Leu Ala His Gly Pro Ser Phe Lys Glu Lys Thr Glu
465                 470                 475                 480

Val Glu Pro Phe Glu Asn Ile Glu Val Tyr Asn Leu Met Cys Asp Leu
                485                 490                 495

Leu Arg Ile Gln Pro Ala Pro Asn Asn Gly Thr His Gly Ser Leu Asn
                500                 505                 510

His Leu Leu Lys Val Pro Phe Tyr Glu Pro Ser His Ala Glu Glu Val
                515                 520                 525

Ser Lys Phe Ser Val Cys Gly Phe Ala Asn Pro Leu Pro Thr Glu Ser
                530                 535                 540

Leu Asp Cys Phe Cys Pro His Leu Gln Asn Ser Thr Gln Leu Glu Gln
545                 550                 555                 560

Val Asn Gln Met Leu Asn Leu Thr Gln Glu Glu Ile Thr Ala Thr Val
                565                 570                 575

Lys Val Asn Leu Pro Phe Gly Arg Pro Arg Val Leu Gln Lys Asn Val
                580                 585                 590

Asp His Cys Leu Leu Tyr His Arg Glu Tyr Val Ser Gly Phe Gly Lys
                595                 600                 605

Ala Met Arg Met Pro Met Trp Ser Ser Tyr Thr Val Pro Gln Leu Gly
                610                 615                 620

Asp Thr Ser Pro Leu Pro Pro Thr Val Pro Asp Cys Leu Arg Ala Asp
625                 630                 635                 640

Val Arg Val Pro Pro Ser Glu Ser Gln Lys Cys Ser Phe Tyr Leu Ala
                645                 650                 655

Asp Lys Asn Ile Thr His Gly Phe Leu Tyr Pro Pro Ala Ser Asn Arg
                660                 665                 670

Thr Ser Asp Ser Gln Tyr Asp Ala Leu Ile Thr Ser Asn Leu Val Pro
                675                 680                 685

Met Tyr Glu Glu Phe Arg Lys Met Trp Asp Tyr Phe His Ser Val Leu
                690                 695                 700

Leu Ile Lys His Ala Thr Glu Arg Asn Gly Val Asn Val Val Ser Gly
705                 710                 715                 720

Pro Ile Phe Asp Tyr Asn Tyr Asp Gly His Phe Asp Ala Pro Asp Glu
                725                 730                 735
```

```
Ile Thr Lys His Leu Ala Asn Thr Asp Val Pro Ile Pro Thr His Tyr
            740                 745                 750

Phe Val Val Leu Thr Ser Cys Lys Asn Lys Ser His Thr Pro Glu Asn
            755                 760                 765

Cys Pro Gly Trp Leu Asp Val Leu Pro Phe Ile Ile Pro His Arg Pro
770                 775                 780

Thr Asn Val Glu Ser Cys Pro Glu Gly Lys Pro Glu Ala Leu Trp Val
785                 790                 795                 800

Glu Glu Arg Phe Thr Ala His Ile Ala Arg Val Arg Asp Val Glu Leu
                805                 810                 815

Leu Thr Gly Leu Asp Phe Tyr Gln Asp Lys Val Gln Pro Val Ser Glu
            820                 825                 830

Ile Leu Gln Leu Lys Thr Tyr Leu Pro Thr Phe Glu Thr Thr Ile Asp
            835                 840                 845

Lys Thr His Thr Cys Pro Pro Cys Pro Ala Pro Glu Leu Leu Gly Gly
            850                 855                 860

Pro Ser Val Phe Leu Phe Pro Pro Lys Pro Lys Asp Thr Leu Met Ile
865                 870                 875                 880

Ser Arg Thr Pro Glu Val Thr Gly Gly Gly Ser Gly Gly Gly Gly Ser
                885                 890                 895

Gly Gly Gly Gly Ser Met Lys Trp Val Thr Phe Leu Leu Leu Leu Phe
                900                 905                 910

Val Ser Gly Ser Ala Phe Ser Arg Gly Val Phe Arg Arg Glu Ala His
            915                 920                 925

Lys Ser Glu Ile Ala His Arg Tyr Asn Asp Leu Gly Glu Gln His Phe
930                 935                 940

Lys Gly Leu Val Leu Ile Ala Phe Ser Gln Tyr Leu Gln Lys Cys Ser
945                 950                 955                 960

Tyr Asp Glu His Ala Lys Leu Val Gln Glu Val Thr Asp Phe Ala Lys
                965                 970                 975

Thr Cys Val Ala Asp Glu Ser Ala Ala Asn Cys Asp Lys Ser Leu His
            980                 985                 990

Thr Leu Phe Gly Asp Lys Leu Cys Ala Ile Pro Asn Leu Arg Glu Asn
            995                 1000                1005

Tyr Gly Glu Leu Ala Asp Cys Cys Thr Lys Gln Glu Pro Glu Arg
    1010                1015                1020

Asn Glu Cys Phe Leu Gln His Lys Asp Asp Asn Pro Ser Leu Pro
    1025                1030                1035

Pro Phe Glu Arg Pro Glu Ala Glu Ala Met Cys Thr Ser Phe Lys
    1040                1045                1050

Glu Asn Pro Thr Thr Phe Met Gly His Tyr Leu His Glu Val Ala
    1055                1060                1065

Arg Arg His Pro Tyr Phe Tyr Ala Pro Glu Leu Leu Tyr Tyr Ala
    1070                1075                1080

Glu Gln Tyr Asn Glu Ile Leu Thr Gln Cys Cys Ala Glu Ala Asp
    1085                1090                1095

Lys Glu Ser Cys Leu Thr Pro Lys Leu Asp Gly Val Lys Glu Lys
    1100                1105                1110

Ala Leu Val Ser Ser Val Arg Gln Arg Met Lys Cys Ser Ser Met
    1115                1120                1125

Gln Lys Phe Gly Glu Arg Ala Phe Lys Ala Trp Ala Val Ala Arg
    1130                1135                1140

Leu Ser Gln Thr Phe Pro Asn Ala Asp Phe Ala Glu Ile Thr Lys
```

```
              1145                1150                1155

Leu Ala Thr Asp Leu Thr Lys Val Asn Lys Glu Cys Cys His Gly
        1160                1165                1170

Asp Leu Leu Glu Cys Ala Asp Asp Arg Ala Glu Leu Ala Lys Tyr
        1175                1180                1185

Met Cys Glu Asn Gln Ala Thr Ile Ser Ser Lys Leu Gln Thr Cys
        1190                1195                1200

Cys Asp Lys Pro Leu Leu Lys Lys Ala His Cys Leu Ser Glu Val
        1205                1210                1215

Glu His Asp Thr Met Pro Ala Asp Leu Pro Ala Ile Ala Ala Asp
        1220                1225                1230

Phe Val Glu Asp Gln Glu Val Cys Lys Asn Tyr Ala Glu Ala Lys
        1235                1240                1245

Asp Val Phe Leu Gly Thr Phe Leu Tyr Glu Tyr Ser Arg Arg His
        1250                1255                1260

Pro Asp Tyr Ser Val Ser Leu Leu Leu Arg Leu Ala Lys Lys Tyr
        1265                1270                1275

Glu Ala Thr Leu Glu Lys Cys Cys Ala Glu Ala Asn Pro Pro Ala
        1280                1285                1290

Cys Tyr Gly Thr Val Leu Ala Glu Phe Gln Pro Leu Val Glu Glu
        1295                1300                1305

Pro Lys Asn Leu Val Lys Thr Asn Cys Asp Leu Tyr Glu Lys Leu
        1310                1315                1320

Gly Glu Tyr Gly Phe Gln Asn Ala Ile Leu Val Arg Tyr Thr Gln
        1325                1330                1335

Lys Ala Pro Gln Val Ser Thr Pro Thr Leu Val Glu Ala Ala Arg
        1340                1345                1350

Asn Leu Gly Arg Val Gly Thr Lys Cys Cys Thr Leu Pro Glu Asp
        1355                1360                1365

Gln Arg Leu Pro Cys Val Glu Asp Tyr Leu Ser Ala Ile Leu Asn
        1370                1375                1380

Arg Val Cys Leu Leu His Glu Lys Thr Pro Val Ser Glu His Val
        1385                1390                1395

Thr Lys Cys Cys Ser Gly Ser Leu Val Glu Arg Arg Pro Cys Phe
        1400                1405                1410

Ser Ala Leu Thr Val Asp Glu Thr Tyr Val Pro Lys Glu Phe Lys
        1415                1420                1425

Ala Glu Thr Phe Thr Phe His Ser Asp Ile Cys Thr Leu Pro Glu
        1430                1435                1440

Lys Glu Lys Gln Ile Lys Lys Gln Thr Ala Leu Ala Glu Leu Val
        1445                1450                1455

Lys His Lys Pro Lys Ala Thr Ala Glu Gln Leu Lys Thr Val Met
        1460                1465                1470

Asp Asp Phe Ala Gln Phe Leu Asp Thr Cys Cys Lys Ala Ala Asp
        1475                1480                1485

Lys Asp Thr Cys Phe Ser Thr Glu Gly Pro Asn Leu Val Thr Arg
        1490                1495                1500

Cys Lys Asp Ala Leu Ala
        1505

<210> SEQ ID NO 63
<211> LENGTH: 3447
<212> TYPE: DNA
<213> ORGANISM: Artificial Sequence
```

<220> FEATURE:
<223> OTHER INFORMATION: ENPP121-ENPP3-Fc nucleotide sequence

<400> SEQUENCE: 63

| | | | | | |
|---|---|---|---|---|---|
| atggaaaggg | acggatgcgc | cggtggtgga | tctcgcggag | gcgaaggtgg | aagggcccct | 60 |
| agggaaggac | ctgccggaaa | cggaaggac | aggggacgct | ctcacgccgc | tgaagctcca | 120 |
| ggcgaccctc | aggccgctgc | ctctctgctg | gctcctatgg | acgtcggaga | agaaccctg | 180 |
| gaaaaggccg | ccagggccag | gactgccaag | gaccccaaca | cctacaagat | catctccctc | 240 |
| ttcactttcg | ccgtcggagt | caacatctgc | ctgggattca | ccgccgaaaa | gcaaggcagc | 300 |
| tgcaggaaga | agtgctttga | tgcatcattt | agaggactgg | agaactgccg | gtgtgatgtg | 360 |
| gcatgtaaag | accgaggtga | ttgctgctgg | gattttgaag | acacctgtgt | ggaatcaact | 420 |
| cgaatatgga | tgtgcaataa | atttcgttgt | ggagagacca | gattagaggc | cagcctttgc | 480 |
| tcttgttcag | atgactgttt | gcagaggaaa | gattgctgtg | ctgactataa | gagtgtttgc | 540 |
| caaggagaaa | cctcatggct | ggaagaaaac | tgtgacacag | cccagcagtc | tcagtgccca | 600 |
| gaagggtttg | acctgccacc | agttatcttg | ttttctatgg | atggatttag | agctgaatat | 660 |
| ttatacacat | gggatacttt | aatgccaaat | atcaataaac | tgaaaacatg | tggaattcat | 720 |
| tcaaaataca | tgagagctat | gtatcctacc | aaaaccttcc | caaatcatta | caccattgtc | 780 |
| acgggcttgt | atccagagtc | acatggcatc | attgacaata | atatgtatga | tgtaaatctc | 840 |
| aacaagaatt | tttcactttc | ttcaaaggaa | caaaataatc | cagcctggtg | gcatgggcaa | 900 |
| ccaatgtggc | tgacagcaat | gtatcaaggt | ttaaaagccg | ctacctactt | ttggcccgga | 960 |
| tcagaagtgg | ctataaatgg | ctcctttcct | tccatataca | tgccttacaa | cggaagtgtc | 1020 |
| ccatttgaag | agaggatttc | tacactgtta | aatggctgg | acctgcccaa | agctgaaaga | 1080 |
| cccaggtttt | ataccatgta | ttttgaagaa | cctgattcct | ctggacatgc | aggtggacca | 1140 |
| gtcagtgcca | gagtaattaa | agccttacag | gtagtagatc | atgcttttgg | gatgttgatg | 1200 |
| gaaggcctga | agcagcggaa | tttgcacaac | tgtgtcaata | tcatccttct | ggctgaccat | 1260 |
| ggaatggacc | agacttattg | taacaagatg | gaatacatga | ctgattattt | tcccagaata | 1320 |
| aacttcttct | acatgtacga | agggcctgcc | ccccgcatcc | gagctcataa | tatacctcat | 1380 |
| gacttttta | gttttaattc | tgaggaaatt | gttagaaacc | tcagttgccg | aaaacctgat | 1440 |
| cagcatttca | agccctattt | gactcctgat | ttgccaaagc | gactgcacta | tgccaagaac | 1500 |
| gtcagaatcg | acaaagttca | tctctttgtg | gatcaacagt | ggctggctgt | taggagtaaa | 1560 |
| tcaaatacaa | attgtggagg | aggcaaccat | ggttataaca | atgagtttag | gagcatggag | 1620 |
| gctatctttc | tggcacatgg | acccagtttt | aaagagaaga | ctgaagttga | accatttgaa | 1680 |
| aatattgaag | tctataacct | aatgtgtgat | cttctacgca | ttcaaccagc | accaaacaat | 1740 |
| ggaacccatg | gtagtttaaa | ccatcttctg | aaggtgcctt | tttatgagcc | atcccatgca | 1800 |
| gaggaggtgt | caaagttttc | tgtttgtggc | tttgctaatc | cattgcccac | agagtctctt | 1860 |
| gactgtttct | gccctcacct | acaaaatagt | actcagctgg | aacaagtgaa | tcagatgcta | 1920 |
| aatctcaccc | aagaagaaat | aacagcaaca | gtgaaagtaa | atttgccatt | tgggaggcct | 1980 |
| agggtactgc | agaagaacgt | ggaccactgt | ctcctttacc | acagggaata | tgtcagtgga | 2040 |
| tttggaaaag | ctatgaggat | gcccatgtgg | agttcataca | cagtccccca | gttgggagac | 2100 |
| acatcgcctc | tgcctcccac | tgtcccagac | tgtctgcggg | ctgatgtcag | ggttcctcct | 2160 |
| tctgagagcc | aaaaatgttc | cttctattta | gcagacaaga | atatcaccca | cggcttcctc | 2220 |

| | | | | |
|---|---|---|---|---|
| tatcctcctg | ccagcaatag | aacatcagat | agccaatatg | atgctttaat tactagcaat | 2280 |
| ttggtaccta | tgtatgaaga | attcagaaaa | atgtgggact | acttccacag tgttcttctt | 2340 |
| ataaaacatg | ccacagaaag | aaatggagta | atgtggtta | gtggaccaat atttgattat | 2400 |
| aattatgatg | ccattttga | tgctccagat | gaaattacca | acatttagc caacactgat | 2460 |
| gttcccatcc | caacacacta | ctttgtggtg | ctgaccagtt | gtaaaacaa gagccacaca | 2520 |
| ccggaaaact | gccctgggtg | gctggatgtc | ctacccttta | tcatccctca ccgacctacc | 2580 |
| aacgtggaga | gctgtcctga | aggtaaacca | gaagctcttt | gggttgaaga aagatttaca | 2640 |
| gctcacattg | cccgggtccg | tgatgtagaa | cttctcactg | gcttgactt ctatcaggat | 2700 |
| aaagtgcagc | ctgtctctga | aattttgcaa | ctaaagacat | atttaccaac atttgaaacc | 2760 |
| actattgaca | aaactcacac | atgcccaccg | tgcccagcac | ctgaactcct gggggaccg | 2820 |
| tcagtcttcc | tcttccccc | aaaacccaag | gacaccctca | tgatctcccg gacccctgag | 2880 |
| gtcacatgcg | tggtggtgga | cgtgagccac | gaagaccctg | aggtcaagtt caactggtac | 2940 |
| gtggacggcg | tggaggtgca | taatgccaag | acaaagccgc | gggaggagca gtacaacagc | 3000 |
| acgtaccgtg | tggtcagcgt | cctcaccgtc | ctgcaccagg | actggctgaa tggcaaggag | 3060 |
| tacaagtgca | aggtctccaa | caaagccctc | ccagccccca | tcgagaaaac catctccaaa | 3120 |
| gccaagggc | agccccgaga | accacaggtg | tacaccctgc | ccccatcccg ggaggagatg | 3180 |
| accaagaacc | aggtcagcct | gacctgcctg | gtcaaaggct | tctatcccag cgacatcgcc | 3240 |
| gtggagtggg | agagcaatgg | gcagccggag | aacaactaca | agaccacgcc tcccgtgctg | 3300 |
| gactccgacg | gctccttctt | cctctatagc | aagctcaccg | tggacaagag caggtggcag | 3360 |
| caggggaacg | tcttctcatg | ctccgtgatg | catgaggctc | tgcacaacca ctacacgcag | 3420 |
| aagagcctct | ccctgtcccc | gggtaaa | | | 3447 |

<210> SEQ ID NO 64
<211> LENGTH: 4638
<212> TYPE: DNA
<213> ORGANISM: Artificial Sequence
<220> FEATURE:
<223> OTHER INFORMATION: ENPP121-ENPP3-Albumin nucleotide sequence

<400> SEQUENCE: 64

| | | | | |
|---|---|---|---|---|
| atggaaggg | acggatgcgc | cggtggtgga | tctcgcggag | gcgaaggtgg aagggcccct | 60 |
| agggaaggac | ctgccggaaa | cggaagggac | aggggacgct | ctcacgccgc tgaagctcca | 120 |
| ggcgaccctc | aggccgctgc | ctctctgctg | gctcctatgg | acgtcggaga agaaccctg | 180 |
| gaaaaggccg | ccagggccag | gactgccaag | gaccccaaca | cctacaagat catctccctc | 240 |
| ttcactttcg | ccgtcggagt | caacatctgc | ctgggattca | ccgccgaaaa gcaaggcagc | 300 |
| tgcaggaaga | agtgctttga | tgcatcattt | agaggactgg | agaactgccg gtgtgatgtg | 360 |
| gcatgtaaag | accgaggtga | ttgctgctgg | gattttgaag | acacctgtgt ggaatcaact | 420 |
| cgaatatgga | tgtgcaataa | atttcgttgt | ggagagacca | gattagaggc cagcctttgc | 480 |
| tcttgttcag | atgactgttt | gcagaggaaa | gattgctgtg | ctgactataa gagtgtttgc | 540 |
| caaggagaaa | cctcatggct | ggaagaaaac | tgtgacacag | cccagcagtc tcagtgccca | 600 |
| gaagggtttg | acctgccacc | agttatcttg | ttttctatgg | atggatttag agctgaatat | 660 |
| ttatacacat | gggatacttt | aatgccaaat | atcaataaac | tgaaaacatg tggaattcat | 720 |
| tcaaaataca | tgagagctat | gtatcctacc | aaaaccttcc | caaatcatta caccattgtc | 780 |
| acgggcttgt | atccagagtc | acatggcatc | attgacaata | atatgtatga tgtaaatctc | 840 |

```
aacaagaatt tttcactttc ttcaaaggaa caaaataatc cagcctggtg gcatgggcaa    900
ccaatgtggc tgacagcaat gtatcaaggt ttaaaagccg ctacctactt ttggcccgga    960
tcagaagtgg ctataaatgg ctccttcct tccatataca tgccttacaa cggaagtgtc   1020
ccatttgaag agaggatttc tacactgtta aaatggctgg acctgcccaa agctgaaaga   1080
cccaggtttt ataccatgta ttttgaagaa cctgattcct ctggacatgc aggtggacca   1140
gtcagtgcca gagtaattaa agccttacag gtagtagatc atgcttttgg gatgttgatg   1200
gaaggcctga agcagcggaa tttgcacaac tgtgtcaata tcatccttct ggctgaccat   1260
ggaatggacc agacttattg taacaagatg gaatacatga ctgattattt tcccagaata   1320
aacttcttct acatgtacga agggcctgcc ccccgcatcc gagctcataa tatacctcat   1380
gactttttta gttttaattc tgaggaaatt gttagaaacc tcagttgccg aaaacctgat   1440
cagcatttca gccctatttt gactcctgat ttgccaaagc gactgcacta tgccaagaac   1500
gtcagaatcg acaaagttca tctctttgtg gatcaacagt ggctggctgt taggagtaaa   1560
tcaaatacaa attgtggagg aggcaaccat ggttataaca atgagtttag gagcatggag   1620
gctatctttc tggcacatgg acccagtttt aaagagaaga ctgaagttga accatttgaa   1680
aatattgaag tctataacct aatgtgtgat cttctacgca ttcaaccagc accaaacaat   1740
ggaacccatg gtagtttaaa ccatcttctg aaggtgcctt tttatgagcc atcccatgca   1800
gaggaggtgt caaagttttc tgtttgtggc tttgctaatc cattgcccac agagtctctt   1860
gactgtttct gccctcacct acaaaatagt actcagctgg aacaagtgaa tcagatgcta   1920
aatctcaccc aagaagaaat aacagcaaca gtgaaagtaa atttgccatt tgggaggcct   1980
agggtactgc agaagaacgt ggaccactgt ctcctttacc acaggaaata tgtcagtgga   2040
tttggaaaag ctatgaggat gcccatgtgg agttcataca cagtcccccca gttgggagac   2100
acatcgcctc tgcctcccac tgtcccagac tgtctgcggg ctgatgtcag ggttcctcct   2160
tctgagagcc aaaaatgttc cttctatttg gcagacaaga atatcaccca cggcttcctc   2220
tatcctcctg ccagcaatag aacatcagat agccaatatg atgctttaat tactagcaat   2280
ttggtaccta tgtatgaaga attcagaaaa atgtgggact acttccacag tgttcttctt   2340
ataaaacatg ccacagaaag aaatggagta aatgtggtta gtggaccaat atttgattat   2400
aattatgatg ccattttga tgctccagat gaaattacca acatttagc caacactgat   2460
gttcccatcc caacacacta ctttgtggtg ctgaccagtt gtaaaaacaa gagccacaca   2520
ccggaaaact gccctgggtg gctggatgtc ctacccttta tcatccctca ccgacctacc   2580
aacgtggaga gctgtcctga aggtaaacca gaagctcttt gggttgaaga aagatttaca   2640
gctcacattg cccgggtccg tgatgtagaa cttctcactg gcttgactt ctatcaggat   2700
aaagtgcagc ctgtctctga aattttgcaa ctaaagacat atttaccaac atttgaaacc   2760
actattggtg gaggagctc tggtggaggc ggtagcggag gcggagggtc gatgaagtgg   2820
gtaaccttta tttcccttct ttttctcttt agctcggctt attccagggg tgtgtttcgt   2880
cgagatgcac acaagagtga ggttgctcat cggtttaaag atttgggaga agaaaatttc   2940
aaagccttgg tgttgattgc ctttgctcag tatcttcagc agtgtccatt tgaagatcat   3000
gtaaaattag tgaatgaagt aactgaattt gcaaaaacat gtgttgctga tgagtcagct   3060
gaaaattgtg acaaatcact tcatacccctt tttggagaca attatgcac agttgcaact   3120
cttcgtgaaa cctatggtga aatggctgac tgctgtgcaa acaagaacc tgagagaaat   3180
```

```
gaatgcttct tgcaacacaa agatgacaac ccaaacctcc cccgattggt gagaccagag      3240
gttgatgtga tgtgcactgc ttttcatgac aatgaagaga cattttttgaa aaaatactta    3300 tatgaaattg ccagaagaca tccttacttt tatgccccgg aactccttttt ctttgctaaa   3360 aggtataaag ctgcttttac agaatgttgc caagctgctg ataaagctgc ctgcctgttg     3420
ccaaagctcg atgaacttcg ggatgaaggg aaggcttcgt ctgccaaaca gagactcaag    3480
tgtgccagtc tccaaaaatt tggagaaaga gctttcaaag catgggcagt agctcgcctg    3540
agccagagat ttcccaaagc tgagtttgca gaagtttcca agttagtgac agatcttacc   3600
aaagtccaca cggaatgctg ccatggagat ctgcttgaat gtgctgatga cagggcggac    3660
cttgccaagt atatctgtga aaatcaagat tcgatctcca gtaaactgaa ggaatgctgt   3720
gaaaaacctc tgttggaaaa atcccactgc attgccgaag tggaaaatga tgagatgcct   3780
gctgacttgc cttcattagc tgctgatttt gttgaaagta aggatgtttg caaaaactat    3840
gctgaggcaa aggatgtctt cctgggcatg ttttttgtatg aatatgcaag aaggcatcct   3900
gattactctg tcgtgctgct gctgagactt gccaagacat atgaaaccac tctagagaag    3960
tgctgtgccg ctgcagatcc tcatgaatgc tatgccaaag tgttcgatga atttaaacct    4020
cttgtggaag agcctcagaa tttaatcaaa caaaattgtg agcttttttga gcagcttgga   4080 gagtacaaat tccagaatgc gctattagtt cgttacacca agaaagtacc ccaagtgtca    4140
actccaactc ttgtagaggt ctcaagaaac ctaggaaaag tgggcagcaa atgttgtaaa    4200
catcctgaag caaaaagaat gccctgtgca gaagactatc tatccgtggt cctgaaccag    4260
ttatgtgtgt tgcatgagaa aacgccagta agtgacagag tcaccaaatg ctgcacagaa    4320
tccttggtga acaggcgacc atgcttttca gctctggaag tcgatgaaac atacgttccc    4380
aaagagttta atgctgaaac attccacttc catgcagata tatgcacact ttctgagaag    4440
gagagacaaa tcaagaaaca aactgcactt gttgagctcg tgaaacacaa gcccaaggca    4500 acaaagagc aactgaaagc tgttatggat gatttcgcag cttttgtaga gaagtgctgc     4560
aaggctgacg ataaggagac ctgctttgcc gaggagggta aaaaacttgt tgctgcaagt    4620
caagctgcct taggctta                                                  4638
```

<210> SEQ ID NO 65
<211> LENGTH: 8852
<212> TYPE: DNA
<213> ORGANISM: Artificial Sequence
<220> FEATURE:
<223> OTHER INFORMATION: hNPP3-hFc-pcDNA3 nucleotide sequence

<400> SEQUENCE: 65

```
gacggatcgg gagatctccc gatccctat ggtcgactct cagtacaatc tgctctgatg        60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180 ttaggggttag gcgttttgcg ctgcttcgcg atgtacgggc cagatatacg cgttgacatt    240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

-continued

```
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caatgggcg       780 gtaggcgtgt acggtgggag gtctatataa gcagagctct ctggctaact agagaaccca      840
ctgcttactg gcttatcgaa attaatacga ctcactatag ggagacccaa gcttatggaa      900
agggacggat gcgccggtgg tggatctcgc ggaggcgaag gtggaagggc cctagggaa       960 ggacctgccg aaacggaag ggacagggga cgctctcacg ccgctgaagc tccaggcgac      1020
cctcaggccg ctgcctctct gctggctcct atggacgtcg gagaagaacc cctggaaaag     1080
gccgccaggg ccaggactgc caaggacccc aacacctaca agatcatctc cctcttcact     1140
ttcgccgtcg gagtcaacat ctgcctggga ttcaccgccg aaaagcaagg cagctgcagg     1200
aagaagtgct tgatgcatc atttagagga ctggagaact gccggtgtga tgtggcatgt     1260
aaagaccgag gtgattgctg ctgggatttt gaagacacct gtgtggaatc aactcgaata     1320
tggatgtgca ataaatttcg ttgtggagag accagattag aggccagcct tgctcttgt      1380 tcagatgact gtttgcagag gaaagattgc tgtgctgact ataagagtgt ttgccaagga     1440
gaaacctcat ggctggaaga aaactgtgac acagcccagc agtctcagtg cccagaaggg     1500
tttgacctgc caccagttat cttgtttct atggatggat ttagagctga atatttatac      1560
acatgggata cttttaatgcc aaatatcaat aaactgaaaa catgtggaat tcattcaaaa    1620
tacatgagag ctatgtatcc taccaaaacc ttcccaaatc attacaccat tgtcacgggc     1680
ttgtatccag agtcacatgg catcattgac aataatatgt atgatgtaaa tctcaacaag     1740
aatttttcac tttcttcaaa ggaacaaaat aatccagcct ggtggcatgg gcaaccaatg     1800
tggctgacag caatgtatca aggtttaaaa gccgctacct acttttggcc cggatcagaa     1860
gtggctataa atggctcctt tccttccata tacatgcctt acaacggaag tgtcccattt     1920
gaagagagga tttctacact gttaaaatgg ctggacctgc ccaaagctga agacccagg      1980 ttttatacca tgtattttga agaacctgat tcctctggac atgcaggtgg accagtcagt     2040
gccagagtaa ttaaagcctt acaggtagta gatcatgctt tgggatgtt gatgaaggc      2100 ctgaagcagc ggaatttgca caactgtgtc aatatcatcc ttctggctga ccatggaatg    2160
gaccagactt attgtaacaa gatggaatac atgactgatt attttcccag aataaacttc    2220
ttctacatgt acgaagggcc tgccccccgc atccgagctc ataatatacc tcatgacttt    2280
tttagtttta attctgagga aattgttaga acctcagtt gccgaaaacc tgatcagcat     2340
ttcaagccct atttgactcc tgatttgcca agcgactgc actatgccaa gaacgtcaga     2400
atcgacaaag ttcatctctt tgtggatcaa cagtggctgg ctgttaggag taaatcaaat    2460
acaaattgtg gaggaggcaa ccatggttat aacaatgagt ttaggagcat ggaggctatc    2520
tttctggcac atggacccag ttttaaagag aagactgaag ttgaaccatt tgaaaatatt    2580
gaagtctata acctaatgtg tgatcttcta cgcattcaac cagcaccaaa caatggaacc    2640
catggtagtt taaaccatct tctgaaggtg ccttttttatg agccatccca tgcagaggag    2700
gtgtcaaagt tttctgtttg tggctttgct aatccattgc ccacagagtc tcttgactgt    2760
ttctgccctc acctacaaaa tagtactcag ctggaacaag tgaatcagat gctaaatctc    2820
acccaagaag aaataacagc aacagtgaaa gtaaatttgc catttgggag gcctagggta   2880
ctgcagaaga acgtggacca ctgtctcct taccacaggg aatatgtcag tggatttgga    2940
```

```
aaagctatga ggatgcccat gtggagttca tacacagtcc cccagttggg agacacatcg    3000
cctctgcctc ccactgtccc agactgtctg cgggctgatg tcagggttcc tccttctgag    3060
agccaaaaat gttccttcta tttagcagac aagaatatca cccacggctt cctctatcct    3120
cctgccagca atagaacatc agatagccaa tatgatgctt taattactag caatttggta    3180
cctatgtatg aagaattcag aaaaatgtgg gactacttcc acagtgttct tcttataaaa    3240
catgccacag aaagaaatgg agtaaatgtg gttagtggac caatatttga ttataattat    3300
gatggccatt ttgatgctcc agatgaaatt accaaacatt tagccaacac tgatgttccc    3360
atcccaacac actactttgt ggtgctgacc agttgtaaaa acaagagcca cacaccggaa    3420
aactgccctg ggtggctgga tgtcctaccc tttatcatcc ctcaccgacc taccaacgtg    3480
gagagctgtc ctgaaggtaa accagaagct ctttgggttg aagaaagatt tacagctcac    3540
attgcccggg tccgtgatgt agaacttctc actgggcttg acttctatca ggataaagtg    3600
cagcctgtct ctgaaatttt gcaactaaag acatatttac caacatttga accactatt     3660 gacaaaactc acacatgccc accgtgccca gcacctgaac tcctgggggg accgtcagtc    3720
ttcctcttcc ccccaaaacc caaggacacc ctcatgatct cccggacccc tgaggtcaca    3780
tgcgtggtgg tggacgtgag ccacgaagac cctgaggtca agttcaactg gtacgtggac    3840
ggcgtggagg tgcataatgc caagacaaag ccgcgggagg agcagtacaa cagcacgtac    3900
cgtgtggtca gcgtcctcac cgtcctgcac caggactggc tgaatggcaa ggagtacaag    3960
tgcaaggtct ccaacaaagc cctcccagcc cccatcgaga aaaccatctc caaagccaaa    4020
gggcagcccc gagaaccaca ggtgtacacc ctgcccccat cccgggagga tgaccaag     4080 aaccaggtca gcctgacctg cctggtcaaa ggcttctatc ccagcgacat cgccgtggag    4140
tgggagagca atgggcagcc ggagaacaac tacaagacca cgcctcccgt gctggactcc    4200
gacggctcct tcttcctcta tagcaagctc accgtggaca agagcaggtg gcagcagggg    4260
aacgtcttct catgctccgt gatgcatgag gctctgcaca accactacac gcagaagagc    4320
ctctccctgt ccccgggtaa atgaaattct gcagatatcc atcacactgg cggccgctcg    4380
agcatgcatc tagagggccc tattctatag tgtcacctaa atgctagagc tcgctgatca    4440
gcctcgactg tgccttctag ttgccagcca tctgttgttt gcccctcccc cgtgccttcc    4500
ttgaccctgg aaggtgccac tcccactgtc ctttcctaat aaaatgagga aattgcatcg    4560
cattgtctga gtaggtgtca ttctattctg ggggtgggg tggggcagga cagcaagggg     4620
gaggattggg aagacaatag caggcatgct ggggatgcgg tgggctctat ggcttctgag    4680
gcggaaagaa ccagctgggg ctctaggggg tatccccacg cgccctgtag cggcgcatta    4740
agcgcggcgg gtgtggtggt tacgcgcagc gtgaccgcta cacttgccag cgccctagcg    4800
cccgctcctt tcgctttctt cccttccttt ctcgccacgt tcgccggctt tccccgtcaa    4860
gctctaaatc gggcatccc tttagggttc cgatttagtg ctttacggca cctcgacccc     4920
aaaaaacttg attagggtga tggttcacgt agtgggccat cgccctgata gacggttttt    4980
cgccctttga cgttggagtc acgttctttt aatagtggac tcttgttcca aactggaaca    5040
acactcaacc ctatctcggt ctattctttt gatttataag ggattttggg gatttcggcc    5100
tattggttaa aaatgagct gatttaacaa aaatttaacg cgaattaatt ctgtggaatg     5160
tgtgtcagtt agggtgtgga aagtcccag gctccccagg caggcagaag tatgcaaagc      5220
atgcatctca attagtcagc aaccaggtgt ggaaagtccc caggctcccc agcaggcaga    5280
agtatgcaaa gcatgcatct caattagtca gcaaccatag tcccgcccct aactccgccc    5340
```

```
atcccgcccc taactccgcc cagttccgcc cattctccgc cccatggctg actaattttt    5400
tttatttatg cagaggccga ggccgcctct gcctctgagc tattccagaa gtagtgagga    5460
ggcttttttg gaggcctagg cttttgcaaa aagctcccgg gagcttgtat atccattttc    5520
ggatctgatc aagagacagg atgaggatcg tttcgcatga ttgaacaaga tggattgcac    5580
gcaggttctc cggccgcttg ggtggagagg ctattcggct atgactgggc acaacagaca    5640
atcggctgct ctgatgccgc cgtgttccgg ctgtcagcgc aggggcgccc ggttcttttt    5700
gtcaagaccg acctgtccgg tgccctgaat gaactgcagg acgaggcagc gcggctatcg    5760
tggctggcca cgacgggcgt tccttgcgca gctgtgctcg acgttgtcac tgaagcggga    5820
agggactggc tgctattggg cgaagtgccg gggcaggatc tcctgtcatc tcaccttgct    5880
cctgccgaga agtatccat catggctgat gcaatgcggc ggctgcatac gcttgatccg    5940
gctacctgcc cattcgacca ccaagcgaaa catcgcatcg agcgagcacg tactcggatg    6000
gaagccggtc ttgtcgatca ggatgatctg gacgaagagc atcaggggct cgcgccagcc    6060
gaactgttcg ccaggctcaa ggcgcgcatg cccgacggcg aggatctcgt cgtgacccat    6120
ggcgatgcct gcttgccgaa tatcatggtg gaaaatggcc gcttttctgg attcatcgac    6180
tgtggccggc tgggtgtggc ggaccgctat caggacatag cgttggctac ccgtgatatt    6240
gctgaagagc ttggcggcga atgggctgac cgcttcctcg tgctttacgg tatcgccgct    6300
cccgattcgc agcgcatcgc cttctatcgc cttcttgacg agttcttctg agcgggactc    6360
tggggttcga aatgaccgac caagcgacgc ccaacctgcc atcacgagat tcgattcca    6420 ccgccgcctt ctatgaaagg ttgggcttcg gaatcgtttt ccgggacgcc ggctggatga    6480
tcctccagcg cggggatctc atgctggagt tcttcgccca ccccaacttg tttattgcag    6540
cttataatgg ttacaaataa agcaatagca tcacaaattt cacaaataaa gcatttttt    6600 cactgcattc tagttgtggt ttgtccaaac tcatcaatgt atcttatcat gtctgtatac    6660
cgtcgacctc tagctagagc ttggcgtaat catggtcata gctgtttcct gtgtgaaatt    6720
gttatccgct cacaattcca cacaacatac gagccggaag cataaagtgt aaagcctggg    6780
gtgcctaatg agtgagctaa ctcacattaa ttgcgttgcg ctcactgccc gctttccagt    6840
cgggaaacct gtcgtgccag ctgcattaat gaatcggcca acgcgcgggg agaggcggtt    6900
tgcgtattgg gcgctcttcc gcttcctcgc tcactgactc gctgcgctcg tcgttcggc    6960 tgcggcgagc ggtatcagct cactcaaagg cggtaatacg ttatccaca gaatcagggg    7020 ataacgcagg aaagaacatg tgagcaaaag gccagcaaaa ggccaggaac cgtaaaaagg    7080
ccgcgttgct ggcgtttttc cataggctcc gcccccctga cgagcatcac aaaaatcgac    7140
gctcaagtca gaggtggcga aacccgacag gactataaag ataccaggcg tttccccctg    7200
gaagctccct cgtgcgctct cctgttccga cctgccgct taccggatac ctgtccgcct    7260
ttctcccttc gggaagcgtg gcgctttctc aatgctcacg ctgtaggtat ctcagttcgg    7320
tgtaggtcgt tcgctccaag ctgggctgtg tgcacgaacc ccccgttcag cccgaccgct    7380
gcgccttatc cggtaactat cgtcttgagt ccaacccggt aagacacgac ttatcgccac    7440
tggcagcagc cactggtaac aggattagca gagcgaggta tgtaggcggt gctacagagt    7500
tcttgaagtg gtggcctaac tacggctaca ctagaaggac agtatttggt atctgcgctc    7560
tgctgaagcc agttaccttc ggaaaaagag ttggtagctc ttgatccggc aaacaaacca    7620
ccgctggtag cggtggtttt tttgtttgca agcagcagat tacgcgcaga aaaaaaggat    7680
```

-continued

```
ctcaagaaga tcctttgatc ttttctacgg ggtctgacgc tcagtggaac gaaaactcac      7740
gttaagggat tttggtcatg agattatcaa aaaggatctt cacctagatc cttttaaatt      7800
aaaaatgaag ttttaaatca atctaaagta tatatgagta aacttggtct gacagttacc      7860
aatgcttaat cagtgaggca cctatctcag cgatctgtct atttcgttca tccatagttg      7920
cctgactccc cgtcgtgtag ataactacga tacgggaggg cttaccatct ggccccagtg      7980
ctgcaatgat accgcgagac ccacgctcac cggctccaga tttatcagca ataaaccagc      8040
cagccggaag ggccgagcgc agaagtggtc ctgcaacttt atccgcctcc atccagtcta      8100
ttaattgttg ccgggaagct agagtaagta gttcgccagt taatagtttg cgcaacgttg      8160
ttgccattgc tacaggcatc gtggtgtcac gctcgtcgtt tggtatggct tcattcagct      8220
ccggttccca acgatcaagg cgagttacat gatcccccat gttgtgcaaa aaagcggtta      8280
gctccttcgg tcctccgatc gttgtcagaa gtaagttggc cgcagtgtta tcactcatgg      8340
ttatggcagc actgcataat tctcttactg tcatgccatc cgtaagatgc ttttctgtga      8400
ctggtgagta ctcaaccaag tcattctgag aatagtgtat gcggcgaccg agttgctctt      8460
gcccggcgtc aatacgggat aataccgcgc cacatagcag aactttaaaa gtgctcatca      8520
ttggaaaacg ttcttcgggg cgaaaactct caaggatctt accgctgttg agatccagtt      8580
cgatgtaacc cactcgtgca cccaactgat cttcagcatc ttttactttc accagcgttt      8640
ctgggtgagc aaaaacagga aggcaaaatg ccgcaaaaaa gggaataagg gcgacacgga      8700
aatgttgaat actcatactc ttcctttttc aatattattg aagcatttat cagggttatt      8760
gtctcatgag cggatacata tttgaatgta tttagaaaaa taaacaaata ggggttccgc      8820
gcacatttcc ccgaaaagtg ccacctgacg tc                                    8852
```

<210> SEQ ID NO 66
<211> LENGTH: 1152
<212> TYPE: PRT
<213> ORGANISM: Artificial Sequence
<220> FEATURE:
<223> OTHER INFORMATION: ENPP121-Fc

<400> SEQUENCE: 66

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160
```

```
Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
                180                 185                 190

Glu Pro Cys Glu Ser Ile Asn Glu Pro Gln Cys Pro Ala Gly Phe Glu
            195                 200                 205

Thr Pro Pro Thr Leu Leu Phe Ser Leu Asp Gly Phe Arg Ala Glu Tyr
        210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
                260                 265                 270

Gly Ile Ile Asp Asn Lys Met Tyr Asp Pro Lys Met Asn Ala Ser Phe
            275                 280                 285

Ser Leu Lys Ser Lys Glu Lys Phe Asn Pro Glu Trp Tyr Lys Gly Glu
        290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
                340                 345                 350

Val Leu Gln Trp Leu Gln Leu Pro Lys Asp Glu Arg Pro His Phe Tyr
            355                 360                 365

Thr Leu Tyr Leu Glu Glu Pro Asp Ser Ser Gly His Ser Tyr Gly Pro
        370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
                420                 425                 430

Lys Tyr Ile Tyr Leu Asn Lys Tyr Leu Gly Asp Val Lys Asn Ile Lys
            435                 440                 445

Val Ile Tyr Gly Pro Ala Ala Arg Leu Arg Pro Ser Asp Val Pro Asp
450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
                500                 505                 510

Tyr Leu Asp Pro Gln Trp Gln Leu Ala Leu Asn Pro Ser Glu Arg Lys
            515                 520                 525

Tyr Cys Gly Ser Gly Phe His Gly Ser Asp Asn Val Phe Ser Asn Met
        530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575
```

-continued

Leu Asn Leu Thr Pro Ala Pro Asn Asn Gly Thr His Gly Ser Leu Asn
              580                 585                 590

His Leu Leu Lys Asn Pro Val Tyr Thr Pro Lys His Pro Lys Glu Val
          595                 600                 605

His Pro Leu Val Gln Cys Pro Phe Thr Arg Asn Pro Arg Asp Asn Leu
      610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
              645                 650                 655

Leu Pro Tyr Gly Arg Pro Arg Val Leu Gln Lys Glu Asn Thr Ile Cys
          660                 665                 670

Leu Leu Ser Gln His Gln Phe Met Ser Gly Tyr Ser Gln Asp Ile Leu
      675                 680                 685

Met Pro Leu Trp Thr Ser Tyr Thr Val Asp Arg Asn Asp Ser Phe Ser
      690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
              725                 730                 735

Tyr Gly Phe Leu Ser Pro Gln Leu Asn Lys Asn Ser Ser Gly Ile
          740                 745                 750

Tyr Ser Glu Ala Leu Leu Thr Thr Asn Ile Val Pro Met Tyr Gln Ser
      755                 760                 765

Phe Gln Val Ile Trp Arg Tyr Phe His Asp Thr Leu Leu Arg Lys Tyr
      770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
              805                 810                 815

Arg Arg Val Ile Arg Asn Gln Glu Ile Leu Ile Pro Thr His Phe Phe
          820                 825                 830

Ile Val Leu Thr Ser Cys Lys Asp Thr Ser Gln Thr Pro Leu His Cys
      835                 840                 845

Glu Asn Leu Asp Thr Leu Ala Phe Ile Leu Pro His Arg Thr Asp Asn
850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
              885                 890                 895

Gly Leu Ser Phe Tyr Gln Gln Arg Lys Glu Pro Val Ser Asp Ile Leu
          900                 905                 910

Lys Leu Lys Thr His Leu Pro Thr Phe Ser Gln Glu Asp Asp Lys Thr
      915                 920                 925

His Thr Cys Pro Pro Cys Pro Ala Pro Glu Leu Leu Gly Gly Pro Ser
      930                 935                 940

Val Phe Leu Phe Pro Pro Lys Pro Lys Asp Thr Leu Met Ile Ser Arg
945                 950                 955                 960

Thr Pro Glu Val Thr Cys Val Val Val Asp Val Ser His Glu Asp Pro
              965                 970                 975

Glu Val Lys Phe Asn Trp Tyr Val Asp Gly Val Glu Val His Asn Ala
          980                 985                 990

Lys Thr Lys Pro Arg Glu Glu Gln  Tyr Asn Ser Thr Tyr  Arg Val Val

```
              995                 1000                1005
Ser  Val  Leu  Thr  Val  Leu  His  Gln  Asp  Trp  Leu  Asn  Gly  Lys  Glu
     1010                 1015                 1020

Tyr  Lys  Cys  Lys  Val  Ser  Asn  Lys  Ala  Leu  Pro  Ala  Pro  Ile  Glu
     1025                 1030                 1035

Lys  Thr  Ile  Ser  Lys  Ala  Lys  Gly  Gln  Pro  Arg  Glu  Pro  Gln  Val
     1040                 1045                 1050

Tyr  Thr  Leu  Pro  Pro  Ser  Arg  Glu  Glu  Met  Thr  Lys  Asn  Gln  Val
     1055                 1060                 1065

Ser  Leu  Thr  Cys  Leu  Val  Lys  Gly  Phe  Tyr  Pro  Ser  Asp  Ile  Ala
     1070                 1075                 1080

Val  Glu  Trp  Glu  Ser  Asn  Gly  Gln  Pro  Glu  Asn  Asn  Tyr  Lys  Thr
     1085                 1090                 1095

Thr  Pro  Pro  Val  Leu  Asp  Ser  Asp  Gly  Ser  Phe  Phe  Leu  Tyr  Ser
     1100                 1105                 1110

Lys  Leu  Thr  Val  Asp  Lys  Ser  Arg  Trp  Gln  Gln  Gly  Asn  Val  Phe
     1115                 1120                 1125

Ser  Cys  Ser  Val  Met  His  Glu  Ala  Leu  His  Asn  His  Tyr  Thr  Gln
     1130                 1135                 1140

Lys  Ser  Leu  Ser  Leu  Ser  Pro  Gly  Lys
     1145                 1150

<210> SEQ ID NO 67
<211> LENGTH: 1077
<212> TYPE: PRT
<213> ORGANISM: Artificial Sequence
<220> FEATURE:
<223> OTHER INFORMATION: ENPP71-Fc

<400> SEQUENCE: 67

Met  Arg  Gly  Pro  Ala  Val  Leu  Leu  Thr  Val  Ala  Leu  Ala  Thr  Leu  Leu
1                   5                    10                   15

Ala  Pro  Gly  Ala  Gly  Leu  Lys  Pro  Ser  Cys  Ala  Lys  Glu  Val  Lys  Ser
               20                    25                   30

Cys  Lys  Gly  Arg  Cys  Phe  Glu  Arg  Thr  Phe  Gly  Asn  Cys  Arg  Cys  Asp
         35                   40                    45

Ala  Ala  Cys  Val  Glu  Leu  Gly  Asn  Cys  Cys  Leu  Asp  Tyr  Gln  Glu  Thr
    50                   55                   60

Cys  Ile  Glu  Pro  Glu  His  Ile  Trp  Thr  Cys  Asn  Lys  Phe  Arg  Cys  Gly
65                   70                   75                   80

Glu  Lys  Arg  Leu  Thr  Arg  Ser  Leu  Cys  Ala  Cys  Ser  Asp  Asp  Cys  Lys
               85                    90                   95

Asp  Lys  Gly  Asp  Cys  Cys  Ile  Asn  Tyr  Ser  Ser  Val  Cys  Gln  Gly  Glu
         100                  105                  110

Lys  Ser  Trp  Val  Glu  Glu  Pro  Cys  Glu  Ser  Ile  Asn  Glu  Pro  Gln  Cys
         115                  120                  125

Pro  Ala  Gly  Phe  Glu  Thr  Pro  Pro  Thr  Leu  Leu  Phe  Ser  Leu  Asp  Gly
    130                  135                  140

Phe  Arg  Ala  Glu  Tyr  Leu  His  Thr  Trp  Gly  Gly  Leu  Leu  Pro  Val  Ile
145                  150                  155                  160

Ser  Lys  Leu  Lys  Lys  Cys  Gly  Thr  Tyr  Thr  Lys  Asn  Met  Arg  Pro  Val
               165                  170                  175

Tyr  Pro  Thr  Lys  Thr  Phe  Pro  Asn  His  Tyr  Ser  Ile  Val  Thr  Gly  Leu
         180                  185                  190

Tyr  Pro  Glu  Ser  His  Gly  Ile  Ile  Asp  Asn  Lys  Met  Tyr  Asp  Pro  Lys
```

```
              195                 200                 205
Met Asn Ala Ser Phe Ser Leu Lys Ser Lys Glu Lys Phe Asn Pro Glu
210                 215                 220

Trp Tyr Lys Gly Glu Pro Ile Trp Val Thr Ala Lys Tyr Gln Gly Leu
225                 230                 235                 240

Lys Ser Gly Thr Phe Phe Trp Pro Gly Ser Asp Val Glu Ile Asn Gly
                245                 250                 255

Ile Phe Pro Asp Ile Tyr Lys Met Tyr Asn Gly Ser Val Pro Phe Glu
                260                 265                 270

Glu Arg Ile Leu Ala Val Leu Gln Trp Leu Gln Leu Pro Lys Asp Glu
                275                 280                 285

Arg Pro His Phe Tyr Thr Leu Tyr Leu Glu Glu Pro Asp Ser Ser Gly
    290                 295                 300

His Ser Tyr Gly Pro Val Ser Ser Glu Val Ile Lys Ala Leu Gln Arg
305                 310                 315                 320

Val Asp Gly Met Val Gly Met Leu Met Asp Gly Leu Lys Glu Leu Asn
                325                 330                 335

Leu His Arg Cys Leu Asn Leu Ile Leu Ile Ser Asp His Gly Met Glu
                340                 345                 350

Gln Gly Ser Cys Lys Lys Tyr Ile Tyr Leu Asn Lys Tyr Leu Gly Asp
            355                 360                 365

Val Lys Asn Ile Lys Val Ile Tyr Gly Pro Ala Ala Arg Leu Arg Pro
370                 375                 380

Ser Asp Val Pro Asp Lys Tyr Tyr Ser Phe Asn Tyr Glu Gly Ile Ala
385                 390                 395                 400

Arg Asn Leu Ser Cys Arg Glu Pro Asn Gln His Phe Lys Pro Tyr Leu
                405                 410                 415

Lys His Phe Leu Pro Lys Arg Leu His Phe Ala Lys Ser Asp Arg Ile
                420                 425                 430

Glu Pro Leu Thr Phe Tyr Leu Asp Pro Gln Trp Gln Leu Ala Leu Asn
                435                 440                 445

Pro Ser Glu Arg Lys Tyr Cys Gly Ser Gly Phe His Gly Ser Asp Asn
450                 455                 460

Val Phe Ser Asn Met Gln Ala Leu Phe Val Gly Tyr Gly Pro Gly Phe
465                 470                 475                 480

Lys His Gly Ile Glu Ala Asp Thr Phe Glu Asn Ile Glu Val Tyr Asn
                485                 490                 495

Leu Met Cys Asp Leu Leu Asn Leu Thr Pro Ala Pro Asn Asn Gly Thr
                500                 505                 510

His Gly Ser Leu Asn His Leu Leu Lys Asn Pro Val Tyr Thr Pro Lys
            515                 520                 525

His Pro Lys Glu Val His Pro Leu Val Gln Cys Pro Phe Thr Arg Asn
530                 535                 540

Pro Arg Asp Asn Leu Gly Cys Ser Cys Asn Pro Ser Ile Leu Pro Ile
545                 550                 555                 560

Glu Asp Phe Gln Thr Gln Phe Asn Leu Thr Val Ala Glu Glu Lys Ile
                565                 570                 575

Ile Lys His Glu Thr Leu Pro Tyr Gly Arg Pro Arg Val Leu Gln Lys
                580                 585                 590

Glu Asn Thr Ile Cys Leu Leu Ser Gln His Gln Phe Met Ser Gly Tyr
                595                 600                 605

Ser Gln Asp Ile Leu Met Pro Leu Trp Thr Ser Tyr Thr Val Asp Arg
610                 615                 620
```

```
Asn Asp Ser Phe Ser Thr Glu Asp Phe Ser Asn Cys Leu Tyr Gln Asp
625                 630                 635                 640

Phe Arg Ile Pro Leu Ser Pro Val His Lys Cys Ser Phe Tyr Lys Asn
            645                 650                 655

Asn Thr Lys Val Ser Tyr Gly Phe Leu Ser Pro Gln Leu Asn Lys
        660                 665                 670

Asn Ser Ser Gly Ile Tyr Ser Glu Ala Leu Leu Thr Thr Asn Ile Val
675                 680                 685

Pro Met Tyr Gln Ser Phe Gln Val Ile Trp Arg Tyr Phe His Asp Thr
690                 695                 700

Leu Leu Arg Lys Tyr Ala Glu Glu Arg Asn Gly Val Asn Val Val Ser
705                 710                 715                 720

Gly Pro Val Phe Asp Phe Asp Tyr Asp Gly Arg Cys Asp Ser Leu Glu
            725                 730                 735

Asn Leu Arg Gln Lys Arg Arg Val Ile Arg Asn Gln Glu Ile Leu Ile
        740                 745                 750

Pro Thr His Phe Phe Ile Val Leu Thr Ser Cys Lys Asp Thr Ser Gln
        755                 760                 765

Thr Pro Leu His Cys Glu Asn Leu Asp Thr Leu Ala Phe Ile Leu Pro
770                 775                 780

His Arg Thr Asp Asn Ser Glu Ser Cys Val His Gly Lys His Asp Ser
785                 790                 795                 800

Ser Trp Val Glu Glu Leu Leu Met Leu His Arg Ala Arg Ile Thr Asp
            805                 810                 815

Val Glu His Ile Thr Gly Leu Ser Phe Tyr Gln Arg Lys Glu Pro
        820                 825                 830

Val Ser Asp Ile Leu Lys Leu Lys Thr His Leu Pro Thr Phe Ser Gln
        835                 840                 845

Glu Asp Asp Lys Thr His Thr Cys Pro Pro Cys Pro Ala Pro Glu Leu
850                 855                 860

Leu Gly Gly Pro Ser Val Phe Leu Phe Pro Pro Lys Pro Lys Asp Thr
865                 870                 875                 880

Leu Met Ile Ser Arg Thr Pro Glu Val Thr Cys Val Val Val Asp Val
            885                 890                 895

Ser His Glu Asp Pro Glu Val Lys Phe Asn Trp Tyr Val Asp Gly Val
        900                 905                 910

Glu Val His Asn Ala Lys Thr Lys Pro Arg Glu Glu Gln Tyr Asn Ser
        915                 920                 925

Thr Tyr Arg Val Val Ser Val Leu Thr Val Leu His Gln Asp Trp Leu
930                 935                 940

Asn Gly Lys Glu Tyr Lys Cys Lys Val Ser Asn Lys Ala Leu Pro Ala
945                 950                 955                 960

Pro Ile Glu Lys Thr Ile Ser Lys Ala Lys Gly Gln Pro Arg Glu Pro
            965                 970                 975

Gln Val Tyr Thr Leu Pro Pro Ser Arg Glu Glu Met Thr Lys Asn Gln
        980                 985                 990

Val Ser Leu Thr Cys Leu Val Lys Gly Phe Tyr Pro Ser Asp Ile Ala
        995                 1000                1005

Val Glu Trp Glu Ser Asn Gly Gln Pro Glu Asn Asn Tyr Lys Thr
        1010                1015                1020

Thr Pro Pro Val Leu Asp Ser Asp Gly Ser Phe Phe Leu Tyr Ser
        1025                1030                1035
```

<210> SEQ ID NO 68
<211> LENGTH: 1079
<212> TYPE: PRT
<213> ORGANISM: Artificial Sequence
<220> FEATURE:
<223> OTHER INFORMATION: ENPP51-Fc

<400> SEQUENCE: 68

```
Met Thr Ser Lys Phe Leu Leu Val Ser Phe Ile Leu Ala Ala Leu Ser
1               5                   10                  15
Leu Ser Thr Thr Phe Ser Gly Leu Lys Pro Ser Cys Ala Lys Glu Val
                20                  25                  30
Lys Ser Cys Lys Gly Arg Cys Phe Glu Arg Thr Phe Gly Asn Cys Arg
            35                  40                  45
Cys Asp Ala Ala Cys Val Glu Leu Gly Asn Cys Cys Leu Asp Tyr Gln
        50                  55                  60
Glu Thr Cys Ile Glu Pro Glu His Ile Trp Thr Cys Asn Lys Phe Arg
65                  70                  75                  80
Cys Gly Glu Lys Arg Leu Thr Arg Ser Leu Cys Ala Cys Ser Asp Asp
                85                  90                  95
Cys Lys Asp Lys Gly Asp Cys Cys Ile Asn Tyr Ser Ser Val Cys Gln
            100                 105                 110
Gly Glu Lys Ser Trp Val Glu Glu Pro Cys Glu Ser Ile Asn Glu Pro
        115                 120                 125
Gln Cys Pro Ala Gly Phe Glu Thr Pro Pro Thr Leu Leu Phe Ser Leu
    130                 135                 140
Asp Gly Phe Arg Ala Glu Tyr Leu His Thr Trp Gly Gly Leu Leu Pro
145                 150                 155                 160
Val Ile Ser Lys Leu Lys Lys Cys Gly Thr Tyr Thr Lys Asn Met Arg
                165                 170                 175
Pro Val Tyr Pro Thr Lys Thr Phe Pro Asn His Tyr Ser Ile Val Thr
            180                 185                 190
Gly Leu Tyr Pro Glu Ser His Gly Ile Ile Asp Asn Lys Met Tyr Asp
        195                 200                 205
Pro Lys Met Asn Ala Ser Phe Ser Leu Lys Ser Lys Glu Lys Phe Asn
    210                 215                 220
Pro Glu Trp Tyr Lys Gly Glu Pro Ile Trp Val Thr Ala Lys Tyr Gln
225                 230                 235                 240
Gly Leu Lys Ser Gly Thr Phe Phe Trp Pro Gly Ser Asp Val Glu Ile
                245                 250                 255
Asn Gly Ile Phe Pro Asp Ile Tyr Lys Met Tyr Asn Gly Ser Val Pro
            260                 265                 270
Phe Glu Glu Arg Ile Leu Ala Val Leu Gln Trp Leu Gln Leu Pro Lys
        275                 280                 285
Asp Glu Arg Pro His Phe Tyr Thr Leu Tyr Leu Glu Glu Pro Asp Ser
    290                 295                 300
Ser Gly His Ser Tyr Gly Pro Val Ser Ser Glu Val Ile Lys Ala Leu
305                 310                 315                 320
```

```
Gln Arg Val Asp Gly Met Val Gly Met Leu Met Asp Gly Leu Lys Glu
                325                 330                 335
Leu Asn Leu His Arg Cys Leu Asn Leu Ile Leu Ile Ser Asp His Gly
            340                 345                 350
Met Glu Gln Gly Ser Cys Lys Lys Tyr Ile Tyr Leu Asn Lys Tyr Leu
        355                 360                 365
Gly Asp Val Lys Asn Ile Lys Val Ile Tyr Gly Pro Ala Ala Arg Leu
    370                 375                 380
Arg Pro Ser Asp Val Pro Asp Lys Tyr Tyr Ser Phe Asn Tyr Glu Gly
385                 390                 395                 400
Ile Ala Arg Asn Leu Ser Cys Arg Glu Pro Asn Gln His Phe Lys Pro
                405                 410                 415
Tyr Leu Lys His Phe Leu Pro Lys Arg Leu His Phe Ala Lys Ser Asp
            420                 425                 430
Arg Ile Glu Pro Leu Thr Phe Tyr Leu Asp Pro Gln Trp Gln Leu Ala
        435                 440                 445
Leu Asn Pro Ser Glu Arg Lys Tyr Cys Gly Ser Gly Phe His Gly Ser
    450                 455                 460
Asp Asn Val Phe Ser Asn Met Gln Ala Leu Phe Val Gly Tyr Gly Pro
465                 470                 475                 480
Gly Phe Lys His Gly Ile Glu Ala Asp Thr Phe Glu Asn Ile Glu Val
                485                 490                 495
Tyr Asn Leu Met Cys Asp Leu Leu Asn Leu Thr Pro Ala Pro Asn Asn
            500                 505                 510
Gly Thr His Gly Ser Leu Asn His Leu Leu Lys Asn Pro Val Tyr Thr
        515                 520                 525
Pro Lys His Pro Lys Glu Val His Pro Leu Val Gln Cys Pro Phe Thr
    530                 535                 540
Arg Asn Pro Arg Asp Asn Leu Gly Cys Ser Cys Asn Pro Ser Ile Leu
545                 550                 555                 560
Pro Ile Glu Asp Phe Gln Thr Gln Phe Asn Leu Thr Val Ala Glu Glu
                565                 570                 575
Lys Ile Ile Lys His Glu Thr Leu Pro Tyr Gly Arg Pro Arg Val Leu
            580                 585                 590
Gln Lys Glu Asn Thr Ile Cys Leu Leu Ser Gln His Gln Phe Met Ser
        595                 600                 605
Gly Tyr Ser Gln Asp Ile Leu Met Pro Leu Trp Thr Ser Tyr Thr Val
    610                 615                 620
Asp Arg Asn Asp Ser Phe Ser Thr Glu Asp Phe Ser Asn Cys Leu Tyr
625                 630                 635                 640
Gln Asp Phe Arg Ile Pro Leu Ser Pro Val His Lys Cys Ser Phe Tyr
                645                 650                 655
Lys Asn Asn Thr Lys Val Ser Tyr Gly Phe Leu Ser Pro Pro Gln Leu
            660                 665                 670
Asn Lys Asn Ser Ser Gly Ile Tyr Ser Glu Ala Leu Leu Thr Thr Asn
        675                 680                 685
Ile Val Pro Met Tyr Gln Ser Phe Gln Val Ile Trp Arg Tyr Phe His
    690                 695                 700
Asp Thr Leu Leu Arg Lys Tyr Ala Glu Glu Arg Asn Gly Val Asn Val
705                 710                 715                 720
Val Ser Gly Pro Val Phe Asp Phe Asp Tyr Asp Gly Arg Cys Asp Ser
                725                 730                 735
Leu Glu Asn Leu Arg Gln Lys Arg Arg Val Ile Arg Asn Gln Glu Ile
```

```
                    740                 745                 750
Leu Ile Pro Thr His Phe Phe Ile Val Leu Thr Ser Cys Lys Asp Thr
            755                 760                 765

Ser Gln Thr Pro Leu His Cys Glu Asn Leu Asp Thr Leu Ala Phe Ile
        770                 775                 780

Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
                805                 810                 815

Thr Asp Val Glu His Ile Thr Gly Leu Ser Phe Tyr Gln Gln Arg Lys
            820                 825                 830

Glu Pro Val Ser Asp Ile Leu Lys Leu Lys Thr His Leu Pro Thr Phe
        835                 840                 845

Ser Gln Glu Asp Asp Lys Thr His Thr Cys Pro Cys Pro Ala Pro
    850                 855                 860

Glu Leu Leu Gly Gly Pro Ser Val Phe Leu Phe Pro Pro Lys Pro Lys
865                 870                 875                 880

Asp Thr Leu Met Ile Ser Arg Thr Pro Glu Val Thr Cys Val Val Val
                885                 890                 895

Asp Val Ser His Glu Asp Pro Glu Val Lys Phe Asn Trp Tyr Val Asp
            900                 905                 910

Gly Val Glu Val His Asn Ala Lys Thr Lys Pro Arg Glu Glu Gln Tyr
        915                 920                 925

Asn Ser Thr Tyr Arg Val Val Ser Val Leu Thr Val Leu His Gln Asp
    930                 935                 940

Trp Leu Asn Gly Lys Glu Tyr Lys Cys Lys Val Ser Asn Lys Ala Leu
945                 950                 955                 960

Pro Ala Pro Ile Glu Lys Thr Ile Ser Lys Ala Lys Gly Gln Pro Arg
                965                 970                 975

Glu Pro Gln Val Tyr Thr Leu Pro Pro Ser Arg Glu Glu Met Thr Lys
            980                 985                 990

Asn Gln Val Ser Leu Thr Cys Leu Val Lys Gly Phe Tyr Pro Ser Asp
        995                1000                1005

Ile Ala Val Glu Trp Glu Ser Asn Gly Gln Pro Glu Asn Asn Tyr
    1010                1015                1020

Lys Thr Thr Pro Pro Val Leu Asp Ser Asp Gly Ser Phe Phe Leu
    1025                1030                1035

Tyr Ser Lys Leu Thr Val Asp Lys Ser Arg Trp Gln Gln Gly Asn
    1040                1045                1050

Val Phe Ser Cys Ser Val Met His Glu Ala Leu His Asn His Tyr
    1055                1060                1065

Thr Gln Lys Ser Leu Ser Leu Ser Pro Gly Lys
    1070                1075

<210> SEQ ID NO 69
<211> LENGTH: 1472
<212> TYPE: PRT
<213> ORGANISM: Artificial Sequence
<220> FEATURE:
<223> OTHER INFORMATION: ENPP121-ALB

<400> SEQUENCE: 69

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
```

-continued

```
                20                  25                  30
Arg Ser His Ala Ala Glu Ala Pro Gly Asp Pro Gln Ala Ala Ser
            35                  40                  45
Leu Leu Ala Pro Met Asp Val Gly Glu Pro Leu Glu Lys Ala Ala
        50                  55                  60
Arg Ala Arg Thr Ala Lys Asp Pro Asn Thr Tyr Lys Ile Ile Ser Leu
65                  70                  75                  80
Phe Thr Phe Ala Val Gly Val Asn Ile Cys Leu Gly Phe Thr Ala Gly
                85                  90                  95
Leu Lys Pro Ser Cys Ala Lys Glu Val Lys Ser Cys Lys Gly Arg Cys
            100                 105                 110
Phe Glu Arg Thr Phe Gly Asn Cys Arg Cys Asp Ala Ala Cys Val Glu
            115                 120                 125
Leu Gly Asn Cys Cys Leu Asp Tyr Gln Glu Thr Cys Ile Glu Pro Glu
        130                 135                 140
His Ile Trp Thr Cys Asn Lys Phe Arg Cys Gly Glu Lys Arg Leu Thr
145                 150                 155                 160
Arg Ser Leu Cys Ala Cys Ser Asp Asp Cys Lys Asp Lys Gly Asp Cys
                165                 170                 175
Cys Ile Asn Tyr Ser Ser Val Cys Gln Gly Glu Lys Ser Trp Val Glu
            180                 185                 190
Glu Pro Cys Glu Ser Ile Asn Glu Pro Gln Cys Pro Ala Gly Phe Glu
            195                 200                 205
Thr Pro Pro Thr Leu Leu Phe Ser Leu Asp Gly Phe Arg Ala Glu Tyr
        210                 215                 220
Leu His Thr Trp Gly Gly Leu Leu Pro Val Ile Ser Lys Leu Lys Lys
225                 230                 235                 240
Cys Gly Thr Tyr Thr Lys Asn Met Arg Pro Val Tyr Pro Thr Lys Thr
                245                 250                 255
Phe Pro Asn His Tyr Ser Ile Val Thr Gly Leu Tyr Pro Glu Ser His
            260                 265                 270
Gly Ile Ile Asp Asn Lys Met Tyr Asp Pro Lys Met Asn Ala Ser Phe
            275                 280                 285
Ser Leu Lys Ser Lys Glu Lys Phe Asn Pro Glu Trp Tyr Lys Gly Glu
        290                 295                 300
Pro Ile Trp Val Thr Ala Lys Tyr Gln Gly Leu Lys Ser Gly Thr Phe
305                 310                 315                 320
Phe Trp Pro Gly Ser Asp Val Glu Ile Asn Gly Ile Phe Pro Asp Ile
                325                 330                 335
Tyr Lys Met Tyr Asn Gly Ser Val Pro Phe Glu Glu Arg Ile Leu Ala
            340                 345                 350
Val Leu Gln Trp Leu Gln Leu Pro Lys Asp Glu Arg Pro His Phe Tyr
            355                 360                 365
Thr Leu Tyr Leu Glu Glu Pro Asp Ser Ser Gly His Ser Tyr Gly Pro
        370                 375                 380
Val Ser Ser Glu Val Ile Lys Ala Leu Gln Arg Val Asp Gly Met Val
385                 390                 395                 400
Gly Met Leu Met Asp Gly Leu Lys Glu Leu Asn Leu His Arg Cys Leu
                405                 410                 415
Asn Leu Ile Leu Ile Ser Asp His Gly Met Glu Gln Gly Ser Cys Lys
            420                 425                 430
Lys Tyr Ile Tyr Leu Asn Lys Tyr Leu Gly Asp Val Lys Asn Ile Lys
            435                 440                 445
```

```
Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
                500                 505                 510

Tyr Leu Asp Pro Gln Trp Gln Leu Ala Leu Asn Pro Ser Glu Arg Lys
            515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
                580                 585                 590

His Leu Leu Lys Asn Pro Val Tyr Thr Pro Lys His Pro Lys Glu Val
            595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
    675                 680                 685

Met Pro Leu Trp Thr Ser Tyr Thr Val Asp Arg Asn Asp Ser Phe Ser
690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
    755                 760                 765

Phe Gln Val Ile Trp Arg Tyr Phe His Asp Thr Leu Leu Arg Lys Tyr
770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
    835                 840                 845

Glu Asn Leu Asp Thr Leu Ala Phe Ile Leu Pro His Arg Thr Asp Asn
850                 855                 860
```

```
Ser Glu Ser Cys Val His Gly Lys His Asp Ser Ser Trp Val Glu
865                 870                 875                 880

Leu Leu Met Leu His Arg Ala Arg Ile Thr Asp Val Glu His Ile Thr
            885                 890                 895

Gly Leu Ser Phe Tyr Gln Gln Arg Lys Glu Pro Val Ser Asp Ile Leu
                900                 905                 910

Lys Leu Lys Thr His Leu Pro Thr Phe Ser Gln Glu Asp Arg Ser Gly
        915                 920                 925

Ser Gly Gly Ser Met Lys Trp Val Thr Phe Leu Leu Leu Leu Phe Val
    930                 935                 940

Ser Gly Ser Ala Phe Ser Arg Gly Val Phe Arg Arg Glu Ala His Lys
945                 950                 955                 960

Ser Glu Ile Ala His Arg Tyr Asn Asp Leu Gly Glu Gln His Phe Lys
                965                 970                 975

Gly Leu Val Leu Ile Ala Phe Ser Gln Tyr Leu Gln Lys Cys Ser Tyr
            980                 985                 990

Asp Glu His Ala Lys Leu Val Gln Glu Val Thr Asp Phe Ala Lys Thr
        995                 1000                1005

Cys Val Ala Asp Glu Ser Ala Ala Asn Cys Asp Lys Ser Leu His
    1010                1015                1020

Thr Leu Phe Gly Asp Lys Leu Cys Ala Ile Pro Asn Leu Arg Glu
    1025                1030                1035

Asn Tyr Gly Glu Leu Ala Asp Cys Cys Thr Lys Gln Glu Pro Glu
    1040                1045                1050

Arg Asn Glu Cys Phe Leu Gln His Lys Asp Asn Pro Ser Leu
    1055                1060                1065

Pro Pro Phe Glu Arg Pro Glu Ala Glu Ala Met Cys Thr Ser Phe
    1070                1075                1080

Lys Glu Asn Pro Thr Thr Phe Met Gly His Tyr Leu His Glu Val
    1085                1090                1095

Ala Arg Arg His Pro Tyr Phe Tyr Ala Pro Glu Leu Leu Tyr Tyr
    1100                1105                1110

Ala Glu Gln Tyr Asn Glu Ile Leu Thr Gln Cys Cys Ala Glu Ala
    1115                1120                1125

Asp Lys Glu Ser Cys Leu Thr Pro Lys Leu Asp Gly Val Lys Glu
    1130                1135                1140

Lys Ala Leu Val Ser Ser Val Arg Gln Arg Met Lys Cys Ser Ser
    1145                1150                1155

Met Gln Lys Phe Gly Glu Arg Ala Phe Lys Ala Trp Ala Val Ala
    1160                1165                1170

Arg Leu Ser Gln Thr Phe Pro Asn Ala Asp Phe Ala Glu Ile Thr
    1175                1180                1185

Lys Leu Ala Thr Asp Leu Thr Lys Val Asn Lys Glu Cys Cys His
    1190                1195                1200

Gly Asp Leu Leu Glu Cys Ala Asp Asp Arg Ala Glu Leu Ala Lys
    1205                1210                1215

Tyr Met Cys Glu Asn Gln Ala Thr Ile Ser Ser Lys Leu Gln Thr
    1220                1225                1230

Cys Cys Asp Lys Pro Leu Leu Lys Lys Ala His Cys Leu Ser Glu
    1235                1240                1245

Val Glu His Asp Thr Met Pro Ala Asp Leu Pro Ala Ile Ala Ala
    1250                1255                1260

Asp Phe Val Glu Asp Gln Glu Val Cys Lys Asn Tyr Ala Glu Ala
```

```
                     1265                1270                1275

Lys Asp Val Phe Leu Gly Thr Phe Leu Tyr Glu Tyr Ser Arg Arg
            1280                1285                1290

His Pro Asp Tyr Ser Val Ser Leu Leu Leu Arg Leu Ala Lys Lys
    1295                1300                1305

Tyr Glu Ala Thr Leu Glu Lys Cys Cys Ala Glu Ala Asn Pro Pro
1310                1315                1320

Ala Cys Tyr Gly Thr Val Leu Ala Glu Phe Gln Pro Leu Val Glu
    1325                1330                1335

Glu Pro Lys Asn Leu Val Lys Thr Asn Cys Asp Leu Tyr Glu Lys
        1340                1345                1350

Leu Gly Glu Tyr Gly Phe Gln Asn Ala Ile Leu Val Arg Tyr Thr
            1355                1360                1365

Gln Lys Ala Pro Gln Val Ser Thr Pro Thr Leu Val Glu Ala Ala
                1370                1375                1380

Arg Asn Leu Gly Arg Val Gly Thr Lys Cys Cys Thr Leu Pro Glu
    1385                1390                1395

Asp Gln Arg Leu Pro Cys Val Glu Asp Tyr Leu Ser Ala Ile Leu
1400                1405                1410

Asn Arg Val Cys Leu Leu His Glu Lys Thr Pro Val Ser Glu His
    1415                1420                1425

Val Thr Lys Cys Cys Ser Gly Ser Leu Val Glu Arg Arg Pro Cys
        1430                1435                1440

Phe Ser Ala Leu Thr Val Asp Glu Thr Tyr Val Pro Lys Glu Phe
            1445                1450                1455

Lys Ala Glu Thr Phe Thr Phe His Ser Asp Ile Cys Thr Leu
                1460                1465                1470

<210> SEQ ID NO 70
<211> LENGTH: 1396
<212> TYPE: PRT
<213> ORGANISM: Artificial Sequence
<220> FEATURE:
<223> OTHER INFORMATION: NPP71-ALB

<400> SEQUENCE: 70

Met Arg Gly Pro Ala Val Leu Leu Thr Val Ala Leu Ala Thr Leu Leu
1               5                   10                  15

Ala Pro Gly Ala Gly Leu Lys Pro Ser Cys Ala Lys Glu Val Lys Ser
                20                  25                  30

Cys Lys Gly Arg Cys Phe Glu Arg Thr Phe Gly Asn Cys Arg Cys Asp
            35                  40                  45

Ala Ala Cys Val Glu Leu Gly Asn Cys Cys Leu Asp Tyr Gln Glu Thr
        50                  55                  60

Cys Ile Glu Pro Glu His Ile Trp Thr Cys Asn Lys Phe Arg Cys Gly
65                  70                  75                  80

Glu Lys Arg Leu Thr Arg Ser Leu Cys Ala Cys Ser Asp Asp Cys Lys
                85                  90                  95

Asp Lys Gly Asp Cys Cys Ile Asn Tyr Ser Ser Val Cys Gln Gly Glu
            100                 105                 110

Lys Ser Trp Val Glu Glu Pro Cys Glu Ser Ile Asn Glu Pro Gln Cys
        115                 120                 125

Pro Ala Gly Phe Glu Thr Pro Pro Thr Leu Leu Phe Ser Leu Asp Gly
    130                 135                 140

Phe Arg Ala Glu Tyr Leu His Thr Trp Gly Gly Leu Leu Pro Val Ile
```

```
                145                 150                 155                 160
        Ser Lys Leu Lys Lys Cys Gly Thr Tyr Thr Lys Asn Met Arg Pro Val
                        165                 170                 175

Tyr Pro Thr Lys Thr Phe Pro Asn His Tyr Ser Ile Val Thr Gly Leu
                        180                 185                 190

Tyr Pro Glu Ser His Gly Ile Ile Asp Asn Lys Met Tyr Asp Pro Lys
                        195                 200                 205

Met Asn Ala Ser Phe Ser Leu Lys Ser Lys Glu Lys Phe Asn Pro Glu
        210                 215                 220

Trp Tyr Lys Gly Glu Pro Ile Trp Val Thr Ala Lys Tyr Gln Gly Leu
        225                 230                 235                 240

Lys Ser Gly Thr Phe Phe Trp Pro Gly Ser Asp Val Glu Ile Asn Gly
                        245                 250                 255

Ile Phe Pro Asp Ile Tyr Lys Met Tyr Asn Gly Ser Val Pro Phe Glu
                        260                 265                 270

Glu Arg Ile Leu Ala Val Leu Gln Trp Leu Gln Leu Pro Lys Asp Glu
                        275                 280                 285

Arg Pro His Phe Tyr Thr Leu Tyr Leu Glu Glu Pro Asp Ser Ser Gly
                        290                 295                 300

His Ser Tyr Gly Pro Val Ser Ser Glu Val Ile Lys Ala Leu Gln Arg
        305                 310                 315                 320

Val Asp Gly Met Val Gly Met Leu Met Asp Gly Leu Lys Glu Leu Asn
                        325                 330                 335

Leu His Arg Cys Leu Asn Leu Ile Leu Ile Ser Asp His Gly Met Glu
                        340                 345                 350

Gln Gly Ser Cys Lys Lys Tyr Ile Tyr Leu Asn Lys Tyr Leu Gly Asp
                        355                 360                 365

Val Lys Asn Ile Lys Val Ile Tyr Gly Pro Ala Ala Arg Leu Arg Pro
                        370                 375                 380

Ser Asp Val Pro Asp Lys Tyr Tyr Ser Phe Asn Tyr Glu Gly Ile Ala
        385                 390                 395                 400

Arg Asn Leu Ser Cys Arg Glu Pro Asn Gln His Phe Lys Pro Tyr Leu
                        405                 410                 415

Lys His Phe Leu Pro Lys Arg Leu His Phe Ala Lys Ser Asp Arg Ile
                        420                 425                 430

Glu Pro Leu Thr Phe Tyr Leu Asp Pro Gln Trp Gln Leu Ala Leu Asn
                        435                 440                 445

Pro Ser Glu Arg Lys Tyr Cys Gly Ser Gly Phe His Gly Ser Asp Asn
        450                 455                 460

Val Phe Ser Asn Met Gln Ala Leu Phe Val Gly Tyr Gly Pro Gly Phe
        465                 470                 475                 480

Lys His Gly Ile Glu Ala Asp Thr Phe Glu Asn Ile Glu Val Tyr Asn
                        485                 490                 495

Leu Met Cys Asp Leu Leu Asn Leu Thr Pro Ala Pro Asn Asn Gly Thr
                        500                 505                 510

His Gly Ser Leu Asn His Leu Leu Lys Asn Pro Val Tyr Thr Pro Lys
                        515                 520                 525

His Pro Lys Glu Val His Pro Leu Val Gln Cys Pro Phe Thr Arg Asn
        530                 535                 540

Pro Arg Asp Asn Leu Gly Cys Ser Cys Asn Pro Ser Ile Leu Pro Ile
        545                 550                 555                 560

Glu Asp Phe Gln Thr Gln Phe Asn Leu Thr Val Ala Glu Glu Lys Ile
                        565                 570                 575
```

```
Ile Lys His Glu Thr Leu Pro Tyr Gly Arg Pro Arg Val Leu Gln Lys
            580                 585                 590

Glu Asn Thr Ile Cys Leu Leu Ser Gln His Gln Phe Met Ser Gly Tyr
            595                 600                 605

Ser Gln Asp Ile Leu Met Pro Leu Trp Thr Ser Tyr Thr Val Asp Arg
    610                 615                 620

Asn Asp Ser Phe Ser Thr Glu Asp Phe Ser Asn Cys Leu Tyr Gln Asp
625                 630                 635                 640

Phe Arg Ile Pro Leu Ser Pro Val His Lys Cys Ser Phe Tyr Lys Asn
                645                 650                 655

Asn Thr Lys Val Ser Tyr Gly Phe Leu Ser Pro Gln Leu Asn Lys
            660                 665                 670

Asn Ser Ser Gly Ile Tyr Ser Glu Ala Leu Leu Thr Thr Asn Ile Val
            675                 680                 685

Pro Met Tyr Gln Ser Phe Gln Val Ile Trp Arg Tyr Phe His Asp Thr
    690                 695                 700

Leu Leu Arg Lys Tyr Ala Glu Glu Arg Asn Gly Val Asn Val Val Ser
705                 710                 715                 720

Gly Pro Val Phe Asp Phe Asp Tyr Asp Gly Arg Cys Asp Ser Leu Glu
                725                 730                 735

Asn Leu Arg Gln Lys Arg Arg Val Ile Arg Asn Gln Glu Ile Leu Ile
            740                 745                 750

Pro Thr His Phe Phe Ile Val Leu Thr Ser Cys Lys Asp Thr Ser Gln
            755                 760                 765

Thr Pro Leu His Cys Glu Asn Leu Asp Thr Leu Ala Phe Ile Leu Pro
    770                 775                 780

His Arg Thr Asp Asn Ser Glu Ser Cys Val His Gly Lys His Asp Ser
785                 790                 795                 800

Ser Trp Val Glu Glu Leu Leu Met Leu His Arg Ala Arg Ile Thr Asp
                805                 810                 815

Val Glu His Ile Thr Gly Leu Ser Phe Tyr Gln Gln Arg Lys Glu Pro
            820                 825                 830

Val Ser Asp Ile Leu Lys Leu Lys Thr His Leu Pro Thr Phe Ser Gln
    835                 840                 845

Glu Asp Gly Gly Ser Gly Gly Ser Met Lys Trp Val Thr Phe Leu Leu
850                 855                 860

Leu Leu Phe Val Ser Gly Ser Ala Phe Ser Arg Gly Val Phe Arg Arg
865                 870                 875                 880

Glu Ala His Lys Ser Glu Ile Ala His Arg Tyr Asn Asp Leu Gly Glu
                885                 890                 895

Gln His Phe Lys Gly Leu Val Leu Ile Ala Phe Ser Gln Tyr Leu Gln
            900                 905                 910

Lys Cys Ser Tyr Asp Glu His Ala Lys Leu Val Gln Glu Val Thr Asp
    915                 920                 925

Phe Ala Lys Thr Cys Val Ala Asp Glu Ser Ala Ala Asn Cys Asp Lys
    930                 935                 940

Ser Leu His Thr Leu Phe Gly Asp Lys Leu Cys Ala Ile Pro Asn Leu
945                 950                 955                 960

Arg Glu Asn Tyr Gly Glu Leu Ala Asp Cys Cys Thr Lys Gln Glu Pro
                965                 970                 975

Glu Arg Asn Glu Cys Phe Leu Gln His Lys Asp Asp Asn Pro Ser Leu
            980                 985                 990
```

```
Pro Pro Phe Glu Arg Pro Glu Ala  Glu Ala Met Cys Thr  Ser Phe Lys
            995              1000                1005

Glu Asn Pro Thr Thr Phe Met  Gly His Tyr Leu  His Glu Val Ala
1010                1015               1020

Arg Arg His Pro Tyr Phe Tyr  Ala Pro Glu Leu  Leu Tyr Tyr Ala
1025                1030               1035

Glu Gln Tyr Asn Glu Ile Leu  Thr Gln Cys Cys  Ala Glu Ala Asp
1040                1045               1050

Lys Glu Ser Cys Leu Thr Pro  Lys Leu Asp Gly  Val Lys Glu Lys
1055                1060               1065

Ala Leu Val Ser Ser Val Arg  Gln Arg Met Lys  Cys Ser Ser Met
1070                1075               1080

Gln Lys Phe Gly Glu Arg Ala  Phe Lys Ala Trp  Ala Val Ala Arg
1085                1090               1095

Leu Ser Gln Thr Phe Pro Asn  Ala Asp Phe Ala  Glu Ile Thr Lys
1100                1105               1110

Leu Ala Thr Asp Leu Thr Lys  Val Asn Lys Glu  Cys Cys His Gly
1115                1120               1125

Asp Leu Leu Glu Cys Ala Asp  Asp Arg Ala Glu  Leu Ala Lys Tyr
1130                1135               1140

Met Cys Glu Asn Gln Ala Thr  Ile Ser Ser Lys  Leu Gln Thr Cys
1145                1150               1155

Cys Asp Lys Pro Leu Leu Lys  Lys Ala His Cys  Leu Ser Glu Val
1160                1165               1170

Glu His Asp Thr Met Pro Ala  Asp Leu Pro Ala  Ile Ala Ala Asp
1175                1180               1185

Phe Val Glu Asp Gln Glu Val  Cys Lys Asn Tyr  Ala Glu Ala Lys
1190                1195               1200

Asp Val Phe Leu Gly Thr Phe  Leu Tyr Glu Tyr  Ser Arg Arg His
1205                1210               1215

Pro Asp Tyr Ser Val Ser Leu  Leu Leu Arg Leu  Ala Lys Lys Tyr
1220                1225               1230

Glu Ala Thr Leu Glu Lys Cys  Cys Ala Glu Ala  Asn Pro Pro Ala
1235                1240               1245

Cys Tyr Gly Thr Val Leu Ala  Glu Phe Gln Pro  Leu Val Glu Glu
1250                1255               1260

Pro Lys Asn Leu Val Lys Thr  Asn Cys Asp Leu  Tyr Glu Lys Leu
1265                1270               1275

Gly Glu Tyr Gly Phe Gln Asn  Ala Ile Leu Val  Arg Tyr Thr Gln
1280                1285               1290

Lys Ala Pro Gln Val Ser Thr  Pro Thr Leu Val  Glu Ala Ala Arg
1295                1300               1305

Asn Leu Gly Arg Val Gly Thr  Lys Cys Cys Thr  Leu Pro Glu Asp
1310                1315               1320

Gln Arg Leu Pro Cys Val Glu  Asp Tyr Leu Ser  Ala Ile Leu Asn
1325                1330               1335

Arg Val Cys Leu Leu His Glu  Lys Thr Pro Val  Ser Glu His Val
1340                1345               1350

Thr Lys Cys Cys Ser Gly Ser  Leu Val Glu Arg  Arg Pro Cys Phe
1355                1360               1365

Ser Ala Leu Thr Val Asp Glu  Thr Tyr Val Pro  Lys Glu Phe Lys
1370                1375               1380

Ala Glu Thr Phe Thr Phe His  Ser Asp Ile Cys  Thr Leu
```

<210> SEQ ID NO 71
<211> LENGTH: 3456
<212> TYPE: DNA
<213> ORGANISM: Artificial Sequence
<220> FEATURE:
<223> OTHER INFORMATION: ENPP121-Fc nucleotide sequence

<400> SEQUENCE: 71

```
atggaaaggg acggatgcgc cggtggtgga tctcgcggag gcgaaggtgg aagggcccct      60
agggaaggac ctgccggaaa cggaagggac aggggacgct ctcacgccgc tgaagctcca     120
ggcgaccctc aggccgctgc ctctctgctg gctcctatgg acgtcggaga agaaccctg      180
gaaaaggccg ccagggccag gactgccaag gaccccaaca cctacaagat catctccctc     240
ttcactttcg ccgtcggagt caacatctgc ctgggattca ccgccggact gaagcccagc     300
tgcgccaaag aagtgaagtc ctgcaagggc cggtgcttcg agcggacctt cggcaactgc     360
agatgcgacg ccgcctgtgt ggaactgggc aactgctgcc tggactacca ggaaacctgc     420
atcgagcccg agcacatctg gacctgcaac aagttcagat gcggcgagaa gcggctgacc     480
agatccctgt gtgcctgcag cgacgactgc aaggacaagg gcgactgctg catcaactac     540
agcagcgtgt gccagggcga agtcctggtg gtggaagaac cctgcgagag catcaacgag     600
ccccagtgcc ctgccggctt cgagacacct cctaccctgc tgttcagcct ggacggcttt     660
cgggccgagt acctgcacac atggggaggc ctgctgcccg tgatcagcaa gctgaagaag     720
tgcggcacct acaccaagaa catgcggccc gtgtacccca ccaagacctt ccccaaccac     780
tactccatcg tgaccggcct gtaccccgag agccacggca tcatcgacaa caagatgtac     840
gaccccaaga tgaacgccag cttcagcctg aagtccaaag agaagttcaa ccccgagtgg     900
tataagggcg agcccatctg ggtcaccgcc aagtaccagg gcctgaaaag cggcacattc     960
ttttggcccg cagcgacgt ggaaatcaac ggcatcttcc ccgacatcta taagatgtac    1020
aacggcagcg tgcccttcga ggaacggatc ctggctgtgc tgcagtggct gcagctgccc    1080
aaggatgagc ggccccactt ctacacccct tacctggaag aacctgacag cagcggccac    1140
agctacggcc ctgtgtccag cgaagtgatc aaggccctgc agcgggtgga cggcatggtg    1200
ggaatgctga tggacggcct gaaagagctg aacctgcaca gatgcctgaa cctgatcctg    1260
atcagcgacc acggcatgga cagggatccc tgcaagaagt acatctacct gaacaagtac    1320
ctgggcgacg tgaagaacat caaagtgatc tacggcccag cgccagact gaggcctagc    1380
gacgtgcccg acaagtacta cagcttcaac tacgagggaa tcgcccggaa cctgagctgc    1440
agagagccca ccagcacctt caagccctac ctgaagcact tcctgcccaa gcggctgcac    1500
ttcgccaaga gcgacagaat cgagcccctg accttctacc tggaccccca gtggcagctg    1560
gccctgaatc ccagcgagag aaagtactgc ggcagcggct tccacggctc cgacaacgtg    1620
ttcagcaaca tgcaggccct gttcgtgggc tacggacccg ctttaagca cggcatcgag    1680
gccgacacct tcgagaacat cgaggtgtac aatctgatgt gcgacctgct gaatctgacc    1740
cctgccccca caatggcac ccacggcagc ctgaaccatc tgctgaagaa ccccgtgtac    1800
acccctaagc accccaaaga ggtgcaccc ctggtgcagt gccctttcac cagaaacccc    1860
agagacaacc tgggctgtag ctgcaacccc agcatcctgc ccatcgagga cttccagacc    1920
cagttcaacc tgaccgtggc cgaggaaaag atcatcaagc acgagacact gccctacggc    1980
agaccccggg tgctgcagaa agagaacacc atctgcctgc tgagccagca ccagttcatg    2040
```

```
agcggctact cccaggacat cctgatgccc ctgtggacca gctacaccgt ggaccggaac   2100
gacagcttct ccaccgagga tttcagcaac tgcctgtacc aggatttccg gatccccctg   2160
agccccgtgc acaagtgcag cttctacaag aacaacacca aggtgtccta cggcttcctg   2220
agccctcccc agctgaacaa gaacagctcc ggcatctaca gcgaggccct gctgactacc   2280
aacatcgtgc ccatgtacca gagcttccaa gtgatctggc ggtacttcca cgacaccctg   2340
ctgcggaagt acgccgaaga acggaacggc gtgaacgtgg tgtccggccc agtgttcgac   2400
ttcgactacg acggcagatg tgacagcctg gaaaatctgc ggcagaaaag aagagtgatc   2460
cggaaccagg aaattctgat ccctacccac ttctttatcg tgctgacaag ctgcaaggat   2520
accagccaga ccccccctgca ctgcgagaac ctggataccc tggccttcat cctgcctcac   2580
cggaccgaca acagcgagag ctgtgtgcac ggcaagcacg acagctcttg ggtggaagaa   2640
ctgctgatgc tgcaccgggc cagaatcacc gatgtggaac acatcaccgg cctgagcttt   2700
taccagcagc ggaaagaacc cgtgtccgat atcctgaagc tgaaaaccca tctgcccacc   2760
ttcagccagg aagatgacaa gacccacact tgcccccccct gcccagctcc tgaactgctg   2820
ggaggaccct ctgtgttcct gttcccccca aagcccaagg acaccctgat gatctctagg   2880
acccccgaag tcacttgcgt cgtcgtcgac gtgtcccacg aggaccctga agtcaagttc   2940
aactggtacg tcgacggtgt cgaagtccac aacgccaaga ccaagcccag ggaagaacag   3000
tacaactcta cctaccgcgt cgtcagcgtc ctgaccgtcc tgcaccagga ctggctgaac   3060
ggaaaggaat acaagtgcaa ggtgtccaac aaggccctgc ctgcccccat cgaaaagacc   3120
atctctaagg ccaagggaca gccccgcgaa ccccaggtct acaccctgcc accctctagg   3180
gaagaaatga ccaagaacca ggtgtccctg acctgcctgg tcaagggatt ctacccctct   3240
gacatcgccg tcgaatggga atctaacgga cagcccgaaa acaactacaa gaccaccccc   3300
cctgtcctgg actctgacgg atcattcttc ctgtactcta agctgactgt cgacaagtct   3360
aggtggcagc agggaaacgt gttctcttgc tctgtcatgc acgaagccct gcacaaccac   3420
tacacccaga agtctctgtc tctgtccccc ggaaag                           3456
```

<210> SEQ ID NO 72
<211> LENGTH: 4662
<212> TYPE: DNA
<213> ORGANISM: Artificial Sequence
<220> FEATURE:
<223> OTHER INFORMATION: ENPP121-Albumin nucleotide sequence

<400> SEQUENCE: 72

```
atggaaaggg acggatgcgc cggtggtgga tctcgcggag gcgaaggtgg aagggcccct     60
agggaaggac ctgccggaaa cggaagggac aggggacgct ctcacgccgc tgaagctcca    120
ggcgaccctc aggccgctgc ctctctgctg gctcctatgg acgtcggaga agaacccctg    180
gaaaaggccg ccagggccag gactgccaag gaccccaaca cctacaagat catctccctc    240
ttcactttcg ccgtcggagt caacatctgc ctgggattca ccgccggact gaagcccagc    300
tgcgccaaag aagtgaagtc ctgcaagggc cggtgcttcg agcggacctt cggcaactgc    360
agatgcgacg ccgcctgtgt ggaactgggc aactgctgcc tggactacca ggaaacctgc    420
atcgagcccg agcacatctg gacctgcaac aagttcagat gcggcgagaa gcggctgacc    480
agatccctgt gtgcctgcag cgacgactgc aaggacaagg gcgactgctg catcaactac    540
agcagcgtgt gccagggcga gaagtcctgg gtggaagaac cctgcgagag catcaacgag    600
```

```
ccccagtgcc ctgccggctt cgagacacct cctaccctgc tgttcagcct ggacggcttt      660
cgggccgagt acctgcacac atggggaggc ctgctgcccg tgatcagcaa gctgaagaag      720
tgcggcacct acaccaagaa catgcggccc gtgtacccca ccaagacctt ccccaaccac      780
tactccatcg tgaccggcct gtaccccgag agccacggca tcatcgacaa caagatgtac      840
gaccccaaga tgaacgccag cttcagcctg aagtccaaag agaagttcaa ccccgagtgg      900
tataagggcg agcccatctg ggtcaccgcc aagtaccagg gcctgaaaag cggcacattc      960
ttttggcccg gcagcgacgt ggaaatcaac ggcatcttcc ccgacatcta agatgtac      1020
aacggcagcg tgcccttcga ggaacggatc ctggctgtgc tgcagtggct gcagctgccc     1080
aaggatgagc ggccccactt ctacaccctg tacctggaag aacctgacag cagcggccac     1140
agctacggcc ctgtgtccag cgaagtgatc aaggccctgc agcgggtgga cggcatggtg     1200
ggaatgctga tggacggcct gaaagagctg aacctgcaca gatgcctgaa cctgatcctg     1260
atcagcgacc acggcatgga cagggatcc tgcaagaagt acatctacct gaacaagtac     1320
ctgggcgacg tgaagaacat caaagtgatc tacgcccag ccgccagact gaggcctagc      1380
gacgtgcccg acaagtacta cagcttcaac tacgagggaa tcgcccggaa cctgagctgc     1440
agagagccca accagcactt caagcccttac ctgaagcact tcctgcccaa gcggctgcac     1500
ttcgccaaga gcgacagaat cgagcccctg accttctacc tggaccccca gtggcagctg     1560
gccctgaatc ccagcgagag aaagtactgc ggcagcggct ccacggctc cgacaacgtg      1620
ttcagcaaca tgcaggccct gttcgtgggc tacggacccg gctttaagca cggcatcgag     1680
gccgacacct tcgagaacat cgaggtgtac aatctgatgt gcgacctgct gaatctgacc     1740
cctgccccca caatggcac ccacggcagc ctgaaccatc tgctgaagaa ccccgtgtac      1800
acccctaagc cccccaaaga ggtgcacccc ctggtgcagt gccccttcac cagaaacccc     1860
agagacaacc tgggctgtag ctgcaacccc agcatcctgc ccatcgagga cttccagacc     1920
cagttcaacc tgaccgtggc cgaggaaaag atcatcaagc acgagacact gccctacggc     1980
agaccccggg tgctgcagaa agagaacacc atctgcctgc tgagccagca ccagttcatg     2040
agcggctact cccaggacat cctgatgccc ctgtggacca gctacaccgt ggaccggaac     2100
gacagcttct ccaccgagga tttcagcaac tgcctgtacc aggatttccg gatccccctg     2160
agccccgtgc acaagtgcag cttctacaag aacaacacca aggtgtccta cggcttcctg     2220
agccctcccc agctgaacaa gaacagctcc ggcatctaca gcgaggccct gctgactacc     2280
aacatcgtgc ccatgtacca gagcttccaa gtgatctggc ggtacttcca cgacaccctg     2340
ctgcggaagt acgccgaaga acggaacggc gtgaacgtgg tgtccggccc agtgttcgac     2400
ttcgactacg acggcagatg tgacagcctg gaaaatctgc ggcagaaaag aagagtgatc     2460
cggaaccagg aaattctgat ccctaccac ttctttatcg tgctgacaag ctgcaaggat     2520
accagccaga ccccctgca ctgcgagaac ctggatcccc tggccttcat cctgcctcac     2580
cggaccgaca cagcgagag ctgtgtgcac ggcaagcacg acagctcttg ggtggaagaa     2640
ctgctgatgc tgcaccgggc cagaatcacc gatgtggaac acatcaccgg cctgagcttt     2700
taccagcagc ggaaagaacc cgtgtccgat atcctgaagc tgaaaacca tctgcccacc     2760
ttcagccagg aagatggtgg aggaggctct ggtggaggcg tagcggagg cggagggtcg     2820
ggaggttctg gatcaatgaa gtgggtaacc tttatttccc ttcttttttct ctttagctcg    2880
gcttattcca ggggtgtgtt tcgtcgagat gcacacaaga gtgaggttgc tcatcggttt    2940
aaagatttgg gagaagaaaa tttcaaagcc ttggtgttga ttgcctttgc tcagtatctt    3000
```

```
cagcagtgtc catttgaaga tcatgtaaaa ttagtgaatg aagtaactga atttgcaaaa    3060
acatgtgttg ctgatgagtc agctgaaaat tgtgacaaat cacttcatac ccttttttgga   3120 gacaaattat gcacagttgc aactcttcgt gaaacctatg gtgaaatggc tgactgctgt    3180
gcaaaacaag aacctgagag aaatgaatgc ttcttgcaac acaagatgca acccaaac      3240 ctcccccgat tggtgagacc agaggttgat gtgatgtgca ctgcttttca tgacaatgaa    3300
gagacatttt tgaaaaaata cttatatgaa attgccagaa gacatcctta ctttatgcc    3360 ccggaactcc ttttctttgc taaaaggtat aaagctgctt ttacagaatg ttgccaagct    3420
gctgataaag ctgcctgcct gttgccaaag ctcgatgaac ttcgggatga agggaaggct    3480
tcgtctgcca aacagagact caagtgtgcc agtctccaaa aatttggaga aagagctttc    3540
aaagcatggg cagtagctcg cctgagccag agatttccca agctgagtt tgcagaagtt    3600 tccaagttag tgacagatct taccaaagtc cacacggaat gctgccatgg agatctgctt    3660
gaatgtgctg atgacagggc ggaccttgcc aagtatatct gtgaaaatca agattcgatc    3720
tccagtaaac tgaaggaatg ctgtgaaaaa cctctgttgg aaaaatccca ctgcattgcc    3780
gaagtggaaa atgatgagat gcctgctgac ttgccttcat tagctgctga tttttgttgaa  3840 agtaaggatg tttgcaaaaa ctatgctgag gcaaaggatg tcttcctggg catgtttttg    3900
tatgaatatg caagaaggca tcctgattac tctgtcgtgc tgctgctgag acttgccaag    3960
acatatgaaa ccactctaga gaagtgctgt gccgctgcag atcctcatga atgctatgcc    4020
aaagtgttcg atgaatttaa acctcttgtg gaagagcctc agaatttaat caaacaaaat    4080
tgtgagcttt ttgagcagct tggagagtac aaattccaga atgcgctatt agttcgttac    4140
accaagaaag tacccaagt gtcaactcca actcttgtag aggtctcaag aaacctagga    4200
aaagtgggca gcaaatgttg taaacatcct gaagcaaaaa gaatgccctg tcagaagac     4260 tatctatccg tggtcctgaa ccagttatgt gtgttgcatg agaaaacgcc agtaagtgac    4320
agagtcacca aatgctgcac agaatccttg gtgaacaggc gaccatgctt ttcagctctg    4380
gaagtcgatg aaacatacgt tcccaaagag tttaatgctg aaacattcac cttccatgca    4440
gatatatgca cactttctga aaggagaga caaatcaaga acaaactgc acttgttgag    4500 ctcgtgaaac acaagcccaa ggcaacaaaa gagcaactga agctgttat ggatgatttc    4560 gcagcttttg tagagaagtg ctgcaaggct gacgataagg agacctgctt tgccgaggag    4620
ggtaaaaaac ttgttgctgc aagtcaagct gccttaggct ta                      4662
```

<210> SEQ ID NO 73
<211> LENGTH: 3228
<212> TYPE: DNA
<213> ORGANISM: Artificial Sequence
<220> FEATURE:
<223> OTHER INFORMATION: ENPP7-1-Fc nucleotide sequence

<400> SEQUENCE: 73

```
atgagaggac ctgccgtcct gctgaccgtc gccctggcta ccttgctggc cctggtgct         60 ggtgcaccca gctgcgccaa agaagtgaag tcctgcaagg gccggtgctt cgagcggacc       120
ttcggcaact gcagatgcga cgccgcctgt gtggaactgg caactgctg cctggactac        180 caggaaaacct gcatcgagcc cgagcacatc tggaccctgca acaagttcag atgcggcgag    240
aagcggctga ccagatccct gtgtgcctgc agcgacgact gcaaggacaa gggcgactgc       300
tgcatcaact acagcagcgt gtgccaggcc gagaagtcct gggtggaaga accctgcgag       360
```

```
agcatcaacg agccccagtg ccctgccggc ttcgagacac ctcctaccct gctgttcagc    420
ctggacggct ttcgggccga gtacctgcac acatggggag gcctgctgcc cgtgatcagc    480
aagctgaaga agtgcggcac ctacaccaag aacatgcggc ccgtgtaccc caccaagacc    540
ttccccaacc actactccat cgtgaccggc ctgtaccccg agagccacgg catcatcgac    600
aacaagatgt acgaccccaa gatgaacgcc agcttcagcc tgaagtccaa agagaagttc    660
aaccccgagt ggtataaggg cgagcccatc tgggtcaccg ccaagtacca gggcctgaaa    720
agcggcacat tcttttggcc cggcagcgac gtggaaatca acggcatctt ccccgacatc    780
tataagatgt acaacggcag cgtgcccttc gaggaacgga tcctggctgt gctgcagtgg    840
ctgcagctgc ccaaggatga gcggccccac ttctacaccc tgtacctgga agaacctgac    900
agcagcggcc acagctacgg ccctgtgtcc agcgaagtga tcaaggccct gcagcgggtg    960
gacggcatgg tgggaatgct gatggacggc ctgaagagc tgaacctgca cagatgcctg    1020
aacctgatcc tgatcagcga ccacggcatg aacagggat cctgcaagaa gtacatctac    1080
ctgaacaagt acctgggcga cgtgaagaac atcaaagtga tctacggccc agccgccaga    1140
ctgaggccta gcgacgtgcc cgacaagtac tacagcttca actacgaggg aatcgcccgg    1200
aacctgagct gcagagagcc caaccagcac ttcaagccct acctgaagca cttcctgccc    1260
aagcggctgc acttcgccaa gagcgacaga atcgagcccc tgaccttcta cctggacccc    1320
cagtggcagc tggccctgaa tcccagcgag agaaagtact gcggcagcgg cttccacggc    1380
tccgacaacg tgttcagcaa catgcaggcc ctgttcgtgg gctacggacc cggctttaag    1440
cacggcatcg aggccgacac cttcgagaac atcgaggtgt acaatctgat gtgcgacctg    1500
ctgaatctga cccctgcccc caacaatggc acccacggca gcctgaacca tctgctgaag    1560
aaccccgtgt acacccctaa gcaccccaaa gaggtgcacc ccctggtgca gtgccccttc    1620
accagaaacc ccagagacaa cctgggctgt agctgcaacc ccagcatcct gcccatcgag    1680
gacttccaga cccagttcaa cctgaccgtg gccgaggaaa agatcatcaa gcacgagaca    1740 ctgcccctacg gcagaccccg ggtgctgcag aaagagaaca ccatctgcct gctgagccag    1800
caccagttca tgagcggcta ctcccaggac atcctgatgc ccctgtggac cagctacacc    1860
gtggaccgga acgacagctt ctccaccgag gatttcagca actgcctgta ccaggatttc    1920
cggatccccc tgagccccgt gcacaagtgc agcttctaca gaacaacac caaggtgtcc    1980 tacggcttcc tgagccctcc ccagctgaac aagaacagct ccggcatcta cagcgaggcc    2040
ctgctgacta ccaacatcgt gcccatgtac cagagcttcc aagtgatctg gcggtacttc    2100
cacgacaccc tgctgcggaa gtacgccgaa gaacggaacg gcgtgaacgt ggtgtccggc    2160
ccagtgttcg acttcgacta cgacggcaga tgtgacagcc tggaaaatct gcggcagaaa    2220
agaagagtga tccggaacca ggaaattctg atccctaccc acttctttat cgtgctgaca    2280
agctgcaagg ataccagcca gacccccctg cactgcgaga acctggatac cctggccttc    2340
atcctgcctc accggaccga caacagcgag agctgtgtgc acggcaagca cgacagctct    2400
tgggtggaag aactgctgat gctgcaccgg gccagaatca ccgatgtgga acacatcacc    2460
ggcctgagct tttaccagca gcggaaagaa cccgtgtccg atatcctgaa gctgaaaacc    2520
catctgccca ccttcagcca ggaagatgac aagacccaca cttgccccc ctgcccagct    2580 cctgaactgc tgggaggacc ctctgtgttc ctgttccccc caaagccaa ggacaccctg    2640 atgatctcta ggaccccga agtcacttgc gtcgtcgtcg acgtgtccca cgaggaccct    2700
gaagtcaagt tcaactggta cgtcgacggt gtcgaagtcc acaacgccaa gaccaagccc    2760
```

-continued

| | |
|---|---|
| agggaagaac agtacaactc tacctaccgc gtcgtcagcg tcctgaccgt cctgcaccag | 2820 |
| gactggctga acggaaagga atacaagtgc aaggtgtcca acaaggccct gcctgccccc | 2880 |
| atcgaaaaga ccatctctaa ggccaaggga cagccccgcg aaccccaggt ctacaccctg | 2940 |
| ccaccctcta gggaagaaat gaccaagaac caggtgtccc tgacctgcct ggtcaaggga | 3000 |
| ttctacccct ctgacatcgc cgtcgaatgg gaatctaacg gacagcccga aaacaactac | 3060 |
| aagaccaccc ccctgtcct ggactctgac ggatcattct tcctgtactc taagctgact | 3120 |
| gtcgacaagt ctaggtggca gcagggaaac gtgttctctt gctctgtcat gcacgaagcc | 3180 |
| ctgcacaacc actacaccca gaagtctctg tctctgtccc ccggaaag | 3228 |

<210> SEQ ID NO 74
<211> LENGTH: 4434
<212> TYPE: DNA
<213> ORGANISM: Artificial Sequence
<220> FEATURE:
<223> OTHER INFORMATION: ENPP7-NPP1-Albumin nucleotide sequence
<400> SEQUENCE: 74

| | |
|---|---|
| atgagaggac ctgccgtcct gctgaccgtc gccctggcta ccttgctggc cctggtgct | 60 |
| ggtgcaccca gctgcgccaa agaagtgaag tcctgcaagg gccggtgctt cgagcggacc | 120 |
| ttcggcaact gcagatgcga cgccgcctgt gtggaactgg caactgctg cctggactac | 180 |
| caggaaacct gcatcgagcc cgagcacatc tggacctgca acaagttcag atgcggcgag | 240 |
| aagcggctga ccagatccct gtgtgcctgc agcgacgact gcaaggacaa gggcgactgc | 300 |
| tgcatcaact acagcagcgt gtgccagggc gagaagtcct gggtggaaga accctgcgag | 360 |
| agcatcaacg agccccagtg ccctgccggc ttcgagacac ctcctaccct gctgttcagc | 420 |
| ctggacggct tcgggccga gtacctgcac acatggggag gctgctgcc cgtgatcagc | 480 |
| aagctgaaga gtgcggcac ctacaccaag aacatgcggc ccgtgtaccc caccaagacc | 540 |
| ttccccaacc actactccat cgtgaccggc ctgtaccccg agagccacgg catcatcgac | 600 |
| aacaagatgt acgaccccaa gatgaacgcc agcttcagcc tgaagtccaa agagaagttc | 660 |
| aaccccgagt ggtataaggg cgagcccatc tgggtcaccg ccaagtacca gggcctgaaa | 720 |
| agcggcacat ctttttggcc cggcagcgac gtggaaatca acggcatctt ccccgacatc | 780 |
| tataagatgt acaacggcag cgtgcccttc gaggaacgga tcctggctgt gctgcagtgg | 840 |
| ctgcagctgc ccaaggatga gcggccccac ttctacaccc tgtacctgga agaacctgac | 900 |
| agcagcggcc acagctacgg ccctgtgtcc agcgaagtga tcaaggccct gcagcgggtg | 960 |
| gacggcatgg tgggaatgct gatggacggc ctgaagagc tgaacctgca gatgcctg | 1020 |
| aacctgatcc tgatcagcga ccacggcatg gaacagggat cctgcaagaa gtacatctac | 1080 |
| ctgaacaagt acctgggcga cgtgaagaac atcaaagtga tctacggccc agccgccaga | 1140 |
| ctgaggccta gcgacgtgcc cgacaagtac tacagcttca actacgaggg aatcgcccgg | 1200 |
| aacctgagct gcagagagcc caaccagcac ttcaagccct acctgaagca cttcctgccc | 1260 |
| aagcggctgc acttcgccaa gagcgacaga atcgagcccc tgaccttcta cctggacccc | 1320 |
| cagtggcagc tggccctgaa tcccagcgag agaaagtact gcggcagcgg cttccacggc | 1380 |
| tccgacaacg tgttcagcaa catgcaggcc ctgttcgtgg gctacggacc cggctttaag | 1440 |
| cacggcatcg aggccgacac cttcgagaac atcgaggtgt acaatctgat gtgcgacctg | 1500 |
| ctgaatctga cccctgcccc caacaatggc acccacggca gctgaaccca tctgctgaag | 1560 |

-continued

```
aaccccgtgt acaccectaa gcaccccaaa gaggtgcacc ccctggtgca gtgccccttc    1620
accagaaacc ccagagacaa cctgggctgt agctgcaacc ccagcatcct gcccatcgag    1680
gacttccaga cccagttcaa cctgaccgtg gccgaggaaa agatcatcaa gcacgagaca    1740
ctgccctacg gcagacccg ggtgctgcag aaagagaaca ccatctgcct gctgagccag    1800
caccagttca tgagcggcta ctcccaggac atcctgatgc ccctgtggac cagctacacc    1860
gtggaccgga cgacagctt ctccaccgag gatttcagca actgcctgta ccaggatttc    1920
cggatccccc tgagccccgt gcacaagtgc agcttctaca gaacaacac caaggtgtcc    1980
tacggcttcc tgagccctcc ccagctgaac aagaacagct ccggcatcta cagcgaggcc    2040
ctgctgacta ccaacatcgt gcccatgtac cagagcttcc aagtgatctg gcggtacttc    2100
cacgacaccc tgctgcggaa gtacgccgaa gaacggaacg gcgtgaacgt ggtgtccggc    2160
ccagtgttcg acttcgacta cgacggcaga tgtgacagcc tggaaaatct gcggcagaaa    2220
agaagagtga tccggaacca ggaaattctg atccctaccc acttctttat cgtgctgaca    2280
agctgcaagg ataccagcca gacccccctg cactgcgaga acctggatac cctggccttc    2340
atcctgcctc accggaccga caacagcgag agctgtgtgc acggcaagca cgacagctct    2400
tgggtggaag aactgctgat gctgcaccgg gccagaatca ccgatgtgga acacatcacc    2460
ggcctgagct tttaccagca gcggaaagaa cccgtgtccg atatcctgaa gctgaaaacc    2520
catctgccca ccttcagcca ggaagatggt ggaggaggct ctggtggagg cggtagcgga    2580
ggcggagggt cgggaggttc tggatcaatg aagtgggtaa ccttatttc ccttcttttt    2640
ctctttagct cggcttattc cagggtgtg tttcgtcgag atgcacacaa gagtgaggtt    2700
gctcatcggt ttaaagattt gggagaagaa aatttcaaag ccttggtgtt gattgccttt    2760
gctcagtatc ttcagcagtg tccatttgaa gatcatgtaa aattagtgaa tgaagtaact    2820
gaatttgcaa aaacatgtgt tgctgatgag tcagctgaaa attgtgacaa atcacttcat    2880
accctttttg gagacaaatt atgcacagtt gcaactcttc gtgaaaccta tggtgaaatg    2940
gctgactgct gtgcaaaaca agaacctgag agaaatgaat gcttcttgca acacaaagat    3000
gacaacccaa acctccccg attggtgaga ccagaggttg atgtgatgtg cactgctttt    3060
catgacaatg aagagacatt tttgaaaaa tacttatatg aaattgccag aagacatcct    3120
tacttttatg ccccggaact cctttttctt gctaaaaggt ataaagctgc ttttacagaa    3180
tgttgccaag ctgctgataa agctgcctgc ctgttgccaa agctcgatga acttcgggat    3240
gaagggaagg cttcgtctgc caaacagaga ctcaagtgtg ccagtctcca aaaatttgga    3300
gaaagagctt tcaaagcatg ggcagtagct cgcctgagcc agagatttcc caaagctgag    3360
tttgcagaag tttccaagtt agtgacagat cttaccaaag tccacacgga atgctgccat    3420
ggagatctgc ttgaatgtgc tgatgacagg gcggaccttg ccaagtatat ctgtgaaaat    3480
caagattcga tctccagtaa actgaaggaa tgctgtgaaa aacctctgtt ggaaaaatcc    3540
cactgcattg ccgaagtgga aaatgatgag atgcctgctg acttgccttc attagctgct    3600
gatttgttg aaagtaagga tgtttgcaaa aactatgctg aggcaaagga tgtcttcctg    3660
ggcatgtttt tgtatgaata tgcaagaagg catcctgatt actctgtcgt gctgctgctg    3720
agacttgcca agacatatga aaccactcta gagaagtgct gtgccgctgc agatcctcat    3780
gaatgctatg ccaaagtgtt cgatgaattt aaacctcttg tggaagagcc tcagaattta    3840
atcaaacaaa attgtgagct ttttgagcag cttggagagt acaaattcca gaatgcgcta    3900
ttagttcgtt acaccaagaa agtaccccaa gtgtcaactc caactcttgt agaggtctca    3960
```

```
agaaacctag gaaaagtggg cagcaaatgt tgtaaacatc ctgaagcaaa aagaatgccc    4020
tgtgcagaag actatctatc cgtggtcctg aaccagttat gtgtgttgca tgagaaaacg    4080
ccagtaagtg acagagtcac caaatgctgc acagaatcct tggtgaacag gcgaccatgc    4140
ttttcagctc tggaagtcga tgaaacatac gttcccaaag agtttaatgc tgaaacattc    4200
accttccatg cagatatatg cacactttct gagaaggaga gacaaatcaa gaaacaaact    4260
gcacttgttg agctcgtgaa acacaagccc aaggcaacaa aagagcaact gaaagctgtt    4320
atggatgatt tcgcagcttt tgtagagaag tgctgcaagg ctgacgataa ggagacctgc    4380
tttgccgagg agggtaaaaa acttgttgct gcaagtcaag ctgccttagg ctta          4434

<210> SEQ ID NO 75
<211> LENGTH: 2625
<212> TYPE: DNA
<213> ORGANISM: Artificial Sequence
<220> FEATURE:
<223> OTHER INFORMATION: ENPP3 nucleotide sequence

<400> SEQUENCE: 75
atggaatcta cgttgacttt agcaacggaa caacctgtta agaagaacac tcttaagaaa      60
tataaaatag cttgcattgt tcttcttgct ttgctggtga tcatgtcact tggattaggc     120
ctggggcttg gactcaggaa actggaaaag caaggcagct gcaggaagaa gtgctttgat     180
gcatcattta gaggactgga gaactgccgg tgtgatgtgg catgtaaaga ccgaggtgat     240
tgctgctggg attttgaaga cacctgtgtg aatcaactc gaatatggat gtgcaataaa     300
tttcgttgtg gagagaccag attagaggcc agcctttgct cttgttcaga tgactgtttg     360
cagaggaaag attgctgtgc tgactataag agtgtttgcc aaggagaaac ctcatggctg     420
gaagaaaact gtgacacagc ccagcagtct cagtgcccag aagggtttga cctgccacca     480
gttatcttgt tttctatgga tggatttaga gctgaatatt tatacacatg ggatacttta     540
atgccaaata tcaataaact gaaaacatgt ggaattcatt caaaatacat gagagctatg     600
tatcctacca aaaccttccc aaatcattac accattgtca cgggcttgta tccagagtca     660
catggcatca ttgacaataa tatgtatgat gtaaatctca caagaatttt ttcactttct     720
tcaaaggaac aaaataatcc agcctggtgg catgggcaac caatgtggct gacagcaatg     780
tatcaaggtt aaaagccgc tacctacttt tggcccggat cagaagtggc tataaatggc     840 tccttttcctt ccatatacat gccttacaac ggaagtgtcc catttgaaga gaggatttct     900
acactgttaa aatggctgga cctgcccaaa gctgaaagac ccaggtttta taccatgtat     960
tttgaagaac tgattcctc tggacatgca ggtggaccag tcagtgccag agtaattaaa    1020 gcctacagg tagtagatca tgcttttggg atgttgatgg aaggcctgaa gcagcggaat    1080
ttgcacaact gtgtcaatat catccttctg gctgaccatg gaatggacca gacttattgt    1140
aacaagatgg aatacatgac tgattatttt cccagaataa acttcttcta catgtacgaa    1200
gggcctgccc cccgcatccg agctcataat atacctcatg acttttttag ttttaattct    1260
gaggaaattg ttagaaacct cagttgccga aaacctgatc agcatttcaa gcccatttg    1320 actcctgatt tgccaaagcg actgcactat gccaagaacg tcagaatcga caagttcat    1380 ctctttgtgg atcaacagtg gctggctgtt aggagtaaat caaatacaaa ttgtggagga    1440
ggcaaccatg gttataacaa tgagtttagg agcatggagg ctatctttct ggcacatgga    1500
cccagtttta aagagaagac tgaagttgaa ccatttgaaa atattgaagt ctataacca    1560
```

| | |
|---|---|
| atgtgtgatc ttctacgcat tcaaccagca ccaaacaatg gaacccatgg tagtttaaac | 1620 |
| catcttctga aggtgccttt ttatgagcca tcccatgcag aggaggtgtc aaagttttct | 1680 |
| gtttgtggct ttgctaatcc attgcccaca gagtctcttg actgtttctg ccctcaccta | 1740 |
| caaaatagta ctcagctgga acaagtgaat cagatgctaa atctcaccca agaagaaata | 1800 |
| acagcaacag tgaaagtaaa tttgccattt gggaggccta gggtactgca agaacgtg | 1860 |
| gaccactgtc tcctttacca cagggaatat gtcagtggat ttggaaaagc tatgaggatg | 1920 |
| cccatgtgga gttcatacac agtccccag ttgggagaca catcgcctct gcctcccact | 1980 |
| gtcccagact gtctgcgggc tgatgtcagg gttcctcctt ctgagagcca aaaatgttcc | 2040 |
| ttctatttag cagacaagaa tatcacccac ggcttcctct atcctcctgc cagcaataga | 2100 |
| acatcagata gccaatatga tgctttaatt actagcaatt tggtacctat gtatgaagaa | 2160 |
| ttcagaaaaa tgtgggacta cttccacagt gttcttctta taaaacatgc cacagaaaga | 2220 |
| aatggagtaa atgtggttag tggaccaata tttgattata attatgatgg ccatttgat | 2280 |
| gctccagatg aaattaccaa acatttagcc aacactgatt ttcccatccc aacacactac | 2340 |
| tttgtggtgc tgaccagttg taaaaacaag agccacacac ggaaaactg ccctgggtgg | 2400 |
| ctggatgtcc tacccttat catccctcac cgacctacca acgtggagag ctgtcctgaa | 2460 |
| ggtaaaccag aagctctttg ggttgaagaa agatttacag ctcacattgc ccgggtccgt | 2520 |
| gatgtagaac ttctcactgg gcttgacttc tatcaggata aagtgcagcc tgtctctgaa | 2580 |
| attttgcaac taaagacata tttaccaaca tttgaaacca ctatt | 2625 |

<210> SEQ ID NO 76
<211> LENGTH: 2775
<212> TYPE: DNA
<213> ORGANISM: Artificial Sequence
<220> FEATURE:
<223> OTHER INFORMATION: ENPP1 nucleotide sequence

<400> SEQUENCE: 76

| | |
|---|---|
| atggaacggg acggctgtgc cggcggagga tcaagaggcg agaaggcgg cagagcccct | 60 |
| agagaaggac ctgccggcaa cggcagagac agaggcagat ctcatgccgc cgaagccct | 120 |
| ggcgatcctc aggctgctgc ttctctgctg gcccccatgg atgtgggcga ggaacctctg | 180 |
| gaaaaggccg ccagagccag aaccgccaag gaccccaaca cctacaaggt gctgagcctg | 240 |
| gtgctgtccg tgtgcgtgct gaccaccatc ctgggctgca tcttcggcct gaagcccagc | 300 |
| tgcgccaaag aagtgaagtc ctgcaagggc cggtgcttcg agcggacctt cggcaactgc | 360 |
| agatgcgacg ccgcctgtgt ggaactgggc aactgctgcc tggactacca ggaaacctgc | 420 |
| atcgagcccg agcacatctg gacctgcaac aagttcagat gcggcgagaa gcggctgacc | 480 |
| agatccctgt gtgcctgcag cgacgactgc aaggacaagg gcgactgctg catcaactac | 540 |
| agcagcgtgt gccagggcga agtcctggt gtggaagaac cctgcgagag catcaacgag | 600 |
| ccccagtgcc ctgccggctt cgagacacct cctaccctgc tgttcagcct ggacggcttt | 660 |
| cgggccgagt acctgcacac atggggaggc ctgctgcccg tgatcagcaa gctgaagaag | 720 |
| tgcggcacct acaccaagaa catgcggccc gtgtacccca ccaagacctt ccccaaccac | 780 |
| tactccatcg tgaccggcct gtaccccgag agccacggca tcatcgacaa caagatgtac | 840 |
| gaccccaaga tgaacgccag cttcagcctg aagtccaaag agaagttcaa ccccgagtgg | 900 |
| tataagggcg agcccatctg ggtcaccgcc agtaccagg gctgaaaag cggcacattc | 960 |
| ttttggcccg gcagcgacgt ggaaatcaac ggcatcttcc ccgacatcta agatgtac | 1020 |

```
aacggcagcg tgcccttcga ggaacggatc ctggctgtgc tgcagtggct gcagctgccc    1080
aaggatgagc ggccccactt ctacaccctg tacctggaag aacctgacag cagcggccac    1140
agctacggcc ctgtgtccag cgaagtgatc aaggccctgc agcgggtgga cggcatggtg    1200
ggaatgctga tggacggcct gaaagagctg aacctgcaca gatgcctgaa cctgatcctg    1260
atcagcgacc acggcatgga cagggatcc tgcaagaagt acatctacct gaacaagtac    1320
ctgggcgacg tgaagaacat caaagtgatc tacgcccag ccgccagact gaggcctagc    1380
gacgtgcccg acaagtacta cagcttcaac tacgagggaa tcgcccggaa cctgagctgc    1440
agagagccca accagcactt caagccctac ctgaagcact tcctgcccaa gcggctgcac    1500
ttcgccaaga gcgacagaat cgagcccctg accttctacc tggaccccca gtggcagctg    1560
gccctgaatc ccagcgagag aaagtactgc ggcagcggct tccacggctc cgacaacgtg    1620
ttcagcaaca tgcaggccct gttcgtgggc tacggacccg gctttaagca cggcatcgag    1680
gccgacacct tcgagaacat cgaggtgtac aatctgatgt gcgacctgct gaatctgacc    1740
cctgccccca caatggcac ccacggcagc ctgaaccatc tgctgaagaa ccccgtgtac    1800
acccctaagc accccaaaga ggtgcacccc tggtgcagt gccccttcac cagaaacccc    1860
agagacaacc tgggctgtag ctgcaacccc agcatcctgc ccatcgagga cttccagacc    1920
cagttcaacc tgaccgtggc cgaggaaaag atcatcaagc acgagacact gcccctacggc    1980 agacccgggg tgctgcagaa agagaacacc atctgcctgc tgagccagca ccagttcatg    2040
agcggctact cccaggacat cctgatgccc ctgtggacca gctacaccgt ggaccggaac    2100
gacagcttct ccaccgagga tttcagcaac tgcctgtacc aggatttccg gatccccctg    2160
agccccgtgc acaagtgcag cttctacaag aacaacacca aggtgtccta cggcttcctg    2220
agccctcccc agctgaacaa gaacagctcc ggcatctaca gcgaggccct gctgactacc    2280
aacatcgtgc ccatgtacca gagcttccaa gtgatctggc ggtacttcca cgacaccctg    2340
ctgcggaagt acgccgaaga acggaacggc gtgaacgtgg tgtccggccc agtgttcgac    2400
ttcgactacg acggcagatg tgacagcctg gaaaatctgc ggcagaaaag aagagtgatc    2460
cggaaccagg aaattctgat ccctacccac ttctttatcg tgctgacaag ctgcaaggat    2520
accagccaga ccccccctgca ctgcgagaac ctggataccc tggccttcat cctgcctcac    2580
cggaccgaca cagcgagag ctgtgtgcac ggcaagcacg acagctcttg ggtggaagaa    2640
ctgctgatgc tgcaccgggc cagaatcacc gatgtggaac acatcaccgg cctgagcttt    2700
taccagcagc ggaaagaacc cgtgtccgat atcctgaagc tgaaaaccca tctgcccacc    2760
ttcagccagg aagat                                                    2775
```

<210> SEQ ID NO 77
<211> LENGTH: 20
<212> TYPE: DNA
<213> ORGANISM: Artificial Sequence
<220> FEATURE:
<223> OTHER INFORMATION: Chemically synthesized

<400> SEQUENCE: 77

```
ggctgtattc ccctccatcg                                                 20
```

<210> SEQ ID NO 78
<211> LENGTH: 22
<212> TYPE: DNA
<213> ORGANISM: Artificial Sequence
<220> FEATURE:

<223> OTHER INFORMATION: Chemically synthesized

<400> SEQUENCE: 78
ccagttggta acaatgccat gt                                              22

<210> SEQ ID NO 79
<211> LENGTH: 23
<212> TYPE: DNA
<213> ORGANISM: Artificial Sequence
<220> FEATURE:
<223> OTHER INFORMATION: Chemically synthesized

<400> SEQUENCE: 79
ctggttttgt cagtatgtgt gct                                             23

<210> SEQ ID NO 80
<211> LENGTH: 21
<212> TYPE: DNA
<213> ORGANISM: Artificial Sequence
<220> FEATURE:
<223> OTHER INFORMATION: Chemically synthesized

<400> SEQUENCE: 80
ctcaccgcac ctgaatttgt t                                               21

<210> SEQ ID NO 81
<211> LENGTH: 21
<212> TYPE: DNA
<213> ORGANISM: Artificial Sequence
<220> FEATURE:
<223> OTHER INFORMATION: Chemically synthesized

<400> SEQUENCE: 81
ccaaagactc gatccccaga a                                               21

<210> SEQ ID NO 82
<211> LENGTH: 23
<212> TYPE: DNA
<213> ORGANISM: Artificial Sequence
<220> FEATURE:
<223> OTHER INFORMATION: Chemically synthesized

<400> SEQUENCE: 82
tgttagaaag ttcacggtaa ccc                                             23

<210> SEQ ID NO 83
<211> LENGTH: 21
<212> TYPE: DNA
<213> ORGANISM: Artificial Sequence
<220> FEATURE:
<223> OTHER INFORMATION: Chemically synthesized

<400> SEQUENCE: 83
tacgggctgg cgtattcttt g                                               21

<210> SEQ ID NO 84
<211> LENGTH: 21
<212> TYPE: DNA
<213> ORGANISM: Artificial Sequence
<220> FEATURE:
<223> OTHER INFORMATION: Chemically synthesized

<400> SEQUENCE: 84
cactgtaggc tatcagggtg t                                               21

```
<210> SEQ ID NO 85
<211> LENGTH: 21
<212> TYPE: DNA
<213> ORGANISM: Artificial Sequence
<220> FEATURE:
<223> OTHER INFORMATION: Chemically synthesized

<400> SEQUENCE: 85
ccaactcttt tgtgccagag a                                          21

<210> SEQ ID NO 86
<211> LENGTH: 23
<212> TYPE: DNA
<213> ORGANISM: Artificial Sequence
<220> FEATURE:
<223> OTHER INFORMATION: Chemically synthesized

<400> SEQUENCE: 86
ggctacattg gtgttgagct ttt                                        23
```